US011896652B2

(12) United States Patent
High et al.

(10) Patent No.: US 11,896,652 B2
(45) Date of Patent: *Feb. 13, 2024

(54) MODIFIED FACTOR IX, AND COMPOSITIONS, METHODS AND USES FOR GENE TRANSFER TO CELLS, ORGANS, AND TISSUES

(71) Applicant: The Children's Hospital of Philadelphia, Philadelphia, PA (US)

(72) Inventors: Katherine A. High, Merion Station, PA (US); Xavier Anguela, Barcelona (ES)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/050,982

(22) Filed: Oct. 28, 2022

(65) Prior Publication Data

US 2023/0142320 A1 May 11, 2023

Related U.S. Application Data

(63) Continuation of application No. 17/305,649, filed on Jul. 12, 2021, now Pat. No. 11,491,213, which is a continuation of application No. 17/014,782, filed on Sep. 8, 2020, now Pat. No. 11,110,153, which is a continuation of application No. 15/191,357, filed on Jun. 23, 2016, now Pat. No. 10,799,566.

(60) Provisional application No. 62/349,572, filed on Jun. 13, 2016, provisional application No. 62/348,781, filed on Jun. 10, 2016, provisional application No. 62/338,315, filed on May 18, 2016, provisional application No. 62/315,453, filed on Mar. 30, 2016, provisional application No. 62/183,599, filed on Jun. 23, 2015.

(51) Int. Cl.
*A61K 38/48* (2006.01)
*C12N 15/86* (2006.01)
*C12N 9/64* (2006.01)

(52) U.S. Cl.
CPC .......... *A61K 38/4846* (2013.01); *C12N 9/644* (2013.01); *C12N 15/86* (2013.01); *C12Y 304/21022* (2013.01); *C12N 2750/14143* (2013.01)

(58) Field of Classification Search
None
See application file for complete search history.

(56) References Cited

U.S. PATENT DOCUMENTS

| 6,156,303 A | 12/2000 | Russell et al. |
| 6,468,524 B1 | 10/2002 | Chiorini et al. |
| 6,531,298 B2 | 3/2003 | Stafford et al. |
| 6,670,176 B1 | 12/2003 | Samuiski et al. |
| 7,351,813 B2 | 4/2008 | Miao et al. |
| 8,030,065 B2 | 10/2011 | Gray |
| 9,249,405 B2 | 2/2016 | Simioni |
| 9,840,719 B2 | 12/2017 | High et al. |
| 9,982,248 B2 | 5/2018 | Simioni |
| 10,398,787 B2 | 9/2019 | Vandendriessche et al. |
| 10,413,598 B2 | 9/2019 | Nathwani et al. |
| 10,465,180 B2 | 11/2019 | Simioni |
| 10,799,566 B2 * | 10/2020 | High ............. C12Y 304/21022 |
| 11,110,153 B2 * | 9/2021 | High ..................... C12N 9/644 |
| 11,191,847 B2 | 12/2021 | Wang et al. |
| 11,491,213 B2 * | 11/2022 | High ........................ A61P 7/04 |
| 2003/0022378 A1 | 1/2003 | Ehrhardt et al. |
| 2003/0099618 A1 | 5/2003 | Couto et al. |
| 2008/0044386 A1 | 2/2008 | Ji et al. |
| 2008/0153156 A1 | 6/2008 | Gray |
| 2008/0220015 A1 | 9/2008 | Abina |
| 2009/0197338 A1 | 8/2009 | Vandenberghe et al. |
| 2009/0317417 A1 | 12/2009 | Vandenberghe et al. |
| 2010/0286242 A1 | 11/2010 | Bohn et al. |
| 2011/0184049 A1 | 7/2011 | Chuah et al. |
| 2011/0244550 A1 | 10/2011 | Simioni |
| 2011/0263027 A1 | 10/2011 | Gao et al. |
| 2013/0296534 A1 | 11/2013 | Lee et al. |
| 2014/0271550 A1 | 9/2014 | Rabinowitz et al. |
| 2014/0323956 A1 | 10/2014 | Mendell et al. |
| 2014/0336245 A1 | 11/2014 | Mingozzi et al. |
| 2015/0023924 A1 | 1/2015 | High et al. |
| 2015/0273082 A1 | 10/2015 | Nathwani et al. |
| 2016/0201088 A1 | 7/2016 | Gao |
| 2016/0375110 A1 | 12/2016 | High et al. |
| 2018/0071406 A1 | 3/2018 | Chuah et al. |

FOREIGN PATENT DOCUMENTS

| EP | 2796426 A1 | 10/2014 |
| JP | 2004-500880 A | 1/2004 |
| WO | 1999003496 | 1/1999 |

(Continued)

OTHER PUBLICATIONS

McCarty, "Self-complementary AAV Vectors: Advances and Applications" 16(10 Molecular Therapy 1648-1656 (Year: 2008).*
Nair et al., "Computationally designed liver-specific transcriptional modules and hyperactive factor IX improve hepatic gene therapy" 123(20) Blood 3195-3199 (Year: 2014).*
Allen et al., "Two Hepatic Enhancers, HCR.1 and HCR.2, Coordinate the Liver Expression of the Entire Human Apolipoprotein E/C-I/C-IV/C-II Gene Cluster"; J. of Biological Chem.; vol. 272, No. 46, pp. 29113-29119, 1997.

(Continued)

*Primary Examiner* — Nancy J Leith
(74) *Attorney, Agent, or Firm* — Pillsbury Winthrop Shaw Pittman LLP; Robert M. Bedgood

(57) ABSTRACT

The invention relates to modified Factor IX coding sequence, expression cassette, vectors such as viral (e.g., lenti- or adeno-associated viral) vectors, and gene transfer methods and uses. In particular, to target Factor IX nucleic acid to cells, tissues or organs for expression (transcription) of Factor IX.

23 Claims, 50 Drawing Sheets

Specification includes a Sequence Listing.

(56) References Cited

FOREIGN PATENT DOCUMENTS

| WO | 2001/98482 A2 | 12/2001 |
|---|---|---|
| WO | 2004027019 A2 | 4/2004 |
| WO | 2005/037226 A2 | 4/2005 |
| WO | 2006036502 A2 | 4/2006 |
| WO | 2007120542 A2 | 10/2007 |
| WO | 2010/029178 A1 | 3/2010 |
| WO | 2010029178 | 3/2010 |
| WO | 2011005968 | 1/2011 |
| WO | 2011133890 A1 | 10/2011 |
| WO | 2011133933 A2 | 10/2011 |
| WO | 2013/078316 A1 | 5/2013 |
| WO | 2013078400 A1 | 5/2013 |
| WO | 2013123457 A1 | 8/2013 |
| WO | 2013123503 A1 | 8/2013 |
| WO | 2013158879 A1 | 10/2013 |
| WO | 2014/003553 A1 | 1/2014 |
| WO | 2014/016580 A1 | 1/2014 |
| WO | 2015/013313 A2 | 1/2015 |
| WO | 2017075619 | 5/2017 |

OTHER PUBLICATIONS

Anson et al., "The gene structure of human anti-harmophilic factor IX" The EMBO J.; vol. 3, No. 2, pp. 1053-1060, 1984.
Leebeek, et al., "First Results From a Dose-Escalating Study With AAV5 Vector Containing Wild Type Human Factor IX Gene Therapy in Patients With Severe or Moderately-Severe Haemophilia B"; 2 pages; Abstract of oral presentation; "Presentation during EHA21: On Saturday, Jun. 11, 2016"; downloaded on Jan. 10, 2020 from https://library.ehaweb.org/eha/2016/21st/135223/frank.leebeek.first.results.from.a.dose-escalating.study.with.aav5.vector.html?f=m3.
Monahan, P., "Update on a phase 1/2 open-label trial of BAX335, an adeno-associated virus 8 (AAV8) vector-based gene therapy program for hemophilia B. ISTH 2015 Congress, Toronto, Jun. 20-25"; 4 pages; downloaded on Jan. 10, 2020 from https://econnect.baxter.com/assets/downloads/bax335-isth-highlights.pdf.
"Baxalta Reports Continued Progress on Phase 1/2 Clinical Trial of BAX335, Investigational Gene Therapy Treatment for Hemophilia B"; 6 pages; Press release dated Jun. 4, 2015; downloaded on Jan. 10, 2020 from https://www.baxter.com/baxter-newsroom/baxalta-reports-continued-progress-phase-12-clinical-trial-bax335-investigational.
"Baxter Provides Progress Update on Gene Therapy Program, Including Phase I/II Clinical Trial of BAX 335, Investigational Gene Therapy for Hemophilia B"; 5 pages; Press release dated Feb. 12, 2015; downloaded on Jan. 10, 2020 from https://www.baxter.com/baxter-newsroom/baxter-provides-progress-update-gene-therapy-program-including-phase-iii-clinical.
Cantore et al., "Hyperfunctional coagulation factor IX improves the efficacy of gene therapy in hemophilic mice"; Blood; vol. 120, No. 23, pp. 4517-4520, 2012.
Chang et al., Chaging Residue 338 in Human Factor IX from Arginine to Alanine Causes an Increase in Catalytic Activity; J. of Biological Chem., vol. 273, No. 20, pp. 12089-12094, 1998.
Crudele et al., AAV liver expression of FIX-Padua prevents and eradicates FIX inhibitor without increasing thrombogenicity in hemophilia B dogs and mice; Blood, vol. 125, No. 10, 2015.
Faust et al., "CpG-depleted adeno-associated virus vectors evade immune detection"; J Clin Invest; vol. 123, No. 7, pp. 2994-3001, 2013.
Finn et al., "The efficacy and the risk of immunogenicity of FIX Padua (R338L) in hemophilia B dogs treated by AAV muscle gene therapy"; Blood, vol. 120, No. 23, pp. 4521-4523, 2012.
Finn et al., "Factor IX-R338L (FIX Padua) as a Novel Alterntive for the Treatment of Canine Severe Hemophilia B"; Molecular Therapy; vol. 18, supple. 1, No. 615, May 2010.
Hafenrichter et al., "Quantitative Evaluation of Liver-Specific Promoters From Retroviral Vectors After In Vivo Transduction of Hepatocytes"; Blood, vol. 84, No. 10, pp. 3394-3404, 1994.

Kay et al., "Evidence for gene transfer and expression of factor IX in haemophilia B patients treated with an AAV vector"; Nature Genetics, vol. 24, pp. 257-261, 2000.
Kurachi et al., " Role of Intron I in Expression of the Human Factor IX Gene"; J. of Biological Chem.; vol. 270, No. 10, pp. 5276-5528, 1995.
Manno et al., "Successful transduction of liver in hemophilia by AAV-Factor IX and limitations imposed by the host immune response"; Nature Medicine, vol. 12, No. 3, pp. 342-347, 2006.
Miao et al., "Inclusion of the Hepatic Locus Control Region, an Intron, and Untranslated Region Increases and Stabilizes Hepatic Factor IX Gene Expression in Vivo but Not in Vitro"; Molec. Ther., vol. 1, No. 6, pp. 522-532, 2000.
Miesbach et al., "Phase 1-2 Clinical Trial of a Recombinant AAV5 Vector Containing the Human FIX Gene in Patients with Severe or Moderately Severe Haemophilia B"; Abstract; Blood, 124:5948, 2014; 4 pages.
Monahan et al., "Employing a Gain-of-Function Factor IX VariantR338L to Advance the Efficacy and Safetyof Hemophilia B Human Gene Therapy:Preclinical Evaluation Supporting an OngoingAdeno-Associated Virus Clinical Trial"; Human Gene Therapy, vol. 26 pp. 69-81, 2015.
Nathwani et al., "Self-complementary adeno-associated virus vectors containing a novelliver-specific human factor IX expression cassette enable highly efficient transduction of murine and nonhuman primate liver"; Blood, vol. 107, No. 7, pp. 2653-2661, 2006.
Nathwani et al., "Adenovirus-Associated Virus Vector-Mediated Gene Transfer in Hemophilia B"; New England J. of Med., vol. 365, No. 25, pp. 2357-2365, 2011.
Nathwani et al., "Long-Term Safety and Efficacy of Factor IX Gene Therapy in Hemophilia B"; New England J. of Med., vol. 371 No. 21, pp. 1994-2004, 2014.
Reyes-Sandoval & Ertl, "CpG Methylation of a Plasmid Vector Results in Extended Transgene Product Expression by Circumventing Induction of Immune Responses"; Molecular Therapy, vol. 9, No. 2, pp. 249-261, 2004.
Schuettrumpf et al., "Factor variants improve gene therapy efficacy for hemophilia B"; Blood, vol. 105, No. 6, pp. 2316-2323 , 2005.
Shen et al., "Tissue-Specific Regulation of Human $\alpha$1-Antitrypsin Gene Expression in Transgenic Mice" DNA, vol. 8, No. 2, pp. 101-108, 1989.
Vandendriessche et al., "Efficacy and safety of adeno-associated viral vectors based on serotype 8 and 9 vs. lentiviral vectors for hemophilia B gene therapy" J. of Thromb. and Haemos. vol. 5 pp. 16-24, 2007.
Wang et al., "Sustained correction of disease in naive and AAV2-pretreated hemophilia B dogs:AAV2/8-mediated, liver-directed gene therapy"; Blood, vol. 105, No. 8, pp. 3079-3086, 2005.
Yoshitake et al., "Nucleotide Sequence of the Gene for Human Factor IX (Antihemophilic Factor B)"; Biochem., vol. 24, pp. 3736-3750, 1985.
Arruda et al., "Regional intravascular delivery of AAV-2-F.IX to skeletal muscle achieves long-term correction of hemophilia B in a large animal model"; Blood, vol. 105, No. 9, pp. 3458-3464, 2005.
Bauer et al., "The impact of intragenic CpG content on gene expression"; Nucleic Acids Res., vol. 38, No. 12, pp. 3891-3908, 2010.
Francesco Bernardi, "Gain-of-function proteins for gene transfer in hemophilia"; Blood, vol. 105, No. 6, pp. 2243, 2005.
Cancio et al., "Developments in the treatment of hemophilia B: focus on emerging gene therapy"; The Application of Clinical Genetics, vol. 6, pp. 91-101, 2013.
Chao et al., "Sustained and Complete Phenotype Correction of Hemophilia B Mice Following Intramuscular Injection of AAV1 Serotype Vectors"; Molecular Therapy, vol. 4, No. 3, pp. 217-222, 2001.
Linda B. Couto, "Preclinical Gene Therapy Studies for Hemophilia Using Adeno-Associated Virus (AAV) Vectors"; Sem. Thromb. Hemo. 30:161-171 (2004).
Dang et al., "Structure of the Hepatic Control Region of the Human Apolipoprotein E/C-I Gene Locus"; J. of Biological Chemistry, vol. 270, No. 38, pp. 22577-22585, 1995.

(56) References Cited

OTHER PUBLICATIONS

Gao et al., "Novel adeno-associated viruses from rhesus monkeys as vectors for human gene therapy"; PNAS, vol. 99, No. 18, pp. 11854-11859, 2002.
Goodwin and Rottman, "The 3'-Flanking Sequence of the Bovine Growth Hormone Gene Contains Novel Elements Required for Efficient and Accurate Polyadenylation"; J. of Biological Chemistry, vol. 267, No. 23, pp. 16330-16334, 1992.
Hasbrouck and High, "AAV-mediated gene transfer for the treatment of hemophilia B: problems and prospects"; Gene Therapy, vol. 15, pp. 870-875, 2008.
Herzog et al., "Muscle-Directed Gene Transfer and Transient Immune Suppression Result in Sustained Partial Correction of Canine Hemophilia B Caused by a Null Mutation"; Molecular Therapy, vol. 4, No. 3, pp. 192-200, 2001.
Herzog et al., "Long-term correction of canine hemophilia B by gene transfer of blood coagulation factor IX mediated by adeno-associated viral vector"; Nature Medicine Medicine, vol. 5, No. 1, pp. 56-63, 1999.
Katherine A. High, "The gene therapy journey for hemophilia: are we there yet?"; Blood, vol. 120,, No. 23, pp. 4482-4487, 2012.
Katherine A. High, "Clinical Gene Transfer Studies for Hemophilia B"; Seminars in Thrombosis and Hemostasis, vol. 30, No. 2, pp. 257-267, 2004.
Jiang et al., "Effects of transient immuno suppression on adenoassociated, virus-mediated, liver-directed gene transfer in rhesus macaques and implications for human gene therapy"; Blood, vol. 108, No. 10, pp. 3321-3328, 2006.
Jiang et al., "Evidence of Multiyear Factor IX Expression by AAV-Mediated Gene Transfer to Skeletal Muscle in an Individual with Severe Hemophilia B"; Molecular Therapy, vol. 14, No. 3, pp. 452-455, 2006.
Leger et al., "Adeno-Associated Viral Vector-Mediated Transgene Expression Is Independent of DNA Methylation in Primate Liver and Skeletal Muscle"; PloS ONE, vol. 6, issue 6, pp. 1-11, 2011.
Long et al., "Complete Sequence of the cDNA for Human α1-Antitrypsin and the Gene for the S Variant"; Biochemistry, vol. 23, pp. 4828-4837, 1984.
Lu et al., "Preparation of a recombinant adeno-associated viral vector with a mutation of human factor IX in large scale and its expresstion in virtro and in vivo"; Chinese Science Bulletin, vol. 46, No. 1, pp. 1367-1371, 2001.
Lu et al., "Gene therapy for hemophilia B mediated by recombinant adeno-associated viral vector with hFIXR338A, a high catalytic activity mutation of human coagulation factor IX"; Science in China, vol. 44, No. 6, pp. 585-592, 2001.
Manno et al., "AAV-mediated factor IX gene transfer to skeletal muscle in patients with severe hemophilia B"; Blood, vol. 101, No. 8, pp. 2963-2972, 2003.
Mauro and Chappell, "A critical analysis of codon optimization in human therapeutics"; Trends Mol. Med., vol. 20, No. 22, pp. 604-613, 2014.
Chirmule, N. et al., Humoral Immunity to Adeno-Associated Virus Type 2 Vectors Following Administration to Murine and Nonhuman Primate Muscle, Journal of Virology, 2000, 74(5):2420-2425.
Daya et al., Gene Therapy Using Adeno-Associated Virus Vectors, Clinical Microbiology Reviews, 2008, pp. 583-593.
Fumoto et al., Targeted Gene Delivery: Importance of Administration Routes, Intech, 2013, pp. 3-31.
Gao, G., et al., Clades of Adeno-Associated Viruses are Widely Disseminated in Human Tissues, Journal of Virology, 2004, 78(12):6381-6388.
Guo et al., Protein Tolerance to Random Amino Acid Change, PNAS, 2004, 101(25):9205-9210.
Katz et al., Cardiac Gene Therapy: Optimization of Gene Delivery Techniques In Vivo, Human Gene Therapy, 2010, 21:371-380.
Kay et al., Evidence for Gene Transfer and Expression of Factor IX in Haemophilia B Patients Treated with an AAV Vector, Nature Genetics, 2000, 24(3):257-61.

Ketterling, R.P., et al., The Rates of G:C->C:G Transversions at CpG Dinucleotides in the Human Factgor IX Gene, Am. J. Hum. Genet., 1994, 54:831-835.
Lesk et al., Prediction of Protein Function from Protein Sequence and Structure, p. 27 and 28, downloaded Sep. 16, 2007.
Martin et al., Overexpression of Galgt2 in skeletal muscle prevents injury resulting from eccentric contractions in both mdx and wild-type mice, Am. J. Physiol. Cell Physiol., 2009, 296:C476-88.
McIntosh, J., et al., Therapeutic levels of FVIII following a since peripheral vein administration of rAAV vector encoding a novel human factor VIII variant, Blood, 2013, 121(17):3335-3344.
Mingozzi, F. et al., Overcoming Preexisting Humoral Immunity to AAV Using Capsid Decoys, Science Translational Medicine, 2013, 5(192-196):122-130.
Nair, A.R., et al., Effect of different UCOE-promoter combinations in creation of engineered cell lines for the production of Factor VIII, BMC Research Notes, 2011, 4:178.
NCBI, GenBank accession No. EU159410.1 (Jul. 23, 2009) See the whole sequence.
NCBI, GenBank accession No. NM_000132.3 (Sep. 11, 2015) See the who sequence.
Qu, G., et al., Separation of Adeno-Associated Virus Type 2 Empty Particles from Genome Containing Vectors by Anion-Exchange Column Chromatography, Journal of Virological Methods, 2007, 140:183-192.
Rodino-Klapac et al., A translational approach for limb vascular delivery of the micro-dystrophin gene without high volume or high pressure for treatment of Duchenne muscular dystrophy, J. Transl. Med., 2007, 5(45):1-11.
Scallan et al., Human Immunoglobulin Inhibits Liver Transduction by AAV Vectors at Low AAV2 Neutralizing Titers in SCID Mice, Blood, 2005, 107:1810-1817.
Sequence Alignment, 2016.
Simioni, P., et al., X-Linked Thrombophilia with a Mutant Factor IX (Factor IX Padua), The New England Journal of Medicine, 2009, 361(17):1671-1675.
Urabe et al., Removal of Empty Capsids from Type 1 Adeno-Associated Virus Vector Stocks by Anion-Exchange Chromatography Potentiates Transgene Expression, Molecular Therapy, 2006, 13(4):823-28.
Wright, J.F. et al., Manufacturing and Characterizing AAV-Based Vectors for Use in Clinical Studies, Gene Therapy, 2008, 15:840-848.
Halbert, C.L., et al., Adeno-associated virus type 6 (AAV6) vectors mediate efficient transduction of airway epithelial cells in mouse lungs compared to that of AAV2 vectors, Journal of Virology, 2001, 75(14):6615-662.
Hodges, B.L. et al., Long-term transgene expression from plasmid DNA gene therapy vectors is negatively affected by CpG dinucleotides, Molecular Therapy, 2004, 10(2):269-278.
NCBI, GenBank accession No. AAS99242.1 (Jun. 24, 2004).
Rogers, G.L. et al., Role of the vector genome and underlying factor IX mutation in immune responses to AAV gene therapy for hemophilia B., Journal of Translational Medicine, 2014, 12(1):e25 (inner pp. 1-10).
Yew, N.S., et al., CpG-Depleted Plasmid DNA Vectors with Enhanced Safety and Long-Term Gene Expression in vivo, Molecular Therapy, 2002, 5(6):731-738.
Annoni, A., et al., Liver gene therapy by lentiviral vectors reversed anti-factor IX pre-existing immunity in haemophilic mice, EMBO Mol. Med., 2013, 5(11):1684-1697.
Blanchette, V.S., et al., Definitions in hemophilia: communication from the SSC of the ISTH, J. of Thromb. and Haemost., 2014, 12:1935-1939.
White, G.C., II, et al., Definition of Hemophilia, Thromb. Haemost., 2001, 85:550.
Grimm, Dirk, et al., In Vitro and In Vivo Gene Therapy Vector Evolution via Multispecies Interbreeding and Retargeting of Adeno-Associated Viruses, Journal of Virology, 2008, 82(12):5887-5911.
St. Pierre, et al., A refined vector system for the in vitro construction of single-copy transcriptional or translations fusions to lacZ, Gene, 1996, 169:65-68.

(56) References Cited

OTHER PUBLICATIONS

U.S. Appl. No. 17/305,649, Third-Party Submission under 37 CFR 1.290 electronically filed with USPTO on Apr. 22, 2022 along with concise description of relevance, 71 pages.
Von Drygalski, et al., Etranacogene dezaparvovec (AMT-061 phase 2b): normal/near normal FIX activity and bleed cessation in hemophilia B, Blood Advances, Nov. 12, 2019, 3(21):3241-3247.
Montenegro-Miranda, et al., Adeno-Associated Viral Vector Serotype 5 Poorly Transduces Liver in Rat Models, PLOS One, Dec. 2013, 8(12), e82597:1-6.
Exhibit No. 2148 uniQure biopharma B.V., European Application No. 19174517.3, Communication Pursuant to Article 94(3 EPC, dated Apr. 26, 2022.
Exhibit No. 2139, High, K., et a., Immune Responses to AAV and to Factor IX in a Phase I Study of AAV-Mediated, Liver-Directed Gene Transfer for Hemophilia B, Molecular Therapy, May 2004, 9(suppl 1): S383-S384 [*Pfizer v. uniQure* Case No. IPR2021-00926].
Transcript of Lee Pedersen, Ph.D., dated Jul. 8, 2022, *Pfizer, Inc. v. Uniqure Biopharma B.V. (PTAB)* [uniQure 2146: *Pfizer v. unIQure* Case No. IPR2021-00926].
Transcript of Lili Wang, Ph.D., dated Jul. 11, 2022, Transcript of Lee Pedersen, Ph.D., dated Jul. 8, 2022, *Pfizer, Inc. v. Uniqure Biopharma B.V. (PTA)* [uniQure 2146: *Pfizer v. unIQure* Case No. PR2021-00926].
Patent Owner's Sur Reply, Case No. IPR2021-00926, U.S. Pat. No. 9,982,248, dated Jul. 18, 2022, *Pfizer, Inc. v. Uniqure Biopharma B.V. (PTAB)*, pp. 1-47.
Patent Owner's Sur Reply, Case No. IPR2021-00925, U.S. Pat. No. 9,982,248, dated Jul. 18, 2022, *Pfizer, Inc. v. Uniqure Biopharma B.V. (PTAB)*, pp. 1-47.
Videotaped Deposition Taken Remotely via Zoom Videoconference of Paul Clinton Spiegel, Ph.D., on Jun. 7, 2022, Case Nos. IPR2021-00925 (U.S. Pat. No. 9,982,248), IPR2021-00926 (U.S. Pat. No. 9,982,248) and IPR2021-00928 (U.S. Pat. No. 10,465,180), *Pfizer, Inc. v. Uniqure Biopharma B.V. (PTAB)*, pp. 1-199.
Deposition of Christopher Doering, Ph.D. Conducted Remotely, on Jun. 10, 2022, Case Nos. PR2021-00925 (U.S. Pat. No. 9,982,248), IPR2021-00926 (U.S. Pat. No. 9,982,248) and IPR2021-00928 (U.S. Pat. No. 10,465,180), *Pfizer, Inc. v. Uniqure Biopharma B.V. (PTAB)*, pp. 1-160.
Reply Declaration of Lee Pedersen, Ph.D., dated Jun. 17, 2022, Case Nos. IPR2021-00925 (U.S. Pat. No. 9,982,248), IPR2021-00926 (U.S. Pat. No. 9,982,248) and IPR2021-00928 (U.S. Pat. No. 10,465,180), *Pfizer. Inc. v. Uniqure Biopharma B.V. (PTAB)*, pp. 1-74.
Reply Declaration of Lili Wang, Ph.D., dated Jun. 17, 2022, Case Nos. IPR2021-00925 (U.S. Pat. No. 9,982,248), IPR2021-00926 (U.S. Pat. No. 9,982,248) and IPR2021-00928 (U.S. Pat. No. 10,465,180), *Pfizer, Inc. v. Uniqure Biopharma B.V. (PTAB)*, pp. 1-178.
Petitioner's Reply To Patent Owner's Response, dated Jun. 17, 2022, Case No. IPR2021-00928 (U.S. Pat. No. 10,465,180), *Pfizer, Inc. v. Uniqure Biopharma B.V. (PTAB)*, pp. 1-41.
Petitioner's Reply To Patent Owner's Response, dated Jun. 17, 2022, Case No. IPR2021-00926 (U.S. Pat. No. 9,982,248), *Pfizer, Inc. v. Uniqure Biopharma B.V. (PTAB)*, pp. 1-41.
Petitioner's Reply To Patent Owner's Response, dated Jun. 17, 2022, Case No. IPR2021-00925 (U.S. Pat. No. 9,982,248), *Pfizer, Inc. v. Uniqure Biopharma B.V. (PTAB)*, pp. 1-41.
Patent Owner's Sur Reply, Case No. IPR2021-00928, U.S. Pat. No. 10,465,180, dated Jul. 18, 2022, *Pfizer, Inc. v. Uniqure Biopharma B.V. (PTAB)*, pp. 1-46.
McCarty et al., "Adeno-associated virus terminal repeat (TR) mutant generates self-complementary vectors to overcome the rate-limiting step to transduction in vivo"; Gene Therapy, vol. 10, pp. 2112-2118, 2003.

Miesbach et al., "Phase 1-2 Clinical Trial of a Recombinant AAV5 Vector Containing the Human FIX Gene in Patients with Severe or Moderately Severe Haemophilia B"; Blood, vol. 124, issue 21, 2014.
Mingozzi and High, "Immune responses to AAV vectors: overcoming barriers to successful gene therapy"; Blood, vol. 122, No. 1, pp. 23-36, 2013.
Mingozzi et al., "Induction of immune tolerance to coagulation factor IX antigen by in vivo hepatic gene transfer"; J. Clin. Invest., vol. 111, No. 9, pp. 1347-1356, 2003.
Monahan et al., "Direct intramuscular injection with recombinant AAV vectors results in sustained expression in a dog model of hemophilia"; Gene Therapy, vol. 5, pp. 40-49, 1998.
Mount et al., "Sustained phenotypic correction of hemophilia B dogs with a factor IX null mutation by liver-directed gene therapy"; Blood, vol. 99, No. 8, pp. 2670-2676, 2002.
Murphy and High, "Gene therapy for haemophilia"; British J. of Haematology, vol. 140, pp. 479-487, 2008.
Nathwani et al., "Safe and efficient transduction of the liver after peripheral vein infusion of self-complementary AAV vector results in stable therapeutic expression of human FIX in nonhuman primates"; Blood, vol. 109, No. 4, pp. 1414-1421, 2007.
Nathwani et al., "Long-term Safety and Efficacy Following Systemic Administration of a Self-complementary AAV Vector Encoding Human FIX Pseudotyped With Serotype 5 and 8 Capsid Proteins"; Molecular Therapy, vol. 19, No. 5, pp. 876-885, 2011.
Papadakis et al., "Promoters and Control Elements: Designing Expression Cassettes for Gene Therapy"; Current Gene Therapy, vol. 4, pp. 89-113, 2004.
Katherine P. Ponder, "Gene therapy for hemophilia"; Current Opinion Hematology, vol. 13, pp. 301-307, 2006.
Quade-Lyssy et al., "Oral gene therapy for hemophilia B using chitosan-formulated FIX mutants"; J. of thrombosis and Haemostasis, vol. 12, pp. 932-942, 2014.
Raj et al., "Self-complementary adeno-associated viral vectors for gene therapy of hemophilia B: progress and challenges"; Expert Rev. Hematol. 4:539-49 (2011).
Reyes-Sandoval and Ertl, "CpG Methylation of a Plasmid Vector Results in Extended Transgene Product Expression by Circumventing Induction of Immune Responses"; Molecular Therapy, vol. 9, No. 2, pp. 249-261, 2004.
Sabatino et al., "Novel hemophilia B mouse models exhibiting a range of mutations in the Factor IX gene"; Blood, vol. 104, No. 9, pp. 2767-2774, 2004.
Samulski et al., "A Recombinant Plasmid from Which an Infectious Adeno-Associated Virus Genome Can Be Excised In Vitro and Its Use To Study Viral Replication"; J. of Virology, vol. 61., No. 10, pp. 3096-3101, 1987.
Schuttrumpf et al., "Transgene Loss and Changes in the Promoter Methylation Status as Determinants for Expression Duration in Nonviral Gene Transfer for Factor IX"; Human Gene Therapy, vol. 22, pp. 101-106, 2011.
Simioni et al. "Evidence of the first X-linked thrombophilia due to a novel mutation in clotting factor IX gene resulting in hyperfunctional fix: factor IX arginine 338 leucine (factor IX padua)"; International Society on Thrombosis and Haemostasis, vol. 7, suppl. 2, pp. 1-1204, 2009.
Simone et al., "A Far-downstream Hepatocyte-specific Control Region Directs Expression of the Linked Human Apolipoprotein E and C-I Genes in Transgenic Mice"; J. Biological Chemistry, vol. 268, No. 11, pp. 8221-8229, 1993.
Snyder et al., "Persistent and therapeutic concentrations of human factor IX in mice after hepatic gene transfer of recombinant AAV vectors"; Nature Genetics, vol. 16, pp. 270-276, 1997.
Snyder et al., "Correction of hemophilia B in canine and murine models using recombinant adeno-associated viral vectors"; Nature Medicine, vol. 5, No. 1, pp. 64-70, 1999.
Vandenberghe et al., "Heparin binding directs activation of T cells against adeno-associated virus serotype 2 capsid"; Nature Medicine, vol. 12, No. 8, pp. 967-971, 2006.

(56) References Cited

OTHER PUBLICATIONS

Wang et al., "Cross-Presentation of Adeno-Associated Virus Serotype 2 Capsids Activates Cytotoxic T Cells but Does Not Render Hepatocytes Effective Cytolytic Targets"; Human Gene Therapy, vol. 18, pp. 185-194, 2007.
Wang et al., "Sustained Expression of Therapeutic Level of Factor IX in Hemophilia B Dogs by AAV-Mediated Gene Therapy in Liver"; Molecular Therapy, vol. 1, No. 2, pp. 154-158, 2000.
Wang et al., "Sustained correction of bleeding disorder in hemophilia B mice by gene therapy"; Proc. Natl. Acad. Sci., vol. 96, pp. 3906-3910, 1999.
Wu et al., "Optimization of Self-complementary AAV Vectors for Liver-directed Expression Results in Sustained Correction of Hemophilia B at Low Vector Dose"; Molecular Therapy, vol. 16, No. 2, pp. 280-289, 2008.
Yan et al., "Transgenic Mice Can Express Mutant Human Coagulation Factor IX with Higher Level of Clotting Activity"; Biochemical Genetics, vol. 44, Nos. 7/8, pp. 349-360, 2006.
Supplemental information published with Manno, SC, et al., Successful transduction of liver in hemophilia by AAV-Factor IX and limitations imposed by the host immune response, Nature Medicine 12(3):342-347 (2006); Suppl. Fig. 1, Suppl. Tables 1-6, Suppl. Note, Suppl. Methods.
Herzog, RW, et al., Influence of Vector Dose on Factor IX-Specific T and B Cell Responses in Muscle-Directed Gene Therapy, Human Gene Therapy 13:1281-1291 (2002).
High, KA, The gene therapy journey for hemophilia: are we there yet?, Blood 120(23):4482-4487 (2012).
Petition for Inter Partes Review in IPR2021-00925 of U.S. Pat. No. 9,982,248 (May 11, 2021).
Institution Decision in IPR2021-00925 of U.S. Pat. No. 9,982,248 (Nov. 17, 2021).
Patent Owner Preliminary Response in IPR2021-00925 of U.S. Pat. No. 9,982,248 (Aug. 23, 2021).
Patent Owner Response in IPR2021-00925 of U.S. Pat. No. 9,982,248 (Mar. 3, 2022).
Petition for Inter Partes Review in IPR2021-00926 of U.S. Pat. No. 9,982,248 (May 11, 2021).
Institution Decision in IPR2021-00926 of U.S. Pat. No. 9,982,248 (Nov. 17, 2021).
Patent Owner Preliminary Response in IPR2021-00926 of U.S. Pat. No. 9,982,248 (Aug. 23, 2021).
Patent Owner Response in IPR2021-00926 of U.S. Pat. No. 9,982,248 (Mar. 3, 2022).
Petition for Inter Partes Review in IPR2021-00928 of U.S. Appl. No. 10/465,180, filed May 11, 2021.
Institution Decision in IPR2021-00928 of U.S. Appl. No. 10/465,180, filed Nov. 17, 2021.
Patent Owner Preliminary Response in IPR2021-00928 of U.S. Appl. No. 10/465,180, filed Aug. 24, 2021.
Patent Owner Response in IPR2021-00928 of U.S. Appl. No. 10/465,180, filed Mar. 3, 2022.
Declaration Christopher Doering in IPR2021-00925 (Mar. 3, 2022).
Declaration Lee Pedersen in IPR2021-00925 (May 6, 2021).
Transcript Lee Pedersen in IPR2020-00388 (Sep. 17, 2020).
Transcript Lee Pedersen in IPR2021-00925 (Feb. 22, 2022).
Declaration Clint Spiegel in IPR2021-00925 (Feb. 28, 2022).
Declaration Lili Wang in IPR2021-00925 (May 10, 2021).
Transcript of Lili Wang in IPR2020-00388 (Feb. 9, 2021).
Transcript of Lili Wang in IPR2020-00388 (Sep. 15, 2020).
Transcript of Lili Wang in IPR2021-00925 (Feb. 16, 2022).
Van Hylckama Vlieg, A, et al., High levels of factor IX increase the risk of venous thrombosis, Blood 95(12):3678-3682 (2000).
Supplemental Appendix to: Nathwani, A.C., et al., Adenovirus-associated virus vector-mediated gene transfer in hemophilia B, N. Engl. J. Med., 2011; 365:2357-65. DOI: 10.1056/NEJMoa1108046.
U.S. Department of Health and Human Services, National Institutes of Health, Recombinant DNA Advisory Committee, Minutes of the Meeting, Dec. 3-5, pp. 1-57, 2007.

U.S. Department of Health and Human Services, National Institutes of Health, Recombinant DNA Advisory Committee, Minutes of the Meeting, Jun. 7-9, 2011, pp. 1-61, 2011.
Nathwani, A.C., et al., Blood 2006, Supplemental Fig 1.
Nathwani, A.C., et al., Molecular Therapy, 2011, Supplemental Fig 1.
Nathwani, A.C., et al., Molecular Therapy, 2011, Supplemental Fig 2.
Nathwani, A.C., et al., Molecular Therapy, 2011, Supplemental Fig 3.
Supplementary Appendix to: Nathwani, A.C., et al., Long-term safety and efficacy of factor IX gene therapy in hemophilia B, N Engl J Med 2014; 371:1994-2004. DOI: 10.1056/NEJMoa1407309.
Trial Protocol for: Nathwani, A.C., et al., Adenovirus-associated virus vector-mediated gene transfer in hemophilia B, N Engl J Med 2011; 365:2357-65. DOI: 10.1056/NEJMoa1108046.
Davidoff, A.M., et al., Comparison of the Ability of Adeno-associated Viral Vectors Pseudotyped with Serotype 2, 5, and 8 Capsid Proteins to Mediate Efficient Transduction of the Liver in Murine and Nonhuman Primate Models, Molecular Therapy, Jun. 2005, 11(6):875-888.
U.S. Patent and Trademark Office, Patent Trial and Appeal Board, *Prizer, Inc. v. Uniqure Biopharma B.V.*, IPR2020-00388 U.S. Pat. No. 9,249,404 B2, Patent Owner's Revised Non-Contingent Motion to Amend Under 37 C.F.R. § 42.121, filed Dec. 2, 2020 (Paper No. 37).
U.S. Patent and Trademark Office, Patent Trial and Appeal Board, *Prizer, Inc. v. Uniqure Biopharma B.V.*, IPR2020-00388 U.S. Pat. No. 9,249,404 B2, Patent Owner's Motion to Terminate Proceeding, filed Mar. 4, 2021 (Paper No. 48).
U.S. Patent and Trademark Office, Patent Trial and Appeal Board, *Prizer, Inc. v. Uniqure Biopharma B.V.*, IPR2020-00388 U.S. Pat. No. 9,249,404 B2, Patent Owner Preliminary Response, filed Apr. 17, 2020 (Paper No. 8).
U.S. Patent and Trademark Office, Patent Trial and Appeal Board, *Prizer, Inc. v. Uniqure Biopharma B.V.*, IPR2020-00388 U.S. Pat. No. 9,249,404 B2, Preliminary Guidance Patent Owner's Motion to Amend, filed Feb. 3, 2021 (Paper No. 45).
U.S. Patent and Trademark Office, Patent Trial and Appeal Board, *Prizer, Inc. v. Uniqure Biopharma B.V.*, IPR2020-00388 U.S. Pat. No. 9,249,404 B2, Deposition of Lili Wang, Ph.D. on Sep. 15, 2020.
U.S. Patent and Trademark Office, Patent Trial and Appeal Board, *Prizer, Inc. v. Uniqure Biopharma B.V.*, IPR2020-00388 U.S. Pat. No. 9,249,404 B2, Petition for Inter Partes Review of U.S. Pat. No. 9,249,405 UNDER 35 U.S.C. § 311 AND 37 CFR § 42.100, filed Jan. 4, 2020.
U.S. Patent and Trademark Office, Patent Trial and Appeal Board, *Prizer, Inc. v. Uniqure Biopharma B.V.*, IPR2020-00388 U.S. Pat. No. 9,249,404 B2, Petitioner's Opposition to Patent Owner's Revised Non-Contingent Motion To Amend, filed Jan. 21, 2021 (Paper No. 40).
U.S. Patent and Trademark Office, Patent Trial and Appeal Board, *Prizer, Inc. v. Uniqure Biopharma B.V.*, IPR2020-00388 U.S. Pat. No. 9,249,404 B2, Petitioner's Opposition to Patent Owner's Motion to Terminate, filed Mar. 16, 2021 (Paer No. 50).
U.S. Patent and Trademark Office, Patent Trial and Appeal Board, *Prizer, Inc. v. Uniqure Biopharma B.V.*, IPR2020-00388 U.S. Pat. No. 9,249,404 B2, Judgment Grenting Request for Adverse Judgment after Institution of Trial, 37 CFR 42.73(b) entered Mar. 25, 2021 (Paper No. 52).
U.S. Patent and Trademark Office, Patent Trial and Appeal Board, *Prizer, Inc. v. Uniqure Biopharma B.V.*, IPR2020-00388 U.S. Pat. No. 9,249,404 B2, Videotaped Videoconference Deposition of Lee Pedersen, Ph.D on Sep. 17, 2020—9:14 am.
European Patent Office, European Patent Application No. 16815331.0, Communication Pursuant to Rule 114(2) EPC dated Mar. 15, 2021, Third Party Observations, filed Mar. 10, 2021.
Globe Newswire, uniQure N.V. (Nasdaq:QURE) "uniQure Announces Preliminary Topline Results from Low-Dose Cohort in Hemophilia B Phase I/II Gene Therapy Clinical Trial," Conference Call to Discuss Data Scheduled for 8:30am EST, Jan. 7, 2016, Amsterdam, the Netherlands.

(56) References Cited

OTHER PUBLICATIONS

Globe Newswire, uniQure N.V. (Nasdaq:QURE) "uniQure Presents Clinical Data from Ongoing Phase I/II Study in Hemophilia B Demonstrating 6 Months of Sustained Increases in Fa," Conference Call to Discuss Data Scheduled for 8:30am EST / 2:00 pm CET Monday, Jun. 13—Jun. 11, 2016, Amsterdam, the Netherlands.

Dirks, Brain Tumor Stem Cells: Bringing Order to the Chaos of Brain Cancer. Journal of Clinical Oncology, 2008, 26 (17), 2916-2924. DOI:10.1200/jco.2008.17.6792.

Mabey D. Epidemiology of sexually transmitted infections: worldwide, Medicine, 2014, 42(6), p. 287-290, see abstract).

Lopez-Lazaro, M. The migration ability of stem cells can explain the existence of cancer of unknown primary site. Rethinking metastasis. Oncoscience, 2015, 2, 467. doi:10.18632/oncoscience. 159 (see p. 467, right paragraph).

B.Tran and M.A.Rosenthal, Survival comparison between glioblastoma multiforme and other incurable cancers, Journal of Clinical Neuroscience, 2010, vol. 17, Is. 4, p. 417-421).

Russian Application No. 2018102242, Official Notification dated Mar. 23, 2023 [Russian and English Translations].

* cited by examiner

Rh74 VP1 Amino Acid Sequence (SEQ ID NO:1)

MAADGYLPDWLEDNLSEGIREWWDLKPGAPKPKANQQKQDNGRGLVLPGYKYLGPFNGLDKGEPV
NAADAAALEHDKAYDQQLQAGDNPYLRYNHADAEFQERLQEDTSFGGNLGRAVFQAKKRVLEPLGL
VESPVKTAPGKKRPVEPSPQRSPDSSTGIGKKGQQPAKKRLNFGQTGDSESVPDPQPIGEPPAGPSGLGS
GTMAAGGGAPMADNNEGADGVGSSSGNWHCDSTWLGDRVITTSTRTWALPTYNNHLYKQISNGTSG
GSTNDNTYFGYSTPWGYFDFNRFHCHFSPRDWQRLINNNWGFRPKRLNFKLFNIQVKEVTQNEGTKTI
ANNLTSTIQVFTDSEYQLPYVLGSAHQGCLPPFPADVFMIPQYGYLTLNNGSQAVGRSSFYCLEYFPSQ
MLRTGNNFEFSYNFEDVPFHSSYAHSQSLDRLMNPLIDQYLYYLSRTQSTGGTAGTQQLLFSQAGPNN
MSAQAKNWLPGPCYRQQRVSTTLSQNNNSNFAWTGATKYHLNGRDSLVNPGVAMATHKDDEERFFP
SSGVLMFGKQGAGKDNVDYSSVMLTSEEEIKTTNPVATEQYGVVADNLQQQNAAPIVGAVNSQGALP
GMVWQNRDVYLQGPIWAKIPHTDGNFHPSPLMGGFGLKHPPPQILIKNTPVPADPPTTFNQAKLASFIT
QYSTGQVSVEIEWELQKENSKRWNPEIQYTSNYYKSTNVDFAVNTEGTYSEPRPIGTRYLTRNL

Figure 1

Rh74 VP2 Amino Acid (SEQ ID NO:2):

TAPGKKRPVEPSPQRSPDSSTGIGKKGQQPAKKRLNFGQTGDSESVPDPQPIGEPPAGPSGLGSGTMAA
GGGAPMADNNEGADGVGSSSGNWHCDSTWLGDRVITTSTRTWALPTYNNHLYKQISNGTSGGSTND
NTYFGYSTPWGYFDFNRFHCHFSPRDWQRLINNNWGFRPKRLNFKLFNIQVKEVTQNEGTKTIANNLT
STIQVFTDSEYQLPYVLGSAHQGCLPPFPADVFMIPQYGYLTLNNGSQAVGRSSFYCLEYFPSQMLRTG
NNFEFSYNFEDVPFHSSYAHSQSLDRLMNPLIDQYLYYLSRTQSTGGTAGTQQLLFSQAGPNNMSAQA
KNWLPGPCYRQQRVSTTLSQNNNSNFAWTGATKYHLNGRDSLVNPGVAMATHKDDEERFFPSSGVL
MFGKQGAGKDNVDYSSVMLTSEEEIKTTNPVATEQYGVVADNLQQQNAAPIVGAVNSQGALPGMVW
QNRDVYLQGPIWAKIPHTDGNFHPSPLMGGFGLKHPPPQILIKNTPVPADPPTTFNQAKLASFITQYSTG
QVSVEIEWELQKENSKRWNPEIQYTSNYYKSTNVDFAVNTEGTYSEPRPIGTRYLTRNL

Figure 2

Rh74 VP3 Amino Acid (SEQ ID NO:3):

MAAGGGAPMADNNEGADGVGSSSGNWHCDSTWLGDRVITTSTRTWALPTYNNHLYKQISNGTSGGS
TNDNTYFGYSTPWGYFDFNRFHCHFSPRDWQRLINNNWGFRPKRLNFKLFNIQVKEVTQNEGTKTIAN
NLTSTIQVFTDSEYQLPYVLGSAHQGCLPPFPADVFMIPQYGYLTLNNGSQAVGRSSFYCLEYFPSQML
RTGNNFEFSYNFEDVPFHSSYAHSQSLDRLMNPLIDQYLYYLSRTQSTGGTAGTQQLLFSQAGPNNMS
AQAKNWLPGPCYRQQRVSTTLSQNNNSNFAWTGATKYHLNGRDSLVNPGVAMATHKDDEERFFPSS
GVLMFGKQGAGKDNVDYSSVMLTSEEEIKTTNPVATEQYGVVADNLQQQNAAPIVGAVNSQGALPG
MVWQNRDVYLQGPIWAKIPHTDGNFHPSPLMGGFGLKHPPPQILIKNTPVPADPPTTFNQAKLASFITQ
YSTGQVSVEIEWELQKENSKRWNPEIQYTSNYYKSTNVDFAVNTEGTYSEPRPIGTRYLTRNL

Figure 3

4-1 variant VP1 capsid amino acid sequence (SEQ ID NO:4)

```
  1 MAADGYLPDWLEDNLSEGIREWWDLKPGAPKPKANQQKQDNGRGLVLPGYKYLGPFNGLD
 61 KGEPVNAADAAALEHDKAYDQQLQAGDNPYLRYNHADAEFQERLQEDTSFGGNLGRAVFQ
121 AKKRVLEPLGLVESPVKTAPGKKRPVEPSPQRSPDSSTGIGKKGQQPAKKRLNFGQTGDS
181 ESVPDPQPIGEPPAAPSGVGPNTMAAGGGAPMADNNEGADGVGSSSGNWHCDSTWLGDRV
241 ITTSTRTWALPTYNNHLYKQISNGTSGGSTNDNTYFGYSTPWGYFDFNRFHCHFSPRDWQ
301 RLINNNWGFRPKRLNFKLFNIQVKEVTQNEGTKTIANNLTSTIQVFTDSEYQLPYVLGSA
361 HQGCLPPFPADVFMIPQYGYLTLNNGSQAV GRSSFYCLEYFPSQMLRTGNNFEFSYNFED
421 VPFHSSYAHSQSLDRLMNPLIDQYLYYLSRTQSTGGTAGTQQLLFSQAGPNNMSAQAKNW
481 LPGPCYRQQRVSTTLSQNNNSNFAWTGATKYHLNGRDSLVNPGVAMATHKDDEERFFPSS
541 GVLMFGKQGAGKDNVDYSSVMLTSEEEIKTTNPVATEQYGVVADNLQQQNAAPIVGAVNS
601 QGALPGMVWQNRDVYLQGPIWAKIPHTDGNFHPSPLMGGFGLKHPPPQILIKNTPVPADP
661 PTTFNQAKLASFITQYSTGQVSVEIEWELQKENSKRWNPEIQYTSNYYKSTNVDFAVNTE
721 GTYSEPRPIGTRYLTRNL
```

4-1 variant VP2 capsid amino acid sequence (SEQ ID NO:27)

TAPGKKRPVEPSPQRSPDSSTGIGKKGQQPAKKRLNFGQTGDSESVPDPQPIGEPPAAPSGVGPNT
MAAGGGAPMADNNEGADGVGSSSGNWHCDSTWLGDRVITTSTRTWALPTYNNHLYKQISNGTS
GGSTNDNTYFGYSTPWGYFDFNRFHCHFSPRDWQRLINNNWGFRPKRLNFKLFNIQVKEVTQNEG
TKTIANNLTSTIQVFTDSEYQLPYVLGSAHQGCLPPFPADVFMIPQYGYLTLNNGSQAVGRSSFYCL
EYFPSQMLRTGNNFEFSYNFEDVPFHSSYAHSQSLDRLMNPLIDQYLYYLSRTQSTGGTAGTQQLLF
SQAGPNNMSAQAKNWLPGPCYRQQRVSTTLSQNNNSNFAWTGATKYHLNGRDSLVNPGVAMAT
HKDDEERFFPSSGVLMFGKQGAGKDNVDYSSVMLTSEEEIKTTNPVATEQYGVVADNLQQQNAAP
IVGAVNSQGALPGMVWQNRDVYLQGPIWAKIPHTDGNFHPSPLMGGFGLKHPPPQILIKNTPVPADPP
TTFNQAKLASFITQYSTGQVSVEIEWELQKENSKRWNPEIQYTSNYYKSTNVDFAVNTEGTYSEPRPI
GTRYLTRNL

4-1 variant VP3 capsid amino acid sequence (SEQ ID NO:3)

MAAGGGAPMADNNEGADGVGSSSGNWHCDSTWLGDRVITTSTRTWALPTYNNHLYKQISNGTS
GGSTNDNTYFGYSTPWGYFDFNRFHCHFSPRDWQRLINNNWGFRPKRLNFKLFNIQVKEVTQNEG
TKTIANNLTSTIQVFTDSEYQLPYVLGSAHQGCLPPFPADVFMIPQYGYLTLNNGSQAVGRSSFYCL
EYFPSQMLRTGNNFEFSYNFEDVPFHSSYAHSQSLDRLMNPLIDQYLYYLSRTQSTGGTAGTQQLLF
SQAGPNNMSAQAKNWLPGPCYRQQRVSTTLSQNNNSNFAWTGATKYHLNGRDSLVNPGVAMAT
HKDDEERFFPSSGVLMFGKQGAGKDNVDYSSVMLTSEEEIKTTNPVATEQYGVVADNLQQQNAAP
IVGAVNSQGALPGMVWQNRDVYLQGPIWAKIPHTDGNFHPSPLMGGFGLKHPPPQILIKNTPVPADPP
TTFNQAKLASFITQYSTGQVSVEIEWELQKENSKRWNPEIQYTSNYYKSTNVDFAVNTEGTYSEPRPI
GTRYLTRNL

Figure 4

15-1 variant VP1 capsid amino acid sequence (SEQ ID NO:5)

```
1   MAADGYLPDWLEDNLSEGIREWWDLKPGAPKPKANQQRQDNGRGLVLPGYRYLGPFNGLD
61  KGEPVNAADAAALEHDRAYDQQLQAGDNPYLRYNHADAEFQERLQEDTSFGGNLGRAVFQ
121 AKKRVLEPLGLVESPVRTAPGKKRPVEPSPQRSPDSSTGIGKKGQQPARKRLNFGQTGDS
181 ESVPDPQPIGEPPAAPSGVGPNTMAAGGGAPMADNNEGADGVGSSSGNWHCDSTWLGDRV
241 ITTSTRTWALPTYNNHLYRQISNGTSGGSTNDNTYFGYSTPWGYFDFNRFHCHFSPRDWQ
301 RLINNNWGFRPKRLNFKLFNIQVKEVTQNEGTRTIANNLTSTIQVFTDSEYQLPYVLGSA
361 HQGCLPPFPADVFMIPQYGYLTLNNGSQAVGRSSFYCLEYFPSQMLRTGNNFEFSYNFED
421 VPFHSSYAHSQSLDRLMNPLIDQYLYYLSRTQSTGGTAGTQQLLFSQAGPNNMSAQAKNW
481 LPGPCYRQQRVSTTLSQNNNSNFAWTGATKYHLNGRDSLVNPGVAMATHRDDEERFFPSS
541 GVLMFGRQGAGRDNVDYSSVMLTSEEEIRTTNPVATEQYGVVADNLQQQN AAPIVGAVNS
601 QGALPGMVWQNRDVYLQGPIWAKIPHTDGNFHPSPLMGGFGLKHPPPQILIKNTPVPADP
661 PTTFNQAKLASFITQYSTGQVSVEIEWELQKENSKRWNPEIQYTSNYYKSTNVDFAVNTE
721 GTYSEPRPIGTRYLTRNL
```

Figure 5

15-2 variant VP1 capsid amino acid sequence (SEQ ID NO:6)

```
  1 MAADGYLPDWLEDNLSEGIREWWDLKPGAPKPKANQQRQD NGRGLVLPGY RYLGPFNGLD
 61 KGEPVNAADAAALEHDRAYDQQLQAGDNPYLRYNHADAEF QERLQEDTSF GGNLGRAVFQ
121 AKKRVLEPLGLVESPVRTAPGKKRPVEPSPQRSPDSSTGI GKRGQQPARK RLNFGQTGDS
181 ESVPDPQPIGEPPAAPSGVGPNTMAAGGGAPMADNNEGAD GVGSSSGNWH CDSTWLGDRV
241 ITTSTRTWALPTYNNHLYRQISNGTSGGSTNDNTYFGYST PWGYFDFNRF HCHFSPRDWQ
301 RLINNNWGFRPKRLNFKLFNIQVKEVTQNEGTRTIANNLT STIQVFTDSE YQLPYVLGSA
361 HQGCLPPFPADVFMIPQYGYLTLNNGSQAVGRSSFYCLEY FPSQMLRTGN NFEFSYNFED
421 VPFHSSYAHSQSLDRLMNPLIDQYLYYLSRTQSTGGTAGT QQLLFSQAGP NNMSAQAKNW
481 LPGPCYRQQRVSTTLSQNNNSNFAWTGATKYHLNGRDSLV NPGVAMATHR DDEERFFPSS
541 GVLMFGKQGAGRDNVDYSSVMLTSEEEIRTTNPVATEQYG VVADNLQQQN AAPIVGAVNS
601 QGALPGMVWQNRDVYLQGPIWAKIPHTDGNFHPSPLMGGF GLKHPPPQIL IKNTPVPADP
661 PTTFNQAKLASFITQYSTGQVSVEIEWELQKENSKRWNPE IQYTSNYYKS TNVDFAVNTE
721 GTYSEPRPIGTRYLTRNL
```

Figure 6

15-3/15-5 variant VP1 capsid amino acid sequence (SEQ ID NO:7)

```
  1 MAADGYLPDWLEDNLSEGIR EWWDLKPGAPKPKANQQRQD NGRGLVLPGY RYLGPFNGLD
 61 KGEPVNAADAAALEHDRAYDQQLQAGDNPYLRYNHAD 15-4 variant VP1 capsid amino acid sequence (SEQ ID NO:8)

1 MAADGYLPDWLEDNLSEGIREWWDLKPGAP KPKANQQRQD NGRGLVLPGY RYLGPFNGLD
61 KGEPVNAADAAALEHDRAYDQQLQAGDNPY LRYNHADAEF QERLQEDTSF GGNLGRAVFQ
121 AKKRVLEPLGLVESPVRTAPGKKRPVEPSP QRSPDSSTGI GKRGQQPAKK RLNFGQTGDS
181 ESVPDPQPIGEPPAAPSGVGPNTMAAGGGA PMADNNEGAD GVGSSSGNWH CDSTWLGDRV
241 ITTSTRTWALPTYNNHLYRQISNGTSGGST NDNTYFGYST PWGYFDFNRF HCHFSPRDWQ
301 RLINNNWGFRPKRLNFKLFNIQVKEVTQNE GTRTIANNLT STIQVFTDSE YQLPYVLGSA
361 HQGCLPPFPADVFMIPQYGYLTLNNGSQAV GRSSFYCLEY FPSQMLRTGN NFEFSYNFED
421 VPFHSSYAHSQSLDRLMNPLIDQYLYYLSR TQSTGGTAGT QQLLFSQAGP NNMSAQAKNW
481 LPGPCYRQQRVSTTLSQNNNSNFAWTGATK YHLNGRDSLV NPGVAMATHR DDEERFFPSS
541 GVLMFGKQGAGRDNVDYSSVMLTSEEEIRT TNPVATEQYG VVADNLQQQN AAPIVGAVNS
601 QGALPGMVWQNRDVYLQGPIWAKIPHTDGN FHPSPLMGGF GLKHPPPQIL IKNTPVPADP
661 PTTFNQARLASFITQYSTGQVSVEIEWELQ KENSKRWNPE IQYTSNYYKS TNVDFAVNTE
721 GTYSEPRPIGTRYLTRNL

Figure 8

15-6 variant VP1 capsid amino acid sequence (SEQ ID NO:9)

```
1   MAADGYLPDWLEDNLSEGIREWWDLKPGAPKPKANQQRQDNGRGLVLPGY RYLGPFNGLD
61  KGEPVNAADAAALEHDRAYDQQLQAGDNPYLRYNHADAEFQERLQEDTSF GGNLGRAVFQ
121 AKKRVLEPLGLVESPVRTAPGKKRPVEPSPQRSPDSSTGIGKKGQQPAKK RLNFGQTGDS
181 ESVPDPQPIGEPPAAPSGVGPNTMAAGGGAPMADNNEGADGVGSSSGNWH CDSTWLGDRV
241 ITTSTRTWALPTYNNHLYRQISNGTSGGSTNDNTYFGYSTPWGYFDFNRF HCHFSPRDWQ
301 RLINNNWGFRPKRLNFKLFNIQVKEVTQNEGTRTIANNLTSTIQVFTDSE YQLPYVLGSA
361 HQGCLPPFPADVFMIPQYGYLTLNNGSQAVGRSSFYCLEYFPSQMLRTGN NFEFSYNFED
421 VPFHSSYAHSQSLDRLMNPLIDQYLYYLSRTQSTGGTAGTQQLLFSQAGP NNMSAQAKNW
481 LPGPCYRQQRVSTTLSQNNNSNFAWTGATKYHLNGRDSLVNPGVAMATHR DDEERFFPSS
541 GVLMFGRQGAGRDNVDYSSVMLTSEEEIRTTNPVATEQYGVVADNLQQQN AAPIVGAVNS
601 QGALPGMVWQNRDVYLQGPIWAKIPHTDGNFHPSPLMGGFGLKHPPPQIL IKNTPVPADP
661 PTTFNQARLASFITQYSTGQVSVEIEWELQKENSKRWNPEIQYTSNYYKS TNVDFAVNTE
721 GTYSEPRPIGTRYLTRNL
```

Figure 9

FIX39 nucleic acid sequence (SEQ ID NO:10)

ATGCAGAGGGTGAACATGATCATGGCTGAGAGCCCTGGCCTGATCACCATCTGCCTGCTGGGCTA
CCTGCTGTCTGCTGAATGTACAGTTTTTCTTGATCATGAAAATGCCAACAAAATTCTGAATAGACC
AAAGAGGGTATAACTCTGGCAAGCTTGAAGAGTTTGTACAGGGGAATCTGGAGAGAGAGTGTATGG
AAGAGAAGTGCAGCTTTGAGGAAGCCAGAGAAGTGTTTGAAAATACAGAGAGAACAACTGAATT
TTGGAAGCAGTATGTGGATGGTGATCAATGTGAGAGCAATCCCTGCTTGAATGGGGGGAGCTGTA
AAGATGATATCAACAGCTATGAATGTTGGTGTCCCTTTGGATTTGAGGGGAAAAACTGTGAGCTTG
ATGTGACCTGTAATATCAAGAATGGCAGGTGTGAGCAATTTTGCAAGAATTCTGCTGATAACAAA
GTGGTCTGTAGCTGCACTGAGGGATATAGGCTGGCTGAAAACCAGAAGAGCTGTGAACCTGCAGT
GCCTTTTCCCTGTGGGAGAGTGTCTGTGAGCCAAACCAGCAAGCTGACTAGGGCTGAAGCAGTCTT
TCCTGATGTAGATTATGTGAATAGCACTGAGGCTGAGACAATCCTTGACAATATCACTCAGAGCAC
ACAGAGCTTCAATGACTTCACCAGGGTGGTAGGAGGGGAGGATGCCAAGCCTGGGCAGTTCCCCT
GGCAGGTAGTGCTCAATGGAAAAGTGGATGCCTTTTGTGGAGGTTCAATTGTAAATGAGAAGTGG
ATTGTGACTGCAGCCCACTGTGTGGAAACTGGAGTCAAGATTACTGTGGTGGCTGGAGAGCACAA
TATTGAGGAAACTGAGCACACTGAGCAGAAGAGGAATGTGATCAGGATTATCCCCCACCACAACT
ACAATGCTGCTATCAACAAGTACAACCATGACATTGCCCTCCTGGAACTGGATGAACCCCTGGTCT
TGAACAGCTATGTGACACCCATCTGTATTGCTGATAAAGAGTACACCAACATCTTCTTGAAATTTG
GGTCTGGATATGTGTCTGGCTGGGGCAGGGTGTTCCATAAAGGCAGGTCTGCCCTGGTATTGCAGT
ATTTGAGGGTGCCTCTGGTGGATAGAGCAACCTGCTTGCTGAGCACCAAGTTTACAATCTACAACA
ATATGTTCTGTGCAGGGTTCCATGAAGGTGGTAGAGACAGCTGCCAGGGAGATTCTGGGGGTCCC
CATGTGACTGAGGTGGAGGGAACCAGCTTCCTGACTGGGATTATCAGCTGGGGTGAGGAGTGTGC
TATGAAGGGAAAGTATGGGATCTACACAAAAGTATCCAGATATGTGAACTGGATTAAGGAGAAAA
CCAAGCTGACTTGA

Figure 10

FIX19 nucleic acid sequence (SEQ ID NO:11)

ATGCAGCGCGTGAACATGATCATGGCCGAGAGCCCTGGCCTGATTACCATCTGCCTGTTAGGATAT
CTACTCAGTGCTGAATGTACAGTTTTTCTTGATCATGAAAACGCCAACAAAATCCTGAACCGGCCC
AAGCGGTACAACTCAGGCAAGCTGGAAGAGTTCGTGCAGGGCAACCTGGAACGGGAGTGCATGG
AAGAGAAGTGCAGCTTCGAGGAAGCCCGGGAGGTGTTCGAGAACACCGAGCGGACCACCGAGTT
CTGGAAGCAGTACGTGGACGGCGACCAGTGCGAGTCAAACCCCTGCCTGAACGGCGGCAGCTGCA
AGGACGATATCAACAGCTACGAGTGCTGGTGCCCCTTCGGCTTCGAGGGCAAGAACTGCGAGCTG
GACGTGACCTGCAACATCAAGAACGGCCGCTGCGAGCAGTTCTGCAAGAACAGCGCCGACAACAA
GGTGGTGTGCTCATGCACTGAGGGCTACCGGCTGGCCGAGAACCAGAAGAGCTGCGAGCCCGCCG
TGCCCTTCCCCTGCGGCAGAGTGTCCGTGAGCCAGACCAGCAAGCTGACCAGGGCCGAGGCCGTG
TTCCCTGACGTGGACTACGTGAACTCAACCGAGGCCGAGACAATCCTGGACAACATCACCCAGAG
CACCCAGTCCTTCAACGACTTCACCCGGGTGGTGGGCGGCGAGGACGCCAAGCCCGGCCAGTTCC
CTTGGCAGGTGGTGCTGAACGGCAAGGTGGACGCCTTCTGCGGCGGCTCAATCGTGAACGAGAAG
TGGATCGTGACAGCCGCCCACTGCGTGGAGACAGGCGTGAAGATCACCGTGGTGGCCGGCGAACA
CAATATCGAGGAAACCGAGCACACCGAGCAGAAACGGAACGTGATCCGGATTATCCCCCACCACA
ACTACAACGCCGCCATCAACAAGTACAACCACGATATCGCCCTGCTGGAACTGGACGAGCCTCTG
GTGCTGAATTCATACGTGACCCCCATCTGTATCGCCGACAAAGAGTACACCAACATCTTTCTGAAG
TTCGGCAGCGGCTACGTGTCCGGCTGGGGCAGGGTGTTCCACAAGGGCCGCAGCGCCCTGGTGCT
GCAGTACCTGCGGGTGCCCCTGGTGGACAGAGCCACCTGCCTGCGGTCAACCAAGTTCACCATCTA
CAACAACATGTTCTGCGCCGGCTTCCACGAGGGCGGCAGGGACAGCTGCCAGGGCGACAGCGGCG
GACCCCACGTGACCGAGGTGGAGGGCACCAGCTTTCTGACCGGCATCATCTCATGGGGCGAGGAA
TGCGCCATGAAGGGCAAGTACGGAATCTACACTAAGGTGTCAAGATACGTGAACTGGATCAAAGA
GAAAACCAAGCTGACCTGA

Figure 11 pAAV-ApoE_hAAT-FIX39 (SEQ ID NO:12)

```
LOCUS       FIX39                   11125 bp    DNA     circular UNA
DEFINITION  AKA FIX39 Step 4.
ACCESSION   urn.local...e-3um3omk
VERSION     urn.local...e-3um3omk
KEYWORDS    .
SOURCE
  ORGANISM  .

FEATURES             Location/Qualifiers
     repeat_region   1..141
                     /Imported_from="<a
                     href=""http://wishart.biology.ualberta.ca/PlasMapper"">Pla
                     sMapper</a>"
                     /Transferred_From="LAAV-2_ITR"
                     /Transferred_Similarity="100.00%"
                     /modified_by="User"
                     /label="AAV2 ITR"
     enhancer        152..472
                     /created_by="User"
                     /modified_by="User"
                     /Transferred_From="ApoE HCR-1"
                     /Transferred_Similarity="100.00%"
                     /label="ApoE HCR-1"
     promoter        482..878
                     /vntifkey=21
                     /ApEinfo_fwdcolor="#ffff00"
                     /ApEinfo_revcolor="#0080ff"
                     /Transferred_From="hAAT Promoter"
                     /Transferred_Similarity="100.00%"
                     /modified_by="User"
                     /label="hAAT Promoter"
     5'UTR           879..907
                     /created_by="User"
                     /label="FIX 5'UTR"
     CDS             order(908..995,2434..3731)
                     /created_by="User"
                     /Transferred_From="hFIX CDS"
                     /Transferred_Similarity="79.22%"
                     /modified_by="User"
                     /label="hFIX CDS"
     intron          996..2433
                     /created_by="User"
                     /Transferred_From="hFIX Intron"
                     /Transferred_Similarity="100.00%"
                     /modified_by="User"
                     /label="hFIX Intron"
     3'UTR           3732..3779
                     /created_by="User"
                     /label="hF9 3' UTR"
     Terminator      3820..4047
                     /Imported_from="<a
                     href=""http://wishart.biology.ualberta.ca/PlasMapper"">Pla
                     sMapper</a>"
                     /Transferred_From="bGH_PA term"
                     /Transferred_Similarity="100.00%"
                     /label="bGH_PA term"
     repeat_region   complement(4097..4204)
                     /modified_by="User"
                     /label="AAV2 ITR"
     misc_feature    4219..8579
                     /modified_by="User"
                     /label="Lambda Stuffer"
     Gene            complement(8491..8580)
                     /Imported_from="<a
                     href=""http://wishart.biology.ualberta.ca/PlasMapper"">Pla
```

Figure 12A

```
                        sMapper</a>"
                        /Transferred_From="cosN"
                        /Transferred_Similarity="100.00%"
                        /label="cosN"
     rep_origin         8680..8986
                        /modified_by="User"
                        /label="F1 Ori"
     misc._marker       9284..10096
                        /modified_by="User"
                        /label="Kan R"
     rep_origin         complement(10453..11120)
                        /modified_by="User"
                        /label="pUC Ori"
ORIGIN
        1 cctgcaggca gctgcgcgct cgctcgctca ctgaggccgc ccgggcaaag cccgggcgtc
       61 gggcgacctt tggtcgcccg gcctcagtga gcgagcgagc gcgcagagag ggagtggcca
      121 actccatcac tagggggttcc tgcggcctag taggctcaga ggcacacagg agtttctggg
      181 ctcaccctgc ccccttccaa ccctcagtt cccatcctcc agcagctgtt tgtgtgctgc
      241 ctctgaagtc cacactgaac aaacttcagc ctactcatgt ccctaaaatg ggcaaacatt
      301 gcaagcagca aacagcaaac acacagccct cctgcctgc tgaccttgga gctggggcag
      361 aggtcagaga cctctctggg cccatgccac ctccaacatc cactcgaccc cttggaattt
      421 cggtggagag gagcagaggt tgtcctggcg tggtttaggt agtgtgagag gggtaccgg
      481 ggatcttgct accagtggaa cagccactaa ggattctgga gtgagcag agggccagct
      541 aagtggtact ctcccagaga ctgtctgact cacgccaccc cctccacctt ggacacagga
      601 cgctgtggtt tctgagccag gtacaatgac tccttctggt aagtgcagtg gaagctgtac
      661 actgccagg caaagcgtcc gggcagcgta ggcgggcgac tcagatccca gccagtggac
      721 ttagccctg tttgctcctc cgataactgg ggtgaccttg gttaatattc accagcagcc
      781 tccccgttg ccctctgga tccactgctt aaatacggac gaggacaggg ccctgtctcc
      841 tcagcttcag gcaccaccac tgacctggga cagtgaatac cactttcaca atctgctagc
      901 aaaggttatg cagagggtga acatgatcat ggctgagagc cctggcctga tcaccatctg
      961 cctgctgggc tacctgctgt ctgctgaatg tacaggtttg tttccttttt tataatacat
     1021 tgagtatgt tgccttttag atatagaaat atctgattct gtcttcttca ctaaattttg
     1081 attacatgat ttgacagcaa tattgaagag tctaacagcc agcacccagg ttggtaagta
     1141 ctggttcttt gttagctagg ttttcttctt cttcactttt aaaactaaat agatggacaa
     1201 tgcttatgat gcaataaggt ttaataaaca ctgttcagtt cagtatttgg tcatgtaatt
     1261 cctgttaaaa aacagtcatc tccttggttt aaaaaatta aagtgggaa aacaaagaaa
     1321 tagcagaata tagtgaaaaa aaataaccac agtattttg tttggactta ccactttgaa
     1381 atcaaattgg gaaacaaaag cacaaacagt ggccttattt acacaaaaag tctgatttta
     1441 agatatgtga caattcaagg tttcagaagt atgtaaggag gtgtgtctct aattttttaa
     1501 attatatatc ttcaatttaa agttttagtt aaaacataaa gattaaccttt tcattagcaa
     1561 gctgttagtt atcaccaaag cttttcatgg attaggaaaa aatcattttg tctctatctc
     1621 aaacatcttg gagttgatat ttggggaaac acaatactca gttgacttcc ctaggggaga
     1681 aaagcaagct taagaattga cacaaagagt aggaagttag ctattgcaac atatatcact
     1741 ttgttttttc acaactacag tgactttatt tatttcccag aggaaggcat acagggaaga
     1801 aattatccca tttggacaaa cagcatgttc tcacagtaag cacttatcac acttacttgt
     1861 caactttcta gaatcaaatc tagtagctga cagtaccagg atcaggggtg ccaaccctaa
     1921 gcaccccag aaagctgact ggccctgtgg ttcccactcc agacatgatg tcagctgtga
     1981 aatccacctc cctggaccat aattaggctt ctgttcttca ggagacattt gttcaaagtc
     2041 atttgggcaa ccatattctg aaaacagccc agccagggtg atggatcact ttgcaaagat
     2101 cctcaatgag ctattttcaa gtgatgacaa agtgtgaagt taagggctca tttgagaact
     2161 ttcttttca tccaaagtaa attcaaatat gattagaaat ctgacctttt attactggaa
     2221 ttctcttgac taaaagtaaa attgaatttt aattcctaaa tctccatgtg tatacagtac
     2281 tgtgggaaca tcacagattt tggctccatg ccctaaagag aaattggctt tcagattatt
     2341 tggattaaaa acaaagactt tcttaagaga tgtaaaattt tcatgatgtt ttcttttttg
     2401 ctaaaactaa agaattattc ttttacattt cagttttcct tgatcatgaa aatgccaaca
     2461 aaattctgaa tagaccaaag aggtataact ctggcaagct tgaagagttt gtacagggga
     2521 atctggagag agagtgtatg gaagagaagt gcagctttga ggaagccaga gaagtgtttg
     2581 aaaatacaga gagaacaact gaattttgga agcagtatgt ggatggtgat caatgtgaga
     2641 gcaatccctg cttgaatggg gggagctgta agatgatat caacagctat gaatgttggt
     2701 gtccctttgg atttgagggg aaaaactgtg agcttgatgt gacctgtaat atcaagaatg
     2761 gcaggtgta gcaatttttgc aagaattctg ctgataacaa agtggtctgt agctgcactg
     2821 agggatatag gctggctgaa aaccagaaga gctgtgaacc tgcagtgcct tttccctgtg
     2881 ggagagtgtc tgtgagccaa accagcaagc tgactagggc tgaagcagtc tttcctgatg
     2941 tagattatgt gaatagcact gaggctgaga caatccttga caatatcact cagagcacac
     3001 agagcttcaa tgacttcacc agggtggtag gaggggagga tgccaagcct gggcagttcc
     3061 cctggcaggt agtgctcaat ggaaaagtgg atgccttttg tggaggttca attgtaaatg
     3121 agaagtggat tgtgactgca gcccactgtg tggaaactgg agtcaagatt actgtggtgg
```

Figure 12A cont.

```
3181 ctggagagca caatattgag gaaactgagc acactgagca gaagaggaat gtgatcagga
3241 ttatccccca ccacaactac aatgctgcta tcaacaagta caaccatgac attgccctcc
3301 tggaactgga tgaaccctg gtcttgaaca gctatgtgac acccatctgt attgctgata
3361 aagagtacac caacatcttc ttgaaatttg ggtctggata tgtgtctggc tgggcaggg
3421 tgttccataa aggcaggtct gccctggtat tgcagtattt gagggtgcct ctggtggata
3481 gagcaacctg cttgctgagc accaagttta caatctacaa caatatgttc tgtgcagggt
3541 tccatgaagg tggtagagac agctgccagg gagattctgg gggtccccat gtgactgagg
3601 tggagggaac cagcttcctg actgggatta tcagctgggg tgaggagtgt gctatgaagg
3661 gaaagtatgg gatctacaca aaagtatcca gatatgtgaa ctggattaag gagaaaacca
3721 agctgacttg atgaaagatg gatttccaag gttaattcat tggaattgaa aattaacaga
3781 gatctagagc tgaattcctg cagccagggg gatcagcctc tactgtgcct tctagttgcc
3841 agccatctgt tgtttgcccc tccccccttgc cttccttgac cctggaaggt gccactccca
3901 ctgtcctttc ctaataaaat gaggaaattg catcacattg tctgagtagg tgtcattcta
3961 ttctgggggg tggggtgggg caggacagca agggggagga ttgggaagac aatagcaggc
4021 atgctgggga tgcagtgggc tctatggctt ctgaggcaga aagaaccagc tggggctcga
4081 gatccactag gccgcagga accctagtg atggagttgg ccactcctc tctgcgcgct
4141 cgctcgtca ctgaggccgc ccgggctttg ccgggcggc ctcagtgagc gagcgagcgc
4201 gcagctgcct gcaggggcag cttgaaggaa atactaaggc aaaggtactg caagtgctcg
4261 caacattcgc ttatgcggat tattgccgta gtgccgcgac gccggggca agatgcagag
4321 attgccatgg tacaggccgt gcggttgata ttgccaaaac agagctgtgg gggagagttg
4381 tcgagaaaga gtgcggaaga tgcaaaggcg tggctattc aaggatgcca gcaagcgcag
4441 catatcgcgc tgtgacgatg ctaatcccaa accttaccca acccacctgg tcacgcactg
4501 ttaagccgct gtatgacgct ctggtggtgc aatgccacaa agaagagtca atcgcagaca
4561 acattttgaa tgcggtcaca cgttagcagc atgattgcca cggatggcaa catattaacg
4621 gcatgatatt gacttattga ataaaatttgg gtaaatttga ctcaacgatg ggttaattcg
4681 ctcgttgtgg tagtgagatg aaaagaggcg gcgcttacta ccgattccgc ctagttggtc
4741 acttcgacgt atcgtctgga actccaacca tcgcaggcag agaggtctgc aaaatgcaat
4801 cccgaaacag ttcgcaggta atagttagag cctgcataac ggtttcggga ttttttatat
4861 ctgcacaaca ggtaagagca ttgagtcgat aatcgtgaag agtcggcgag cctggttgc
4921 cagtgctctt tccgttgtgc tgaattaagc gaataccgga agcagaaccg gatccaccaa
4981 tgcgtacagg cgtcatcgcc gcccagcaac agcacaaccc aaactgagcc gtagccactg
5041 tctgtcctga attcattagt aatagttacg ctgcggcctt ttacacatga ccttcgtgaa
5101 agcgggtggc aggaggtcgc gctaacaacc tcctgccgtt ttgcccgtgc atatcggtca
5161 cgaacaaatc tgattactaa acacagtagc ctggatttgt tctatcagta atcgaccta
5221 ttcctaatta aatagagcaa atcccttat tggggtaag acatgaagat gccagaaaaa
5281 catgacctgt tggccgccat tctcgcggca aaggaacaag gcatcgggc aatccttgcg
5341 tttgcaatgg cgtaccttcg cggcagatat aatgcggtg cgtttacaaa aacagtaatc
5401 gacgcaacga tgtgcgccat tatcgcctag ttcattcgtg accttctcga cttcgccga
5461 ctaagtagca atctcgctta tataacgagc gtgtttatcg gctacatcgg tactgactcg
5521 attggttcgc ttatcaaacg cttcgctgct aaaaagccg gagtagaaga tggtagaaat
5581 caataatcaa cgtaaggcgt tcctcgatat gctggcgtgg tcggagggaa ctgataacgg
5641 acgtcagaaa accagaaatc atggttatga cgtcattgta ggcggagagc tatttactga
5701 ttactccgat cacctcgca aacttgtcac gctaaaccca aaactcaaat caacaggcgc
5761 cggacgctac cagcttcttt cccgttggtg ggatgcctac cgcaagcagc ttggcctgaa
5821 agacttctct ccgaaaagtc aggacgctgt ggcattgcag cagattaagg agcgtggcgc
5881 tttaacctatg attgatcgtg gtgatatccg tcggccaatc gacgttcga gcaatatctg
5941 ggcttcactg ccgggcgctg gttatggtca gttcgagcat aaggctgaca gcctgattgc
6001 aaaattcaaa gaagcgggcg gaacggtcag agagattgat gtatgagcag agtcaccgcg
6061 attatctccg ctctggttat ctgcatcatc gtctgcctgt catgggctgt taatcattac
6121 cgtgataacg ccattaccta caaagcccag cgcgacaaaa atgccagaga actgaagctg
6181 gcgaacgcgg caattactga catgcagatg cgtcagcgtg atgttgctgc gctcgatgca
6241 aaatacacga aggagttagc tgatgctaaa gctgaaaatg atgctctgcg tgatgatgtt
6301 gccgctggtc gtcgtcggtt gcacatcaaa gcagtctgtc agtcagtgcg tgaagccacc
6361 accgctcg gcgtggataa tgcagcctcc cccgactgg cagacaccgc tgaacgggat
6421 tatttcaccc tcagagagag gctgatcact atgcaaaaac aactggaagg aacccagaag
6481 tatattaatg agcagtgcag atagagttgc ccatatcgat gggcaactca tgcaattatt
6541 gtgagcaata cacgcgct tccagcggag tataaatgcc taaagtaata aaaccgagca
6601 atccatttac gaatgtttgc tgggttctg ttttaacaac attttctgcg ccgccacaaa
6661 ttttggctgc atcgacagtt ttcttctgcc caattccaga aacgaagaaa tgatgggtga
6721 tggtttcctt tggtgctact gctgccggtt tgttttgaac agtaaacgtc tgttgagcac
6781 atcctgtaat aagcagggcc agcgcagtag cgagtagcat tttttcatg gtgttattcc
6841 cgatgctttt tgaagttcgc agaatcgtat gtgtagaaaa ttaaacaaac cctaaacaat
6901 gagttgaaat ttcatattgt taatatttat caggtgcgat gaatcgtcat
6961 tgtattcccg gattaactat gtccacagcc ctgacggga acttctctgc gggagtgtcc
7021 gggaataatt aaaacgatgc acacagggtt tagcgcgtac acgtattgca ttatgccaac
7081 gccccggtgc tgacacggaa gaaaccggac gttatgattt agcgtggaaa gatttgtgta
7141 gtgttctgaa tgctctcagt aaatagtaat gaattatcaa aggtatagta atatcttta
7201 tgttcatgga tatttgtaac ccatcggaaa actcctgctt tagcaagatt ttccctgtat
```

Figure 12A cont.

```
7261 tgctgaaatg tgatttctct tgatttcaac ctatcatagg acgtttctat aagatgcgtg
7321 tttcttgaga atttaacatt tacaaccttt ttaagtcctt ttattaacac ggtgttatcg
7381 ttttctaaca cgatgtgaat attatctgtg gctagatagt aaatataatg tgagacgttg
7441 tgacgtttta gttcagaata aaacaattca cagtctaaat cttttcgcac ttgatcgaat
7501 atttctttaa aaatggcaac ctgagccatt ggtaaaacct tccatgtgat acgagggcgc
7561 gtagtttgca ttatcgtttt tatcgtttca atctggtctg acctccttgt gttttgttga
7621 tgatttatgt caaatattag gaatgttttc acttaatagt attggttgcg taacaaagtg
7681 cggtcctgct ggcattctgg agggaaatac aaccgacaga tgtatgtaag gccaacgtgc
7741 tcaaatcttc atacagaaag atttgaagta atattttaac cgctagatga agagcaagcg
7801 catggagcga caaaatgaat aaagaacaat ctgctgatga tccctccgtg gatctgattc
7861 gtgtaaaaaa tatgcttaat agcaccattt ctatgagtta ccctgatgtt gtaattgcat
7921 gtatagaaca taaggtgtct ctggaagcat tcagagcaat tgaggcagcg ttggtgaagc
7981 acgataataa tatgaaggat tattccctgg tggttgactg atcaccataa ctgctaatca
8041 ttcaaactat ttagtctgtg acagagccaa cacgcagtct gtcactgtca ggaaagtggt
8101 aaaactgcaa ctcaattact gcaatgccct cgtaattaag tgaatttaca atatcgtcct
8161 gttcggaggg aagaacgcgg gatgttcatt cttcatcact tttaattgat gtatatgctc
8221 tcttttctga cgttagtctc cgacggcagg cttcaatgac ccaggctgag aaattcccgg
8281 acccttttg ctcaagagcg atgttaattt gttcaatcat ttggttagga aagcggatgt
8341 tgcgggttgt tgttctgcgg gttctgttct tcgttgacat gaggttgccc cgtattcagt
8401 gtcgctgatt tgtattgtct gaagttgttt ttacgttaag ttgatgcaga tcaattaata
8461 cgatacctgc gtcataattg attatttgac gtgtttgat ggcctccacg cacgttgtga
8521 tatgtagatg ataatcatta tcactttacg ggtccttcc ggtgatccga caggttacgg
8581 ggcggcgacc tgcctgatgc ggtattttct ccttacgcat ctgtgcgta tttcacaccg
8641 catacgtcaa agcaaccata gtacgcgccc tgtagcgcg cattaagcgc ggcgggtgtg
8701 gtggttacgc gcagcgtgac cgctacactt gccagcgcct tagcgcccgc tcctttcgct
8761 ttcttccctt cctttctcgc cacgttcgcc ggctttcccc gtcaagctct aaatcggggg
8821 ctcccttag ggttccgatt tagtgcttta cggcacctcg accccaaaaa acttgatttg
8881 ggtgatggtt cacgtagtgg gccatcgccc tgatagacgg ttttcgccc tttgacgttg
8941 gagtccacgt tctttaaatag tggactcttg ttccaaactg gaacaacact caactctatc
9001 tcgggctatt cttttgattt agacctgcag gcatgcaagc ttggcactgg ccgtcgtttt
9061 acaacgtcgt gactgggaaa accctggcgt tacccaactt aatcgccttg cagcacatcc
9121 ccctttcgcc agctggcgta atagcgaaga ggcccgcacc gatcgccctt cccaacagtt
9181 gcgcagcctg aatggcgaat gcgatttatt caacaaagcc gccgtcccgt caagtcagcg
9241 taatgctctg ccagtgttac aaccaattaa ccaattctga ttagaaaaac tcatcgagca
9301 tcaaatgaaa ctgcaattta ttcatatcag gattatcaat accatatttt tgaaaaagcc
9361 gtttctgtaa tgaaggagaa aactcaccga ggcagttcca taggatgca agatcctggt
9421 atcggtctgc gattccgact cgtccaacat caatacaacc tattaatttc ccctcgtcaa
9481 aataaggtt atcaagtgag aaatcaccat gagtgacgac tgaatccggt gagaatggca
9541 aaagcttatg catttctttc cagacttgtt caacaggcca gccattacgc tcgtcatcaa
9601 aatcactcgc atcaaccaaa ccgttattca ttcgtgattg cgcctgagcg agacgaaata
9661 cgcgatcgct gttaaaagga caattacaaa caggaatcga atgcaaccgg cgcaggaaca
9721 ctgccagcgc atcaacaata ttttcacctg aatcaggata ttcttctaat acctggaatg
9781 ctgttttccc ggggatcgca gtggtgagta accatgcatc atcaggagta cggataaaat
9841 gcttgatggt cggaagaggc ataaattccg tcagccagtt tagtctgacc atctcatctg
9901 taacatcatt ggcaacgcta cctttgccat gtttcagaaa caactctggc gcatcgggct
9961 tcccatacaa tcgatagatt gtcgcacctg attgcccgac attatcgcga gcccatttat
10021 acccatataa atcagcatcc atgttgagaat ttaatcgcgg cttcgagcaa gacgtttccc
10081 gttgaatatg gctcataaca cccccttgtat tactgtttat gtaagcagac agttttattg
10141 ttcatgatga tatattttta tcttgtgcaa tgtaacatca gagattttga gacacaacgt
10201 ggctttgttg aataaatcga acttttgctg agttgaagga tcagatcacg catctcccg
10261 acaacgcaga ccgttccgtg gcaaagcaaa agttcaaaat caccaactgg tccacctaca
10321 acaaagctct catcaaccgt ggctccctca ctttctggct ggatgatggg gcgattcagg
10381 cctggtatga gtcagcaaca ccttcttcac gaggcagacc tctgacgga gttccactga
10441 gcgtcagacc ccgtagaaaa gatcaaagga tcttcttgag atccttttt tctgcgcgta
10501 atctgctgct tgcaaacaaa aaaaccaccg ctaccagcgg tggtttgttt gccggatcaa
10561 gagctaccaa ctcttttcc gaaggtaact ggcttcagca gagcgcagat accaaatact
10621 gttcttctag tgtagccgta gttaggccac cacttcaaga actctgtagc accgcctaca
10681 tacctcgctc tgctaatcct gttaccagtg gctgctgcca gtggcgataa gtcgtgtctt
10741 accgggttgg actcaagacg atagttaccg gataaggcgc agcggtcggg ctgaacgggg
10801 ggttcgtgca cacagcccag cttggagcga acgacctaca ccgaactgag atacctacag
10861 cgtgagctat gagaaagcgc cacgcttccc gaagggagaa aggcggacag gtatccggta
10921 agcggcaggg tcgaacagg agagcgcacg agggagcttc cagggggaaa cgcctggtat
10981 ctttatagtc ctgtcgggtt tcgccacctc tgacttgagc gtcgattttt gtgatgctcg
11041 tcagggggc ggagcctatg gaaaaacgcc agcaacgcgg ccttttacg gttcctggcc
11101 ttttgctggc cttttgctca catgt
```

Figure 12A cont.

phFIX39v2 (SEQ ID NO:26)

```
LOCUS       phFIX39v2              11199 bp    DNA     circular UNA
FEATURES             Location/Qualifiers
     repeat_region   1..141
                     /label="AAV2 ITR"
     enhancer        192..472
                     /label="ApoE HCR-1"
     promoter        492..673
                     /label="hAAT Promoter"
     CDS             order(908..995,1434..5731)
                     /label="hFIX CDS"
     intron          996..2433
                     /label="hFIX Intron"
     3'UTR           3732..3779
                     /label="bF9 3' UTR"
     Terminator      3820..4047
                     /label="bGH PA term"
     repeat_region   complement(4097..4237)
                     /label="AAV2 ITR"
     misc_feature    4248..8713
                     /label="Eukaryotic Stuffer"
     rep_origin      8754..9060
                     /label="F1 Ori"
     CDS             complement(9355..10170)
                     /label="Kanamycin resistance"
     rep_origin      complement(10527..11194)
                     /label="pUC Ori"
ORIGIN
```

Figure 12B

```
2101 ctctaaagag ctatttcaa gtgatgacaa agtgtgaagt taagggtca tttgaaaatt
2161 tctctttcta tucaagtaa attcaaatat gattagaaat ctgacttttt acttactgaa
2221 tactctgac aaaagaaaa atgaattct aattcaaca ncnctaggtg aaaagagaa
2281 tgtgggaaca taacagttt tggcteau cctaaagag aattgaaca caagatttt
2341 tggattaaaa acaagctt tcttaagaga tgtaaatct tcatgatgt tctcttctg
2401 ctaaaachaa agaatnaatc attnacattc aagtttct tgatcatgaa aatgccaaa
2461 aactctgaa tagaccaaag aagtataact ctgtaagct tgaagagttt gtataggga
2521 atctgtagag tgtctatg gaaaaat goagttta gtagcaaa gagtgttg
2581 aaaatacaga gagacaat gaattgga agaagtatgt ggctggtgat naatgaga
2641 gtaatccctg ntgaatgg aggagtgaa aagatgtat caccgctat gactgttg
2701 gtccttgg attgaggg aaaactgty agttgatgt gactgtat atcagaatg
2761 gaagtgtga gcattttag atgaattca ctgataaa aagggactg agctgacng
2821 agagtatag gctagctgaa aaacagaaaa gctgtgacc tgctctcct tttcctgtg
2881 gagagtgtg tgtgaccaa accgcaagc tgacaaggc tgagcagc ttctctgctg
2941 tagatatagt gaatgract gagctgaga caatccttga castatnct cagagcaca
3001 agagcttcaa tgactcact agtgttat gagcgatga tgtcaagct gagagtcc
3061 cctggcagt agcgtcaat ggaaagtgg atgcttctg tgaggttca aatgtaaang
3121 agaagtgga tgtgctga gocactgtg tggaaatgg agtaagatt actgtggtg
3181 ctgagagtca cactatgag gaaactgac atgctgagga gaagagaat gtgtcagga
3241 thaacccnn cactcaatac aatgctgcta acaaaagta caccaacgan atgccnat
3301 tggaactgga tgaaccctg gtcttgaaa gatatgac acaatgt attgctgata
3361 aagtgtcat ctacctctt tgaaatt ugtctgaca tgtgtgc tggcagagg
3401 ngatcaaaa aggcaggct ggctgtat tgcagnatt ggggtgct ctgtgaaaa
3461 gagcaactg ctgctgagc accaagtcta aaactacaa acacatgtc tgtgaggt
3521 tctcaaagg tngtagaga atctgcag aantcctg ggatccat atactgaga
3581 tggagtgac cagttong aatggata tagcttgg ngggatgt gctgaagg
3641 gaaagtgtg gatctacaca aagtaacaa gatagaga ctggattag ggaaaatca
3701 agtgaantg atgaagatg gatctcaa gctacttat tggattgaa aatcaacga
3761 gancagaan tgaactctg aaaocggg patcagctc tacgagct tctagtgac
3821 agctatctgc tatgagca aaaactgcac accactgaa actgacaggt gtcactccta
3881 cagctcttc ctagtaaat gagaaattg tatctcactg tctgagtagg tgtcattcta
3941 tcagggag tgggtagg cagaaacga agacgaga ctgggaaga aatagagn
4001 aagtcggga tgcagtcga tctatcct ctgagtaga aagaatgc tgggtctg
4061 gatccactag ngctcagga actctagto atggagtg ccatctcc tutgcagct
4121 ngctagctca ctgagcatcg ggaacaag ptcgcactga ctongggct tgacaggaga
4201 gcttcaaqtgn cgagcgagg gccagotgc atgtagggc ccatggcag atgcaccacc
4261 tgtctcagtg caaagccctg cctaagtagg ctggctcaaa gaccatgtgt ctggctgtaa
4321 ctccaattga ttgtcagcat caatataact tgtccaacac tgttatatac tggtattgat
4381 agttacaact gaacatattt gtttaagcaa ttggaattaa gaattcacat gcaatgatat
4441 cagggtcctt ctcctctggt tagtgtattg ggggaaatt ggacatctct cagctcagta
4501 ggctagttag gccaggatgg atgcatcca cagccctgg gcagagagat tatgatgtag
4561 ctagtctgac tcctgacaaa gacttgcttc ctggagcttc tactactttc tggtgatgg
4621 ctaagaaata tggttgtgtt cttttaagtc tgaagagcat tatttttgcc aaccctgac
4681 caaacatcct tgccaaggaa aaggcctaaa atatatttgc atttaaagat attacaaact
4741 acttggtttt ggaatgtttg gcctttcagg atcatagcta tcaaaatatt agctatttgg
4801 ggtatgagat gtctgcttgg tcaaggacaa gttcttaaaa acatcatgtt ggggaataat
4861 gggaaaatg ggaaggctta tgctctgagt aagacatctg agttatcatc tgtcaaacat
4921 ttttgttagt catagtctaa tgggagcctg ttttccctct ttaatataca ttcacatctg
4981 aatttatgct cttcattgac aatgccagcc cagaacaaca gctcttaccc tttggttttc
5041 ttcctaacct ttaactccaa tgtaaccatt acctgccatt tcagtaaaac cattattctc
5101 cctacttacc cacccaagtt gtacaataaa gagtgtttgc tctcactcat atacaaagca
5161 aattcatttg tttgtgatgt acagcttgct atgcccacag atgtggtttg cctagtcctt
5221 tgctctaggt catttgactg ggaacagatg ggatgctcac tttggttttt aatggttaac
5281 tagtcattga aatgcattc atcaaataat cttagaggat aattgtttaa atgtctgtcc
5341 agactagctt tgtagagcca ggtgccatta cacatgtcac cttcttattt ctcttaattg
5401 aatttttatc atctgagata ggaataatag agggcttttt caagtgaaga tattactata
5461 gtctaaagac cttagtgtaa catcctggcc cctaaggaaa aacaagttct ggttcataca
5521 tataataact ttgcatgtta tctgccactg agatgtgtcc taatccaaca gaaaggattg
5581 aatctctgta gctaggtgta cagggcaaga gctgtacagg gaacctttaa agatagcttc
5641 aggccaaagc tgaggaaagt ggatggagac tggggaaaat gctaagacat tttaaagatt
5701 ttcttttaggt caaaaataga ataagaaata gaccatttcc ctggacattt tctgtaggtt
5761 aatactgtta actattggta aatgcatatg ctacaactta atatgtctgc tttgtgagtt
5821 tagcattgtc tccttgtcat tccagaaatg aaatggcaaa tacatttaaa tcagaactaa
```

Figure 12B cont.

```
5881 aaagggggaac agggtataaa ggctcaattt agtcacatca tttcccttc tcacccacc
5941 cctttaaacc agatgtttgc caatgcatta acaatgcaga tgtttcctga aagaaagttt
6001 agtaactcaa gcagacacct tattttcttt tcaagcagaa aagactatga gatggtggtt
6061 gtggttgttc tgggagggag aagatataaa tgatacacat tatttcaaat catttcatga
6121 cctcactgca cacttatagt tattgtacct gttgtctttt tgctgtcaag cctagctaag
6181 atcatttgga atgttcaaga tcactcatac atgcatgtgc acacatacac atgcacatat
6241 gttcactccc tatttcatcc acatgaacta agattactga tgtgtacaga ttcaaagcac
6301 ttttattctt ttccaaaggc aagaagctga gctactttcc agaatagttg tgaaagaccc
6361 tgtcatactt ctgcattgtt tcctccacac cacctccatc cagttcctta tgaatggtta
6421 ctggttttca aaaatatgag ataaattgag tgtataaaag tcatttttag acaaaatgaa
6481 acaggaaatg aaagaaacca gaatctctcc tcatttgtgg atgggccagc tccaccatgt
6541 catggttaat ctgcagggag gaaatactag atttgattgc agatcagact gcagcaaacc
6601 tgctgtgact aaggcatcaa gagaaagcca gcaacagctg gggcttcagt ggtgaaaaca
6661 ttatatatct agctttgaaa tatgaaatac tgtttagcag tgtcacctag aaaagagtgt
6721 ttcaaaatgc tgatgcttca taagaacctt tctcttcaga gttgttctt ttatctttca
6781 aattagccag ggtgggaaat aaagtgatca cttggtgaag aaatctcaca aagaagaaca
6841 tagagagttc actttcatct ggagtaatga acagattgaa caaactagaa atggttagtc
6901 tgttaaagaa aaggtgtagg tgagctgttt gcaagagcca caagggaaag gggaagacaa
6961 cttctttgtg gacttaaggg tgaaagttgc aagcaggcaa gaccattctg acctccatta
7021 agaaagccct ttccaaccaa caaccactgg gttggttact caggttgggc agcattggga
7081 gcaaatgttg attgaacaaa tgtttgtcag aattgttgac ttaaagagct gttctgtcac
7141 tggggacagc agcagctaga tagccccatt cagggagagg gcatttgttc acctggccag
7201 agatcagagc aggctaaggg actgctggga tcctgtccag ctttgagacc tacagagcc
7261 atgttcacct agcaggtatc ccttctgagg tcactctcat ttcttacctt attccagggc
7321 tttcacctca gcttgccagg ctggagccaa gggccaaggc agctcacct tgttggctat
7381 ggtagcttcc caggagcccc ctatggttca ggaacagctc tgcctgcccc atcctgtttg
7441 ctacctccta aagccaaagg cactggtggg ccaggccagc ttctaaagtc acacaaggtt
7501 agaaggttcc tgacaggaag ggcttgaggc caatggaagg aggtacttca gttcccct cc
7561 agatgcccag tgatggctc agagctcctt gagaacttgg gaaaggaagc agggtctctg
7621 aagaaatact tcaggagtag aaagaggaag ctagagggtt aaatgcacta cacaggaaca
7681 gaaatgagtt tttcttagag ttagtatatg tctagaggtg tagtaaacta aaacaagtct
7741 tgaattgcat acagccactt agggaagaaa tgaaaaacct tgaatattag tgaaaaaagg
7801 gaaactgcaa cccctgtatt actagatagc tttcatcaac agctcaaaac agacagattt
7861 ttataggttt actgtgtgca ctttaataca agggcagtgg ttcagaacta gtcaggtcct
7921 gaaaaggatt taccaaatgt tgagtgtgcc ctctagtgtt cacacttccc agctttcttc
7981 ctataaaggt ggatcaaggc acttgcttac aactggaact gaaatcctcc aagtggaact
8041 agacattgag atggagaaaa tattcattgt ccactgtaat tatgcaagga atatccagtt
8101 gagataatgg acttgcctct tatctaataa taccaggct caatgggtca ctgctttgtc
8161 cactttgccc aaaattcaag cacagctaag ttgatatttt aggacaaagg cagcttacta
8221 tccagccaga ggggagtaga atatggttaa gagagagtgg aaagaatgaa tgagccctgc
8281 tattcctcac tgcctggatg gctataagca cagcccttat ggaggcctta ggtcttgctt
8341 cataatattc cagtttgaaa agggtttgaa aagacctcct agaaaaatca gtagtttttc
8401 tcttttgagt aacatgtagc aaaaaaaatt tcatcatgta ggtacaggga acaccctaat
8461 aactattaat ctcaaggagt caagccagtg tgttcctaa tgtatctgct gtatccccat
8521 gaagcaaatt ttgccatcag agaaactgac tcatggggaa aaaatccaag gacctcaaat
8581 caccaaaaga agccattcct cagatttgcc taagcttaga cttccctgtc tctcattgtg
8641 tgttgctttc aatgcagtta cataaatggc ttttttgttt atgcaccaaa aacactaatt
8701 catctgcaaa gctataggtc aaagcaacca tagtatgcac cctgctagct ggcgcattaa
8761 gcgcggcggg tgtggtggtt acgcgcagcg tgaccgctac acttgccagc gcttagcgc
8821 ccgctccttt cgctttcttc ccttccttc tgccacgtt cgcggcttt ccccgtcaag
8881 ctctaaatcg gggctccct ttagggttcc gatttagtgc tttacggcac ctcgacccca
8941 aaaaacttga tttgggtgat ggttcacgta gtgggccatc gccctgatag acggtttttc
9001 gccctttgac gttggagtcc acgttcttta atagtggact cttgttccaa actggaacaa
9061 cactcaactc tatctcgggc tattcttttg atttagacct gcaggcatgc aagcttggca
9121 ctggccgtcg ttttacaacg tcgtgactgg gaaaaccctg gcgttaccca acttaatcgc
9181 cttgcagcac atccccttt cgccagctgg cgtaatagcg aagaggcccg caccgatcgc
9241 ccttcccaac agttgcgcag cctgaatggc gaatgcgatt tattcaacaa agccgccgtc
9301 ccgtcaagtc agcgtaatgc tctgccagtg ttacaaccaa ttaaccaatt ctgattagaa
9361 aaactcatcg agcatcaaat gaaactgcaa tttattcata tcaggattat caataccata
9421 tttttgaaaa agccgtttct gtaatgaagg agaaaactca ccgaggcagt tccataggat
9481 ggcaagatcc tggtatcggt ctgcgattcc gactcgtcca acatcaatac aacctattaa
9541 tttcccctcg tcaaaaataa ggttatcaag tgagaaatca ccatgagtga cgactgaatc
9601 cggtgagaat ggcaaaagct tatgcatttc tttccagact tgttcaacag gccagccatt
```

Figure 12B cont.

```
 9661 acgctcgtca tcaaaatcac tcgcatcaac caaaccgtta ttcattcgtg attgcgcctg
 9721 agcgagacga aatacgcgat cgctgttaaa aggacaatta caaacaggaa tcgaatgcaa
 9781 ccggcgcagg aacactgcca gcgcatcaac aatattttca cctgaatcag gatattcttc
 9841 taataccctgg aatgctgttt tcccgggat cgcagtggtg agtaaccatg catcatcagg
 9901 agtacggata aaatgcttga tggtcggaag aggcataaat tccgtcagcc agtttagtct
 9961 gaccatctca tctgtaacat cattggcaac gctacctttg ccatgtttca gaaacaactc
10021 tggcgcatcg ggcttcccat acaatcgata gattgtcgca cctgattgcc cgacattatc
10081 gcgagcccat ttatacccat ataaatcagc atccatgttg gaatttaatc gcggcttcga
10141 gcaagacgtt tcccgttgaa tatggctcat aacacccctt gtattactgt ttatgtaagc
10201 agacagtttt attgttcatg atgatatatt tttatcttgt gcaatgtaac atcagagatt
10261 ttgagacaca acgtggcttt gttgaataaa tcgaacttt gctgagttga aggatcagat
10321 cacgcatctt cccgacaacg cagaccgttc cgtggcaaag caaaagttca aaatcaccaa
10381 ctggtccacc tacaacaaag ctctcatcaa ccgtggctcc ctcactttct ggctggatga
10441 tgggcgatt caggcctggt atgagtcagc aacaccttct tcacgaggca gacctctcga
10501 cggagttcca ctgagcgtca gaccccgtag aaaagatcaa aggatcttct tgagatcctt
10561 ttttttctgcg cgtaatctgc tgcttgcaaa caaaaaaacc accgctacca gcggtggttt
10621 gtttgccgga tcaagagcta ccaactcttt ttccgaaggt aactggcttc agcagagcgc
10681 agataccaaa tactgttctt ctagtgtagc cgtagttagg ccaccacttc aagaactctg
10741 tagcaccgcc tacatacctc gctctgctaa tcctgttacc agtggctgct gccagtggcg
10801 ataagtcgtg tcttaccggg ttggactcaa gacgatagtt accggataag cgcagcggt
10861 cgggctgaac gggggttcg tgcacacagc ccagcttgga gcgaacgacc tacaccgaac
10921 tgagatacct acagcgtgag ctatgagaaa gcgccacgct tcccgaaggg agaaaggcgg
10981 acaggtatcc ggtaagcggc agggtcggaa caggagagcg cacgagggag cttccagggg
11041 gaaacgcctg gtatctttat agtcctgtcg ggtttcgcca cctctgactt gagcgtcgat
11101 ttttgtgatg ctcgtcaggg gggcggagcc tatggaaaaa cgccagcaac gcggcctttt
11161 tacggttcct ggccttttgc tggccttttg ctcacatgt
```

Figure 12B cont.

pAAV-ApoE_hAAT-FIX39 (SEQ ID NO:12)

Figure 13 pAAV-ApoE_hAAT-FIX3 pAAV-ApoE_hAAT-FIX3

Figure 13 cont.

pAAV-ApoE_hAAT-FIX3

Figure 13 cont.

pAAV-ApoE_hAAT-FIX3

Figure 13 cont.

pAAV-ApoE_hAAT-FIX3

Figure 13 cont.

pAAV-ApoE_hAAT-FIX3

Figure 13 cont.

pAAV-ApoE_hAAT-FIX3

Figure 13 cont.

pAAV-ApoE_hAAT-FIX3

Figure 13 cont.

pAAV-ApoE_hAAT-FIX3

TCTGTTGAGCATATCCTGTAATAAGCAGGCCAGCGCAGTAGCGAGTAGCATTTTTTCATGGTGTTATTCCCGATGCTTTTGAAGTTCGCAG

AATCGTATGTGTAGAAAATTAAACAAACCCTAAACAATGAGTGGAAATTTCATATTGTTAATATGTATTAATGTATGTCAGGTCGATGAATCG

TCATTGTATTCCTGGATTAACTATGTCCACAGCCCTCACGGGGAACTTCTCTCGGGATGTCCCGGGATAATTAAAACGATGCACACAGGGTT

TAGCGCGTACACGTATTGCATTATGCCAACGCCCCGGTGCTGACACGGAAGAAACCGGACGTTATGATTTAGCGTGGAAAGATTTGTGAGTGT

TCTGAATGCTCTCAGTAAATAGTAATGAATTATCAAAGGTATAGTAATATCTTTTATGTTCATGGATATTTGTAACCCATCGGAAAACTCCTGC

TTTAGCAAGATTTCCCTGTATTGCTGAAATGTAAATTCTCTTGATTTCAACCTATCATAGGACGTTCTATAAGATGCAGGTTTCCTCAGGAA

TTAACATTAACAACCGTATTTAAGTCCTTTTATTAACACGGTGTTATCCTTTTCGAACACGAGTGAATAATATCTAGCGCTAGATAGTAAACAT

AATGTGAGACGTTGTGACGTTTTAGTTCAGAATAAAACAATTCACAGTCTAAATCTTTTCCACTTGATCGAATATTTCTTTAAAAATAGGCAAC

Figure 13 cont.

pAAV-ApoE_hAAT-FIX3

Figure 13 cont.

pAAV-ApoE_hAAT-FIX3

Figure 13 cont.

pAAV-ApoE_hAAT-FIX3

Figure 13 cont.

pAAV-ApoE_hAAT-FIX3

Figure 13 cont.

pAAV-ApoE_hAAT-FIX3

Figure 13 cont.

Intron A nucleic acid sequence (SEQ ID NO:17):

GTTTGTTTCCTTTTTTATAATACATTGAGTATGCTTGCCTTTTAGATATAGAAATATCTGATTCTGTC
TTCTTCACTAAATTTTGATTACATGATTTGACAGCAATATTGAAGAGTCTAACAGCCAGCACCCAG
GTTGGTAAGTACTGGTTCTTTGTTAGCTAGGTTTTCTTCTTCTTCACTTTTAAAACTAAATAGATGG
ACAATGCTTATGATGCAATAAGGTTTAATAAACACTGTTCAGTTCAGTATTTGGTCATGTAATTCCT
GTTAAAAAACAGTCATCTCCTTGGTTTAAAAAAATTAAAAGTGGGAAAACAAAGAAATAGCAGAA
TATAGTGAAAAAAAATAACCACAGTATTTTTGTTTGGACTTACCACTTTGAAATCAAATTGGGAAA
CAAAAGCACAAACAGTGGCCTTATTTACACAAAAAGTCTGATTTTAAGATATGTGACAATTCAAG
GTTTCAGAAGTATGTAAGGAGGTGTGTCTCTAATTTTTTAAATTATATATCTTCAATTTAAAGTTTT
AGTTAAAACATAAAGATTAACCTTTCATTAGCAAGCTGTTAGTTATCACCAAAGCTTTTCATGGAT
TAGGAAAAAATCATTTTGTCTCTATCTCAAACATCTTGGAGTTGATATTTGGGGAAACACAATACT
CAGTTGAGTTCCCTAGGGGAGAAAAGCAAGCTTAAGAATTGACACAAAGAGTAGGAAGTTAGCTA
TTGCAACATATATCACTTTGTTTTTTCACAACTACAGTGACTTTATTTATTTCCCAGAGGAAGGCAT
ACAGGGAAGAAATTATCCCATTTGGACAAACAGCATGTTCTCACAGTAAGCACTTATCACACTTAC
TTGTCAACTTTCTAGAATCAAATCTAGTAGCTGACAGTACCAGGATCAGGGGTGCCAACCCTAAGC
ACCCCCAGAAAGCTGACTGGCCCTGTGGTTCCCACTCCAGACATGATGTCAGCTGTGAAATCCACC
TCCCTGGACCATAATTAGGCTTCTGTTCTTCAGGAGACATTTGTTCAAAGTCATTTGGGCAACCATA
TTCTGAAAACAGCCCAGCCAGGGTGATGGATCACTTTGCAAAGATCCTCAATGAGCTATTTTCAAG
TGATGACAAAGTGTGAAGTTAAGGGCTCATTTGAGAACTTTCTTTTTCATCCAAAGTAAATTCAAA
TATGATTAGAAATCTGACCTTTTATTACTGGAATTCTCTTGACTAAAAGTAAAATTGAATTTTAATT
CCTAAATCTCCATGTGTATACAGTACTGTGGGAACATCACAGATTTTGGCTCCATGCCCTAAAGAG
AAATTGGCTTTCAGATTATTTGGATTAAAAACAAAGACTTTCTTAAGAGATGTAAAATTTTCATGA
TGTTTTCTTTTTGCTAAAACTAAAGAATTATTCTTTTACATTTCAG

Figure 14

FIX39 nucleic acid sequence including intron A (intron A is underlined) (SEQ ID NO:25)

ATGCAGAGGGTGAACATGATCATGGCTGAGAGCCCTGGCCTGATCACCATCTGCCTGCTGGGCTAC
CTGCTGTCTGCTGAATGTACAGGTTTGTTTCCTTTTTTATAATACATTGAGTATGCTTGCCTTTTAGA
TATAGAAATATCTGATTCTGTCTTCTTCACTAAATTTTGATTACATGATTTGACAGCAATATTGAAG
AGTCTAACAGCCAGCACCCAGGTTGGTAAGTACTGGTTCTTTGTTAGCTAGGTTTTCTTCTTCTTCA
CTTTTAAAACTAAATAGATGGACAATGCTTATGATGCAATAAGGTTTAATAAACACTGTTCAGTTC
AGTATTTGGTCATGTAATTCCTGTTAAAAACAGTCATCTCCTTGGTTTAAAAAAATTAAAAGTGG
GAAAACAAAGAAATAGCAGAATATAGTGAAAAAAAATAACCACAGTATTTTGTTTGGACTTACC
ACTTTGAAATCAAATTGGGAAACAAAAGCACAAACAGTGGCCTTATTTACACAAAAAGTCTGATT
TTAAGATATGTGACAATTCAAGGTTTCAGAAGTATGTAAGGAGGTGTGTCTCTAATTTTTTAAATT
ATATATCTTCAATTTAAAGTTTTAGTTAAAACATAAAGATTAACCTTTCATTAGCAAGCTGTTAGTT
ATCACCAAAGCTTTTCATGGATTAGGAAAAAATCATTTTGTCTCTATCTCAAACATCTTGGAGTTG
ATATTTGGGGAAACACAATACTCAGTTGAGTTCCCTAGGGGAGAAAAGCAAGCTTAAGAATTGAC
ACAAAGAGTAGGAAGTTAGCTATTGCAACATATATCACTTTGTTTTTTCACAACTACAGTGACTTT
ATTTATTTCCCAGAGGAAGGCATACAGGGAAGAAATTATCCCATTTGGACAAACAGCATGTTCTCA
CAGTAAGCACTTATCACACTTACTTGTCAACTTTCTAGAATCAAATCTAGTAGCTGACAGTACCAG
GATCAGGGGTGCCAACCCTAAGCACCCCAGAAAGCTGACTGGCCCTGTGGTTCCCACTCCAGAC
ATGATGTCAGCTGTGAAATCCACCTCCCTGGACCATAATTAGGCTTCTGTTCTTCAGGAGACATTT
GTTCAAAGTCATTTGGGCAACCATATTCTGAAAACAGCCCAGCCAGGGTGATGGATCACTTTGCAA
AGATCCTCAATGAGCTATTTTCAAGTGATGACAAAGTGTGAAGTTAAGGGCTCATTTGAGAACTTT
CTTTTTCATCCAAAGTAAATTCAAATATGATTAGAAATCTGACCTTTTATTACTGGAATTCTCTTGA
CTAAAAGTAAAATTGAATTTTAATTCCTAAATCTCCATGTGTATACAGTACTGTGGGAACATCACA
GATTTTGGCTCCATGCCCTAAAGAGAAATTGGCTTTCAGATTATTTGGATTAAAAACAAAGACTTT
CTTAAGAGATGTAAAATTTTCATGATGTTTTCTTTTTGCTAAAACTAAAGAATTATTCTTTTACAT
TTCAGTTTTTCTTGATCATGAAAATGCCAACAAAATTCTGAATAGACCAAAGAGGGTATAACTCTGG
CAAGCTTGAAGAGTTTGTACAGGGGAATCTGGAGAGAGAGTGTATGGAAGAGAAGTGCAGCTTTG
AGGAAGCCAGAGAAGTGTTTGAAAATACAGAGAGAACAACTGAATTTTGGAAGCAGTATGTGGAT
GGTGATCAATGTGAGAGCAATCCCTGCTTGAATGGGGGGAGCTGTAAAGATGATATCAACAGCTA
TGAATGTTGGTGTCCCTTTGGATTTGAGGGGAAAAACTGTGAGCTTGATGTGACCTGTAATATCAA
GAATGGCAGGTGTGAGCAATTTTGCAAGAATTCTGCTGATAACAAAGTGGTCTGTAGCTGCACTGA
GGGATATAGGCTGGCTGAAAACCAGAAGAGCTGTGAACCTGCAGTGCCTTTTCCCTGTGGGAGAG
TGTCTGTGAGCCAAACCAGCAAGCTGACTAGGGCTGAAGCAGTCTTTCCTGATGTAGATTATGTGA
ATAGCACTGAGGCTGAGACAATCCTTGACAATATCACTCAGAGCACACAGAGCTTCAATGACTTC
ACCAGGGTGGTAGGAGGGGAGGATGCCAAGCCTGGGCAGTTCCCTGGCAGGTAGTGCTCAATGG
AAAAGTGGATGCCTTTTGTGGAGGTCAATTGTAAATGAGAAGTGGATTGTGACTGCAGCCCACTG
TGTGGAAACTGGAGTCAAGATTACTGTGGTGGCTGGAGAGCACAATATTGAGGAAACTGAGCACA
CTGAGCAGAAGAGGAATGTGATCAGGATTATCCCCCACCACAACTACAATGCTGCTATCAACAAG
TACAACCATGACATTGCCCTCCTGGAACTGGATGAACCCCTGGTCTTGAACAGCTATGTGACACCC
ATCTGTATTGCTGATAAGGAGTACACCAACATCTTCTTGAAATTTGGGTCTGGATATGTGTCTGGCT
GGGGCAGGGTGTTCCATAAAGGCAGGTCTGCCCTGGTATTGCAGTATTTGAGGGTGCCTCTGGTGG
ATAGAGCAACCTGCTTGCTGAGCACCAAGTTTACAATCTACAACAATATGTTCTGTGCAGGGTTCC
ATGAAGGTGGTAGAGACAGCTGCCAGGGAGATTCTGGGGGTCCCCATGTGACTGAGGTGGAGGGA
ACCAGCTTCCTGACTGGGATTATCAGCTGGGGTGAGGAGTGTGCTATGAAGGGAAAGTATGGGAT
CTACACAAAAGTATCCAGATATGTGAACTGGATTAAGGAGAAAACCAAGCTGACTTGA

Figure 15

Transduction efficiency of the AAV-4-1 variant capsid (SEQ ID NO:4) analyzed in an *in vitro* setting

MODIFIED FACTOR IX, AND COMPOSITIONS, METHODS AND USES FOR GENE TRANSFER TO CELLS, ORGANS, AND TISSUES

RELATED APPLICATIONS

This patent application is a continuation application of U.S. patent application Ser. No. 17/305,649, filed Jul. 12, 2021, which is a continuation application of U.S. patent application no. 17/014,782, filed Sep. 8, 2020, now U.S. Pat. No. 11,110,153, issued Sep. 7, 2021, which is a continuation application of U.S. patent application Ser. No. 15/191,357, filed Jun. 23, 2016, now U.S. Pat. No. 10,799,566, issued Oct. 13, 2020, which claims the benefit of U.S. patent application No. 62/183,599, filed Jun. 23, 2015, application No. 62/315,453, filed Mar. 30, 2016, application No. 62/338,315, filed May 18, 2016, application No. 62/348,781, filed Jun. 10, 2016 and application No. 62/349,572, filed Jun. 13, 2016, all of which applications are expressly incorporated herein by reference in their entirety.

SEQUENCE LISTING

This application contains a Sequence Listing which has been submitted electronically in WIPO Standard ST.26 (XML format) and is hereby incorporated by reference in its entirety. Said Sequence Listing copy, created on Oct. 28, 2022, is named "074659-0571338_SEQUENCE_LISTING.xml" and is 66,584 bytes in size.

INTRODUCTION

Genetic disorders, caused by absence or a defect in a desirable gene (loss of function) or expression of an undesirable or defective gene (gain of function) lead to a variety of diseases. One example of a loss of function genetic disorder is hemophilia, an inherited bleeding disorder caused by deficiency in either coagulation factor VIII (FVIII, hemophilia A) or factor IX (FIX, hemophilia B). One example of a gain of function genetic disorder is Huntington's disease, a disease caused by a pathologic "HTT" gene (encodes the huntingtin protein) that encodes a mutated protein that accumulates within and leads to gradual destruction of neurons, particularly in the basal ganglia and the cerebral cortex.

Current treatment for hemophilia consists in the intravenous administration of recombinant clotting factor either on demand, in case a bleeding occurs, or prophylactically. However, this therapeutic approach has several drawbacks such as the need for repeated infusions, the cost of the treatment, the risk of developing anti-therapeutic factor immune responses, and the risk of potentially fatal bleedings. These limitations have prompted the development of gene-based therapies for hemophilia. To this end, hemophilia is ideal for gene transfer based therapy as 1) the therapeutic window is very wide, as levels just above 1% of normal already can result in a change in phenotype from severe to moderate, and levels of 100% are not associated to any side effects; 2) tissue specific expression of the therapeutic transgene is not strictly required; and 3) there is a considerable experience in measuring the endpoints of therapeutic efficacy.

Currently, adeno-associated virus (AAV) vectors are recognized as the gene transfer vectors of choice since they have the best safety and efficacy profile for the delivery of genes in vivo. Of the AAV serotypes isolated so far, AAV2 and AAV8 have been used to target the liver of humans affected by severe hemophilia B.

SUMMARY

The invention provides nucleic acid sequences, expression vectors (e.g., vector genomes) and plasmids, compositions and viral vectors in which the nucleic acid encodes Factor IX (e.g., human Factor IX). The nucleic acid encoding Factor IX is modified to reduce the number of CpG (cytosine-guanine) dinucleotides relative to a comparison FIX coding sequence. In a particular embodiment, a modified nucleic acid encoding Factor IX has a reduced number of CpG di-nucleotides compared to a wild-type or native sequence encoding human Factor IX.

Modified nucleic acids encoding Factor IX, such as FIX modified to reduce the number of CpG (cytosine-guanine) dinucleotides, can be included in vectors, such as viral vectors. Representative viral vectors include lenti- and parvo-viral vectors (e.g., adenoviral or adeno-associated virus (AAV) vectors) which target, for example, hepatocyte cells of the liver, among other cell types. As a vector for nucleic acid sequence delivery, AAV vectors drive expression of the polynucleotide in cells. Polynucleotides that encode proteins, such as a modified nucleic acid encoding Factor IX, are able to be expressed after administration, optionally at therapeutic levels.

Accordingly, there are provided recombinant AAV vectors that include (encapsidate, package) vector genomes that include a modified nucleic acid encoding Factor IX. In particular embodiments, a recombinant AAV particle encapsidates or packages a vector genome. Such invention recombinant AAV particles include a viral vector genome which includes a heterologous polynucleotide sequence (e.g., modified nucleic acid encoding Factor IX, such as FIX modified to reduce the number of CpG (cytosine-guanine) dinucleotides). In one embodiment, a vector genome that includes a modified nucleic acid encoding Factor IX, such as FIX modified to reduce the number of CpG (cytosine-guanine) dinucleotides is encapsidated or packaged by an AAV capsid or an AAV capsid variant.

In the invention recombinant AAV vectors, the heterologous polynucleotide sequence may be transcribed and subsequently translated into a protein. In various aspects, the heterologous polynucleotide sequence encodes a therapeutic protein. In particular aspects, the protein is a blood clotting factor (e.g., Factor IX, Factor XIII, Factor X, Factor VIII, Factor VIIa, or protein C). In more particular aspects, the vector includes a modified nucleic acid encoding Factor IX (e.g., modified nucleic acid encoding Factor IX, such as FIX modified to reduce the number of CpG (cytosine-guanine) dinucleotides).

AAV and AAV variants such as capsid variants can deliver polynucleotides and/or proteins that provide a desirable or therapeutic benefit, thereby treating a variety of diseases. For example, AAV1, AAV2, AAV3, AAV4, AAV5, AAV6, AAV7, AAV8, AAV9, AAV10, AAV11, Rh10, Rh74 or AAV-2i8, and variants thereof and AAV capsid variants (e.g., 4-1) are useful vectors to deliver to cells, tissues and organs, therapeutic genes (e.g., Factor IX) to treat hemophilia A, B, etc.

In the invention recombinant viral and AAV vectors that include (encapsidate, package) vector genome (viral or AAV) include additional elements that function in cis or in trans. In particular embodiments, a recombinant viral (e.g., AAV) vector that includes (encapsidate, package) a vector genome also has: one or more inverted terminal repeat (ITR)

sequences that flank the 5' or 3' terminus of the heterologous polynucleotide sequence (e.g., modified nucleic acid encoding Factor IX, such as FIX modified to reduce the number of CpG (cytosine-guanine) dinucleotides); an expression control element that drives transcription (e.g., a promoter or enhancer) of the heterologous polynucleotide sequence (e.g., modified nucleic acid encoding Factor IX, such as FIX modified to reduce the number of CpG (cytosine-guanine) dinucleotides), such as a constitutive or regulatable control element, or tissue-specific expression control element; an intron sequence, a stuffer or filler polynucleotide sequence; and/or a poly-adenylation sequence located 3' of the heterologous polynucleotide sequence.

Accordingly, vectors can further include an intron, an expression control element (e.g., a constitutive or regulatable control element, or a tissue-specific expression control element or promoter such as for liver expression, e.g., a human $\alpha_1$-anti-trypsin (hAAT) Promoter and/or apolipoprotein E (ApoE) HCR-1 and/or HCR-2 enhancer), one or more adeno-associated virus (AAV) inverted terminal repeats (ITRs) (e.g., an ITR sequence of any of: AAV1, AAV2, AAV3, AAV4, AAV5, AAV6, AAV7, AAV8, AAV9, AAV10, AAV11, Rh10, Rh74 or AAV-2i8 AAV serotypes) and/or a filler polynucleotide sequence. Position of such additional elements can vary. In particular aspects, an intron is within the sequence encoding human FIX protein, and/or the expression control element is operably linked to the sequence encoding human FIX protein, and/or the AAV ITR(s) flanks the 5' or 3'end of the sequence encoding human FIX protein, and/or wherein the filler polynucleotide sequence flanks the 5' or 3'end of the sequence encoding human FIX protein.

In various embodiments, a FIX nucleic acid modified to reduce the number of CpG (cytosine-guanine) dinucleotides can have 1-5 fewer, 5-10 fewer, 10-15 fewer, 15-20 fewer, 20-25 fewer, 25-30 fewer, 30-40 fewer, 40-55, 55-75, fewer, 75-100, 100-150 fewer, 150-200 fewer CpG di-nucleotides than native or wild-type sequence encoding human Factor IX. In particular aspects, a FIX nucleic acid modified as set forth herein encodes human FIX protein which is expressed at levels greater than or comparable to a wild-type or native sequence encoding human Factor IX not having a reduced number of CpG di-nucleotides.

In additional embodiments, an intron, an expression control element (e.g., a constitutive or regulatable control element, or a tissue-specific expression control element or promoter such as for liver expression, e.g., a human $\alpha_1$-anti-trypsin (hAAT) Promoter and/or apolipoprotein E (ApoE) HCR-1 and/or HCR-2 enhancer), one or more adeno-associated virus (AAV) inverted terminal repeats (ITRs) (e.g., an ITR sequence of any of: AAV1, AAV2, AAV3, AAV4, AAV5, AAV6, AAV7, AAV8, AAV9, AAV10, AAV11, Rh10, Rh74 or AAV-2i8 AAV serotypes) and/or a filler polynucleotide sequence can be modified to reduce the number of CpG (cytosine-guanine) dinucleotides as compared to a counterpart native or wild-type expression control element, adeno-associated virus (AAV) inverted terminal repeats (ITRs) and/or a filler polynucleotide sequence. In particular aspects, an expression control element, adeno-associated virus (AAV) inverted terminal repeat (ITR) and/or a filler polynucleotide sequence has 1-5 fewer, 5-10 fewer, 10-15 fewer, 15-20 fewer, 20-25 fewer, 25-30 fewer, 30-40 fewer, 40-55, 55-75, fewer, 75-100, 100-150 fewer, 150-200 fewer CpG di-nucleotides than native or wild-type counterpart sequence.

Exemplary AAV vectors include AAV capsid sequence of any of AAV1, AAV2, AAV3, AAV4, AAV5, AAV6, AAV7, AAV8, AAV9, AAV10, AAV11, Rh10, Rh74 or AAV-2i8, or a capsid variant of AAV1, AAV2, AAV3, AAV4, AAV5, AAV6, AAV7, AAV8, AAV9, AAV10, AAV11, Rh10, Rh74 or AAV-2i8. Recombinant AAV particles of the invention also include AAV1, AAV2, AAV3, AAV4, AAV5, AAV6, AAV7, AAV8, AAV9, AAV10, AAV11, Rh10, Rh74 or AAV-2i8, and variants thereof. Particular capsid variants include capsid variants of such as AAV1, AAV2, AAV3, AAV4, AAV5, AAV6, AAV7, AAV8, AAV9, AAV10, AAV11, Rh10, Rh74 or AAV-2i8, such as a capsid sequence with an amino acid substitution, deletion or insertion/addition. In particular aspects, a substitution is made in the Rh74 VP1 capsid sequence (SEQ ID NO: 1), for example at any one of amino acid positions 195, 199, 201 or 202. In more particular aspects, substituted residues correspond to an A, V, P or N amino acid at any one of amino acid positions 195, 199, 201 or 202 of Rh74 VP1 capsid sequence. In further particular aspects, the capsid sequence has an A residue at amino acid position 195; a V residue at amino acid positions 199, a P residue at amino acid position 201, or an N residue at amino acid position 202 of Rh74 VP1 capsid sequence. In additional particular aspects, the capsid sequence has any two, three or all four of the following: an A residue at amino acid position 195; a V residue at amino acid positions 199, a P residue at amino acid position 201, or an N residue at amino acid position 202 of Rh74 VP1 capsid sequence.

In more particular aspects, a capsid variant comprises any of SEQ ID NOS:4-9. additional embodiments, an AAV vector has a capsid sequence with an AAV VP1, VP2 and/or VP3 sequence having 90% or more sequence identity to any VP1, VP2 and/or VP3 of any AAV serotype. In particular aspects, an AAV vector has a capsid sequence with a VP1, VP2 and/or VP3 capsid sequence having 90% or more identity to AAV1, AAV2, AAV3, AAV4, AAV5, AAV6, AAV7, AAV8, AAV9, AAV10, AAV11, Rh10, Rh74 or AAV-2i8 VP1, VP2 and/or VP3 sequences. In more particular aspects, an AAV vector has a capsid sequence with a VP1, VP2 or VP3 capsid sequence selected from any of: AAV1, AAV2, AAV3, AAV4, AAV5, AAV6, AAV7, AAV8, AAV9, AAV10, AAV11, Rh10, Rh74 or AAV-2i8 AAV serotypes.

In additional embodiments, a recombinant vector genome includes a modified nucleic acid encoding Factor IX, such as FIX modified to reduce the number of CpG (cytosine-guanine) dinucleotides and a filler or stuffer polynucleotide sequence. In particular aspects, modified nucleic acid encoding Factor IX has a length less than about 4.7 kb. In further particular aspects, modified nucleic acid encoding Factor IX has a length less than 4.7 kb and is flanked by one or more AAV ITRs, or positioned within two adeno-associated virus (AAV) ITR sequences. In additional particular aspects, a filler or stuffer polynucleotide sequence has a length that when combined with modified nucleic acid encoding Factor IX the total combined length of the Factor IX encoding nucleic acid sequence and filler or stuffer polynucleotide sequence is between about 3.0-5.5 kb, or between about 4.0-5.0 kb, or between about 4.3 kb-4.8 kb.

Filler or stuffer polynucleotide sequences can be located in the vector sequence at any desired position such that it does not prevent a function or activity of the vector. In one aspect, a filler or stuffer polynucleotide sequence is positioned between a 5' and/or 3' ITR (e.g., an ITR of AAV1, AAV2, AAV3, AAV4, AAV5, AAV6, AAV7, AAV8, AAV9, AAV10, AAV11, Rh10, Rh74 or AAV-2i8, and variants thereof) that flanks the respective 5' and/or 3' termini of a Factor IX encoding nucleic acid sequence, such as FIX with a reduced number of CpG (cytosine-guanine) dinucleotides.

In another aspect, a filler or stuffer polynucleotide sequence is positioned within a 5' and/or 3' ITR that flanks the respective 5' and/or 3' termini of a Factor IX encoding nucleic acid sequence, such as FIX with a reduced number of CpG dinucleotides. In an additional aspect, a filler or stuffer polynucleotide sequence is positioned adjacent to 5' and/or 3' ITR that flanks the respective 5' and/or 3' termini of a Factor IX encoding nucleic acid sequence, such as FIX with a reduced number of CpG dinucleotides. In a further aspect, a filler or stuffer polynucleotide sequence is positioned within a modified nucleic acid encoding Factor IX, such as FIX with a reduced number of CpG dinucleotides, e.g., analogous to an intron within a genomic nucleic acid.

Accordingly, in various embodiments, a filler or stuffer polynucleotide sequence is positioned adjacent to an AAV ITR sequence; positioned within two adeno-associated virus (AAV) ITR sequences; positioned outside two adeno-associated virus (AAV) ITR sequences; or there are two filler or stuffer polynucleotide sequences, a first filler or stuffer polynucleotide sequence positioned within two adeno-associated virus (AAV) ITR sequences, and a second filler or stuffer polynucleotide sequence positioned outside two adeno-associated virus (AAV) ITR sequences.

In more particular aspects, a filler or stuffer polynucleotide sequence has a length that when combined with a modified nucleic acid encoding Factor IX, such as FIX with a reduced number of CpG dinucleotides, the total combined length of the heterologous polynucleotide sequence and filler or stuffer polynucleotide sequence is between about 3.0 kb-5.5 kb, between about 4.0-5.0 kb, or between about 4.3 kb-4.8 kb, when positioned within two adeno-associated virus (AAV) ITR sequences. In other more particular aspects, a filler or stuffer polynucleotide sequence has a length greater than 4.7 kb, between about 5.0-10.0 kb, or between about 6.0-8.0 kb, when positioned outside two adeno-associated virus (AAV) ITR sequences.

Typically, a filler or stuffer polynucleotide sequence is inert or innocuous and has no function or activity. In various particular aspects, a filler or stuffer polynucleotide sequence is not a bacterial polynucleotide sequence, a filler or stuffer polynucleotide sequence is not a sequence that encodes a protein or peptide, a filler or stuffer polynucleotide sequence is a sequence distinct from any of: the heterologous polynucleotide sequence (e.g., modified nucleic acid encoding Factor IX), an AAV inverted terminal repeat (ITR) sequence, an expression control element, an origin of replication, a selectable marker or a poly-adenylation (poly-A) signal sequence.

In various additional particular aspects, a filler or stuffer polynucleotide sequence is an intron sequence that is related to or unrelated to the heterologous polynucleotide sequence (e.g., modified nucleic acid encoding Factor IX, such as FIX with a reduced number of CpG dinucleotides). In particular aspects, the intron sequence is positioned within the heterologous polynucleotide sequence (e.g., modified nucleic acid encoding Factor IX, such as FIX with a reduced number of CpG dinucleotides). In other particular aspects, the intron sequence is related to the heterologous polynucleotide sequence (e.g., modified nucleic acid encoding Factor IX, such as FIX with a reduced number of CpG dinucleotides) as the intron is in genomic DNA, such as the genomic DNA that encodes a protein which protein is also encoded by the heterologous polynucleotide sequence (e.g., modified nucleic acid encoding Factor IX).

Invention recombinant lenti- and parvo-virus (e.g., AAV) vectors such as AAV1, AAV2, AAV3, AAV4, AAV5, AAV6, AAV7, AAV8, AAV9, AAV10, AAV11, Rh10, Rh74 and AAV-2i8, and variants such as capsid variant (e.g., 4-1) particles that include (encapsidate, package) recombinant AAV vector genome can be included within cells. In such embodiments, cells can comprise packaging cells that produce or can be lysed to produce virus (AAV) particles, or target cells in which it is desired to express the heterologous polynucleotide sequence. Accordingly, cells that comprise modified Factor IX encoding nucleic acid, such as FIX with a reduced number of CpG dinucleotides, vectors and lenti- and parvo-virus (e.g., AAV) vectors such as AAV1, AAV2, AAV3, AAV4, AAV5, AAV6, AAV7, AAV8, AAV9, AAV10, AAV11, Rh10, Rh74 and AAV-2i8, and variants (e.g., such as 4-1) particles are provided.

In additional embodiments, a nucleic acid sequence encoding human FIX protein, wherein said nucleic acid has a reduced number of CpG di-nucleotides compared to native sequence encoding human Factor IX, or an expression vector or plasmid comprising a nucleic acid sequence encoding human FIX protein, wherein said nucleic acid has a reduced number of CpG di-nucleotides compared to native sequence encoding human Factor IX is include in a composition. In a particular aspect, such nucleic acid sequences can be included in a pharmaceutical composition. Accordingly, invention recombinant lenti- and parvo-virus (e.g., AAV) vectors such as AAV1, AAV2, AAV3, AAV4, AAV5, AAV6, AAV7, AAV8, AAV9, AAV10, AAV11, Rh10, Rh74 and AAV-2i8, and variants (e.g., such as 4-1) particles that include (encapsidate, package) vector genome can be included within pharmaceutical compositions. Such compositions are useful for administration of recombinant vector (e.g., AAV) and virus particles such as AAV1, AAV2, AAV3, AAV4, AAV5, AAV6, AAV7, AAV8, AAV9, AAV10, AAV11, Rh10, Rh74 or AAV-2i8, and variants (e.g., 4-1) that include (encapsidate, package) vector (e.g., AAV) genomes to a subject.

Invention recombinant lenti- and parvo-virus (e.g., AAV) vectors such as AAV1, AAV2, AAV3, AAV4, AAV5, AAV6, AAV7, AAV8, AAV9, AAV10, AAV11, Rh10, Rh74 and AAV-2i8, and variant (e.g., such as 4-1) particles that include (encapsidate, package) vector genome may be employed in various methods and uses. Accordingly, there are provided methods and uses for delivering or transferring a heterologous polynucleotide sequence (e.g., modified nucleic acid encoding Factor IX, such as FIX with a reduced number of CpG dinucleotides) into an organism or cell, such as a mammal or a cell of a mammal.

In one embodiment, a method or use includes administering a lenti- or parvo-virus (e.g., AAV) vector such as AAV1, AAV2, AAV3, AAV4, AAV5, AAV6, AAV7, AAV8, AAV9, AAV10, AAV11, Rh10, Rh74 and AAV-2i8, or variant that includes a heterologous polynucleotide sequence (e.g., modified nucleic acid encoding Factor IX such as FIX with a reduced number of CpG dinucleotides) particle in a vector genome (encapsidate, package) to a mammal or a cell of a mammal under suitable conditions to deliver or transfer the heterologous polynucleotide sequence into the mammal or the cell of a mammal. In one aspect, the method or use transfers/delivers the heterologous polynucleotide (e.g., modified nucleic acid encoding Factor IX, such as FIX with a reduced number of CpG dinucleotides) into the mammal and/or cell. In another aspect, the method allows transfer/delivery of the heterologous polynucleotide (e.g., modified nucleic acid encoding Factor IX, such as FIX with a reduced number of CpG dinucleotides) into the cell, subsequent transcription to form a transcript and subsequent translation to form a gene product (e.g., Factor IX).

In additional embodiments, a method or use is for treating a subject (e.g., mammal) deficient or in need of protein expression or function includes providing a lenti- or parvo-virus (e.g., AAV) vector such as AAV1, AAV2, AAV3, AAV4, AAV5, AAV6, AAV7, AAV8, AAV9, AAV10, AAV11, Rh10, Rh74 or AAV-2i8, or a variant, a plurality of such viral (e.g., AAV) particles, or a pharmaceutical composition of lenti- or parvo-virus (e.g., AAV) vectors such as AAV1, AAV2, AAV3, AAV4, AAV5, AAV6, AAV7, AAV8, AAV9, AAV10, AAV11, Rh10, Rh74 or AAV-2i8, or variant, particle or plurality of such viral (e.g., AAV) particles; and administering the viral particle, plurality of viral particles, or pharmaceutical composition of viral particles or plurality of viral particles to the subject (e.g., mammal). The heterologous polynucleotide sequence (e.g., modified nucleic acid encoding Factor IX, such as FIX with a reduced number of CpG dinucleotides) so administered may be subsequently expressed in the subject (e.g., mammal).

Methods and uses for administration or delivery include any mode compatible with a subject. In particular embodiments, a lenti- or parvo-virus (e.g., AAV) vector such as AAV1, AAV2, AAV3, AAV4, AAV5, AAV6, AAV7, AAV8, AAV9, AAV10, AAV11, Rh10, Rh74 and AAV-2i8, and variants, or plurality of such viral particles is administered or delivered parenterally, such as intravenously, intraarterially, intramuscularly, subcutaneously, or via catheter.

Subjects include mammals, such as humans and non-humans (e.g., primates). In particular embodiments, a subject would benefit from or is in need of expression of a heterologous polynucleotide sequence. In a more particular embodiment, a subject would benefit from Factor IX expression or function, e.g., such as a subject that expresses reduced amount of Factor IX, such as a subject with hemophilia B.

In accordance with the invention, methods of producing recombinant lenti- and parvo-virus (e.g., AAV) vectors such as AAV1, AAV2, AAV3, AAV4, AAV5, AAV6, AAV7, AAV8, AAV9, AAV10, AAV11, Rh10, Rh74 and AAV-2i8, and variants, that include (encapsidate, package) vector genome are provided. In one embodiment, a method includes introducing into a packaging cell a recombinant vector (e.g., AAV) plasmid to produce a productive viral infection; and culturing the packaging cells under conditions to produce recombinant viral particles. In another embodiment, a method of producing recombinant viral or AAV particles with reduced amounts of recombinant viral particles in which the recombinant viral vector includes contaminating nucleic acid, includes introducing into a packaging cell a recombinant vector (e.g., AAV) plasmid; and culturing the packaging cells under conditions to produce recombinant viral particles, wherein the recombinant viral particles produced have reduced numbers of viral particles with vector genomes that contain contaminating nucleic acid compared to the numbers of viral particles that contain contaminating nucleic acid produced under conditions in which a filler or stuffer polynucleotide sequence is absent from the recombinant viral vector. In particular aspects, the contaminating nucleic acid is bacterial nucleic acid; or a sequences other than the heterologous polynucleotide sequence, or ITR, promoter, enhancer, origin of replication, poly-A sequence, or selectable marker.

Packaging cells include mammalian cells. In particular embodiments, a packaging cell includes helper (e.g., AAV) functions to package the (heterologous polynucleotide) sequence (e.g., modified nucleic acid encoding Factor IX, such as FIX with a reduced number of CpG dinucleotides), expression vector (e.g., vector genome), into a viral particle (e.g., AAV particle). In particular aspects, a packaging cell provides AAV Rep and/or Cap proteins (e.g., Rep78 or/and Rep68 proteins); a packaging cell is stably or transiently transfected with polynucleotide(s) encoding Rep and/or Cap protein sequence(s); and/or a packaging cell is stably or transiently transfected with Rep78 and/or Rep68 protein polynucleotide encoding sequence(s).

In the invention recombinant lenti- or parvo-virus (e.g., AAV) vectors, and accompanying cis (e.g., expression control elements, ITRs, polyA) or trans (e.g., capsid proteins, packaging functions such as Rep/Cap protein) elements can be based upon any organism, species, strain or serotype. Invention recombinant viral (e.g., AAV) particles are typically based upon AAV1, AAV2, AAV3, AAV4, AAV5, AAV6, AAV7, AAV8, AAV9, AAV10, AAV11, Rh10, Rh74 and AAV-2i8, and variants, but also include hybrids or chimeras of different serotypes. Representative AAV serotypes include, without limitation, AAV1, AAV2, AAV3, AAV4, AAV5, AAV6, AAV7, AAV8, AAV9, AAV10, AAV11, Rh10, Rh74 and AAV-2i8 serotypes. Accordingly, invention recombinant viral (e.g., AAV) particles comprising vector genomes can include a capsid protein from a different serotype, a mixture of serotypes, or hybrids or chimeras of different serotypes, such as a VP1, VP2 or VP3 capsid protein of AAV1, AAV2, AAV3, AAV4, AAV5, AAV6, AAV7, AAV8, AAV9, AAV10, AAV11, Rh10, Rh74 or AAV-2i8 serotype. Furthermore, invention recombinant lenti- or parvo-virus (e.g., AAV) vectors such as AAV1, AAV2, AAV3, AAV4, AAV5, AAV6, AAV7, AAV8, AAV9, AAV10, AAV11, Rh10, Rh74 and AAV-2i8, sequences, plasmids, vector genomes, can include elements from any one serotype, a mixture of serotypes, or hybrids or chimeras of different serotypes. In various embodiments, a recombinant AAV vector includes a, ITR, Cap, Rep, and/or sequence derived from AAV1, AAV2, AAV3, AAV4, AAV5, AAV6, AAV7, AAV8, AAV9, AAV10, AAV11, Rh10, Rh74 and/or AAV-2i8 serotype, or a mixture, hybrid or chimera of any of the foregoing AAV serotypes.

ADDITIONAL EMBODIMENTS OF THE DISCLOSURE

Embodiment 1. A nucleic acid sequence encoding human Factor IX protein, wherein said nucleic acid has a reduced number of CpG di-nucleotides compared to a wild-type sequence encoding human Factor IX.

Embodiment 2. An expression vector or plasmid comprising a nucleic acid sequence encoding human Factor IX protein, wherein said nucleic acid has a reduced number of CpG di-nucleotides compared to native sequence encoding human Factor IX, and/or wherein if one or more sequences additional to the nucleic acid sequence encoding human Factor IX are present in said vector or plasmid said additional sequences optionally have a reduced number of CpG di-nucleotides compared to a counterpart native or wild-type sequence.

Embodiment 3. The nucleic acid sequence encoding human Factor IX protein of Embodiment 1, expression vector or plasmid of Embodiment 2, or composition of Embodiment 3, further comprising an intron, an expression control element, one or more adeno-associated virus (AAV) inverted terminal repeats (ITRs) and/or a filler polynucleotide sequence, optionally wherein said intron, expression control element, adeno-associated virus (AAV) inverted terminal repeats (ITRs) and/or filler polynucleotide sequence has a reduced number of CpG di-nucleotides compared to a counterpart native or wild-type expression control element, adeno-associated virus (AAV) inverted terminal repeats (ITRs) and/or filler polynucleotide sequence.

Embodiment 4. The nucleic acid sequence encoding human Factor IX protein of Embodiment 4, wherein the intron is within the sequence encoding human Factor IX protein, or wherein the expression control element is operably linked to the sequence encoding human Factor IX protein, or wherein the AAV ITR(s) flanks the 5' or 3'end of the sequence encoding human Factor IX protein, or wherein the filler polynucleotide sequence flanks the 5' or 3'end of the sequence encoding human Factor IX protein.

Embodiment 5. The nucleic acid sequence encoding human FIX protein of any of Embodiments 1-5, wherein the sequence encoding human FIX protein, intron, expression control element, ITR(s) and/or filler polynucleotide sequence has 1-5 fewer CpG di-nucleotides than native sequence encoding human Factor IX.

Embodiment 6. The nucleic acid sequence encoding human FIX protein of any of Embodiments 1-5, wherein the sequence encoding human FIX protein, intron, expression control element, ITR(s) and/or filler polynucleotide sequence has 5-10 fewer CpG di-nucleotides than native sequence encoding human Factor IX.

Embodiment 7. The nucleic acid sequence encoding human FIX protein of any of Embodiments 1-5, wherein the sequence encoding human FIX protein, intron, expression control element, ITR(s) and/or filler polynucleotide sequence has 10-15 fewer CpG di-nucleotides than native sequence encoding human Factor IX.

Embodiment 8. The nucleic acid sequence encoding human FIX protein of any of Embodiments 1-5, wherein the sequence encoding human FIX protein, intron, expression control element, ITR(s) and/or filler polynucleotide sequence has 15-20 fewer CpG di-nucleotides than native sequence encoding human Factor IX.

Embodiment 9. The nucleic acid sequence encoding human FIX protein of any of Embodiments 1-5, wherein the sequence encoding human FIX protein, intron, expression control element, ITR(s) and/or filler polynucleotide sequence has 20-25 fewer CpG di-nucleotides than native sequence encoding human Factor IX.

Embodiment 10. The nucleic acid sequence encoding human FIX protein of any of Embodiments 1-5, wherein the sequence encoding human FIX protein, intron, expression control element, ITR(s) and/or filler polynucleotide sequence has 25-30 fewer CpG di-nucleotides than native sequence encoding human Factor IX.

Embodiment 11. The nucleic acid sequence encoding human FIX protein of any of Embodiments 1-5, wherein the sequence encoding human FIX protein, intron, expression control element, ITR(s) and/or filler polynucleotide sequence has 30-40 fewer CpG di-nucleotides than native sequence encoding human Factor IX.

Embodiment 12. The nucleic acid sequence encoding human FIX protein of any of Embodiments 1-5, wherein the sequence encoding human FIX protein, intron, expression control element, ITR(s) and/or filler polynucleotide sequence has 40-55 fewer CpG di-nucleotides than native sequence encoding human Factor IX.

Embodiment 13. The nucleic acid sequence encoding human FIX protein of any of Embodiments 1-5, wherein the sequence encoding human FIX protein, intron, expression control element, ITR(s) and/or filler polynucleotide sequence is devoid of any CpG di-nucleotides.

Embodiment 14. The nucleic acid sequence encoding human FIX protein of any of Embodiments 1-5, wherein the sequence encoding human FIX protein comprises a sequence with 80% or more identity to SEQ ID NO: 10, and encodes functional Factor IX as determined by a clotting assay.

Embodiment 15. The nucleic acid sequence encoding human FIX protein of any of Embodiments 1-5, wherein the sequence encoding human FIX protein comprises a sequence with 90% or more identity to SEQ ID NO: 10, and encodes functional Factor IX as determined by a clotting assay.

Embodiment 16. The nucleic acid sequence encoding human FIX protein of any of Embodiments 1-5, wherein the sequence encoding human FIX protein comprises a sequence with 95% or more identity to SEQ ID NO: 10, and encodes functional Factor IX as determined by a clotting assay.

Embodiment 17. The nucleic acid sequence encoding human FIX protein of any of Embodiments 1-5, wherein the sequence encoding human FIX protein comprises SEQ ID NOs:10, 25 or 26.

Embodiment 18. The nucleic acid sequence encoding human FIX protein of any of Embodiments 1-5, wherein the native sequence encoding human Factor IX comprises the sequence set forth in SEQ ID NO:11.

Embodiment 19. The nucleic acid sequence encoding human FIX protein of any of Embodiments 1-5, wherein the intron sequence comprises the sequence set forth in SEQ ID NO:17.

Embodiment 20. The nucleic acid sequence encoding human FIX protein of any of Embodiments 1-5, wherein the expression control element comprises an enhancer sequence comprising the sequence set forth as SEQ ID NO: 14.

Embodiment 21. The nucleic acid sequence encoding human FIX protein of any of Embodiments 1-5, wherein the expression control element comprises a promoter sequence comprising the sequence set forth as SEQ ID NO:15.

Embodiment 22. The nucleic acid sequence encoding human FIX protein of any of Embodiments 1-5, wherein the sequence of the one or more adeno-associated virus (AAV) inverted terminal repeats (ITRs) comprises the sequence set forth as SEQ ID NO:13 and/or SEQ ID NO:20.

Embodiment 23. The nucleic acid sequence encoding human FIX protein of any of Embodiments 1-5, wherein the filler polynucleotide sequence comprises a sequence set forth as SEQ ID NO:21.

Embodiment 24. The nucleic acid sequence encoding human FIX protein of any of Embodiments 1-5, wherein the sequence encoding human FIX protein has reduced ability to induce an immune response.

Embodiment 25. The nucleic acid sequence encoding human FIX protein of any of Embodiments 1-5, wherein the sequence encoding human FIX protein is expressed at levels greater than or comparable to native sequence encoding human Factor IX not having a reduced number of CpG di-nucleotides.

Embodiment 26. The nucleic acid sequence encoding human Factor IX protein of any of Embodiments 1-5, wherein the expression control element comprises a constitutive or regulatable control element, or a tissue-specific expression control element or promoter.

Embodiment 27. The nucleic acid sequence encoding human Factor IX protein of any of Embodiments 1-5, wherein the expression control element comprises a an element that confers expression in liver.

Embodiment 28. The nucleic acid sequence encoding human FIX protein of any of Embodiments 1-5, wherein the expression control element comprises a human α1-antitrypsin (hAAT) Promoter and/or apolipoprotein E (ApoE) HCR-1 and/or HCR-2 enhancer.

Embodiment 29. The nucleic acid sequence encoding human Factor IX protein of any of Embodiments 1-5, further comprising a poly-adenylation sequence located 3' of the nucleic acid sequence encoding human Factor IX.

Embodiment 30. The nucleic acid sequence encoding human Factor IX protein of Embodiment 29, wherein the poly-adenylation sequence is located 3' of the nucleic acid sequence encoding human Factor IX comprises a bGH poly-adenylation sequence.

Embodiment 31. The nucleic acid sequence encoding human FIX protein of Embodiment 29, wherein the poly adenylation sequence located 3' of the nucleic acid sequence encoding human Factor IX comprises a poly-adenylation sequence having all CpG di-nucleotides removed therefrom.

Embodiment 32. The nucleic acid sequence encoding human FIX protein of Embodiment 31, wherein the poly-adenylation sequence comprises the sequence set forth as SEQ ID NO:19.

Embodiment 33. The nucleic acid sequence encoding human FIX protein of Embodiment 4 or 5, wherein the filler polynucleotide sequence is located 3' of the sequence encoding human FIX protein.

Embodiment 34. The nucleic acid sequence encoding human FIX protein of Embodiment 4 or 5, wherein the AAV ITR(s) flanks the 3'end of the sequence encoding human FIX protein.

Embodiment 35. The nucleic acid sequence encoding human FIX protein of Embodiment 34, wherein the filler polynucleotide sequence is located 3' of the AAV ITR(s) flanking the 3'end of the sequence encoding human FIX protein.

Embodiment 36. The nucleic acid sequence encoding human FIX protein of Embodiment 4 or 5, wherein the filler polynucleotide sequence comprises a lambda phage sequence.

Embodiment 37. A plasmid sequence encoding human FIX protein comprising the nucleic acid sequence encoding human FIX protein of any of Embodiments 1-36, further comprising one or more origins of replication and/or a nucleic acid encoding resistance to an antibiotic.

Embodiment 38. A plasmid sequence encoding human FIX protein comprising SEQ ID NO: 12 or 26.

Embodiment 39. A viral vector comprising the sequence encoding human FIX protein or expression vector comprising the nucleic acid sequence encoding human FIX protein of any of Embodiments 1-5.

Embodiment 40. A viral vector according to Embodiment 39, wherein said viral vector is a lenti- or adeno-viral vector.

Embodiment 41. A viral vector according to Embodiment 39, wherein said viral vector is an adeno-associated viral (AAV) vector.

Embodiment 42. The AAV vector of Embodiment 41, comprising an ITR sequence of any of: AAV1, AAV2, AAV3, AAV4, AAV5, AAV6, AAV7, AAV8, AAV9, AAV10, AAV11, Rh10, Rh74 or AAV-2i8 AAV serotypes.

Embodiment 43. The AAV vector of Embodiment 41, wherein the capsid sequence of the vector comprises a VP1, VP2 and/or VP3 capsid sequence having 90% or more identity to AAV1, AAV2, AAV3, AAV4, AAV5, AAV6, AAV7, AAV8, AAV9, AAV10, AAV11, Rh10, Rh74 or AAV-2i8 VP1, VP2 and/or VP3 sequences.

Embodiment 44. The AAV vector of Embodiment 41, wherein the capsid sequence of the vector comprises a VP1, VP2 or VP3 capsid sequence selected from any of: AAV1, AAV2, AAV3, AAV4, AAV5, AAV6, AAV7, AAV8, AAV9, AAV10, AAV11, Rh10, Rh74 or AAV-2i8 AAV serotypes.

Embodiment 45. The AAV vector of Embodiment 41, wherein the capsid sequence of the vector comprises a VP1 sequence having 90% or more sequence identity to SEQ ID NO: 1, or 1-50 amino acid substitutions, deletions or additions thereto; a VP2 sequence having 90% or more sequence identity to SEQ ID NO:2, or 1-50 amino acid substitutions, deletions or additions thereto; and/or
a VP3 sequence having 90% or more sequence identity to SEQ ID NO:3, or 1-50 amino acid substitutions, deletions or additions thereto.

Embodiment 46. The AAV vector of Embodiment 41, wherein the capsid sequence of the vector has an amino acid substitution at any one of amino acid positions 195, 199, 201 or 202, of the VP1 capsid sequence set forth as SEQ ID NO: 1, or an amino acid substitution of an arginine for a lysine in the VP1 capsid sequence set forth as SEQ ID NO:1.

Embodiment 47. The AAV vector of Embodiment 41, wherein the capsid sequence of the vector has residues of any of A, V, P or N amino acids at any one of amino acid positions 195, 199, 201 or 202 of the VP1 capsid sequence set forth as SEQ ID NO:1.

Embodiment 48. The AAV vector of Embodiment 41, wherein the capsid sequence of the vector has an A residue at amino acid position 195; a V residue at amino acid positions 199, a P residue at amino acid position 201, or an N residue at amino acid position 202 of the VP1 capsid sequence set forth as SEQ ID NO:1.

Embodiment 49. The AAV vector of Embodiment 41, wherein the capsid sequence of the vector has any two, three or four of an A residue at amino acid position 195; a V residue at amino acid positions 199, a P residue at amino acid position 201, or an N residue at amino acid position 202 of the VP1 capsid sequence set forth as SEQ ID NO:4.

Embodiment 50. The AAV vector of Embodiment 41, wherein the capsid sequence of the vector comprises a VP1 capsid sequence having 90% or more identity to any of SEQ ID NOs:4-9.

Embodiment 51. The AAV vector of Embodiment 41, wherein the capsid sequence of the vector comprises a VP1 capsid sequence comprises any of SEQ ID NOs:4-9.

Embodiment 52. A pharmaceutical composition comprising the nucleic acid sequence encoding human FIX protein of any of Embodiments 1-38 and/or a viral vector of Embodiments 39-51.

Embodiment 53. A pharmaceutical composition according to Embodiment 52, further comprising empty capsid AAV.

Embodiment 54. A pharmaceutical composition according to Embodiment 53 wherein said empty capsid is selected from serotype AAV AAV1, AAV2, AAV3, AAV4, AAV5, AAV6, AAV7, AAV8, AAV9, AAV10 and AAV11.

Embodiment 55. An expression vector comprising SEQ ID NO:11 or SEQ ID NO:25.

Embodiment 56. The expression vector of Embodiment 55, further comprising an enhancer sequence comprising the sequence set forth as SEQ ID NO:14.

Embodiment 57. The expression vector of Embodiment 55, further comprising a promoter sequence comprising the sequence set forth as SEQ ID NO:15.

Embodiment 58. The expression vector of Embodiment 55, further comprising an upstream and/or downstream AAV2 ITR as set forth in SEQ ID NO: 12 or 26, wherein said upstream ITR is positioned 5' of the enhancer and/or said downstream AAV2 ITR is positioned 3' of hFIX exons 2-8 set forth in SEQ ID NO:12 or 26.

Embodiment 59. The expression vector of Embodiment 55, further comprising a polyA sequence positioned 3' of the hFIX exons 2-8 as set forth in SEQ ID NO: 12 or 26 and positioned 5' of the downstream AAV2 ITR.

Embodiment 60. An AAV vector comprising the expression vector of any of Embodiments 55-59.

Embodiment 61. The AAV vector of Embodiment 60, wherein the capsid sequence comprises a VP1 capsid sequence comprises any of SEQ ID NOs:4-9.

Embodiment 62. A method for delivering or transferring a nucleic acid sequence into a cell, comprising contacting the nucleic acid sequence, expression vector, or virus vector of any of Embodiments 1-61 to said mammalian cell, under conditions allowing transduction of said cell, thereby delivering or transferring the nucleic acid sequence into the mammalian cell.

Embodiment 63. A method for delivering or transferring a nucleic acid sequence into a mammal or a cell of a mammal, comprising administering the nucleic acid sequence, expression vector, or virus vector of any of Embodiments 1-61 to said mammal or a cell of said mammal, thereby delivering or transferring the nucleic acid sequence into the mammal or cell of the mammal.

Embodiment 64. A method of treating a mammal in need of Factor IX protein, comprising: (a) providing a nucleic acid sequence, expression vector, or virus vector of any of Embodiments 1-61; and (b) administering an amount of the nucleic acid sequence, expression vector, or virus vector of any of Embodiments 1-61 to the mammal wherein said Factor IX is expressed in the mammal.

Embodiment 65. The method of any of Embodiments 62-64, wherein said Factor XI protein is expressed in a cell, tissue or organ of said mammal.

Embodiment 66. The method of Embodiment 65, wherein the cell comprises a secretory cell.

Embodiment 67. The method of Embodiment 65, wherein the cell comprises an endocrine cell.

Embodiment 68. The method of Embodiment 65, wherein the cell comprises hepatocyte, a neural cell, a glial cell, a retinal cell, an epithelial cell, a lung cell or a totipotent, pluripotent or multipotent stem cell.

Embodiment 69. The method of Embodiment 65, wherein the tissue or organ of said mammal comprises liver, brain, central nervous system, spinal cord, eye, retina or lung.

Embodiment 70. The method of any of Embodiments 62-69, wherein the mammal produces an insufficient amount of Factor IX protein, or a defective or aberrant Factor IX protein.

Embodiment 71. The method of any of Embodiments 62-69, wherein the mammal has hemophilia B.

Embodiment 72. The method of any of Embodiments 62-69, wherein the nucleic acid sequence, expression vector, or virus vector is delivered to the mammal intravenously, intraarterially, intramuscularly, subcutaneously, orally, by intubation, via catheter, dermally, intra-cranially, via inhalation, intra-cavity, or mucosally.

Embodiment 73. The method of any of Embodiments 62-69, wherein the mammal is human.

Embodiment 74. The method of any of Embodiments 62-69, wherein the mammal is sero-positive or sero-negative for an AAV1, AAV2, AAV3, AAV4, AAV5, AAV6, AAV7, AAV8, AAV9, AAV10, AAV11 or AAV-Rh74 serotype.

Embodiment 75. The method of any of Embodiments 62-69, further comprising administering empty capsid AAV.

Embodiment 76. The method of any of Embodiments 62-69, further comprising administering empty capsid of AAV1, AAV2, AAV3, AAV4, AAV5, AAV6, AAV7, AAV8, AAV9, AAV10, AAV11 and/or AAV-Rh74 serotype.

Embodiment 77. The method of any of Embodiments 62-69, further comprising administering empty capsid AAV of the same serotype as the AAV vector administered.

Embodiment 78. The method of any of Embodiments 62-69, wherein said Factor IX protein is expressed in the mammal at levels having a therapeutic effect on the mammal.

Embodiment 79. The method of any of Embodiments 62-69, wherein said Factor IX protein is expressed in the mammal at levels having a therapeutic effect for at least 1, 2, 3, 4, 5, 6, 7, 8, 9, 10, 11, 12, 13 or 14 days, weeks or months.

Embodiment 80. The method of any of Embodiments 62-69, wherein said Factor IX protein is present in the mammal at levels of about 20% FIX activity or greater than 20% activity for at least 1, 2, 3, 4, 5, 6, 7, 8, 9, 10, 11, 12, 13 or 14 continuous days, weeks or months.

Embodiment 81. The method of any of Embodiments 62-69, wherein the virus vector is administered at a dose in a range from about $1\times10^{10}$-$1\times10^{11}$, $1\times10^{11}$-$1\times10^{12}$, $1\times10^{12}$-$1\times10^{13}$, or $1\times10^{13}$-$1\times10^{14}$ vector genomes per kilogram (vg/kg) of the mammal.

Embodiment 82. The method of any of Embodiments 62-69, wherein the virus vector is administered at a dose of less than $1\times10^{12}$ vector genomes per kilogram (vg/kg) of the mammal, and said Factor IX protein is produced in the mammal at levels of about 20% activity or greater than 20% activity for at least 1, 2, 3, 4, 5, 6, 7, 8, 9, 10, 11, 12, 13 or 14 continuous days, weeks or months Embodiment 83. The method of any of Embodiments 62-69, wherein the virus vector is administered at a dose of about $5\times10^{11}$ vector genomes per kilogram (vg/kg) of the mammal, and said Factor IX protein is produced in the mammal at levels of about 20% activity or greater than 20% activity for at least 1, 2, 3, 4, 5, 6, 7, 8, 9, 10, 11, 12, 13 or 14 continuous days, weeks or months.

Embodiment 84. The method of any of Embodiments 62-69, wherein said nucleic acid sequence, expression vector, or virus vector administered to the mammal does not produce a substantial immune response against the Factor IX protein and/or the virus vector.

Embodiment 85. The method of any of Embodiments 62-69, wherein a substantial immune response against Factor IX protein and/or the virus vector is not produced for at least 1, 2, 3, 4, 5, 6, 7, 8, 9, 10, 11, 12, 13 or 14 continuous days, weeks or months.

Embodiment 86. The method of any of Embodiments 62-69, wherein the mammal does not produce a substantial immune response against the Factor IX protein.

Embodiment 87. The method of Embodiments 62-69, wherein said mammal does not develop an immune response against the Factor IX protein sufficient to decrease or block the Factor IX protein therapeutic effect.

Embodiment 88. The method of any of Embodiments 62-69, wherein the mammal does not produce a substantial immune response against Factor IX protein sufficient to decrease or block the Factor IX protein therapeutic effect for at least 1, 2, 3, 4, 5, 6, 7, 8, 9, 10, 11, 12, 13 or 14 continuous days, weeks or months.

Embodiment 89. The method of any of Embodiments 62-69, wherein said mammal does not develop an immune response against the Factor IX protein sufficient to decrease or block the Factor IX protein therapeutic effect for at least 1, 2, 3, 4, 5, 6, 7, 8, 9, 10, 11, 12, 13 or 14 continuous days, weeks or months.

Embodiment 90. The method of any of Embodiments 62-69, wherein said mammal does not develop an immune response against AAV vector sufficient to decrease or block the Factor IX protein therapeutic effect.

Embodiment 91. The method of any of Embodiments 62-69, wherein said mammal does not develop an immune response against AAV vector sufficient to decrease or block the Factor IX protein therapeutic effect for at least 1, 2, 3, 4, 5, 6, 7, 8, 9, 10, 11, 12, 13 or 14 continuous days, weeks or months.

Embodiment 92. The method of any of Embodiments 62-69, wherein said Factor IX protein is expressed in the mammal in amounts or at activity levels having a therapeutic effect on the mammal without administering an immunosuppressing agent (e.g., steroid).

Embodiment 93. The method of Embodiments any of Embodiments 62-69, wherein said Factor IX protein is expressed in the mammal in amounts or at activity levels having a therapeutic effect without administering an immunosuppressing agent (e.g., steroid) for at least 1, 2, 3, 4, 5, 6, 7, 8, 9, 10, 11, 12, 13 or 14 days, weeks or months.

Embodiment 94. The method of any of Embodiments 62-69, wherein said mammal does not develop abnormally high levels of liver ALT, AST and/or LDH enzymes for at least 1, 2, 3, 4, 5, 6, 7, 8, 9, 10, 11, 12, 13 or 14 continuous days, weeks or months.

Embodiment 95. The method of any of Embodiments 62-69, wherein said mammal does not develop abnormally high levels of liver ALT, AST and/or LDH enzymes for at least 1, 2, 3, 4, 5, 6, 7, 8, 9, 10, 11, 12, 13 or 14 continuous days, weeks or months to require using an immunosuppressing agent (e.g., steroid).

Embodiment 96. The method of any of Embodiments 62-69, wherein said Factor IX protein is expressed in the mammal at levels greater than the circulating levels of FIX needed to reduce the duration, severity or frequency of spontaneous joint bleeds or cerebral bleeding for at least 1, 2, 3, 4, 5, 6, 7, 8, 9, 10, 11, 12, 13 or 14 continuous weeks or months.

Embodiment 97. The method of any of Embodiments 62-69, wherein said Factor IX protein is expressed in the mammal at levels for at least 1, 2, 3, 4, 5, 6, 7, 8, 9, 10, 11, 12, 13 or 14 continuous days, weeks or months such that no recombinant FIX protein is needed or administered after AAV vector administration.

Embodiment 98. A recombinant AAV vector for treating hemophilia B, comprising a capsid and a genome, wherein said capsid comprises a VP1 protein having the amino acid sequence of SEQ ID NO:4; and wherein said genome is single-stranded and comprises the following elements in 5' to 3' order:
(a) a first AAV2 ITR,
(b) an ApoE HCR-1 enhancer,
(c) an AAT promoter,
(d) a codon-optimized nucleic acid encoding a human Factor IX Padua, wherein the nucleic acid lacks at least one CpG dinucleotide otherwise present,
(e) a polyadenylation sequence; and
(f) a second AAV2 ITR.

Embodiment 99. The rAAV vector of Embodiment 98, wherein
(a) the nucleic acid sequence of the first AAV2 ITR consists of nucleotides 1-141 of SEQ ID NO: 12,
(b) the nucleic acid sequence of said ApoE HCR-1 enhancer consists of nucleotides 152-472 of SEQ ID NO: 12,
(c) the nucleic acid sequence of said ATT promoter consists of nucleotides 482-878 of SEQ ID NO: 12,
(d) the nucleic acid sequence of said nucleic acid encoding human Factor IX Padua variant consists of nucleotides 908-3731 of SEQ ID NO: 12,
(e) the nucleic acid sequence of said polyadenylation sequence consists of nucleotides 3820-4047 of SEQ ID NO: 12; and
(f) the nucleic acid sequence of said second AAV2 ITR consists of nucleotides 4097-4204 of SEQ ID NO: 12.

Embodiment 100. The rAAV vector of Embodiment 99, wherein the genome comprises a nucleic acid sequence corresponding to nucleotides 1-4204 of SEQ ID NO: 12.

Embodiment 101. A method for treating a human subject with hemophilia B comprising administering to said subject a therapeutically effective amount of the rAAV vector of any one of Embodiments 98 or 99.

Embodiment 102. The method of Embodiment 101, wherein said subject has severe hemophilia B, and wherein said treatment is effective to reduce the hemophilia symptoms from severe to those of moderate or mild hemophilia B.

Embodiment 103. The method of Embodiment 101, wherein said treatment is effective to achieve a level of plasma FIX activity that is at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% of normal FIX activity.

Embodiment 104. The method of Embodiment 103, wherein said treatment is effective to achieve the level of plasma FIX activity for a sustained period of at least 3 months, 4 months, 5 months, 6 months, 7 months, 8 months, 9 months, 10 months, 11 months, 12 months, 13 months, 14 months, 15 months, 16 months, 17 months, 1.5 years, 2 years, 2.5 years, 3 years, 3.5 years, 4 years, 4.5 years, or 5 years.

Embodiment 105. The method of Embodiment 104, wherein said treatment is effective to achieve at least 1% plasma FIX activity for a sustained period of at least 6 months, 1 year, 2 years, 3 years, 4 years, or 5 years.

Embodiment 106. The method of Embodiment 104, wherein said treatment is effective to achieve at least 5% plasma FIX activity for a sustained period of at least 6 months, 1 year, 2 years, 3 years, 4 years, or 5 years.

Embodiment 107. The method of Embodiment 104, wherein said treatment is effective to achieve at least 10% plasma FIX activity for a sustained period of at least 6 months, 1 year, 2 years, 3 years, 4 years, or 5 years.

Embodiment 108. The method of Embodiment 104, wherein said treatment is effective to achieve at least 20% plasma FIX activity for a sustained period of at least 6 months, 1 year, 2 years, 3 years, 4 years, or 5 years.

Embodiment 109. The method of Embodiment 104, wherein said treatment is effective to achieve at least 30% plasma FIX activity for a sustained period of at least 6 months, 1 year, 2 years, 3 years, 4 years, or 5 years.

Embodiment 110. The method of Embodiment 104, wherein said treatment is effective to achieve at least 40% plasma FIX activity for a sustained period of at least 6 months, 1 year, 2 years, 3 years, 4 years, or 5 years.

Embodiment 111. The method of Embodiment 104, wherein said treatment is effective to achieve at least 20% plasma FIX activity for a sustained period of at least 6 months.

Embodiment 112. The method of Embodiment 111, wherein the therapeutically effective amount of said AAV vector is about $5.0 \times 10^{11}$ vg/kg.

Embodiment 113. The method of Embodiment 101, wherein the treatment is effective to reduce the frequency with which an average human subject having severe hemophilia B requires FIX protein replacement therapy to maintain adequate hemostasis by about 5%, 10%, 15%, 20%, 25%, 30%, 35%, 40%, 45%, 50%, 55%, 60%, 65%, 70%, 75%, 80%, 85%, 90%, 95%, or 100%.

Embodiment 114. The method of Embodiment 101, wherein the treatment is effective to reduce the frequency of spontaneous bleeding into the joints of a human subject with severe hemophilia B by about 5%, 10%, 15%, 20%, 25%, 30%, 35%, 40%, 45%, 50%, 55%, 60%, 65%, 70%, 75%, 80%, 85%, 90%, 95%, or 100%, compared to the average untreated human subject with severe hemophilia B.

Embodiment 115. The method of Embodiment 103, wherein said AAV vector results in an antibody titer against the capsid that is not greater than 1:2, 1:3, 1:4, 1:5, 1:6, 1:7, 1:8, 1:9, 1:10, 1:11, 1:12, 1:13, 1:14, 1:15, or 1:20, when determined at least 4 weeks after administration.

Embodiment 116. The method of Embodiment 103, wherein said AAV vector results in a T cell immune response against the capsid as measured using an ELISPOT assay resulting in not more than 10, 20, 30, 40, 50, 100, 200, 300, 400, or 500 spot-forming units per 1 million PBMCs when determined at least 4 weeks after administration.

Embodiment 117. The method of Embodiment 103, wherein said AAV vector results in an elevated liver enzyme level not more than 0%, 10%, 20%, 30%, 40%, 50%, 60%, 70%, 80%, 90%, 100%, 200%, 300%, 400%, or 500%, of the upper limit of normal (ULN) value for the enzyme.

Embodiment 118. The method of Embodiment 117, wherein said enzyme is alanine aminotransferase (ALT), aspartate aminotransferase (AST), or lactate dehydrogenase (LDH).

Embodiment 119. The method of Embodiment 101, wherein said treatment is effective to achieve a mean plasma FIX activity that is at least 1%, 5%, 10%, 20%, 30%, or 40%, of normal, with a standard deviation less than 15, 14, 13, 12, 11, 10, 9, 8, 7, 6, 5, 4, 3, 2, or 1, when measured at least 8 weeks after the vector is administered.

Embodiment 120. The method of any one of Embodiments 101-119, wherein said AAV vector is administered in a pharmaceutical composition comprising empty capsids wherein said empty capsids comprise a VP1 protein having the amino acid sequence of SEQ ID NO:4.

Embodiment 121. The method of Embodiment 120, wherein the ratio of said empty capsids to said AAV vector is about 2:1, 3:1, 4:1, 5:1, 6:1, 7:1, 8:1, 9:1, or 10:1.

Embodiment 122. A host cell comprising a contiguous nucleic acid sequence identical to the nucleic acid sequence from 1-4204 of SEQ ID NO: 12.

Embodiment 123. The host cell of Embodiment 122, further comprising AAV rep protein, AAV capsid protein and adenovirus helper protein(s).

Embodiment 124. The host cell of Embodiment 123, wherein the AAV capsid protein comprising SEQ ID NO:4, or a sequence having 90% or more identity thereto.

Embodiment 125. The host cell of Embodiment 123, wherein the host cell expresses FIX Padua protein.

Embodiment 126. A method of producing an AAV vector comprising the nucleic acid sequence from 1-4204 of SEQ ID NO: 12, comprising culturing a host cell of Embodiment 123 under conditions allowing packing of the nucleic acid sequence from 1-4204 of SEQ ID NO: 12 into AAV particles thereby producing AAV vector.

Embodiment 127. The method of Embodiment 126, further comprising purifying or isolating the AAV vector so produced.

Embodiment 128. An AAV vector produced by the method of Embodiment 126.

Embodiment 129. An isolated or purified AAV vector produced by the method of Embodiment 127.

BRIEF DESCRIPTION OF THE DRAWINGS

FIG. 1 shows the amino acid sequence of Rh74 VP1.
FIG. 2 shows the amino acid sequence or Rh74 VP2.
FIG. 3 shows the amino acid sequence of Rh74 VP3.
FIG. 4 shows the amino acid sequence of capsid variant 4-1 VP1 protein.
FIG. 5 shows the amino acid sequence of capsid variant 15-1.
FIG. 6 shows the amino acid sequence of capsid variant 15-2.
FIG. 7 shows the amino acid sequence of capsid variant 15-3/15-5.
FIG. 8 shows the amino acid sequence of capsid variant 15-4.
FIG. 9 shows the amino acid sequence of capsid variant 15-6.
FIG. 10 shows the nucleic acid sequence of FIX39.
FIG. 11 shows the nucleic acid sequence of FIX19.
FIG. 12A shows the sequence of the FIX39 plasmid.
FIG. 12B shows the sequence of the phFIX39v2 plasmid.
FIG. 14 shows the Intron A nucleic acid sequence. According to certain embodiments, pharmaceutical compositions comprising AAV vectors include those comprising the 4-1 capsid variant proteins (VP1, VP2 and VP3), comprise an excess of empty capsids greater than the concentration of AAV vectors (i.e.,
FIG. 15 shows the nucleic acid sequence of FIX39+Intron A.

DETAILED DESCRIPTION

Figure 13:
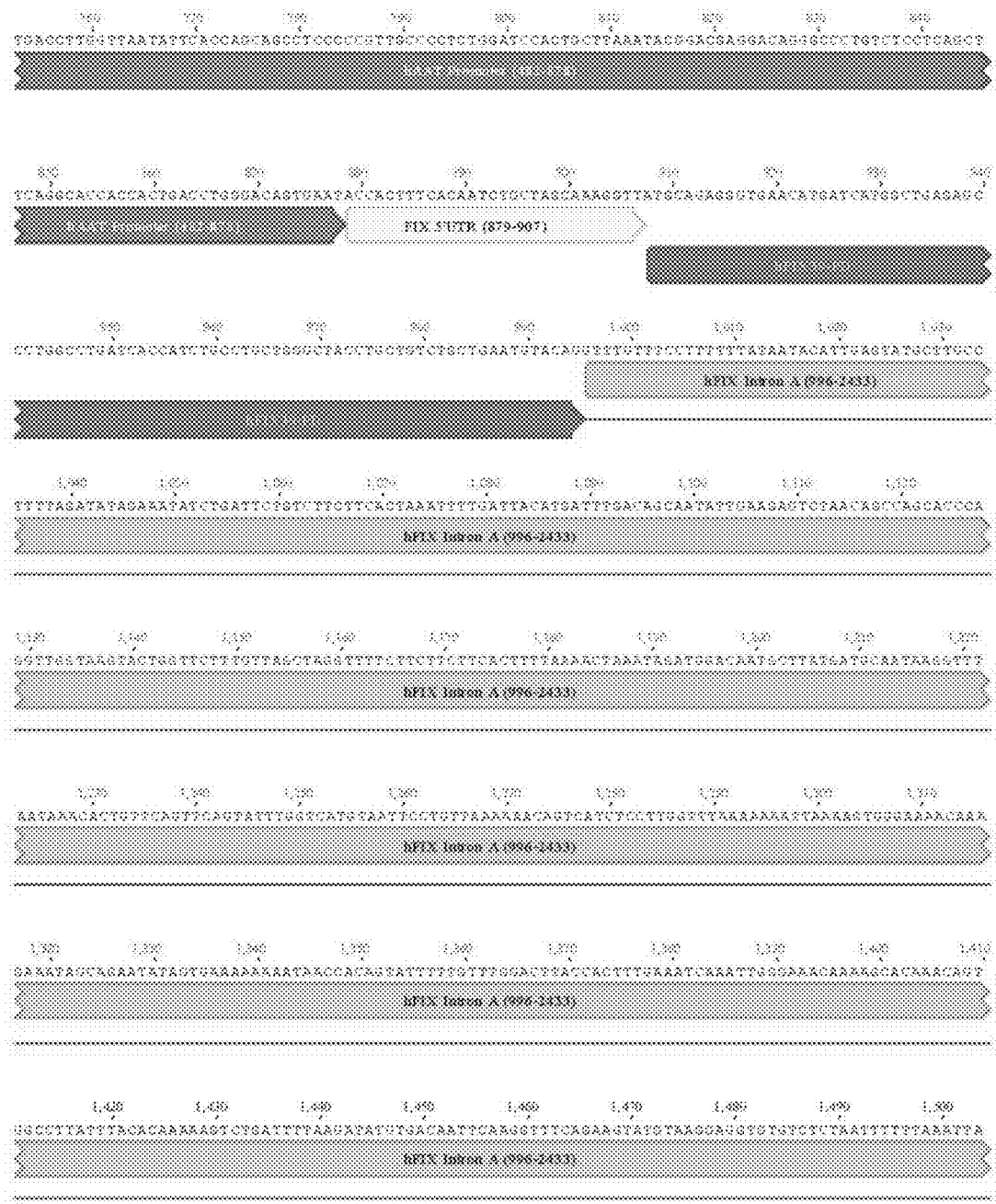
FIG. 13 shows a map of the FIX39 plasmid (SEQ ID NO:12).

The invention is based, at least in part, on development of modified nucleic acid sequences encoding proteins, such as human FIX protein. In various embodiments, a modified nucleic acid has a reduced number of CpG (cytosine-guanine) di-nucleotides compared to a reference nucleic acid sequence encoding Factor IX, such as a native (wild-type) sequence encoding human Factor IX. In further embodiments, such modified nucleic acids having a reduced number of CpG di-nucleotides compared to a reference Factor IX encoding nucleic acid (e.g., a native sequence encoding human Factor IX) are included within expression vectors (e.g., vector genomes) or plasmids.

The invention also includes compositions, such as compositions including a modified nucleic acid sequence encoding human FIX. In such compositions, a modified nucleic acid has a reduced number of CpG di-nucleotides relative to a reference sequence such as a native (wild-type) sequence encoding human Factor IX. Compositions also include expression vectors (e.g., viral vectors/vector genomes) and plasmids that include such modified nucleic acid sequences encoding human FIX protein having a reduced number of CpG di-nucleotides.

In particular aspects, a nucleic acid sequence encoding human FIX protein has 1-5 fewer CpG di-nucleotides than native sequence encoding human Factor IX; or has 5-10 fewer CpG di-nucleotides than native (wild-type) sequence encoding human Factor IX; or has 10-15 fewer CpG di-nucleotides than native (wild-type) sequence encoding human Factor IX; or has 15-20 fewer CpG di-nucleotides than native (wild-type) sequence encoding human Factor IX; or has 20-25 fewer CpG di-nucleotides than native (wild-type) sequence encoding human Factor IX; or has 25-30 fewer CpG di-nucleotides than native (wild-type) sequence encoding human Factor IX; or has 30-40 fewer CpG di-nucleotides than native (wild-type) sequence encoding human Factor IX; or has 40-55 fewer CpG di-nucleotides than native (wild-type) sequence encoding human Factor IX; or is completely devoid of any CpG di-nucleotides.

Modified nucleic acids encoding Factor IX, such as FIX with a reduced number of CpG dinucleotide, may further include one or more additional cis elements. Representative cis elements include, without limitation, expression control elements, introns, ITRs, stop codons, polyA sequences, and/or filler polynucleotide sequences. In particular embodiments, such cis-acting elements can also be modified. For example cis acting elements such as expression control elements, introns, ITRs, poly-A sequences, and/or filler polynucleotide sequences can have a reduced number of CpG di-nucleotides. In one aspect, one or more cis acting elements, such as expression control elements, introns, ITRs, poly-A sequences, and/or filler polynucleotide sequences, are devoid of CpG di-nucleotides. In particular aspects, one or more cis acting elements such as expression control elements, introns, ITRs, poly-A sequences, and/or filler polynucleotide sequences has 1-5 fewer CpG di-nucleotides than a reference cis-acting element; or has 5-10 fewer CpG di-nucleotides than a reference cis-acting element; or has 10-15 fewer CpG di-nucleotides than a reference cis-acting element; or has 15-20 fewer CpG di-nucleotides than a reference cis-acting element; or has 20-25 fewer CpG di-nucleotides than a reference cis-acting element; or has 25-30 fewer CpG di-nucleotides than a reference cis-acting element; or has 30-40 fewer CpG di-nucleotides than a reference cis-acting element; or has 40-55 fewer CpG di-nucleotides than a reference cis element; or is devoid of any CpG di-nucleotides.

The invention also includes viral vectors that include a modified nucleic acid sequence encoding human FIX protein, such as FIX with a reduced number of CpG dinucleotides. In particular embodiments, a vector includes a lenti- or parvo-viral vector, such as an adeno-viral vector. In a more particular embodiment, a modified nucleic acid sequence encoding human FIX protein, such as FIX with a reduced number of CpG dinucleotides, is comprised in an adeno-associated virus (AAV) vector.

In further particular embodiments, adeno-associated virus (AAV) vectors include capsids derived from AAV1, AAV2, AAV3, AAV4, AAV5, AAV6, AAV7, AAV8, AAV9, AAV10, AAV11, Rh10, Rh74 and AAV-2i8, as well as variants (e.g., capsid variants, such as amino acid insertions, additions and substitutions) thereof. As will be appreciated by one of ordinary skill in the art, AAV capsids typically include a VP1 protein and two shorter proteins, called VP2 and VP3, that are essentially amino-terminal truncations of VP1. Depending on the capsid and other factors known to those of ordinary skill, the three capsid proteins VP1, VP2 and VP3 are typically present in a capsid at a ratio approximating 1:1:10, respectively, although this ratio, particularly of VP3, can vary significantly and should not to be considered limiting in any respect.

AAV variants include AAV-Rh74 variants, for example AAV capsid variants of the Rh74 VP1 capsid sequence (SEQ ID NO: 1; FIG. 1), including but not limited to variants 4-1, 15-1, 15-2, 15-3/15-5, 15-4 and 15-6 described in Table 1. Rh74 VP2 and Rh74 VP3 amino acid sequences are provided in SEQ ID NO:2 (FIG. 2) and SEQ ID NO:3 (FIG. 3), respectively.

TABLE 1

AAV capsid variants

| Variant | Amino Acid Substitutions and Indicated Positions in Rh74 VP1 Capsid | Sequence Identifier | Figure |
|---|---|---|---|
| 4-1 | G195A-L199V-S201P-G202N | SEQ ID NO: 4 | FIG. 4 |
| 15-1 | G195A-L199V-S201P-G202N K(137/259/333/530/552/569/38/51/77/169/547)R | SEQ ID NO: 5 | FIG. 5 |
| 15-2 | G195A-L199V-S201P-G202N K(137/259/333/530/552/569/38/51/77/163/169)R | SEQ ID NO: 6 | FIG. 6 |
| 15-3/ 15-5 | G195A-L199V-S201P-G202N K(137/259/333/530/552/569/38/51/77/163/547)R (variant 15-3) G195A-L199V-S201P-G202N K(137/259/333/530/552/569/38/51/77/547/163)R (variant 15-5) | SEQ ID NO: 7 | FIG. 7 |
| 15-4 | G195A-L199V-S201P-G202N K(137/259/333/530/552/569/38/51/77/163/668)R | SEQ ID NO: 8 | FIG. 8 |
| 15-6 | G195A-L199V-S201P-G202N K(137/259/333/530/552/569/38/51/77/547/688)R | SEQ ID NO: 9 | FIG. 9 |

4-1 variant (SEQ ID NO:4) had an alanine, a valine, a proline, and an asparagine substitution at amino acid positions 195, 199, 201 and 202, respectively, of VP1 capsid. The 4-1 variant VP1 capsid amino acid sequence, with substituted residues a, v, p and n, underlined and in bold is shown in FIG. 4 (SEQ ID NO:4). For variant 4-1, the VP2 sequence consists of SEQ ID NO:27, and the VP3 sequence consists of SEQ ID NO:3, respectively.

15-1, 15-2, 15-3, 15-4, 1-5 and 15-6 variants also had an alanine, a valine, a proline, and an asparagine substitution at amino acid positions 195, 199, 201 and 202, respectively, of VP1 capsid. In addition, these variants had multiple arginine substitutions of lysine at various positions. The 15-1 variant VP1 capsid amino acid sequence (SEQ ID NO:5) is shown in FIG. 5; the 15-2 variant VP1 capsid amino acid sequence (SEQ ID NO:6) is shown in FIG. 6; the 15-3/15-5 variant VP1 capsid amino acid sequence (SEQ ID NO:7) is shown in FIG. 7; the 15-4 variant VP1 capsid amino acid sequence (SEQ ID NO:8) is shown in FIG. 8; and the 15-6 variant VP1 capsid amino acid sequence (SEQ ID NO:9) is shown in FIG. 9. Examples of capsids that may be used herein include, but are not limited to, those described in United States patent publication no. 2015/0023924.

Accordingly, lenti- and parvo-viral vectors such as AAV vectors and viral vector variants such as AAV variants (e.g., capsid variants such as 4-1, 15-1, 15-2, 15-3/15-5, 15-4 and 15-6) that include (encapsidate or package) vector genome including modified nucleic acid sequence encoding human FIX protein, such as FIX with a reduced number of CpG dinucleotides, are provided.

In exemplary studies, AAV-Rh74 mediated gene transfer/delivery produced protein expression levels that were significantly higher than several other serotypes. In particular, AAV-Rh74 vector and capsid variants (e.g., 4-1) target genes for delivery to the liver with efficiency at least comparable to the gold standard for liver transduction, AAV8, in hemophilia B dogs and/or in mice and/or macaques.

As set forth herein, viral vectors such as lenti- and parvo-virus vectors, including AAV serotypes and variants provide a means for delivery of polynucleotide sequences into cells ex vivo, in vitro and in vivo, which can encode proteins such that the cells express the encoded proteins. For example, a recombinant AAV vector can include a heterologous polynucleotide encoding a desired protein or peptide (e.g., Factor IX). Vector delivery or administration to a subject (e.g., mammal) therefore provides encoded proteins and peptides to the subject. Thus, viral vectors such as lenti- and parvo-virus vectors, including AAV serotypes and variants such as capsid variants (e.g., 4-1) can be used to transfer/deliver heterologous polynucleotides for expression, and optionally for treating a variety of diseases.

In particular embodiments, a recombinant vector (e.g., AAV) is a parvovirus vector. Parvoviruses are small viruses with a single-stranded DNA genome. "Adeno-associated viruses" (AAV) are in the parvovirus family.

Parvoviruses including AAV are viruses useful as gene therapy vectors as they can penetrate cells and introduce nucleic acid/genetic material so that the nucleic acid/genetic material may be stably maintained in cells. In addition, these viruses can introduce nucleic acid/genetic material into specific sites, for example, such as a specific site on chromosome 19. Because AAV are not associated with pathogenic disease in humans, AAV vectors are able to deliver heterologous polynucleotide sequences (e.g., therapeutic proteins and agents) to human patients without causing substantial AAV pathogenesis or disease.

AAV and AAV variants (e.g., capsid variants such as 4-1) serotypes (e.g., VP1, VP2, and/or VP3 sequences) may or may not be distinct from other AAV serotypes, including, for example, AAV1-AAV11, Rh74 or Rh10 (e.g., distinct from VP1, VP2, and/or VP3 sequences of any of AAV1-AAV11, Rh74 or Rh10 serotypes).

As used herein, the term "serotype" is a distinction used to refer to an AAV having a capsid that is serologically distinct from other AAV serotypes. Serologic distinctiveness is determined on the basis of the lack of cross-reactivity between antibodies to one AAV as compared to another AAV. Such cross-reactivity differences are usually due to differences in capsid protein sequences/antigenic determinants (e.g., due to VP1, VP2, and/or VP3 sequence differences of AAV serotypes). Despite the possibility that AAV variants including capsid variants may not be serologically distinct from a reference AAV or other AAV serotype, they differ by at least one nucleotide or amino acid residue compared to the reference or other AAV serotype.

Under the traditional definition, a serotype means that the virus of interest has been tested against serum specific for all existing and characterized serotypes for neutralizing activity and no antibodies have been found that neutralize the virus of interest. As more naturally occurring virus isolates of are discovered and/or capsid mutants generated, there may or may not be serological differences with any of the currently existing serotypes. Thus, in cases where the new virus (e.g., AAV) has no serological difference, this new virus (e.g., AAV) would be a subgroup or variant of the corresponding serotype. In many cases, serology testing for neutralizing activity has yet to be performed on mutant viruses with capsid sequence modifications to determine if they are of another serotype according to the traditional definition of serotype. Accordingly, for the sake of convenience and to avoid repetition, the term "serotype" broadly refers to both serologically distinct viruses (e.g., AAV) as well as viruses (e.g., AAV) that are not serologically distinct that may be within a subgroup or a variant of a given serotype.

Recombinant vector (e.g., AAV) plasmids, vector (e.g., AAV) genomes, as well as methods and uses thereof, include any viral strain or serotype. As a non-limiting example, a recombinant vector (e.g., AAV) plasmid or vector (e.g., AAV) genome can be based upon any AAV genome, such as AAV-1, -2, -3, -4, -5, -6, -7, -8, -9, -10, -11, -rh74, -rh10 or AAV-2i8, for example. Such vectors can be based on the same of strain or serotype (or subgroup or variant), or be different from each other. As a non-limiting example, a recombinant vector (e.g., AAV) plasmid or vector (e.g., AAV) genome based upon one serotype genome can be identical to one or more of the capsid proteins that package the vector. In addition, a recombinant vector (e.g., AAV) plasmid or vector (e.g., AAV) genome can be based upon an AAV (e.g., AAV2) serotype genome distinct from one or more of the capsid proteins that package the vector, in which case at least one of the three capsid proteins could be a AAV1, AAV2, AAV3, AAV4, AAV5, AAV6, AAV7, AAV8, AAV9, AAV10, AAV11, Rh10, Rh74 or AAV-2i8 or variant such as AAV-Rh74 variant (e.g., capsid variants such as 4-1, 15-1, 15-2, 15-3/15-5, 15-4 and 15-6), for example.

AAV vectors therefore include gene/protein sequences identical to gene/protein sequences characteristic for a particular serotype. As used herein, an "AAV vector related to AAV1" refers to one or more AAV proteins (e.g., VP1, VP2, and/or VP3 sequences) that has substantial sequence identity to one or more polynucleotides or polypeptide sequences that comprise AAV1. Analogously, an "AAV vector related to AAV8" refers to one or more AAV proteins (e.g., VP1, VP2, and/or VP3 sequences) that has substantial sequence identity to one or more polynucleotides or polypeptide sequences that comprise AAV8. An "AAV vector related to AAV-Rh74" refers to one or more AAV proteins (e.g., VP1, VP2, and/or VP3 sequences) that has substantial sequence identity to one or more polynucleotides or polypeptide sequences that comprise AAV-Rh74. (see, e.g., VP1, VP2, VP3 of FIGS. 1-3). Such AAV vectors related to another serotype, e.g., AAV1, AAV2, AAV3, AAV4, AAV5, AAV6, AAV7, AAV8, AAV9, AAV10, AAV11, Rh10, Rh74 or AAV-2i8, can therefore have one or more distinct sequences from AAV1, AAV2, AAV3, AAV4, AAV5, AAV6, AAV7, AAV8, AAV9, AAV10, AAV11, Rh10, Rh74 and AAV-2i8, but can exhibit substantial sequence identity to one or more genes and/or proteins, and/or have one or more functional characteristics of AAV1, AAV2, AAV3, AAV4, AAV5, AAV6, AAV7, AAV8, AAV9, AAV10, AAV11, Rh10, Rh74 or AAV-2i8 (e.g., such as cell/tissue tropism). Exemplary non-limiting AAV-Rh74 and related AAV variants such as AAV-Rh74 or related AAV such as AAV-Rh74 variants (e.g., capsid variants such as 4-1, 15-1, 15-2, 15-3/15-5, 15-4 and 15-6) sequences include VP1, VP2, and/or VP3 set forth herein, for example, in FIGS. 1-9.

In various exemplary embodiments, an AAV vector related to a reference serotype has a polynucleotide, polypeptide or subsequence thereof that includes or consists of a sequence at least 80% or more (e.g., 85%, 90%, 95%, 96%, 97%, 98%, 99%, 99.5%, etc.) identical to one or more AAV1, AAV2, AAV3, AAV4, AAV5, AAV6, AAV7, AAV8, AAV9, AAV10, AAV11, Rh10, Rh74 or AAV-2i8 (e.g., such as AAV-Rh74 VP1, VP2, and/or VP3 sequences set forth in FIGS. 1-9).

Methods and uses of the invention include AAV sequences (polypeptides and nucleotides), AAV-Rh74 sequences (polypeptides and nucleotides) and subsequences thereof that exhibit less than 100% sequence identity to a reference AAV serotype such as AAV1, AAV2, AAV3, AAV4, AAV5, AAV6, AAV7, AAV8, AAV9, AAV10, AAV11, Rh10, or AAV-2i8, for example, AAV-Rh74 gene or protein sequence (e.g., VP1, VP2, and/or VP3 sequences set forth in FIGS. 1-9), but are distinct from and not identical to known AAV genes or proteins, such as AAV1, AAV2, AAV3, AAV4, AAV5, AAV6, AAV7, AAV8, AAV9, AAV10, AAV11, Rh10, Rh74 or AAV-2i8, genes or proteins, etc. In one embodiment, an AAV polypeptide or subsequence thereof includes or consists of a sequence at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical to any reference AAV sequence or subsequence thereof, such as AAV1, AAV2, AAV3, AAV4, AAV5, AAV6, AAV7, AAV8, AAV9, AAV10, AAV11, Rh10, Rh74 or AAV-2i8 (e.g., VP1, VP2 and/or VP3 sequences set forth in FIGS. 1-9). In particular aspects, an AAV variant has one, two, three or four of the four amino acid substitutions (e.g., capsid variant 4-1, 15-1, 15-2, 15-3/15-5, 15-4 and 15-6).

Recombinant vectors (e.g., AAV), including AAV1, AAV2, AAV3, AAV4, AAV5, AAV6, AAV7, AAV8, AAV9, AAV10, AAV11, Rh10, Rh74 or AAV-2i8 and variant, related, hybrid and chimeric sequences, can be constructed using recombinant techniques that are known to the skilled artisan, to include one or more heterologous polynucleotide sequences (transgenes) flanked with one or more functional AAV ITR sequences. Such vectors can have one or more of the wild type AAV genes deleted in whole or in part, for example, a rep and/or cap gene, but retain at least one functional flanking ITR sequence, as necessary for the rescue, replication, and packaging of the recombinant vector into an AAV vector particle. An AAV vector genome would therefore include sequences required in cis for replication and packaging (e.g., functional ITR sequences)

The terms "polynucleotide" and "nucleic acid" are used interchangeably herein to refer to all forms of nucleic acid, oligonucleotides, including deoxyribonucleic acid (DNA) and ribonucleic acid (RNA). Polynucleotides include genomic DNA, cDNA and antisense DNA, and spliced or unspliced mRNA, rRNA tRNA and inhibitory DNA or RNA (RNAi, e.g., small or short hairpin (sh)RNA, microRNA (miRNA), small or short interfering (si)RNA, trans-splicing RNA, or antisense RNA). Polynucleotides include naturally occurring, synthetic, and intentionally modified or altered polynucleotides (e.g., having reduced CpG dinucleotides). Polynucleotides can be single, double, or triplex, linear or circular, and can be of any length. In discussing polynucleotides, a sequence or structure of a particular polynucleotide may be described herein according to the convention of providing the sequence in the 5' to 3' direction.

A "heterologous" polynucleotide refers to a polynucleotide inserted into a vector (e.g., AAV) for purposes of vector mediated transfer/delivery of the polynucleotide into a cell. Heterologous polynucleotides are typically distinct from vector (e.g., AAV) nucleic acid, i.e., are non-native with respect to viral (e.g., AAV) nucleic acid. Once transferred/delivered into the cell, a heterologous polynucleotide, contained within the vector, can be expressed (e.g., transcribed, and translated if appropriate). Alternatively, a transferred/delivered heterologous polynucleotide in a cell, contained within the vector, need not be expressed. Although the term "heterologous" is not always used herein in reference to polynucleotides, reference to a polynucleotide even in the absence of the modifier "heterologous" is intended to include heterologous polynucleotides in spite of the omission. An example of a heterologous sequence would be a Factor IX encoding nucleic acid, for example, a modified nucleic acid encoding Factor IX, such as a nucleic acid having reduced CpG dinucleotides relative to a reference nucleic acid sequence.

The "polypeptides," "proteins" and "peptides" encoded by the "polynucleotide sequences," include full-length native sequences, as with naturally occurring proteins, as well as functional subsequences, modified forms or sequence variants so long as the subsequence, modified form or variant retains some degree of functionality of the native full-length protein. In methods and uses of the invention, such polypeptides, proteins and peptides encoded by the polynucleotide sequences can be but are not required to be identical to the endogenous protein that is defective, or whose expression is insufficient, or deficient in the treated mammal.

In the invention lenti- and parvo-viral vectors, such as an adeno-viral vector and AAV vectors, including AAV1, AAV2, AAV3, AAV4, AAV5, AAV6, AAV7, AAV8, AAV9, AAV10, AAV11, Rh10, Rh74 or AAV-2i8 and related AAV variants such as AAV-Rh74 variants (e.g., capsid variants such as 4-1, 15-1, 15-2, 15-3/15-5, 15-4 and 15-6) can be used to introduce/deliver polynucleotides stably or transiently into cells and progeny thereof. The term "transgene" is used herein to conveniently refer to such a heterologous polynucleotide that is intended or has been introduced into a cell or organism. Transgenes include any polynucleotide, such as a gene that encodes a polypeptide or protein (e.g., Factor IX).

For example, in a cell having a transgene, the transgene has been introduced/transferred by way of vector, such as AAV, "transduction" or "transfection" of the cell. The terms "transduce" and "transfect" refer to introduction of a molecule such as a polynucleotide into a cell or host organism.

A cell into which the transgene has been introduced is referred to as a "transduced cell." Accordingly, a "transduced" cell (e.g., in a mammal, such as a cell or tissue or organ cell), means a genetic change in a cell following incorporation of an exogenous molecule, for example, a polynucleotide or protein (e.g., a transgene) into the cell. Thus, a "transduced" cell is a cell into which, or a progeny thereof in which an exogenous molecule has been introduced, for example. The cell(s) can be propagated and the introduced protein expressed, or nucleic acid transcribed. For gene therapy uses and methods, a transduced cell can be in a subject.

The introduced polynucleotide may or may not be integrated into nucleic acid of the recipient cell or organism. If an introduced polynucleotide becomes integrated into the nucleic acid (genomic DNA) of the recipient cell or organism it can be stably maintained in that cell or organism and further passed on to or inherited by progeny cells or organisms of the recipient cell or organism. Finally, the introduced nucleic acid may exist in the recipient cell or host organism only transiently.

Cells that may be transduced include a cell of any tissue or organ type, of any origin (e.g., mesoderm, ectoderm or endoderm). Non-limiting examples of cells include liver (e.g., hepatocytes, sinusoidal endothelial cells), pancreas (e.g., beta islet cells), lung, central or peripheral nervous system, such as brain (e.g., neural, glial or ependymal cells) or spine, kidney, eye (e.g., retinal, cell components), spleen, skin, thymus, testes, lung, diaphragm, heart (cardiac), muscle or psoas, or gut (e.g., endocrine), adipose tissue (white, brown or beige), muscle (e.g., fibroblasts), synoviocytes, chondrocytes, osteoclasts, epithelial cells, endothelial cells, salivary gland cells, inner ear nervous cells or hema-topoietic (e.g., blood or lymph) cells. Additional examples include stem cells, such as pluripotent or multipotent progenitor cells that develop or differentiate into liver (e.g., hepatocytes, sinusoidal endothelial cells), pancreas (e.g., beta islet cells), lung, central or peripheral nervous system, such as brain (e.g., neural, glial or ependymal cells) or spine, kidney, eye (retinal, cell components), spleen, skin, thymus, testes, lung, diaphragm, heart (cardiac), muscle or psoas, or gut (e.g., endocrine), adipose tissue (white, brown or beige), muscle (e.g., fibroblasts), synoviocytes, chondrocytes, osteoclasts, epithelial cells, endothelial cells, salivary gland cells, inner ear nervous cells or hematopoietic (e.g., blood or lymph) cells.

A "therapeutic molecule" in one embodiment is a peptide or protein that may alleviate or reduce symptoms that result from an absence or defect in a protein in a cell or subject. Alternatively, a "therapeutic" peptide or protein encoded by a transgene is one that confers a benefit to a subject, e.g., to correct a genetic defect, to correct a gene (expression or functional) deficiency.

Non-limiting examples of heterologous polynucleotides encoding gene products (e.g., therapeutic proteins) which are useful in accordance with the invention include those that may be used in the treatment of a disease or disorder including, but not limited to, blood clotting disorders such as hemophilia A, hemophilia B, thalassemia, and anemia.

All mammalian and non-mammalian forms of polynucleotides encoding gene products, including the non-limiting genes and proteins disclosed herein are expressly included, either known or unknown. Thus, the invention includes genes and proteins from non-mammals, mammals other than humans, and humans, which genes and proteins function in a substantially similar manner to the human genes and proteins described herein. Non-limiting examples of mammalian non-human Factor IX sequences are described in Yoshitake et al., 1985, supra; Kurachi et al., 1995, supra; Jallat et al., 1990, supra; Kurachi et al., 1982, Proc. Natl. Acad. Sci. USA 79:6461-6464; Jaye et al., 1983, Nucl. Acids Res. 11:2325-2335; Anson et al., 1984, EMBO J. 3: 1053-1060; Wu et al., 1990, Gene 86:275-278; Evans et al., *Proc Natl Acad Sci USA* 86:10095 (1989), Blood 74:207-212; Pendurthi et al., 1992, Thromb. Res. 65:177-186; Sakar et al., 1990, Genomics 1990, 6:133-143; and, Katayama et al., 1979, Proc. Natl. Acad. Sci. USA 76:4990-4994.

Polynucleotides, polypeptides and subsequences thereof include modified and variant forms. As used herein, the terms "modify" or "variant" and grammatical variations thereof, mean that a polynucleotide, polypeptide or subsequence thereof deviates from a reference sequence. Modified and variant sequences may therefore have substantially the same, greater or less activity or function than a reference sequence, but at least retain partial activity or function of the reference sequence. In particular embodiments, a modified nucleic acid encodes Factor IX, and has been modified to reduce the number of CpG dinucleotides compared to a reference Factor IX encoding nucleic acid (e.g., wild-type Factor IX sequence, such as a human or other mammalian Factor IX gene sequence).

Variants also include gain and loss of function variants. For example, wild type human Factor IX DNA sequences, which protein variants or mutants retain activity, or are therapeutically effective, or are comparably or even more therapeutically active than invariant human Factor IX in the methods and uses of the invention. In one non-limiting example of a naturally occurring human Factor IX variant, called the "Padua", human Factor IX has a L (leucine) at position 338 instead of an R (arginine). The Padua FIX has greater catalytic and coagulant activity compared to human Factor IX lacking the Padua mutation. Changing Residue 338 in Human Factor IX from Arginine to Alanine Causes an Increase in Catalytic Activity (Chang et al., J. Biol. Chem., 273:12089-94 (1998)). In another particular example, collagen IV serves to trap Factor IX, meaning that when introduced into the muscle tissue of a mammal some of the Factor IX is not available for participation in blood coagulation because it is retained in the interstitial spaces in the muscle tissue. A mutation in the sequence of Factor IX that results in a protein with reduced binding to collagen IV (e.g., loss of function) is a useful mutant, for example, for treatment of hemophilia. An example of such a mutant Factor IX gene encodes a human FIX protein with the amino acid alanine in place of lysine in the fifth amino acid position from the beginning of the mature protein.

Non-limiting examples of modifications include one or more nucleotide or amino acid substitutions (e.g., 1-3, 3-5, 5-10, 10-15, 15-20, 20-25, 25-30, 30-40, 40-50, 50-100, or more nucleotides or residues), such as substituting a CpG for an alternative dinucleotide in a transgene (e.g., a Factor IX encoding gene, such as FIX encoding gene with a reduced number of CpG dinucleotides). An example of an amino acid substitution is a conservative amino acid substitution in a capsid sequence. Another example of an amino acid substitution is an arginine for a lysine residue (e.g., one or more arginine substitution of a lysine as set forth in any of 4-1, 15-1, 15-2, 15-3/15-5, 15-4 and/or 15-6). Further modifications include additions (e.g., insertions or 1-3, 3-5, 5-10, 10-15, 15-20, 20-25, 25-30, 30-40, 40-50, 50-100, or more nucleotides or residues) and deletions (e.g., subsequences or fragments) of a reference sequence. In particular embodiments, a modified or variant sequence retains at least part of a function or an activity of unmodified sequence. Such modified forms and variants can have the same, less than, or greater, but at least a part of, a function or activity of a reference sequence, for example, as described herein.

As set forth herein, a variant can have one or more non-conservative or a conservative amino acid sequence differences or modifications, or both. A "conservative substitution" is the replacement of one amino acid by a biologically, chemically or structurally similar residue. Biologically similar means that the substitution does not destroy a biological activity. Structurally similar means that the amino acids have side chains with similar length, such as alanine, glycine and serine, or a similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like. Particular examples of conservative substitutions include the substitution of a hydrophobic residue such as isoleucine, valine, leucine or methionine for another, the substitution of a polar residue for another, such as the substitution of arginine for lysine, glutamic for aspartic acids, or glutamine for asparagine, and the like. For example, conservative amino acid substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. A "conservative substitution" also includes the use of a substituted amino acid in place of an unsubstituted parent amino acid.

Accordingly, the invention includes gene and protein variants (e.g., of polynucleotides encoding proteins described herein) which retain one or more biological activities (e.g., function in blood clotting, etc.). Variants can differ from a reference sequence, such as naturally occurring polynucleotides, proteins or peptides. Such variants of polynucleotides, proteins or polypeptides include proteins or polypeptides which have been or may be modified using recombinant DNA technology such that the polynucleotide, protein or polypeptide possesses altered or additional properties.

At the nucleotide sequence level, a naturally and non-naturally occurring variant gene will typically be at least about 50% identical, more typically about 70% identical, even more typically about 80% identical to the reference gene. Thus, for example, a FIX gene with a reduced number of CpG dinucleotides may have 80% or more identity to wild-type FIX gene, or 80-85%, 85-90%, 90-95%, or more identity to wild-type FIX gene, e.g., 96%, 97%, 98%, or 99% or more identity to wild-type FIX gene.

At the amino acid sequence level, a naturally and non-naturally occurring variant protein will typically be at least about 70% identical, more typically about 80% identical, even more typically about 90% or more identity to the reference protein, although substantial regions of non-identity are permitted in non-conserved regions (e.g., less, than 70% identical, such as less than 60%, 50% or even 40%). In other embodiments, the sequences have at least 60%, 70%, 75% or more identity (e.g., 80%, 85% 90%, 95%, 96%, 97%, 98%, 99% or more identity) to a reference sequence.

The term "identity," "homology" and grammatical variations thereof, mean that two or more referenced entities are the same, when they are "aligned" sequences. Thus, by way of example, when two polypeptide sequences are identical, they have the same amino acid sequence, at least within the referenced region or portion. Where two polynucleotide sequences are identical, they have the same polynucleotide sequence, at least within the referenced region or portion. The identity can be over a defined area (region or domain) of the sequence. An "area" or "region" of identity refers to a portion of two or more referenced entities that are the same. Thus, where two protein or nucleic acid sequences are identical over one or more sequence areas or regions they share identity within that region. An "aligned" sequence refers to multiple polynucleotide or protein (amino acid) sequences, often containing corrections for missing or additional bases or amino acids (gaps) as compared to a reference sequence The identity can extend over the entire length or a portion of the sequence. In particular aspects, the length of the sequence sharing the percent identity is 2, 3, 4, 5 or more contiguous polynucleotide or amino acids, e.g., 6, 7, 8, 9, 10, 11, 12, 13, 14, 15, 16, 17, 18, 19, 20, etc. contiguous polynucleotides or amino acids. In additional particular aspects, the length of the sequence sharing identity is 21 or more contiguous polynucleotide or amino acids, e.g., 21, 22, 23, 24, 25, 26, 27, 28, 29, 30, 31, 32, 33, 34, 35, 36, 37, 38, 39, 40, etc. contiguous polynucleotides or amino acids. In further particular aspects, the length of the sequence sharing identity is 41 or more contiguous polynucleotide or amino acids, e.g. 42, 43, 44, 45, 45, 47, 48, 49, 50, etc., contiguous polynucleotides or amino acids. In yet further particular aspects, the length of the sequence sharing identity is 50 or more contiguous polynucleotide or amino acids, e.g., 50-55, 55-60, 60-65, 65-70, 70-75, 75-80, 80-85, 85-90, 90-95, 95-100, 100-110, etc. contiguous polynucleotide or amino acids.

The terms "homologous" or "homology" mean that two or more referenced entities share at least partial identity over a given region or portion. "Areas, regions or domains" of homology or identity mean that a portion of two or more referenced entities share homology or are the same. Thus, where two sequences are identical over one or more sequence regions they share identity in these regions. "Substantial homology" means that a molecule is structurally or functionally conserved such that it has or is predicted to have at least partial structure or function of one or more of the structures or functions (e.g., a biological function or activity) of the reference molecule, or relevant/corresponding region or portion of the reference molecule to which it shares homology.

The extent of identity (homology) between two sequences can be ascertained using a computer program and/or mathematical algorithm. Such algorithms that calculate percent sequence identity (homology) generally account for sequence gaps and mismatches over the comparison region or area. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch-2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

Polynucleotides include additions and insertions, for example, one or more heterologous domains. An addition (e.g., heterologous domain) can be a covalent or non-covalent attachment of any type of molecule to a composition. Typically additions and insertions (e.g., a heterologous domain) confer a complementary or a distinct function or activity.

Additions and insertions include chimeric and fusion sequences, which is a polynucleotide or protein sequence having one or more molecules not normally present in a reference native (wild type) sequence covalently attached to the sequence. The terms "fusion" or "chimeric" and grammatical variations thereof, when used in reference to a molecule means that a portions or part of the molecule contains a different entity distinct (heterologous) from the molecule—as they do not typically exist together in nature. That is, for example, one portion of the fusion or chimera, includes or consists of a portion that does not exist together in nature, and is structurally distinct.

The term "vector" refers to a plasmid, virus (e.g., AAV vector), or other vehicle that can be manipulated by insertion or incorporation of a polynucleotide. Such vectors can be used for genetic manipulation (i.e., "cloning vectors"), to introduce/transfer polynucleotides into cells, and to transcribe or translate the inserted polynucleotide in cells. A vector nucleic acid sequence generally contains at least an origin of replication for propagation in a cell and optionally additional elements, such as a heterologous polynucleotide sequence, expression control element (e.g., a promoter, enhancer, intron, ITR(s), selectable marker (e.g., antibiotic resistance), poly-Adenine (also referred to as poly-adenylation) sequence.

A viral vector is derived from or based upon one or more nucleic acid elements that comprise a viral genome. Particular viral vectors include lenti- and parvo-virus vectors, such as adeno-associated virus (AAV) vectors.

As used herein, the term "recombinant," as a modifier of viral vector, such as recombinant lenti- or parvo-virus (e.g., AAV) vectors, as well as a modifier of sequences such as recombinant polynucleotides and polypeptides, means that the compositions (e.g., AAV or sequences) have been manipulated (i.e., engineered) in a fashion that generally does not occur in nature. A particular example of a recombinant vector, such as an AAV vector would be where a polynucleotide that is not normally present in the wild-type viral (e.g., AAV) genome is inserted within the viral genome. For example, an example of a recombinant polynucleotide would be where a heterologous polynucleotide (e.g., gene) encoding a protein is cloned into a vector, with or without 5', 3' and/or intron regions that the gene is normally associated within the viral (e.g., AAV) genome. Although the term "recombinant" is not always used herein in reference to vectors, such as viral and AAV vectors, as well as sequences such as polynucleotides and polypeptides, recombinant forms of viral, AAV, and sequences including polynucleotides and polypeptides, are expressly included in spite of any such omission.

A recombinant viral "vector" or "AAV vector" is derived from the wild type genome of a virus, such as AAV by using molecular methods to remove the wild type genome from the virus (e.g., AAV), and replacing with a non-native nucleic acid, such as a heterologous polynucleotide sequence (e.g., modified nucleic acid sequence encoding human FIX, such as FIX with a reduced number of CpG dinucleotides). Typically, for AAV one or both inverted terminal repeat (ITR) sequences of AAV genome are retained in the AAV vector. A "recombinant" viral vector (e.g., AAV) is distinguished from a viral (e.g., AAV) genome, since all or a part of the viral genome has been replaced with a non-native sequence with respect to the viral (e.g., AAV) genomic nucleic acid such as a heterologous polynucleotide sequence (e.g., modified nucleic acid sequence encoding human FIX, such as FIX with a reduced number of CpG dinucleotides). Incorporation of a non-native sequence (e.g., modified nucleic acid sequence encoding human FIX, such as FIX with a reduced number of CpG dinucleotides) therefore defines the viral vector (e.g., AAV) as a "recombinant" vector, which in the case of AAV can be referred to as a "rAAV vector."

A recombinant vector (e.g., lenti-, parvo-, AAV) sequence can be packaged—referred to herein as a "particle" for subsequent infection (transduction) of a cell, ex vivo, in vitro or in vivo. Where a recombinant vector sequence is encapsidated or packaged into an AAV particle, the particle can also be referred to as a "rAAV." Such particles include proteins that encapsidate or package the vector genome. Particular examples include viral envelope proteins, and in the case of AAV, capsid proteins.

For a recombinant plasmid, a vector "genome" refers to the portion of the recombinant plasmid sequence that is ultimately packaged or encapsidated to form a viral (e.g., AAV) particle. In cases where recombinant plasmids are used to construct or manufacture recombinant vectors, the vector genome does not include the portion of the "plasmid" that does not correspond to the vector genome sequence of the recombinant plasmid. This non vector genome portion of the recombinant plasmid is referred to as the "plasmid backbone," which is important for cloning and amplification of the plasmid, a process that is needed for propagation and recombinant virus production, but is not itself packaged or encapsidated into virus (e.g., AAV) particles.

Thus, a vector "genome" refers to the portion of the vector plasmid that is packaged or encapsidated by virus (e.g., AAV), and which contains a heterologous polynucleotide sequence. The non vector genome portion of the recombinant plasmid is the "plasmid backbone" that is important for cloning and amplification of the plasmid, e.g., has a selectable marker, such as Kanamycin, but is not itself packaged or encapsidated by virus (e.g., AAV).

Amounts of rAAV that encapsidate/package vector genomes can be determined, for example, by quantitative PCR. This assay measures the physical number of packaged vector genomes by real-time quantitative polymerase chain reaction and can be performed at various stages of the manufacturing/purification process, for example, on bulk AAV vector and final product.

Recombinant vector sequences are manipulated by insertion or incorporation of a polynucleotide. As disclosed herein, a vector plasmid generally contains at least an origin of replication for propagation in a cell and one or more expression control elements.

Vector sequences including AAV vectors can include one or more "expression control elements." Typically, expression control elements are nucleic acid sequence(s) that influence expression of an operably linked polynucleotide. Control elements, including expression control elements as set forth herein such as promoters and enhancers, present within a vector are included to facilitate proper heterologous polynucleotide transcription and if appropriate translation (e.g., a promoter, enhancer, splicing signal for introns, maintenance of the correct reading frame of the gene to permit in-frame translation of mRNA and, stop codons etc.). Such elements typically act in cis, referred to as a "cis acting" element, but may also act in trans.

Expression control can be effected at the level of transcription, translation, splicing, message stability, etc. Typically, an expression control element that modulates transcription is juxtaposed near the 5' end (i.e., "upstream") of a transcribed polynucleotide (e.g., of a modified nucleic acid encoding Factor IX, such as FIX with a reduced number of CpG dinucleotides). Expression control elements can also be located at the 3' end (i.e., "downstream") of the transcribed sequence or within the transcript (e.g., in an intron). Expression control elements can be located adjacent to or at a distance away from the transcribed sequence (e.g., 1-10, 10-25, 25-50, 50-100, 100 to 500, or more nucleotides from the polynucleotide), even at considerable distances. Nevertheless, owing to the polynucleotide length limitations of certain vectors, such as AAV vectors, such expression control elements will typically be within 1 to 1000 nucleotides from the transcribed polynucleotide.

Functionally, expression of operably linked heterologous polynucleotide is at least in part controllable by the element (e.g., promoter) such that the element modulates transcription of the polynucleotide and, as appropriate, translation of the transcript. A specific example of an expression control element is a promoter, which is usually located 5' of the transcribed sequence. Another example of an expression control element is an enhancer, which can be located 5', 3' of the transcribed sequence, or within the transcribed sequence.

A "promoter" as used herein can refer to a nucleic acid (e.g., DNA) sequence that is located adjacent to a polynucleotide sequence that encodes a recombinant product. A promoter is typically operatively linked to an adjacent sequence, e.g., heterologous polynucleotide (e.g., modified nucleic acid encoding Factor IX). A promoter typically increases an amount expressed from a heterologous polynucleotide as compared to an amount expressed when no promoter exists.

An "enhancer" as used herein can refer to a sequence that is located adjacent to the heterologous polynucleotide. Enhancer elements are typically located upstream of a promoter element but also function and can be located downstream of or within a DNA sequence (e.g., a heterologous polynucleotide). Hence, an enhancer element can be located 100 base pairs, 200 base pairs, or 300 or more base pairs upstream or downstream of a heterologous polynucleotide. Enhancer elements typically increase expressed of a heterologous polynucleotide above increased expression afforded by a promoter element.

Expression control elements (e.g., promoters) include those active in a particular tissue or cell type, referred to herein as a "tissue-specific expression control elements/ promoters." Tissue-specific expression control elements are typically active in specific cell or tissue (e.g., liver, brain, central nervous system, spinal cord, eye, retina, bone, muscle, lung, pancreas, heart, kidney cell, etc.). Expression control elements are typically active in these cells, tissues or organs because they are recognized by transcriptional activator proteins, or other regulators of transcription, that are unique to a specific cell, tissue or organ type.

Examples of promoters active in skeletal muscle include promoters from genes encoding skeletal α-actin, myosin light chain 2A, dystrophin, muscle creatine kinase, as well as synthetic muscle promoters with activities higher than naturally-occurring promoters (see, e.g., Li, et al., *Nat. Biotech.* 17:241-245 (1999)). Examples of promoters that are tissue-specific for liver are the human alpha 1-antitrypsin (hAAT) promoter; albumin, Miyatake, et al. *J. Virol.*, 71:5124-32 (1997); hepatitis B virus core promoter, Sandig, et al., *Gene Ther.* 3:1002-9 (1996); alpha-fetoprotein (AFP), Arbuthnot, et al., *Hum. Gene. Ther.*, 7:1503-14 (1996)], bone (osteocalcin, Stein, et al., *Mol. Biol. Rep.*, 24:185-96 (1997); bone sialoprotein, Chen, et al., *J. Bone Miner. Res.* 11:654-64 (1996)), lymphocytes (CD2, Hansal, et al., *J. Immunol.*, 161:1063-8 (1998); immunoglobulin heavy chain; T cell receptor a chain), neuronal (neuron-specific enolase (NSE) promoter, Andersen, et al., *Cell. Mol. Neurobiol.*, 13:503-15 (1993); neurofilament light-chain gene, Piccioli, et al., *Proc. Natl. Acad. Sci. USA*, 88:5611-5 (1991); the neuron-specific vgf gene, Piccioli, et al., *Neuron*, 15:373-84 (1995); among others. An example of an enhancer active in liver is apolipoprotein E (apoE) HCR-1 and HCR-2 (Allan et al., *J. Biol. Chem.*, 272:29113-19 (1997)).

Expression control elements also include ubiquitous or promiscuous promoters/enhancers which are capable of driving expression of a polynucleotide in many different cell types. Such elements include, but are not limited to the cytomegalovirus (CMV) immediate early promoter/enhancer sequences, the Rous sarcoma virus (RSV) promoter/ enhancer sequences and the other viral promoters/enhancers active in a variety of mammalian cell types, or synthetic elements that are not present in nature (see, e.g., Boshart et al, *Cell*, 41:521-530 (1985)), the SV40 promoter, the dihydrofolate reductase promoter, the cytoplasmic β-actin promoter and the phosphoglycerol kinase (PGK) promoter.

Expression control elements also can confer expression in a manner that is regulatable, that is, a signal or stimuli increases or decreases expression of the operably linked heterologous polynucleotide. A regulatable element that increases expression of the operably linked polynucleotide in response to a signal or stimuli is also referred to as an "inducible element" (i.e., is induced by a signal). Particular examples include, but are not limited to, a hormone (e.g., steroid) inducible promoter. A regulatable element that decreases expression of the operably linked polynucleotide in response to a signal or stimuli is referred to as a "repressible element" (i.e., the signal decreases expression such that when the signal, is removed or absent, expression is increased). Typically, the amount of increase or decrease conferred by such elements is proportional to the amount of signal or stimuli present; the greater the amount of signal or stimuli, the greater the increase or decrease in expression. Particular non-limiting examples include zinc-inducible sheep metallothionine (MT) promoter; the steroid hormone-inducible mouse mammary tumor virus (MMTV) promoter; the T7 polymerase promoter system (WO 98/10088); the tetracycline-repressible system (Gossen, et al., *Proc. Natl. Acad. Sci. USA,* 89:5547-5551 (1992)); the tetracycline-inducible system (Gossen, et al., *Science.* 268:1766-1769 (1995); see also Harvey, et al., *Curr. Opin. Chem. Biol.* 2:512-518 (1998)); the RU486-inducible system (Wang, et al., *Nat. Biotech.* 15:239-243 (1997) and Wang, et al., *Gene Ther.* 4:432-441 (1997)]; and the rapamycin-inducible system (Magari, et al., *J. Clin. Invest.* 100:2865-2872 (1997); Rivera, et al., *Nat. Medicine.* 2:1028-1032 (1996)). Other regulatable control elements which may be useful in this context are those which are regulated by a specific physiological state, e.g., temperature, acute phase, development.

Expression control elements also include the native elements(s) for the heterologous polynucleotide. A native control element (e.g., promoter) may be used when it is desired that expression of the heterologous polynucleotide should mimic the native expression. The native element may be used when expression of the heterologous polynucleotide is to be regulated temporally or developmentally, or in a tissue-specific manner, or in response to specific transcriptional stimuli. Other native expression control elements, such as introns, polyadenylation sites or Kozak consensus sequences may also be used.

As used herein, the term "operable linkage" or "operably linked" refers to a physical or functional juxtaposition of the components so described as to permit them to function in their intended manner. In the example of an expression control element in operable linkage with a nucleic acid, the relationship is such that the control element modulates expression of the nucleic acid. More specifically, for example, two DNA sequences operably linked means that the two DNAs are arranged (cis or trans) in such a relationship that at least one of the DNA sequences is able to exert a physiological effect upon the other sequence.

Accordingly, modified nucleic acid sequences encoding human FIX protein, and vectors and plasmids, including viral vectors such as lenti- and parvovirus vectors, including AAV vectors, as well as compositions thereof, can include additional nucleic acid elements. These elements include, without limitation one or more copies of an AAV ITR sequence, an expression control (e.g., promoter/enhancer) element, a transcription termination signal or stop codon, 5' or 3' untranslated regions (e.g., polyadenylation (polyA) sequences) which flank a polynucleotide sequence, or an intron, such as all or a portion of intron I of genomic human Factor IX (SEQ ID NO: 13).

Nucleic acid elements further include, for example, filler or stuffer polynucleotide sequences, for example to improve packaging and reduce the presence of contaminating nucleic acid, e.g., to reduce packaging of the plasmid backbone. As disclosed herein, AAV vectors typically accept inserts of DNA having a defined size range which is generally about 4 kb to about 5.2 kb, or slightly more. Thus, for shorter sequences, inclusion of a stuffer or filler in the insert fragment in order to adjust the length to near or at the normal size of the virus genomic sequence acceptable for AAV vector packaging into virus particle. In various embodiments, a filler/stuffer nucleic acid sequence is an untranslated (non-protein encoding) segment of nucleic acid. In particular embodiments of an AAV vector, a heterologous polynucleotide sequence has a length less than 4.7 kb and the filler or stuffer polynucleotide sequence has a length that when combined (e.g., inserted into a vector) with the heterologous polynucleotide sequence has a total length between about 3.0-5.5 kb, or between about 4.0-5.0 Kb, or between about 4.3-4.8 Kb.

An intron can also function as a filler or stuffer polynucleotide sequence in order to achieve a length for AAV vector packaging into a virus particle. Introns and intron fragments (e.g. portion of intron I of FIX) that function as a filler or stuffer polynucleotide sequence also can enhance expression. Inclusion of an intron element may enhance expression compared with expression in the absence of the intron element (Kurachi et al., 1995, supra).

The use of introns is not limited to the inclusion of Factor IX intron I sequences, but also include other introns, which introns may be associated with the same gene (e.g., where the nucleic acid encodes Factor IX, the intron is derived from an intron present in Factor IX genomic sequence) or associated with a completely different gene or other DNA sequence. Accordingly, other untranslated (non-protein encoding) regions of nucleic acid, such as introns found in genomic sequences from cognate (related) genes (the heterologous polynucleotide sequence encodes all or a portion of same protein encoded by the genomic sequence) and non-cognate (unrelated) genes (the heterologous polynucleotide sequence encodes a protein that is distinct from the protein encoded by the genomic sequence) can also function as filler or stuffer polynucleotide sequences in accordance with the invention.

A "portion of intron I" as used herein, is meant region of intron I having a nucleotide length of from about 0.1 kb to about 1.7 kb, which region enhances expression of Factor IX, typically by about 1.5-fold or more on a plasmid or viral vector template when compared with expression of FIX in the absence of a portion of intron I. A more specific portion is a 1.3 kb portion of intron I. A non-limiting example of a sequence of Factor IX intron I is intron A, a chimera composed of the 5' part and the 3' part of FIX first intron as set forth in SEQ ID NO: 13.

Expression control elements, ITRs, poly A sequences, filler or stuffer polynucleotide sequences can vary in length. In particular aspects, an expression control element, ITR, polyA, or a filler or stuffer polynucleotide sequence is a sequence between about 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, or 2,000-2,500 nucleotides in length.

According to one non-limiting embodiment, an AAV vector comprises an AAV capsid comprising the 4-1 capsid variant VP1 protein (SEQ ID NO:4) and a genome for expressing a heterologous gene in a transduced mammalian cell.

The capsid of this vector may further comprise the VP2 and VP3 proteins from the 4-1 capsid variant (SEQ ID NO:27 and SEQ ID NO:3, respectively). According to certain non-limiting embodiments, the VP1 protein and VP2 proteins are in a stoichiometric ratio of approximately 1:1

(or some other ratio), and the VP3 protein is in a ratio to either VP1 or VP2, or both VP1 and VP2, in an approximate ratio of about 5:1, 6:1, 7:1, 8:1, 9:1, 10:1, 11:1, 12:1, 13:1, 14:1, 15:1, 16:1, 17:1, 18:1, 19:1, 20:1, or some other ratio.

In some embodiments, a genome of an AAV vector, including without limitation one having a capsid comprising the 4-1 capsid variant proteins (VP1, VP2, VP3), comprises a heterologous nucleic acid sequence encoding human Factor IX (FIX) protein. In some embodiments, FIX protein is wild type, and in other embodiments FIX protein contains a substitution mutation or other mutation that alters the protein's activity. In some embodiments, the mutation increases FIX catalytic activity and/or activity of the protein as a procoagulant. In some embodiments, FIX protein is the Padua FIX protein, with an Arg to Ala substitution at the amino acid corresponding to position 338 of FIX protein. According to some embodiments, a gene encoding human FIX (including FIX Padua) is codon optimized, for example, by reducing or even eliminating CpG dinucleotides. Other types of codon optimization are possible as well.

In some embodiments, a genome of the AAV vector further comprises inverted terminal repeats (ITRs) from AAV2 positioned at the left and right ends (i.e., 5' and 3' termini, respectively) of the genome. In some embodiments, a left ITR comprises or consists of nucleotides 1-141 from SEQ ID NO: 12 (disclosed herein as SEQ ID NO:13), and a right ITR comprises or consists of nucleotides 4097-4204 from SEQ ID NO: 12 (disclosed herein as SEQ ID NO:20). Each ITR may be separated from other elements in the vector genome by a nucleic acid sequence of variable length.

In other embodiments, a genome of the AAV vector further comprises an expression control element, including a promoter, and optionally an enhancer. In some embodiments, an AAV vector genome comprises both a promoter and an enhancer, which may be constitutive, inducible, or tissue specific. In some embodiments, a promoter, or an enhancer, or both are tissue specific. According to an exemplary embodiment, both enhancer and promoter are preferentially active in hepatocytes, compared to certain other cell types. According to one embodiment, an enhancer is all or a portion of the human ApoE HCR-1 enhancer, and a promoter is all or a portion of the human alpha-1 antitrypsin (AAT) promoter. In some embodiments, an AAV vector genome includes a human ApoE HCR-1 enhancer comprising or consisting of nucleotides 152-472 from SEQ ID NO: 12 (disclosed herein as SEQ ID NO:14), and includes a human AAT promoter comprising or consisting of nucleotides 482-878 from SEQ ID NO: 12 (disclosed herein as SEQ ID NO:15). In some embodiments, an ApoE HCR-1 enhancer is positioned 5' of an AAT promoter, and the sequences may be contiguous, or separated by another nucleotide sequence. According to some embodiments, an enhancer and promoter are positioned 5' of a nucleic acid sequence coding Factor IX, and may be contiguously joined to the first exon of a Factor IX gene, or may be separated therefrom by 5' untranslated sequence (UTR) from a human Factor IX gene, or some other sequence serving as a spacer. In an exemplary non-limiting embodiment, a 5' UTR sequence comprises or consists of nucleotides 879-907 from SEQ ID NO: 12.

In some embodiments, gene encoding FIX, including naturally occurring FIX Padua, includes one or more introns present in a human Factor IX genomic sequence. In other embodiments, all introns may be excluded, an example of which is disclosed as the nucleic acid sequence of SEQ ID NO: 10 and referred to herein as the coding sequence for "FIX39." If present, an intron can behave as a stuffer or filler sequence as described herein. The entire gene can be codon-optimized to deplete or eliminate CpG dinucleotides.

In a particular non-limiting embodiment, a gene encoding human Factor IX used in an AAV vector comprises or consists of nucleotides 908-3731 from SEQ ID NO:12, which encodes the FIX Padua and is codon-optimized to eliminate CpG dinucleotides. This sequence includes an exon 1 (nucleotides 908-995 from SEQ ID NO: 12), a first intron (sometimes known as intron I; nucleotides 996-2433 from SEQ ID NO: 12), and exons 2-8 (nucleotides 2434-3731 from SEQ ID NO: 12).

In certain embodiments, a gene encoding Factor IX may be followed at its 3' end by 3' UTR sequence from a human Factor IX gene (such as without limitation nucleotides 3732-3779 from SEQ ID NO: 12 and/or by a polyadenylate (polyA) sequence from a Factor IX gene, or another gene. In one non-limiting example, the polyA sequence can be from the bovine growth hormone (bGH) gene, and can comprise or consist of nucleotides 3820-4047 from SEQ ID NO:12. In some embodiments, a 3'UTR can be variably spaced from the polyA sequence by an intervening sequence of nucleotides.

In some embodiments, the elements described above can be combined into one AAV vector genome. According to one non-limiting example, an AAV vector can have a genome comprising, in 5' to 3' order, a left AAV ITR, the ApoE HCR-1 enhancer (or portion thereof), the hAAT promoter (or portion thereof), a portion of human Factor IX 5'UTR, nucleic acid encoding human Factor IX Padua (including optionally one or more introns, such as intron I), a portion of human Factor IX 3' UTR, a polyA sequence from bGH (or portion thereof), and at the right an AAV2 ITR. In some of these embodiments, a left AAV2 ITR has the nucleic acid sequence of SEQ ID NO:13; an ApoE HCR-1 enhancer has the nucleic acid sequence of SEQ ID NO:14; a hAAT promoter has the nucleic acid sequence of SEQ ID NO: 15; a 5' UTR has the nucleic acid sequence of SEQ ID NO: 16; a gene encoding FIX Padua (including intron I) encodes the FIX protein encoded by nucleic acid sequence of SEQ ID NO:10; the 3' UTR has a nucleic acid sequence of SEQ ID NO: 18; a polyA region has the nucleic acid sequence of SEQ ID NO:19; and a right AAV2 ITR has a nucleic acid sequence of SEQ ID NO:20.

According to certain embodiments, a genome of an AAV vector comprises or consists of nucleotides 1-4204 from SEQ ID NO:12, or a sequence that is at least 95%, 96%, 97%, 98%, or 99% identical thereto. In some of these embodiments, a capsid comprises the 4-1 VP1 capsid protein variant (SEQ ID NO:4) and the corresponding VP2 and VP2 capsid proteins. In a particular non-limiting embodiment of an AAV vector, referred to herein as "AAV-FIX39-Padua," the vector includes a capsid formed from 4-1 capsid variant proteins (VP1, VP2, VP3), and a single-stranded genome comprising a nucleic acid sequence corresponding to nucleotides 1-4204 from SEQ ID NO:12.

AAV "empty capsids" as used herein do not contain a vector genome (hence, the term "empty"), in contrast to "genome containing capsids" which contain an AAV vector genome. Empty capsids are virus-like particles in that they react with one or more antibodies that reacts with the intact (genome containing AAV vector) virus.

Empty capsids can be included in AAV vector preparations. If desired, AAV empty capsids can be added to AAV vector preparations, or administered separately to a subject in accordance with the methods herein.

Although not wishing to be bound by theory, AAV empty capsids are believed to bind to or react with antibodies against the AAV vectors, thereby functioning as a decoy to reduce inactivation of the AAV vector. Such a decoy acts to absorb antibodies directed against the AAV vector thereby increasing or improving AAV vector transgene transduction of cells (introduction of the transgene), and in turn increased cellular expression of the transcript and/or encoded protein.

Empty capsids can be generated and purified at a quality and their quantities determined. For example, empty capsid titer can be measured by spectrophotometry by optical density at 280 nm wavelength (based on Sommer et al., Mol. Ther. 2003 January; 7(1):122-8).

Empty-AAV or empty capsids are sometimes naturally found in AAV vector preparations. Such natural mixtures can be used in accordance with the invention, or if desired be manipulated to increase or decrease the amount of empty capsid and/or vector. For example, the amount of empty capsid can optionally be adjusted to an amount that would be expected to reduce the inhibitory effect of antibodies that react with an AAV vector that is intended to be used for vector-mediated gene transduction in the subject. The use of empty capsids is described in US Publication 2014/0336245.

In various embodiments, AAV empty capsids are formulated with AAV vectors and/or administered to a subject. In particular aspects, AAV empty capsids are formulated with less than or an equal amount of vector (e.g., about 1.5 to 100-fold AAV vectors to AAV empty capsids, or about a 1:1 ratio of AAV vectors to AAV empty capsids). In other particular aspects, AAV vectors are formulated with an excess of AAV empty capsids (e.g., greater than 1 fold AAV empty capsids to AAV vectors, e.g., 1.5 to 100-fold AAV empty capsids to AAV vectors). Optionally, subjects with low to negative titer AAV NAb can receive lower amounts of empty capsids (1 to 10 fold AAV empty capsids to AAV vectors, 2-6 fold AAV empty capsids to AAV vectors, or about 4-5 fold AAV empty capsids to AAV vectors).

According to certain embodiments, pharmaceutical compositions comprising AAV vectors include those comprising the 4-1 capsid variant proteins (VP1, VP2 and VP3), comprise an excess of empty capsids greater than the concentration of AAV vectors (i.e., those containing a vector genome) in the composition. A ratio of empty capsids to AAV vectors can be about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10 to 1, or some other ratio.

In some embodiments, empty capsids comprise the same VP1, VP2, and VP3 capsid proteins that are present in the AAV vectors. In other embodiments, empty capsids comprise VP1, VP2 and VP3 proteins having a different amino acid sequence than those found in the AAV vectors. Typically, although not necessarily, if the capsid proteins of the empty capsids and capsids of the AAV vectors are not identical in sequence, they will be of the same serotype.

According to some embodiments, a composition comprises an AAV vector described herein as AAV-FIX39-Padua (or one having the same capsid and a genome sequence at least 95%, 96%, 97%, 98% or 99% identical thereto) and optionally an excess of empty capsids comprising the same capsid proteins, wherein the ratio of empty capsids to the AAV vector is about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10 to 1, or some other ratio. In some embodiments, the ratio in the composition of AAV-FIX39-Padua to empty capsids is about 1:5. In other embodiments, compositions comprising AAV-FIX39-Padua and empty capsids are administered to a human subject having hemophilia B, including severe, moderate, or mild hemophilia B.

A "selectable marker gene" refers to a gene that when expressed confers a selectable phenotype, such as antibiotic resistance (e.g., kanamycin), on a transduced cell. A "reporter" gene is one that provides a detectable signal. A non-limiting example of a reporter gene is the luciferase gene.

Nucleic acid, polynucleotides, expression vectors (e.g., vector genomes), plasmids, including modified forms can be made using various standard cloning, recombinant DNA technology, via cell expression or in vitro translation and chemical synthesis techniques. Purity of polynucleotides can be determined through sequencing, gel electrophoresis and the like. For example, nucleic acids can be isolated using hybridization or computer-based database screening techniques. Such techniques include, but are not limited to: (1) hybridization of genomic DNA or cDNA libraries with probes to detect homologous nucleotide sequences; (2) antibody screening to detect polypeptides having shared structural features, for example, using an expression library; (3) polymerase chain reaction (PCR) on genomic DNA or cDNA using primers capable of annealing to a nucleic acid sequence of interest; (4) computer searches of sequence databases for related sequences; and (5) differential screening of a subtracted nucleic acid library.

The term "isolated," when used as a modifier of a composition, means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane. The term "isolated" does not exclude combinations produced by the hand of man, for example, a recombinant vector (e.g., rAAV) sequence, or virus particle that packages or encapsidates a vector genome and a pharmaceutical formulation. The term "isolated" also does not exclude alternative physical forms of the composition, such as hybrids/chimeras, multimers/oligomers, modifications (e.g., phosphorylation, glycosylation, lipidation) or derivatized forms, or forms expressed in host cells produced by the hand of man.

Methods and uses of the invention provide a means for delivering (transducing) heterologous polynucleotides (transgenes) into host cells, including dividing and/or non-dividing cells. The recombinant vector (e.g., rAAV) sequences, vector genomes, recombinant virus particles, methods, uses and pharmaceutical formulations of the invention are additionally useful in a method of delivering, administering or providing a nucleic acid, or protein to a subject in need thereof, as a method of treatment. In this manner, the nucleic acid is transcribed and the protein may be produced in vivo in a subject. The subject may benefit from or be in need of the nucleic acid or protein because the subject has a deficiency of the nucleic acid or protein, or because production of the nucleic acid or protein in the subject may impart some therapeutic effect, as a method of treatment or otherwise.

In general, recombinant lenti- or parvo-virus vector (e.g., AAV) sequences, vector genomes, recombinant virus particles, methods and uses may be used to deliver any heterologous polynucleotide (transgene) with a biological effect to treat or ameliorate one or more symptoms associated with any disorder related to insufficient or undesirable gene expression. Recombinant lenti- or parvo-virus vector (e.g., AAV) sequences, plasmids, vector genomes, recombinant virus particles, methods and uses may be used to provide therapy for various disease states.

Invention nucleic acids, vectors, recombinant vectors (e.g., rAAV), vector genomes, and recombinant virus particles, methods and uses permit the treatment of genetic diseases. In general, disease states fall into two classes: deficiency states, usually of enzymes, which are generally inherited in a recessive manner, and unbalanced states, at least sometimes involving regulatory or structural proteins, which are inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. The use of site-specific integration of nucleic acid sequences to correct defects is also possible.

Illustrative examples of disease states include, but are not limited to: blood coagulation disorders such as hemophilia A, hemophilia B, thalassemia, and anemia.

In accordance with the invention, treatment methods and uses are provided that include invention nucleic acids, vectors, recombinant vectors (e.g., rAAV), vector genomes, and recombinant virus particles. Methods and uses of the invention are broadly applicable to providing, or increasing or stimulating, gene expression or function, e.g., gene addition or replacement.

In one embodiment, a method or use of the invention includes: (a) providing a modified nucleic acid encoding Factor IX, such as FIX with a reduced number of CpG dinucleotides, such as in a vector or a vector genome, wherein the modified nucleic acid sequence is operably linked to an expression control element conferring transcription of said sequence; and (b) administering an amount of the modified nucleic acid to the mammal such that Factor IX is expressed in the mammal.

In another embodiment, a method or use of the invention includes delivering or transferring a modified nucleic acid encoding Factor IX sequence, such as FIX with a reduced number of CpG dinucleotides, into a mammal or a cell of a mammal, by administering a viral (e.g., AAV) particle or plurality of viral (e.g., AAV) particles (e.g., such as capsid variants (e.g., 4-1)) comprising a vector genome, the vector genome comprising the modified nucleic acid encoding Factor IX, such as FIX with a reduced number of CpG dinucleotides (and optionally an ITR, intron, polyA, a filler/stuffer polynucleotide sequence) to a mammal or a cell of a mammal, thereby delivering or transferring the modified nucleic acid encoding Factor IX into the mammal or cell of the mammal.

In particular aspects of invention methods and uses disclosed herein, expression of the nucleic acid provides a therapeutic benefit to the mammal (e.g., human). In a more particular aspect, expression of Factor IX provides a therapeutic benefit to the mammal (e.g., human), such as a mammal that has hemophilia B. In various further particular aspects, a filler/stuffer polynucleotide sequence is included in the vector sequence such that the combined length with the modified nucleic acid encoding Factor IX, such as FIX with a reduced number of CpG dinucleotides, has a total length of between about 3.0 Kb-5.5 Kb, or between about 4.0 Kb-5.0 Kb, or between about 4.3 Kb-4.8 kb.

Methods and uses of the invention include treatment methods, which result in any therapeutic or beneficial effect. In various invention methods and uses, further included are inhibiting, decreasing or reducing one or more adverse (e.g., physical) symptoms, disorders, illnesses, diseases or complications caused by or associated with the disease. For a bleeding disorder such as hemophilia, a therapeutic or beneficial effect includes, but is not limited to, reduced bruising, reduced blood clotting time, reduced bleeding episodes (duration, severity, frequency). For example, reduced duration, severity or frequency of joint or cerebral (brain) bleeding episodes. For a bleeding disorder such as hemophilia, a therapeutic or beneficial effect also includes, but is not limited to, reduced dosage of a supplemental clotting factor protein (e.g., Factor IX protein) or elimination of administration of a supplemental clotting factor protein (e.g., Factor IX protein).

A therapeutic or beneficial effect of treatment is therefore any objective or subjective measurable or detectable improvement or benefit provided to a particular subject. A therapeutic or beneficial effect can but need not be complete ablation of all or any particular adverse symptom, disorder, illness, or complication of a disease. Thus, a satisfactory clinical endpoint is achieved when there is an incremental improvement or a partial reduction in an adverse symptom, disorder, illness, or complication caused by or associated with a disease, or an inhibition, decrease, reduction, suppression, prevention, limit or control of worsening or progression of one or more adverse symptoms, disorders, illnesses, or complications caused by or associated with the disease, over a short or long duration (hours, days, weeks, months, etc.).

Compositions, such as nucleic acids, vectors, recombinant vectors (e.g., rAAV), vector genomes, and recombinant virus particles including vector genomes, and methods and uses of the invention, can be administered in a sufficient or effective amount to a subject in need thereof. An "effective amount" or "sufficient amount" refers to an amount that provides, in single or multiple doses, alone or in combination, with one or more other compositions (therapeutic agents such as a drug), treatments, protocols, or therapeutic regimens agents, a detectable response of any duration of time (long or short term), an expected or desired outcome in or a benefit to a subject of any measurable or detectable degree or for any duration of time (e.g., for minutes, hours, days, months, years, or cured).

One skilled in the art can determine whether administration of a single rAAV/vector dose is sufficient or whether are to administer multiple doses of rAAV/vector. For example, if FIX levels decreases below a pre-determined level (e.g., less than the minimum that provides a therapeutic benefit), one skilled in the art can determine if appropriate to administer additional doses of rAAV/vector.

The dose to achieve a therapeutic effect, e.g., the dose in vector genomes/per kilogram of body weight (vg/kg), will vary based on several factors including, but not limited to: route of administration, the level of heterologous polynucleotide expression required to achieve a therapeutic effect, the specific disease treated, any host immune response to the viral vector, a host immune response to the heterologous polynucleotide or expression product (protein), and the stability of the protein expressed. One skilled in the art can determine a rAAV/vector genome dose range to treat a patient having a particular disease or disorder based on the aforementioned factors, as well as other factors. Generally, doses will range from at least $1 \times 10^8$, or more, for example, $1 \times 10^9$, $1 \times 10^{10}$, $1 \times 10^{11}$ $1 \times 10^{12}$, $1 \times 10^{13}$ or $1 \times 10^{14}$, or more, vector genomes per kilogram (vg/kg) of the weight of the subject, to achieve a therapeutic effect.

In some embodiments, a therapeutically effective dose of an AAV vector, including, for example, AAV-FIX39-Padua, or one having the same capsid and a genome sequence at least 95%, 96%, 97%, 98% or 99% identical thereto, is one that is sufficient, when administered to a subject, for example, a human, with hemophilia B or other deficiency of Factor IX activity, to convert severe hemophilia B to moderate or mild hemophilia B, or even to result in an apparently disease-free state. In other embodiments, a therapeutically effective dose of an AAV vector is one that is sufficient to allow a human subject with hemophilia B to forego Factor IX replacement therapy entirely, or reduce the frequency with which replacement FIX is administered to maintain adequate hemostasis. As understood by those of skill in the art, factor replacement therapy is the current standard of care for hemophilia B, but requires frequent injections of recombinantly produced human Factor IX to compensate for the patient's inability to produce sufficient levels of functional clotting factor.

It is generally accepted that severe hemophilia B is characterized by frequent bleeding (for example, at least once or twice per week), often spontaneously (without preceding trauma), into a subject's muscles or joints. Less than 1% of FIX activity found in healthy humans is associated with severe hemophilia B. It is generally accepted that human subjects with moderate hemophilia B bleed less frequently than those with severe hemophilia B, for example, about once per month, but will bleed for a longer time than normal after surgery, trauma, or dental work. It is generally accepted that human subjects with moderate disease do not often bleed spontaneously. FIX activity 1%-5% of normal is associated with moderate hemophilia B. Generally, human subjects with mild hemophilia B bleed excessively, if at all, only as a result of surgery or major trauma. Generally, mild hemophilia is associated with 6%-40% of normal FIX activity. Generally, individuals who are considered healthy, having no symptoms of hemophilia B, have a range of about 50% to 150% of normal FIX activity. Additional information can be found in Fijnvandraat, et al., Diagnosis and management of hemophilia, Br. Med. J., 344:36-40 (2012).

Factor IX activity can be measured in a variety of ways known to those of skill in the art. For example, one exemplary non-limiting assay is the one-stage activated partial thromboplastin time (APTT) assay to determine FIX clotting activity in a plasma sample obtained from a subject. FIX activity is frequently expressed in international units (IU), where 1 IU is defined as the FIX clotting activity present in 1 ml of pooled plasma from normal donors. Using this convention, severe hemophilia B is associated with less than 0.01 IU/ml FIX levels, moderate disease is associated with 0.02-0.05 IU/ml FIX levels, mild disease is associated with 0.06-0.40 IU/ml FIX levels, and being disease-free is associated with 0.50-1.50 IU/ml FIX levels.

As will be appreciated by one of skill in the art, a Factor IX variant, such as naturally occurring FIX Padua variant, that has higher catalytic activity compared to wild type human FIX, can produce a given level of FIX activity (e.g., 1 IU/ml) at a lower concentration of active protein compared to "non-Padua" FIX.

In certain embodiments, a therapeutically effective dose of an AAV vector, including, for example, AAV-FIX39-Padua, or one having the same capsid and a genome sequence at least 95%, 96%, 97%, 98% or 99% identical thereto, is one that is sufficient, when administered to a subject, for example, a human, with severe, moderate or mild hemophilia B, to achieve plasma FIX activity that is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% 40%, 41%, 42%, 43%, 44%, 45%, 46%, 47%, 48%, 49%, or 50%, or more of normal FIX activity. In other embodiments, a therapeutically effective dose is one that achieves 1% or greater FIX activity in a subject otherwise lacking such activity, for example, from 1.5-10%, 10-15%, 15-20%, 20-25%, 25-30% or greater FIX activity in a subject.

With respect to treating a subject with hemophilia B, a therapeutically effective dose of an AAV vector including, for example, AAV-FIX39-Padua, or one having the same capsid and a genome sequence at least 98% or 99% identical thereto, may be at least $1 \times 10^{10}$ vector genomes (vg) per kilogram (vg/kg) of the weight of the subject, or between about $1 \times 10^{10}$ to $1 \times 10^{11}$ vg/kg of the weight of the subject, or between about $1 \times 10^{11}$ to $1 \times 10^{11}$ vg/kg (e.g., about $1 \times 10^{11}$ to $2 \times 10^{11}$ vg/kg or about $2 \times 10^{11}$ to $3 \times 10^{11}$ vg/kg or about $3 \times 10^{11}$ to $4 \times 10^{11}$ vg/kg or about $4 \times 10^{11}$ to $5 \times 10^{11}$ vg/kg or about $5 \times 1^{01}$ to $6 \times 10^{11}$ vg/kg or about $6 \times 10^{11}$ to $7 \times 10^{11}$ vg/kg or about $7 \times 10^{11}$ to $8 \times 10^{11}$ vg/kg or about $8 \times 10^{11}$ to $9 \times 10^{11}$ vg/kg or about $9 \times 10^{11}$ to $1 \times 10^{11}$ vg/kg) of the weight of the subject, or between about $1 \times 10^{12}$ to $1 \times 10^{13}$ vg/kg of the weight of the subject, to achieve a desired therapeutic effect. Additional doses can be in a range of about $5 \times 10^{10}$ to $1 \times 10^{10}$ vector genomes (vg) per kilogram (vg/kg) of the weight of the subject, or in a range of about $1 \times 10^{10}$ to $5 \times 10^{11}$ vg/kg of the weight of the subject, or in a range of about $5 \times 10^{11}$ to $1 \times 10^{12}$ vg/kg of the weight of the subject, or in a range of about $1 \times 10^{12}$ to $5 \times 10^{13}$ vg/kg of the weight of the subject, to achieve a desired therapeutic effect. In other embodiments, a therapeutically effective dose of an AAV vector is about $2.0 \times 10^{11}$ vg/kg, $2.1 \times 10^{11}$ vg/kg, $2.2 \times 10^{11}$ vg/kg, $2.3 \times 10^{11}$ vg/kg, $2.4 \times 10^{11}$ vg/kg, $2.5 \times 10^{11}$ vg/kg, $2.6 \times 10^{11}$ vg/kg, $2.7 \times 10^{11}$ vg/kg, $2.8 \times 10^{11}$ vg/kg, $2.9 \times 10^{11}$ vg/kg, $3.0 \times 10^{11}$ vg/kg, $3.1 \times 10^{11}$ vg/kg, $3.2 \times 10^{11}$ vg/kg, $3.3 \times 10^{11}$ vg/kg, $3.4 \times 10^{11}$ vg/kg, $3.5 \times 10^{11}$ vg/kg, $3.6 \times 10^{11}$ vg/kg, $3.7 \times 10^{11}$ vg/kg, $3.8 \times 10^{11}$ vg/kg, $3.9 \times 10^{11}$ vg/kg, $4.0 \times 10^{11}$ vg/kg, $4.1 \times 10^{11}$ vg/kg, $4.2 \times 10^{11}$ vg/kg, $4.3 \times 10^{11}$ vg/kg, $4.4 \times 10^{11}$ vg/kg, $4.5 \times 10^{11}$ vg/kg, $4.6 \times 10^{11}$ vg/kg, $4.7 \times 10^{11}$ vg/kg, $4.8 \times 10^{11}$ vg/kg, $4.9 \times 10^{11}$ vg/kg, $5.0 \times 10^{11}$ vg/kg, $5.1 \times 10^{11}$ vg/kg, $5.2 \times 10^{11}$ vg/kg, $5.3 \times 10^{11}$ vg/kg, $5.4 \times 10^{11}$ vg/kg, $5.5 \times 10^{11}$ vg/kg, $5.6 \times 10^{11}$ vg/kg, $5.7 \times 10^{11}$ vg/kg, $5.8 \times 10^{11}$ vg/kg, $5.9 \times 10^{11}$ vg/kg, $6.0 \times 10^{11}$ vg/kg, $6.1 \times 10^{11}$ vg/kg, $6.2 \times 10^{11}$ vg/kg, $6.3 \times 10^{11}$ vg/kg, $6.4 \times 10^{11}$ vg/kg, $6.5 \times 10^{11}$ vg/kg, $6.6 \times 10^{11}$ vg/kg, $6.7 \times 10^{11}$ vg/kg, $6.8 \times 10^{11}$ vg/kg, $6.9 \times 10^{11}$ vg/kg, $7.0 \times 10^{11}$ vg/kg, $7.1 \times 10^{11}$ vg/kg, $7.2 \times 10^{11}$ vg/kg, $7.3 \times 10^{11}$ vg/kg, $7.4 \times 10^{11}$ vg/kg, $7.5 \times 10^{11}$ vg/kg, $7.6 \times 10^{11}$ vg/kg, $7.7 \times 10^{11}$ vg/kg, $7.8 \times 10^{11}$ vg/kg, $7.9 \times 10^{11}$ vg/kg, or $8.0 \times 10^{11}$ vg/kg, or some other dose. In any of these embodiments, an AAV vector can be AAV-FIX39-Padua, or an AAV vector having the same capsid and a genome sequence at least 95%, 96%, 97%, 98% or 99% identical thereto, which may be administered to a subject in a pharmaceutically acceptable composition alone, or with empty capsids of the same capsid type at an empty to vector ratio of about 2:1, 3:1, 4:1, 5:1, 6:1, 7:1, 8:1, 9:1, 10:1, or some other ratio.

The doses of an "effective amount" or "sufficient amount" for treatment (e.g., to ameliorate or to provide a therapeutic benefit or improvement) typically are effective to provide a response to one, multiple or all adverse symptoms, consequences or complications of the disease, one or more adverse symptoms, disorders, illnesses, pathologies, or complications, for example, caused by or associated with the disease, to a measurable extent, although decreasing, reducing, inhibiting, suppressing, limiting or controlling progression or worsening of the disease is a satisfactory outcome.

An effective amount or a sufficient amount can but need not be provided in a single administration, may require multiple administrations, and, can but need not be, administered alone or in combination with another composition (e.g., agent), treatment, protocol or therapeutic regimen. For example, the amount may be proportionally increased as indicated by the need of the subject, type, status and severity of the disease treated or side effects (if any) of treatment. In addition, an effective amount or a sufficient amount need not be effective or sufficient if given in single or multiple doses without a second composition (e.g., another drug or agent), treatment, protocol or therapeutic regimen, since additional doses, amounts or duration above and beyond such doses, or additional compositions (e.g., drugs or agents), treatments, protocols or therapeutic regimens may be included in order to be considered effective or sufficient in a given subject. Amounts considered effective also include amounts that result in a reduction of the use of another treatment, therapeutic regimen or protocol, such as administration of recombinant clotting factor protein for treatment of a clotting disorder (e.g., hemophilia A or B).

An effective amount or a sufficient amount need not be effective in each and every subject treated, nor a majority of treated subjects in a given group or population. An effective amount or a sufficient amount means effectiveness or sufficiency in a particular subject, not a group or the general population. As is typical for such methods, some subjects will exhibit a greater response, or less or no response to a given treatment method or use.

The term "ameliorate" means a detectable or measurable improvement in a subject's disease or symptom thereof, or an underlying cellular response. A detectable or measurable improvement includes a subjective or objective decrease, reduction, inhibition, suppression, limit or control in the occurrence, frequency, severity, progression, or duration of the disease, or complication caused by or associated with the disease, or an improvement in a symptom or an underlying cause or a consequence of the disease, or a reversal of the disease.

Thus, a successful treatment outcome can lead to a "therapeutic effect," or "benefit" of decreasing, reducing, inhibiting, suppressing, limiting, controlling or preventing the occurrence, frequency, severity, progression, or duration of a disease, or one or more adverse symptoms or underlying causes or consequences of the disease in a subject. Treatment methods and uses affecting one or more underlying causes of the disease or adverse symptoms are therefore considered to be beneficial. A decrease or reduction in worsening, such as stabilizing the disease, or an adverse symptom thereof, is also a successful treatment outcome.

A therapeutic benefit or improvement therefore need not be complete ablation of the disease, or any one, most or all adverse symptoms, complications, consequences or underlying causes associated with the disease. Thus, a satisfactory endpoint is achieved when there is an incremental improvement in a subject's disease, or a partial decrease, reduction, inhibition, suppression, limit, control or prevention in the occurrence, frequency, severity, progression, or duration, or inhibition or reversal of the disease (e.g., stabilizing one or more symptoms or complications), over a short or long duration of time (hours, days, weeks, months, etc.). Effectiveness of a method or use, such as a treatment that provides a potential therapeutic benefit or improvement of a disease, can be ascertained by various methods, such as blood clot formation time, etc.

According to some embodiments, a therapeutically effective dose of an AAV vector is one that is sufficient, when administered to a human subject with hemophilia B, to result in FIX activity above a certain level for a sustained period of time. In some of these embodiments, an effective dose of an AAV vector results in at least 1% normal FIX activity in human subjects with hemophilia B for a sustained period of at least 3 months, 4 months, 5 months, 6 months, 7 months, 8 months, 9 months, 10 months, 11 months, 12 months, 13 months, 14 months, 15 months, 16 months, 17 months, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, or more. In other embodiments, an effective dose of an AAV vector results in at least 5% normal FIX activity for a sustained period of at least 3, 4, 5, 6, 7, 8, 9, 10, 11, 12, 13, 14, 15, 16, or 17 months, or at least 1.5, 2, 2.5, 3, 3.5, 4, 4.5, 5, 5.5, 6, 6.5, 7, 7.5, 8, 8.5, 9, 9.5, 10 years, or more. In other embodiments, an effective dose of an AAV vector results in at least 10% normal FIX activity for a sustained period of at least 3, 4, 5, 6, 7, 8, 9, 10, 11, 12, 13, 14, 15, 16, or 17 months, or at least 1.5, 2, 2.5, 3, 3.5, 4, 4.5, 5, 5.5, 6, 6.5, 7, 7.5, 8, 8.5, 9, 9.5, 10 years, or more. In other embodiments, an effective dose of an AAV vector results in at least 15% normal FIX activity for a sustained period of at least 3, 4, 5, 6, 7, 8, 9, 10, 11, 12, 13, 14, 15, 16, or 17 months, or at least 1.5, 2, 2.5, 3, 3.5, 4, 4.5, 5, 5.5, 6, 6.5, 7, 7.5, 8, 8.5, 9, 9.5, 10 years, or more. In other embodiments, an effective dose of an AAV vector results in at least 20% normal FIX activity for a sustained period of at least 3, 4, 5, 6, 7, 8, 9, 10, 11, 12, 13, 14, 15, 16, or 17 months, or at least 1.5, 2, 2.5, 3, 3.5, 4, 4.5, 5, 5.5, 6, 6.5, 7, 7.5, 8, 8.5, 9, 9.5, 10 years, or more. In other embodiments, an effective dose of an AAV vector results in at least 25% normal FIX activity for a sustained period of at least 3, 4, 5, 6, 7, 8, 9, 10, 11, 12, 13, 14, 15, 16, or 17 months, or at least 1.5, 2, 2.5, 3, 3.5, 4, 4.5, 5, 5.5, 6, 6.5, 7, 7.5, 8, 8.5, 9, 9.5, 10 years, or more. In other embodiments, an effective dose of an AAV vector results in at least 30% normal FIX activity for a sustained period of at least 3, 4, 5, 6, 7, 8, 9, 10, 11, 12, 13, 14, 15, 16, or 17 months, or at least 1.5, 2, 2.5, 3, 3.5, 4, 4.5, 5, 5.5, 6, 6.5, 7, 7.5, 8, 8.5, 9, 9.5, 10 years, or more. In other embodiments, an effective dose of an AAV vector results in at least 35% normal FIX activity for a sustained period of at least 3, 4, 5, 6, 7, 8, 9, 10, 11, 12, 13, 14, 15, 16, or 17 months, or at least 1.5, 2, 2.5, 3, 3.5, 4, 4.5, 5, 5.5, 6, 6.5, 7, 7.5, 8, 8.5, 9, 9.5, 10 years, or more. In other embodiments, an effective dose of an AAV vector results in at least 40% normal FIX activity for a sustained period of at least 3, 4, 5, 6, 7, 8, 9, 10, 11, 12, 13, 14, 15, 16, or 17 months, or at least 1.5, 2, 2.5, 3, 3.5, 4, 4.5, 5, 5.5, 6, 6.5, 7, 7.5, 8, 8.5, 9, 9.5, 10 years, or more. In other embodiments, an effective dose of an AAV vector results in at least 45% normal FIX activity for a sustained period of at least 3, 4, 5, 6, 7, 8, 9, 10, 11, 12, 13, 14, 15, 16, or 17 months, or at least 1.5, 2, 2.5, 3, 3.5, 4, 4.5, 5, 5.5, 6, 6.5, 7, 7.5, 8, 8.5, 9, 9.5, 10 years, or more. In any of these embodiments, the AAV vector can be AAV-FIX39-Padua, or an AAV vector having the same capsid and a genome sequence at least 95%, 96%, 97%, 98% or 99% identical thereto, which may be administered to a subject in a pharmaceutically acceptable composition alone, or with empty capsids of the same capsid type at an empty to vector ratio of about 2:1, 3:1, 4:1, 5:1, 6:1, 7:1, 8:1, 9:1, 10:1, or some other ratio.

According to other embodiments, a therapeutically effective dose of an AAV vector is one that is sufficient, when administered to a human subject with severe or moderate hemophilia B, to result in FIX activity that is at least 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, or 45%, of normal for a sustained period of at least 6 months. In some embodiments, the dose of AAV-FIX39-Padua, or an AAV vector having the same capsid and a genome sequence at least 95%, 96%, 97%, 98% or 99% identical thereto, is about $5.0 \times 10^{11}$ vg/kg, which may be administered in a pharmaceutically acceptable composition alone, or with empty capsids of the same capsid type at an empty to vector ratio of about 2:1, 3:1, 4:1, 5:1, 6:1, 7:1, 8:1, 9:1, 10:1, or some other ratio.

It may be seen that in some human subjects that have received a therapeutically effective dose of an AAV vector, including for example, AAV-FIX39-Padua, or an AAV vector having the same capsid and a genome sequence at least 95%, 96%, 97%, 98% or 99% identical thereto, that FIX activity attributable to the vector declines over an extended period of time (e.g., months or years) to a level that is no longer deemed sufficient (for example, where the subject exhibits symptoms and/or FIX activity characteristic of moderate or severe hemophilia B). In such circumstances, the subject can be dosed again with the same type of AAV vector as in the initial treatment. In other embodiments, particularly if the subject has developed an immune reaction to the initial vector, the patient may be dosed with an AAV vector designed to express FIX in target cells, but having a capsid of a different or variant serotype that is less immunoreactive compared to the first AAV vector.

According to certain embodiments, a therapeutically effective dose of an AAV vector is one that is sufficient, when administered to a human subject with hemophilia B, to reduce or even eliminate the subject's need for recombinant human Factor IX replacement therapy to maintain adequate hemostasis. Thus, in some embodiments, a therapeutically effective dose of an AAV vector can reduce the frequency with which an average human subject having moderate or severe hemophilia B needs FIX replacement therapy to maintain adequate hemostasis by about 5%, 10%, 15%, 20%, 25%, 30%, 35%, 40%, 45%, 50%, 55%, 60%, 65%, 70%, 75%, 80%, 85%, 90%, 95%, or 100%. In related embodiments, a therapeutically effective dose of an AAV vector can reduce the dose of recombinant human Factor IX that an average human subject having moderate or severe hemophilia B needs to maintain adequate hemostasis by about 5%, 10%, 15%, 20%, 25%, 30%, 35%. 40%, 45%, 50%, 55%, 60%, 65%, 70%, 75%, 80%, 85%, 90%, 95%, or 100%. In any of these embodiments, the AAV vector can be AAV-FIX39-Padua, or an AAV vector having the same capsid and a genome sequence at least 95%, 96%, 97%, 98% or 99% identical thereto, which may be administered to a subject in a pharmaceutically acceptable composition alone, or with empty capsids of the same capsid type at an empty to vector ratio of about 2:1, 3:1, 4:1, 5:1, 6:1, 7:1, 8:1, 9:1, 10:1, or some other ratio.

In other embodiments, a therapeutically effective dose of an AAV vector is one that is sufficient, when administered to a human subject with severe hemophilia B, to reduce or even eliminate spontaneous bleeding into the joints. Thus, in some embodiments, a therapeutically effective dose of an AAV vector can reduce the frequency of spontaneous bleeding into the joints of a human subject with severe hemophilia B by about 5%, 10%, 15%, 20%, 25%, 30%, 35%, 40%, 45%, 50%, 55%, 60%, 65%, 70%, 75%, 80%, 85%, 90%, 95%, or 100%, compared to the average untreated human subject with severe hemophilia B. Bleeding into the joints can be detected using magnetic resonance imaging or ultrasonography of the joints, or other techniques familiar to those of skill in the art. In any of these embodiments, the AAV vector can be AAV-FIX39-Padua, or an AAV vector having the same capsid and a genome sequence at least 95%, 96%, 97%, 98% or 99% identical thereto, which may be administered to a subject in a pharmaceutically acceptable composition alone, or with empty capsids of the same capsid type at an empty to vector ratio of about 2:1, 3:1, 4:1, 5:1, 6:1, 7:1, 8:1, 9:1, 10:1, or some other ratio.

Prior efforts to develop AAV vectors to treat hemophilia have been unsuccessful, at least in part it is believed, because of a robust immune response to AAV capsid in prior clinical trials. (See, for example, Nathwani, et al., NEJM 2011; 365(25):2357-2365; and Manno, et al., *Nat Med* 2006; 12(3):342-347). A clinical trial underway has demonstrated that certain embodiments of AAV vectors herein can produce a high level of FIX activity in human subjects with severe hemophilia B, while resulting in no or minimal immune response even as much as 6 months after the AAV vectors were administered (Example 5). Thus, according to certain embodiments, a therapeutically effective dose of an AAV vector is one that when administered to a subject with severe or moderate hemophilia B results in FIX activity adequate to maintain hemostasis, while producing no or minimal immune response over a significant period of time. In certain embodiments, the immune response can be an innate immune response, a humoral immune response, or a cellular immune response, or even all three types of immune response. In some embodiments, the immune response can be against the capsid, vector genome, and/or Factor IX protein produced from transduced cells.

According to certain embodiments, a therapeutically effective dose of an AAV vector results in FIX activity adequate to maintain hemostasis in a subject with hemophilia B, while producing no or minimal humoral (i.e., antibody) immune response against the capsid, genome and/or Factor IX protein produced from transduced cells. The antibody response to a virus, or virus-like particles such as AAV vectors, can be determined by measuring antibody titer in a subject's serum or plasma using techniques familiar to those of skill in the field of immunology. Antibody titer to any component of an AAV vector, such as the capsid proteins, or a gene product encoded by the vector genome and produced in transduced cells, such as Factor IX Padua (or other FIX variant), can be measured using such techniques. Antibody titers are typically expressed as a ratio indicating the dilution before which antibody signal is no longer detectable in the particular assay being used to detect the presence of the antibody. Different dilution factors can be used, for example, 2-fold, 5-fold, 10-fold, or some other dilution factor. Any suitable assay for the presence of an antibody can be used, for example and without limitation, ELISA, FACS, or a reporter gene assay, such as described in WO 2015/006743. Use of other assays is also possible according to the knowledge of those skilled in the art. Antibody titers can be measured at different times after initial administration of an AAV vector.

In certain embodiments, a therapeutically effective dose of an AAV vector results in at least 1%, 5%, 10%, 15%, 20%, 25%, 30%, 35%, 40%, or more FIX activity in subjects with hemophilia B, while producing an antibody titer against the capsid, genome and/or Factor IX protein (such as FIX Padua) produced from transduced cells that is not greater than 1:2, 1:3, 1:4, 1:5, 1:6, 1:7, 1:8, 1:9, 1:10, 1:11, 1:12, 1:13, 1:14, 1:15, 1:20, 1:30, 1:40, 1:50, 1:60, 1:70, 1:80, 1:90, 1:100, 1:200, 1:300, 1:400, 1:500, or more, when determined at 1 week, 2 weeks, 3 weeks, 4 weeks, 5 weeks, 6 weeks, 7 weeks, 8 weeks, 3 months, 4 months, 5 months, 6 months, 7 months, 8 months, 9 months, 10 months, 11 months, 12 months, 18 months, 2 years, 3 years, 4 years, 5 years, or a longer period after the subjects were administered the AAV vector. According to one exemplary non-limiting embodiment, an AAV vector results in at least 20% FIX activity in a subject with severe hemophilia B while inducing an antibody titer against the capsid and/or Factor IX produced by transduced cells that is not greater than 1:2, 1:3 or 1:4, both at 6 months after the AAV vector was administered. In any of these embodiments, the AAV vector can be AAV-FIX39-Padua, or an AAV vector having the same capsid and a genome sequence at least 95%, 96%, 97%, 98% or 99% identical thereto, which may be administered to a subject in a pharmaceutically acceptable composition alone, or with empty capsids of the same capsid type at an empty to vector ratio of about 2:1, 3:1, 4:1, 5:1, 6:1, 7:1, 8:1, 9:1, 10:1, or some other ratio.

As noted above, prior trials using AAV-mediated gene therapy for hemophilia B triggered a self-limiting immune response that prevented the therapy from being effective for a significant period of time without need for high doses of steroids to cause immunosuppression. An important factor appears to have been a cellular immune response that eliminated the liver cells that had been transduced with the AAV vectors under study. This effect was detectable from both an elevation of liver enzymes, suggesting liver damage, and the presence of capsid-specific T cells in the subjects.

In certain embodiments, a therapeutically effective dose of an AAV vector results in FIX activity adequate to maintain hemostasis in a subject with hemophilia B, while producing no or minimal cellular immune response against the capsid and/or Factor IX protein produced from transduced cells. A cellular immune response can be determined in at least two ways: assaying for T cell activity specific for capsid proteins or Factor IX, and testing for the presence of elevated liver enzyme levels that indicate damage to hepatocytes.

In some embodiments, cellular immune response is determined by assaying for T cell activity specific for capsid proteins and/or the Factor IX protein produced by the transduced liver cells. Different assays for T cell response are known in the art. In one exemplary, non-limiting embodiment, T cell response is determined by collecting peripheral blood mononuclear cells (PBMC) from a subject that was previously treated with an AAV vector for treating hemophilia B. The cells are then incubated with peptides derived from the VP1 capsid protein used in the vector, and/or the Factor IX protein, such as FIX Padua, produced by the transduced liver cells. T cells that specifically recognize the capsid protein or Factor IX protein will be stimulated to release cytokines, such as interferon gamma or another cytokine, which can then be detected and quantified using the ELISPOT assay, or another assay familiar to those of skill in the art. (See, e.g., Manno, et al., Nat Med 2006; 12(3):342-347). T cell response can be monitored before and at different times after a subject has received a dose of an AAV vector for treating hemophilia B, for example, weekly, monthly, or some other interval. Thus, according to certain embodiments, a therapeutically effective dose of an AAV vector results in FIX activity adequate to maintain hemostasis in a subject with hemophilia B (for example, FIX activity of at least 1%, 5%, 10%, 20%, 30%, or more), while causing a T cell response as measured using ELISPOT that is not greater than 10, 20, 30, 40, 50, 100, 200, 300, 400, 500, 600, 700, 800, 900, 1000, 1500, 2000, or more, spot-forming units per 1 million PBMCs assayed when measured weekly, monthly, or some other interval after the AAV vector is administered, or at 2 weeks, 1 month, 2 months, 3 months, 6 months, 9 months, 1 year, 2 years, or some different time after the AAV vector is administered. In some of these embodiments, the ELISPOT assay is designed to detect interferon gamma (or some other cytokine) production stimulated by peptides from the AAV vector capsid protein or Factor IX protein (including FIX Padua, or a different variant) produced by transduced liver cells. In any of these embodiments, the AAV vector can be AAV-FIX39-Padua, or an AAV vector having the same capsid and a genome sequence at least 95%, 96%, 97%, 98% or 99% identical thereto, which may be administered to a subject in a pharmaceutically acceptable composition alone, or with empty capsids of the same capsid type at an empty to vector ratio of about 2:1, 3:1, 4:1, 5:1, 6:1, 7:1, 8:1, 9:1, 10:1, or some other ratio.

As a proxy for the cellular immune response against transduced hepatocytes, the presence of greater-than-normal liver enzymes can be assayed using standard methods. While not wishing to be bound by theory, it is believed that T cells specific for certain AAV vectors, such as those used in prior clinical trials, can attack and kill transduced hepatocytes, which transiently releases liver enzymes into the circulation. Exemplary liver enzymes include alanine aminotransferase (ALT), aspartate aminotransferase (AST), and lactate dehydrogenase (LDH), but other enzymes indicative of liver damage can also be monitored. A normal level of these enzymes in the circulation is typically defined as a range that has an upper level, above which the enzyme level is considered elevated, and therefore indicative of liver damage. A normal range depends in part on the standards used by the clinical laboratory conducting the assay. In certain embodiments, a therapeutically effective dose of an AAV vector results in FIX activity adequate to maintain hemostasis in a subject with hemophilia B (for example, FIX activity of at least 1%, 5%, 10%, 20%, 30%, or more), while causing an elevated circulating liver enzyme level, such as that of ALT, AST, or LDH, which is not greater than 0%, 10%, 20%, 30%, 40%, 50%, 60%, 70%, 80%, 90%, 100%, 200%, 300%, 400%, 500%, 600%, 700%, 800%, 900%, 1000%, 1500%, 2000% of the upper limit of normal (ULN) value of their respective ranges, on average, or at the highest level measured in multiple samples drawn from the same subject under treatment at different times (e.g., at weekly or monthly intervals) after administration of the AAV vector. In any of these embodiments, the AAV vector can be AAV-FIX39-Padua, or an AAV vector having the same capsid and a genome sequence at least 95%, 96%, 97%, 98% or 99% identical thereto, which may be administered to a subject in a pharmaceutically acceptable composition alone, or with empty capsids of the same capsid type at an empty to vector ratio of about 2:1, 3:1, 4:1, 5:1, 6:1, 7:1, 8:1, 9:1, 10:1, or some other ratio.

In prior clinical trials using AAV vectors to treat hemophilia B, the investigators needed to co-administer an immunosuppressant drug, such as a steroid, to prevent the subjects receiving treatment from mounting an immune response that would eliminate the transduced cells producing the Factor IX protein. Due to the attenuated immune response seen in subjects undergoing experimental treatment with certain AAV vectors, however, co-administration of immunosuppressing drugs may not be necessary. Thus, in certain embodiments, a therapeutically effective dose of an AAV vector is one that is sufficient to maintain adequate hemostasis in a subject with severe or moderate hemophilia B, without need for co-administration (before, contemporaneously, or after) of an immunosuppressant drug (such as a steroid or other immunosuppressant). Because an immune response is not predictable in all subjects, however, the methods herein of treatment for hemophilia B include AAV vectors that are co-administered with an immunosuppressant drug. Co-administration of an immunosuppressant drug can occur before, contemporaneously with, or after AAV vectors are administered to a subject having hemophilia B. In some embodiments, an immunosuppressant drug is administered to a subject for a period of days, weeks, or months after being administered an AAV vector for treating hemophilia B. Exemplary immunosuppressing drugs include steroids (e.g., without limitation, prednisone or prednisolone) and non-steroidal immunosuppressants, such as cyclosporin, rapamycin, and others. What drug doses and time course of treatment are required to effect sufficient immunosuppression will depend on factors unique to each subject undergoing treatment, but determining dose and treatment time are within the skill of those ordinarily skilled in the art. In some embodiments, an immunosuppressant may need to be administered more than one time.

According to certain embodiments, a therapeutically effective dose of an AAV vector results in a consistent elevation of FIX activity when administered to a population of human subjects with severe or moderate hemophilia B. Consistency can be determined by calculating variability of response in a population of human subjects using statistical methods such the mean and standard deviation (SD), or another statistical technique familiar to those of skill in the art. In some embodiments, a therapeutically effective dose of an AAV vector, when administered to a population of human subjects with severe or moderate hemophilia B results, at 3 months, 6 months, 9 months, 12 months, 15 months, 18 months, 21 months, or 21 months after administration, in a mean FIX activity of 1-5% with a SD of less than 15, 14, 13, 12, 11, 10, 9, 8, 7, 6, 5, 4, 3, 2, or 1; a mean FIX activity of 2.5-7.5% with a SD of less than 15, 14, 13, 12, 11, 10, 9, 8, 7, 6, 5, 4, 3, 2, or 1; a mean FIX activity of 5-10% with a SD of less than 15, 14, 13, 12, 11, 10, 9, 8, 7, 6, 5, 4, 3, 2, or 1; a mean FIX activity of 7.5-12.5% with a SD of less than 15, 14, 13, 12, 11, 10, 9, 8, 7, 6, 5, 4, 3, 2, or 1; a mean FIX activity of 10-15% with a SD of less than 15, 14, 13, 12, 11, 10, 9, 8, 7, 6, 5, 4, 3, 2, or 1; a mean FIX activity of 12.5-17.5% with a SD of less than 15, 14, 13, 12, 11, 10, 9, 8, 7, 6, 5, 4, 3, 2, or 1; a mean FIX activity of 15-20% with a SD of less than 15, 14, 13, 12, 11, 10, 9, 8, 7, 6, 5, 4, 3, 2, or 1; a mean FIX activity of 17.5-22.5% with a SD of less than 15, 14, 13, 12, 11, 10, 9, 8, 7, 6, 5, 4, 3, 2, or 1; a mean FIX activity of 20-25% with a SD of less than 15, 14, 13, 12, 11, 10, 9, 8, 7, 6, 5, 4, 3, 2, or 1; a mean FIX activity of 22.5-27.5% with a SD of less than 15, 14, 13, 12, 11, 10, 9, 8, 7, 6, 5, 4, 3, 2, or 1; a mean FIX activity of 25-30% with a SD of less than 15, 14, 13, 12, 11, 10, 9, 8, 7, 6, 5, 4, 3, 2, or 1; a mean FIX activity of 27.5-32.5% with a SD of less than 15, 14, 13, 12, 11, 10, 9, 8, 7, 6, 5, 4, 3, 2, or 1; a mean FIX activity of 30-35% with a SD of less than 15, 14, 13, 12, 11, 10, 9, 8, 7, 6, 5, 4, 3, 2, or 1; a mean FIX activity of 32.5-37.5% with a SD of less than 15, 14, 13, 12, 11, 10, 9, 8, 7, 6, 5, 4, 3, 2, or 1; a mean FIX activity of 35-40% with a SD of less than 15, 14, 13, 12, 11, 10, 9, 8, 7, 6, 5, 4, 3, 2, or 1; a mean FIX activity of 37.5-42.5% with a SD of less than 15, 14, 13, 12, 11, 10, 9, 8, 7, 6, 5, 4, 3, 2, or 1; a mean FIX activity of 40-45% with a SD of less than 15, 14, 13, 12, 11, 10, 9, 8, 7, 6, 5, 4, 3, 2, or 1; a mean FIX activity of 42.5-47.5% with a SD of less than 15, 14, 13, 12, 11, 10, 9, 8, 7, 6, 5, 4, 3, 2, or 1; or a mean FIX activity of 45-50% with a SD of less than 15, 14, 13, 12, 11, 10, 9, 8, 7, 6, 5, 4, 3, 2, or 1. In any of these embodiments, the AAV vector can be AAV-FIX39-Padua, or an AAV vector having the same capsid and a genome sequence at least 95%, 96%, 97%, 98% or 99% identical thereto, which may be administered to a subject in a pharmaceutically acceptable composition alone, or with empty capsids of the same capsid type at an empty to vector ratio of about 2:1, 3:1, 4:1, 5:1, 6:1, 7:1, 8:1, 9:1, 10:1, or some other ratio.

Invention methods and uses can be combined with any compound, agent, drug, treatment or other therapeutic regimen or protocol having a desired therapeutic, beneficial, additive, synergistic or complementary activity or effect. Exemplary combination compositions and treatments include second actives, such as, biologics (proteins), agents and drugs. Such biologics (proteins), agents, drugs, treatments and therapies can be administered or performed prior to, substantially contemporaneously with or following any other method or use of the invention, for example, a therapeutic method of treating a subject for a blood clotting disease.

The compound, agent, drug, treatment or other therapeutic regimen or protocol can be administered as a combination composition, or administered separately, such as concurrently or in series or sequentially (prior to or following) delivery or administration of a nucleic acid, vector, recombinant vector (e.g., rAAV), vector genome, or recombinant virus particle. The invention therefore provides combinations in which a method or use of the invention is in a combination with any compound, agent, drug, therapeutic regimen, treatment protocol, process, remedy or composition, set forth herein or known to one of skill in the art. The compound, agent, drug, therapeutic regimen, treatment protocol, process, remedy or composition can be administered or performed prior to, substantially contemporaneously with or following administration of a nucleic acid, vector, recombinant vector (e.g., rAAV), vector genome, or recombinant virus particle of the invention, to a subject.

In certain embodiments, a combination composition includes one or more immunosuppressive agents. In certain embodiments a method includes administering or delivering one or more immunosuppressive agents to the mammal. In certain embodiments, a combination composition includes AAV-FIX particles and one or more immunosuppressive agents. In certain embodiments, a method includes administering or delivering AAV-FIX particles to a mammal and administering an immunosuppressive agent to the mammal. The skilled artisan can determine appropriate need or timing of such a combination composition with one or more immunosuppressive agents and administering the immunosuppressive agent to the mammal.

Methods and uses of the invention also include, among other things, methods and uses that result in a reduced need or use of another compound, agent, drug, therapeutic regimen, treatment protocol, process, or remedy. For example, for a blood clotting disease, a method or use of the invention has a therapeutic benefit if in a given subject a less frequent or reduced dose or elimination of administration of a recombinant clotting factor protein to supplement for the deficient or defective (abnormal or mutant) endogenous clotting factor in the subject. Thus, in accordance with the invention, methods and uses of reducing need or use of another treatment or therapy are provided.

The invention is useful in animals including human and veterinary medical applications. Suitable subjects therefore include mammals, such as humans, as well as non-human mammals. The term "subject" refers to an animal, typically a mammal, such as humans, non-human primates (apes, gibbons, gorillas, chimpanzees, orangutans, macaques), a domestic animal (dogs and cats), a farm animal (poultry such as chickens and ducks, horses, cows, goats, sheep, pigs), and experimental animals (mouse, rat, rabbit, guinea pig). Human subjects include fetal, neonatal, infant, juvenile and adult subjects. Subjects include animal disease models, for example, mouse and other animal models of blood clotting diseases and others known to those of skill in the art.

Subjects appropriate for treatment include those having or at risk of producing an insufficient amount or having a deficiency in a functional gene product (protein), or produce an aberrant, partially functional or non-functional gene product (protein), which can lead to disease. Subjects appropriate for treatment in accordance with the invention also include those having or at risk of producing an aberrant, or defective (mutant) gene product (protein) that leads to a disease such that reducing amounts, expression or function of the aberrant, or defective (mutant) gene product (protein) would lead to treatment of the disease, or reduce one or more symptoms or ameliorate the disease. Target subjects therefore include subjects having aberrant, insufficient or absent blood clotting factor production, such as hemophiliacs (e.g., hemophilia B).

Subjects appropriate for treatment in accordance with the invention further include those previously or currently treated with supplemental protein (e.g., recombinant blood clotting factor such as FIX to treat hemophilia). Subjects appropriate for treatment in accordance with the invention moreover include those that have not developed a substantial or detectable immune response against FIX protein, or amounts of inhibitory antibodies against FIX protein that would interfere with or block FIX based gene therapy.

In other embodiments, human pediatric subjects that are determined to have hemophilia B (e.g., by genotyping), but have not yet exhibited any of the symptoms of hemophilia B, can be treated prophylactically with an AAV vector to prevent any such symptoms from occurring in the first place or, in other embodiments, from being as severe as they otherwise would have been in the absence of treatment. In some embodiments, human subjects treated prophylactically in this way are at least 3, 4, 5, 6, 7, 8, 9, 10, 11, 12, 13, 14, 15, 16, 17, 18 months old, or older, when they are administered an AAV vector to produce and maintain FIX activity adequate to maintain hemostasis, and thus prevent or reduce the severity of one or more symptoms of hemophilia B. In any of these embodiments, the AAV vector can be AAV-FIX39-Padua, or an AAV vector having the same capsid and a genome sequence at least 95%, 96%, 97%, 98% or 99% identical thereto, which may be administered to a subject in a pharmaceutically acceptable composition alone, or with empty capsids of the same capsid type at an empty to vector ratio of about 2:1, 3:1, 4:1, 5:1, 6:1, 7:1, 8:1, 9:1, 10:1, or some other ratio.

Administration or in vivo delivery to a subject can be performed prior to development of an adverse symptom, condition, complication, etc. caused by or associated with the disease. For example, a screen (e.g., genetic) can be used to identify such subjects as candidates for invention compositions, methods and uses. Such subjects therefore include those screened positive for an insufficient amount or a deficiency in a functional gene product (protein), or that produce an aberrant, partially functional or non-functional gene product (protein).

Methods and uses of the invention include delivery and administration systemically, regionally or locally, or by any route, for example, by injection or infusion. Such delivery and administration include parenterally, e.g. intravascularly, intravenously, intramuscularly, intraperitoneally, intradermally, subcutaneously, or transmucosal. Exemplary administration and delivery routes include intravenous (i.v.), intraperitoneal (i.p.), intraarterial, subcutaneous, intra-pleural, intubation, intrapulmonary, intracavity, iontophoretic, intraorgan, intralymphatic.

Alternatively or in addition, AAV vector can be delivered to the liver via the portal vein. In another alternative, a catheter introduced into the femoral artery can be used to deliver AAV vectors to liver via the hepatic artery. Non-surgical means can also be employed, such as endoscopic retrograde cholangiopancreatography (ERCP), to deliver AAV vectors directly to the liver, thereby bypassing the bloodstream and AAV neutralizing antibodies. Other ductal systems, such as the ducts of the submandibular gland, can also be used as portals for delivering AAV vectors into a subject that develops or has preexisting anti-AAV antibodies.

Doses can vary and depend upon whether the type, onset, progression, severity, frequency, duration, or probability of the disease to which treatment is directed, the clinical endpoint desired, previous or simultaneous treatments, the general health, age, gender, race or immunological competency of the subject and other factors that will be appreciated by the skilled artisan. The dose amount, number, frequency or duration may be proportionally increased or reduced, as indicated by any adverse side effects, complications or other risk factors of the treatment or therapy and the status of the subject. The skilled artisan will appreciate the factors that may influence the dosage and timing required to provide an amount sufficient for providing a therapeutic or prophylactic benefit.

Methods and uses of the invention as disclosed herein can be practiced within 1-2, 2-4, 4-12, 12-24 or 24-72 hours after a subject has been identified as having the disease targeted for treatment, has one or more symptoms of the disease, or has been screened and is identified as positive as set forth herein even though the subject does not have one or more symptoms of the disease. Of course, methods and uses of the invention can be practiced 1-7, 7-14, 14-21, 21-48 or more days, months or years after a subject has been identified as having the disease targeted for treatment, has one or more symptoms of the disease, or has been screened and is identified as positive as set forth herein.

Invention nucleic acids, vectors, recombinant vectors (e.g., rAAV), vector genomes, and recombinant virus particles and other compositions, agents, drugs, biologics (proteins) can be incorporated into pharmaceutical compositions, e.g., a pharmaceutically acceptable carrier or excipient. Such pharmaceutical compositions are useful for, among other things, administration and delivery to a subject in vivo or ex vivo.

As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering a viral vector or viral particle to a subject.

Such compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Compositions suitable for parenteral administration comprise aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Pharmaceutical compositions and delivery systems appropriate for the compositions, methods and uses of the invention are known in the art (see, e.g., Remington: The Science and Practice of Pharmacy (2003) 20$^{th}$ ed., Mack Publishing Co., Easton, PA; Remington's Pharmaceutical Sciences (1990) 18$^{th}$ ed., Mack Publishing Co., Easton, PA; The Merck Index (1996) 12$^{th}$ ed., Merck Publishing Group, Whitehouse, NJ; Pharmaceutical Principles of Solid Dosage Forms (1993), Technonic Publishing Co., Inc., Lancaster, Pa.; Ansel and Stoklosa, Pharmaceutical Calculations (2001) 11$^{th}$ ed., Lippincott Williams & Wilkins, Baltimore, MD; and Poznansky et al., Drug Delivery Systems (1980), R. L. Juliano, ed., Oxford, N.Y., pp. 253-315).

A "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. Recombinant vector (e.g., rAAV) sequences, vector genomes, recombinant virus particles, and pharmaceutical compositions thereof can be packaged in single or multiple unit dosage form for ease of administration and uniformity of dosage.

The invention provides kits with packaging material and one or more components therein. A kit typically includes a label or packaging insert including a description of the components or instructions for use in vitro, in vivo, or ex vivo, of the components therein. A kit can contain a collection of such components, e.g., a nucleic acid, recombinant vector, virus (e.g., AAV) vector, vector genome or virus particle and optionally a second active, such as another compound, agent, drug or composition.

A kit refers to a physical structure housing one or more components of the kit. Packaging material can maintain the components sterilely, and can be made of material commonly used for such purposes (e.g., paper, corrugated fiber, glass, plastic, foil, ampules, vials, tubes, etc.).

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer, lot numbers, manufacture location and date, expiration dates. Labels or inserts can include information identifying manufacturer information, lot numbers, manufacturer location and date. Labels or inserts can include information on a disease for which a kit component may be used. Labels or inserts can include instructions for the clinician or subject for using one or more of the kit components in a method, use, or treatment protocol or therapeutic regimen. Instructions can include dosage amounts, frequency or duration, and instructions for practicing any of the methods, uses, treatment protocols or prophylactic or therapeutic regimes described herein.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, magnetic tape, or an electrical storage media such as RAM and ROM or hybrids of these such as magnetic/optical storage media, FLASH media or memory type cards.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

All of the features disclosed herein may be combined in any combination. Each feature disclosed in the specification may be replaced by an alternative feature serving a same, equivalent, or similar purpose. Thus, unless expressly stated otherwise, disclosed features (e.g., modified nucleic acid, vector, plasmid, a recombinant vector (e.g., rAAV) sequence, vector genome, or recombinant virus particle) are an example of a genus of equivalent or similar features.

As used herein, the singular forms "a", "and," and "the" include plural referents unless the context clearly indicates otherwise. Thus, for example, reference to "a nucleic acid" includes a plurality of such nucleic acids, reference to "a vector" includes a plurality of such vectors, and reference to "a virus" or "particle" includes a plurality of such virions/particles.

As used herein, all numerical values or numerical ranges include integers within such ranges and fractions of the values or the integers within ranges unless the context clearly indicates otherwise. Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions.

Accordingly, the following examples are intended to illustrate but not limit the scope of the invention claimed.

Example 1. Vector Design/Preparation

A novel Factor IX nucleic acid encoding a high specific activity human factor IX protein having the 338L Padua variant (Simioni P, et al., *N Engl J Med* 2009, 361:1671) was designed ("FIX 39-Padua"; SEQ ID No: 10; FIG. 10). FIX39-Padua is completely devoid of CpG dinucleotides in the FIX coding and intronic sequences. For comparative testing, FIX19 (Mingozzi et al. *Sci. Transl Med.* 2013) was prepared and modified to include the FIX Padua, to rule out any potential confounding effects resulting from the FIX Padua ("FIX 19-Padua"; SEQ ID NO: 11; FIG. 11).

A plasmid ("pAAV-ApoE_hAAT-FIX39"; 11125 bp; SEQ ID NO:12; FIG. 12A) was synthesized and included the FIX39-Padua expression cassette and the elements described in Table 2. A map of pAAV-ApoE_hAAT-FIX39 is shown in FIG. 13.

TABLE 2

| pAAV-ApoE_hAAT-FIX39 | |
|---|---|
| 5' AAV2 ITR | SEQ ID NO: 13 |
| Enhancer (Hepatic Control Region) | SEQ ID NO: 14 |
| hAAT promoter | SEQ ID NO: 15 |
| 5' UTR | SEQ ID NO: 16 |
| FIX39-Padua CDS | SEQ ID NO: 10 (FIG. 10) |
| Intron A | SEQ ID NO: 17 (FIG. 14) |
| 3' UTR | SEQ ID NO: 18 |
| polyA | SEQ ID NO: 19 |
| 3' AAV2 ITR | SEQ ID NO: 20 |
| Lambda stuffer | SEQ ID NO: 21 |
| F1 origin of replication | SEQ ID NO: 22 |
| Kanamycin resistance | SEQ ID NO: 23 |
| pUC origin of replication | SEQ ID NO: 24 |

The sequence of the FIX39-Padua coding sequence and intron A is set forth in SEQ ID NO:25 (FIG. 15). A plasmid was also synthesized that included the FIX19-Padua CDS and the same regulatory elements, the same adeno-associated inverted terminal repeats (ITRs), and the same liver-specific ApoE/hAAT promoter as pAAV-ApoE_hAAT-FIX39.

AAV vector having the 4-1 capsid variant (SEQ ID NO:4) was prepared for the FIX39-Padua ("AAV-FIX39-Padua") and FIX19-Padua ("AAV-FIX19-Padua") transgenes using a triple transfection process followed by double cesium chloride gradient centrifugation (Ayuso E, M et al., Gene Ther 2010, 17:503). Vectors were titrated by quantitative PCR using a linearized plasmid as the standard. For the study described in Example 3, vector was diluted in PBS, 5% sorbitol, 0.001% F68 to a final volume of 200 µl per mouse, for tail vein injection.

Example 2. In Vitro AAV Variant 4-1 Transduction

Figure 16:
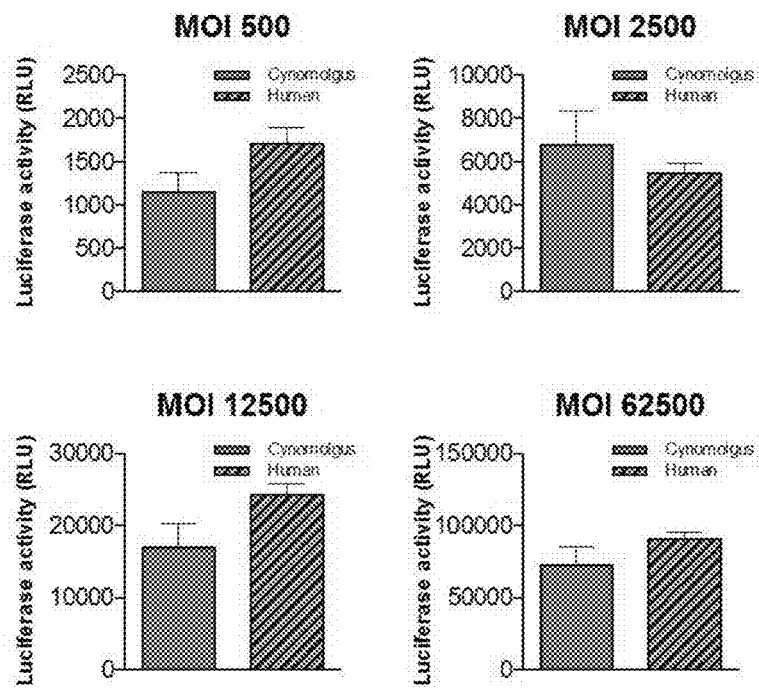
FIG. 16 shows transduction efficiency of the AAV-4-1 capsid variant (SEQ ID NO:4) analyzed in an in vitro setting.

Primary hepatocytes from cynomolgus macaque and human origin were transduced with the 4-1 variant capsid (SEQ ID NO:4) expressing luciferase at four different multiplicities of infection (MOI) ranging from 500 to 62,500 vector genomes per cell. Seventy-two hours after transduction, luciferase expression was analyzed. As shown in FIG. 16, the ratio of transduced human hepatocytes relative to non-human primate hepatocytes ranged from 0.8 to 1.5, depending on the MOI used. These data generated in vitro appear to be consistent with previous observations in vivo when comparing expression of coagulation factor IX in cynomolgus macaques and human subjects.

Example 3. Potency Study

A study was conducted to evaluate the potency of AAV-FIX39-Padua versus AAV-FIX19-Padua in mice. Groups of 5 mice were injected at 8-10 weeks of age with either $1 \times 10^{11}$ or $1 \times 10^{12}$ vg/kg of AAV-FIX39-Padua and AAV-FIX19-Padua. Following vector administration, blood was collected by retro-orbital bleeding using heparinized capillary tubes; plasma was isolated by centrifugation at 9000 rpm for 10 minutes at 4° C. and stored frozen at −80° C. until assayed.

Plasma collected was used to evaluate hFIX transgene expression. Human FIX levels in plasma were measured using an ELISA kit (Affinity Biologicals, Ancaster, ON, Canada).

Activity levels of human FIX were measured by activated partial thromboplastin time (aPTT) assay. The aPTT assay was performed by mixing sample plasma in a 1:1:1 volume-ratio with human FIX-deficient plasma (George King Biomedical, Inc) and aPTT reagent (Trinity Biotech), followed by a 180 s incubation period at 37° C. Coagulation was initiated by addition of 25 mM calcium chloride. Time to clot formation was measured using a STart 4 coagulation instrument (Diagnostica Stago). A standard curve was generated with pooled normal plasma from George King starting at a 1:5 dilution in TBS pH 7.4 (48 µl+192 µl) followed by serial 1:2 dilutions (120 µl+120 µl). The human standard curve was used to calculate the activity of each sample at week 17 after vector administration; activity in two untreated mice was also measured. FIX activity in untreated mice was averaged and then subtracted from the treated samples to calculate the extra (i.e. human) activity due to the FIX Padua protein.

Figure 17:
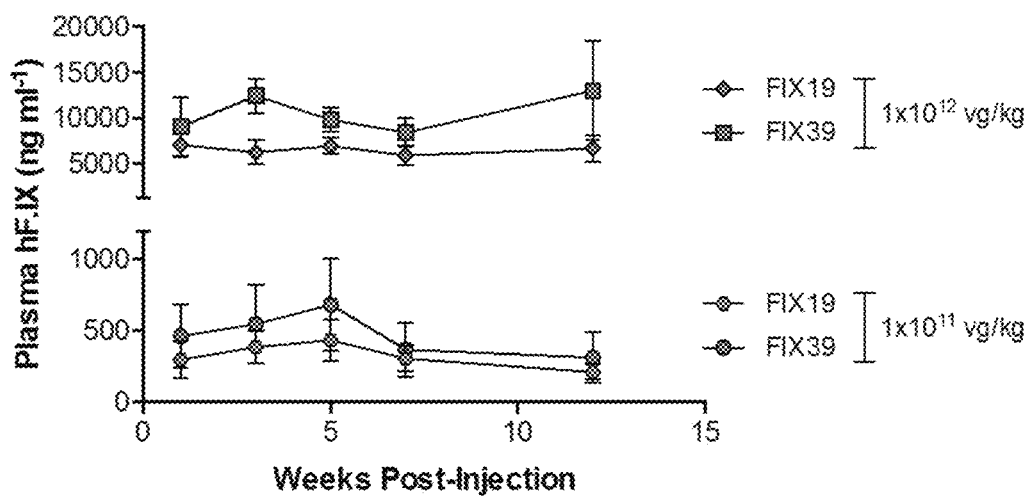
FIG. 17 shows levels of hFIX in plasma of wild-type mice following intravenous injection at week 8 of life with either $1 \times 10^{11}$ or $1 \times 10^{12}$ vg/kg of AAV-FIX39-Padua (square/circle) and AAV-FIX19-Padua (diamond/hexagon). Human FIX plasma levels were assayed by ELISA and represent multiple measurements, obtained by serial bleeding, on the same group of animals during the course of the study (n=5 mice in each cohort). Error bars denote standard error of the mean.

As shown in FIG. 17, AAV-FIX39-Padua and AAV-FIX19-Padua appear to express substantially equivalent levels of FIX.

Seventeen weeks after vector administration, human FIX activity was measured in those mice treated with a vector dose of $1 \times 10^{12}$ vg/kg. The activity-to-antigen ratio ranged between 5.2 and 7.5, with an average value of 6.4 for both FIX19-Padua and FIX39-Padua groups (Table 3).

TABLE 3

Human FIX activity values

| Animal ID | Antigen (% of normal) | Activity (% of normal) | Ratio |
|---|---|---|---|
| 01-FIX19 | 53.9 | 352.7 | 6.5 |
| 02-FIX19 | 95.6 | 631.8 | 6.6 |
| 03-FIX19 | 120.6 | 882.3 | 7.3 |
| 04-FIX19 | 132.9 | 797.1 | 6.0 |
| 05-FIX19 | 105.2 | 599.7 | 5.7 |
| 06-FIX39 | 163.1 | 1092.8 | 6.7 |
| 07-FIX39 | 108.2 | 670.3 | 6.2 |
| 08-FIX39 | 121.1 | 781.2 | 6.4 |
| 09-FIX39 | 152.3 | 1147.8 | 7.5 |
| 10-FIX39 | 134.1 | 702.1 | 5.2 |
| Average | | | |
| AAV-FIX19-Padua | 101.7 | 652.7 | 6.4 |
| AAV-FIX39-Padua | 135.8 | 878.8 | 6.4 |

While these results suggest that the potency of both expression cassettes is substantially similar, the two constructs were also analyzed in the setting of plasmid hydrodynamic tail vein injection. The rationale for evaluating FIX levels derived of in vivo administration of naked DNA was to compare both expression cassettes without the potential interference of differences in AAV tittering, vector manufacturing, etc.

Figure 18:
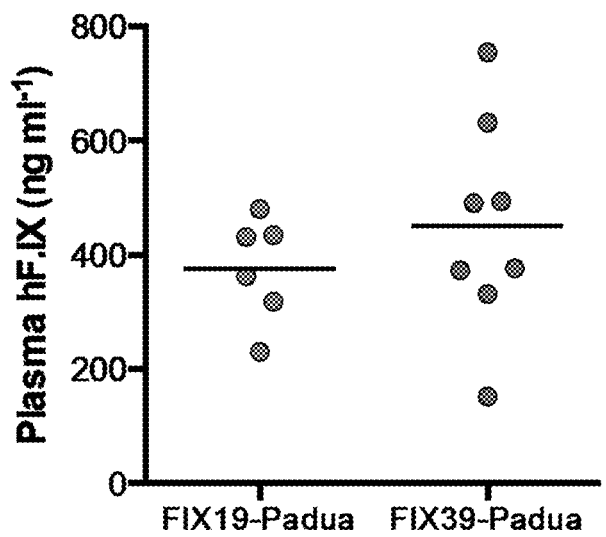
FIG. 18 shows circulating levels of human FIX in mouse plasma 24 hours following hydrodynamic tail vein injection of 5 μg of pFIX19-Padua or pFIX39-Padua plasmids. P=0.3337.

As shown in FIG. 18, both naked expression cassettes were equally potent at driving FIX expression, confirming the data obtained in the AAV setting. These results indicate that the FIX19-Padua and FIX39-Padua expression cassettes have similar potency.

Example 4. AAV-FIX39-Padua Gene Therapy

A clinical study is being conducted to determine safety and kinetics of a single IV infusion of AAV-FIX39-Padua. The AAV 4-1 capsid variant used has been shown in preclinical studies to have good safety and efficacy, the ability to achieve sustained FIX activity levels of ~35% in NHPs at $1 \times 10^{12}$ vg/kg after 3 months of vector infusion; and cross reacting neutralizing antibodies (Ab) to the AAV 4-1 capsid variant are approximately 10% less prevalent than AAV8. The design of the study is provided in Table 4.

TABLE 4

AAV-FIX39-Padua Clinical Study Design

| | |
|---|---|
| Safety and Tolerability of AAVFIX39-Padua | Clinically significant in vital signs, lab values and clinical assessments (including number of bleeds and QoL) from baseline |
| Kinetics of AAVFIX39-Padua steady-state | Transgene FIX activity levels and antigen levels at peak and |
| Dosing | Starting, Middle and Highest Dose Cohorts will each include 2-5 subjects |
| Design | Open-label, non-randomized, dose escalation |
| Participating countries | USA and potentially Europe, Japan and Canada |
| Sample size | Up to 15 subjects |
| Eligibility | Ages Eligible for Study: 18 Years and older Genders Eligible for Study: Male Accepts Healthy Volunteers: No |
| Inclusion Criteria | Able to provide informed consent and comply with requirements of the study Males ≥18 y.o. with confirmed diagnosis of hemophilia B (≤2 IU/dL or ≤2% endogenous factor IX) Received ≥50 exposure days to factor IX products A minimum of an average of 4 bleeding events per year requiring episodic treatment of factor IX infusions or prophylactic factor IX infusions No measurable factor IX inhibitor as assessed by the central laboratory and have no prior history of inhibitors to factor IX protein Agree to use reliable barrier contraception until 3 consecutive samples are negative for vector sequences |
| Exclusion Criteria | Evidence of active hepatitis B or C Currently on antiviral therapy for hepatitis B or C Have significant underlying liver disease Have serological evidence* of HIV-1 or HIV-2 with CD4 counts ≤200/mm3 (*subjects who are HIV+ and stable with CD4 count ≥200/mm3 and undetectable viral load are eligible to enroll) Have detectable antibodies reactive with 4-1 variant AAV capsid (SEQ ID NO: 4) |

TABLE 4-continued

AAV-FIX39-Padua Clinical Study Design

| | |
|---|---|
| Screening Visit | Participated in a gene transfer trial within the last 52 weeks or an investigational drug within the last 12 weeks<br>Unable or unwilling to comply with study assessments<br>Eligibility evaluation<br>AAV NAb titer is the major screen failure (highly recommend referring subjects to CHOP'S AAV NAb titer protocol for phone screening) |
| Day 0 Visit | FIX product incremental recovery then vector infusion |
| Follow-up Visits (~17 visits) | Safety and kinetic evaluations |
| End-of Study Visit (at week 52) | Final safety evaluation |

Example 5. Clinical Results

Four subjects with hemophilia B were administered a single IV infusion of AAV-FIX39-Padua vector. The first two subjects, ages 23 and 18 respectively, had no prior history of liver disease, while the third, age 47, had a history of HCV infection but had cleared spontaneously. All four subjects had been screened for neutralizing antibodies to the novel AAV capsid and found to be negative.

Subjects were infused intravenously with $5\times10^{11}$ vg/kg of AAV-FIX39-Padua vector over a period of ~1 hour. The total AAV-FIX39-Padua vector administered to each subject is shown in FIGS. 20-23, which had been combined with the indicated amount of AAV empty capsids.

FIGS. 19-23 show study results, with AAV-FIX39-Padua vector administered at day 0. The results show increased Factor IX production in all four subjects, as reflected by increased FIX activity throughout the study evaluation period.

The initial increase in FIX activity from day 0 to about day 3 is due to administration of 100 IU/Kg Alprolix™ or BeneFIX™, which are recombinant FIX-Fc fusion protein having an approximate half-life of about 82 hours. Factor IX activity attributable to the AAV-FIX39 Padua vector begins at about day 6-8 after AAV vector infusion.

Figure 19:
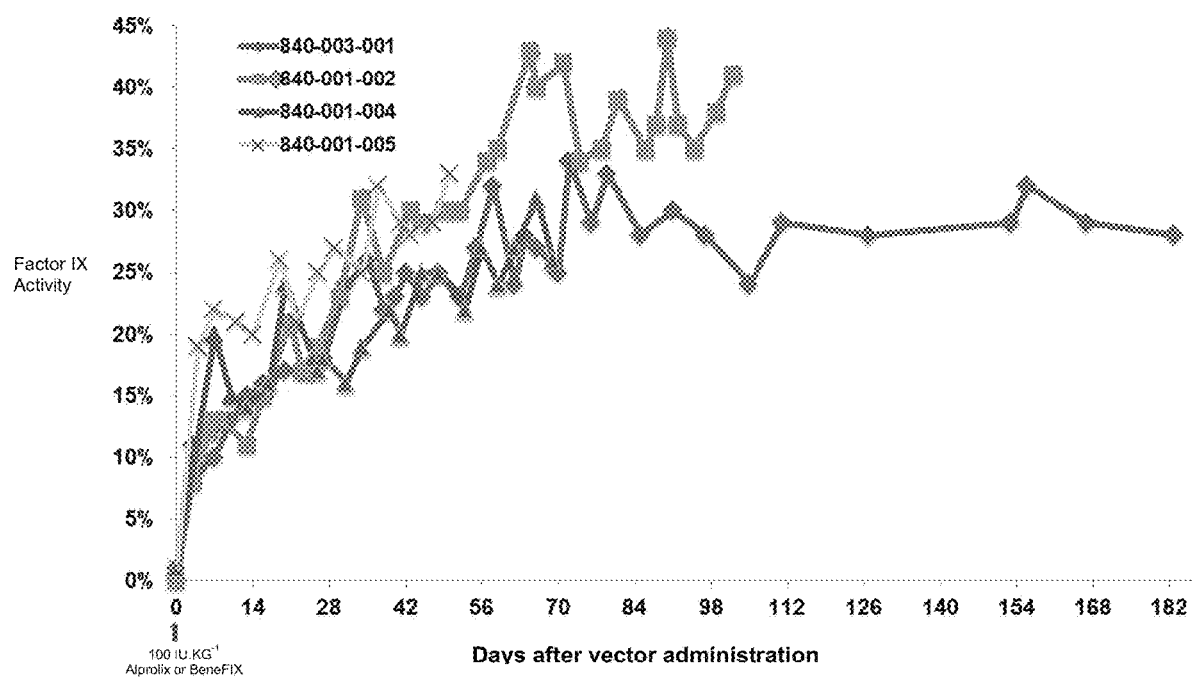
FIG. 19 shows a data summary of four human hemophilia B patients administered a single infusion of an AAV-FIX Padua variant (FIX39) bearing vector in accordance with the invention, and the FIX activity (%) over the ensuing evaluation periods (183, 102, 69 and 50 days, respectively).
Figure 20A:
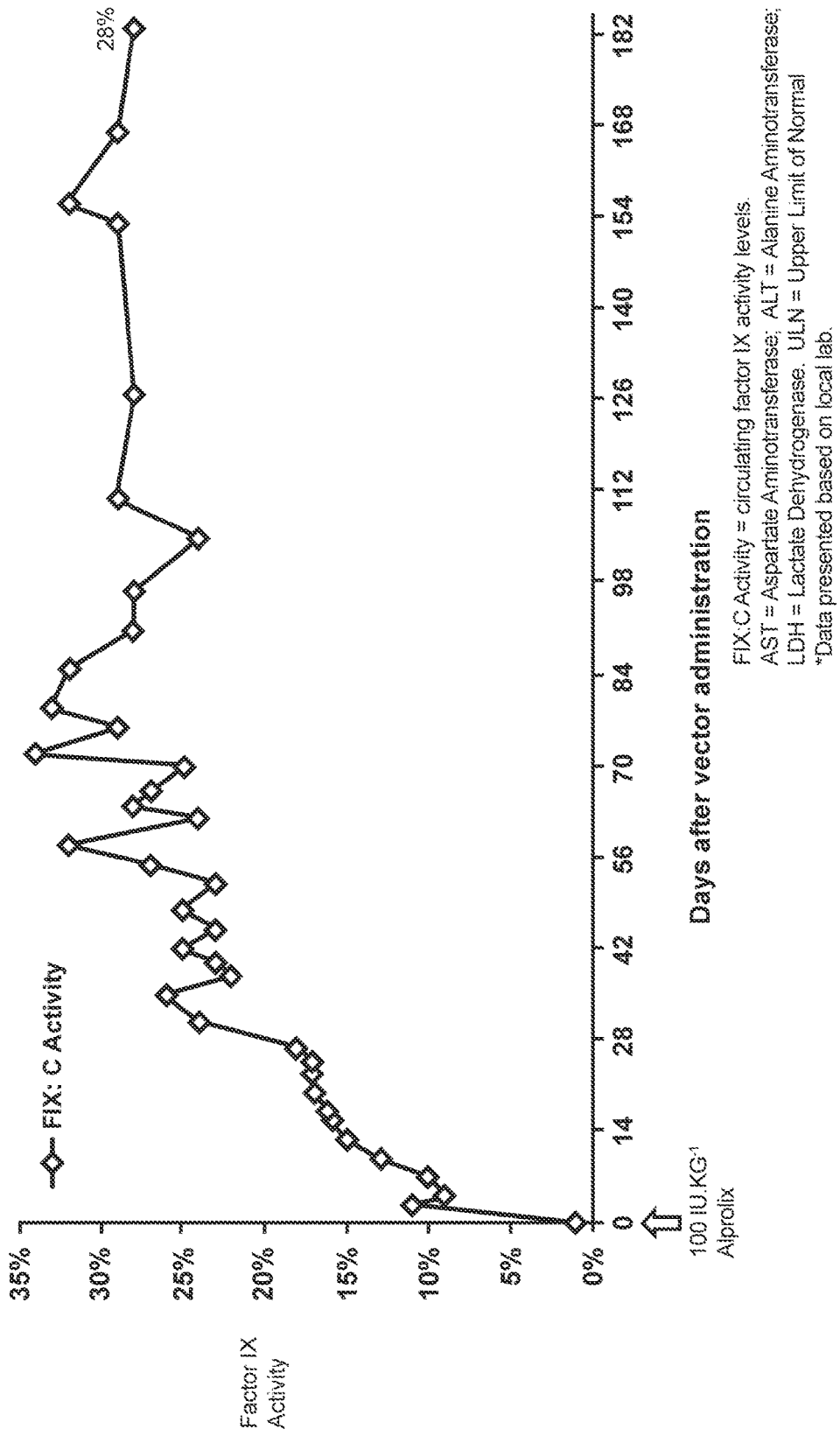
FIG. 20A shows the FIX activity (%) data of the first human hemophilia B patient administered the single infusion of AAV-FIX Padua variant (FIX39) bearing vector, over the 183 day evaluation period.
Figure 20B:
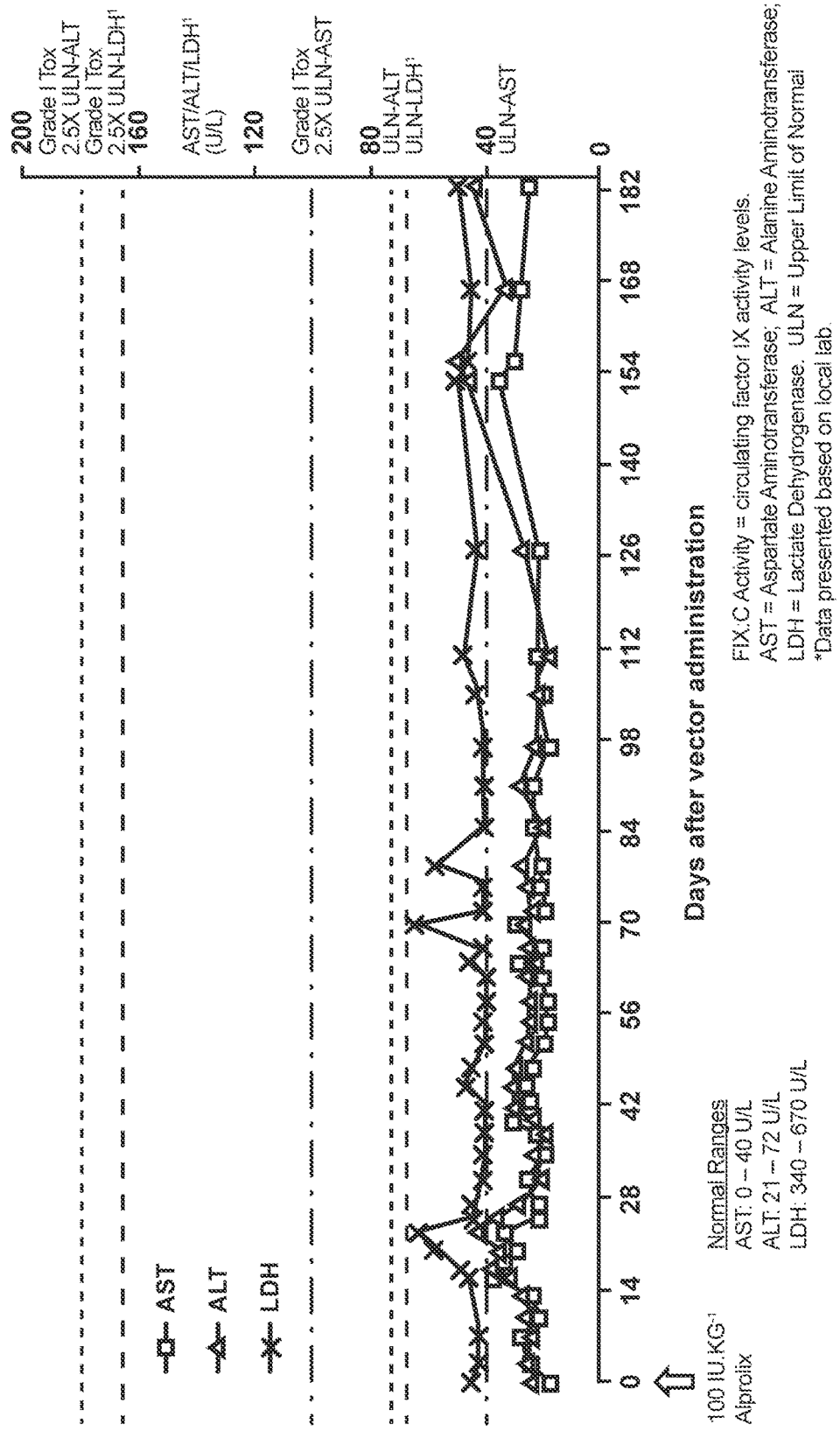
FIG. 20B shows liver function test (ALT, AST and LDH enzymes) data of the first human hemophilia B patient administered the single infusion of AAV-FIX Padua variant (FIX39) bearing vector, over the 183 day evaluation period. The plotted LDH values (LDH$^1$) have been divided by 10 in order to be shown with the ALT and AST values.
Figure 21A:
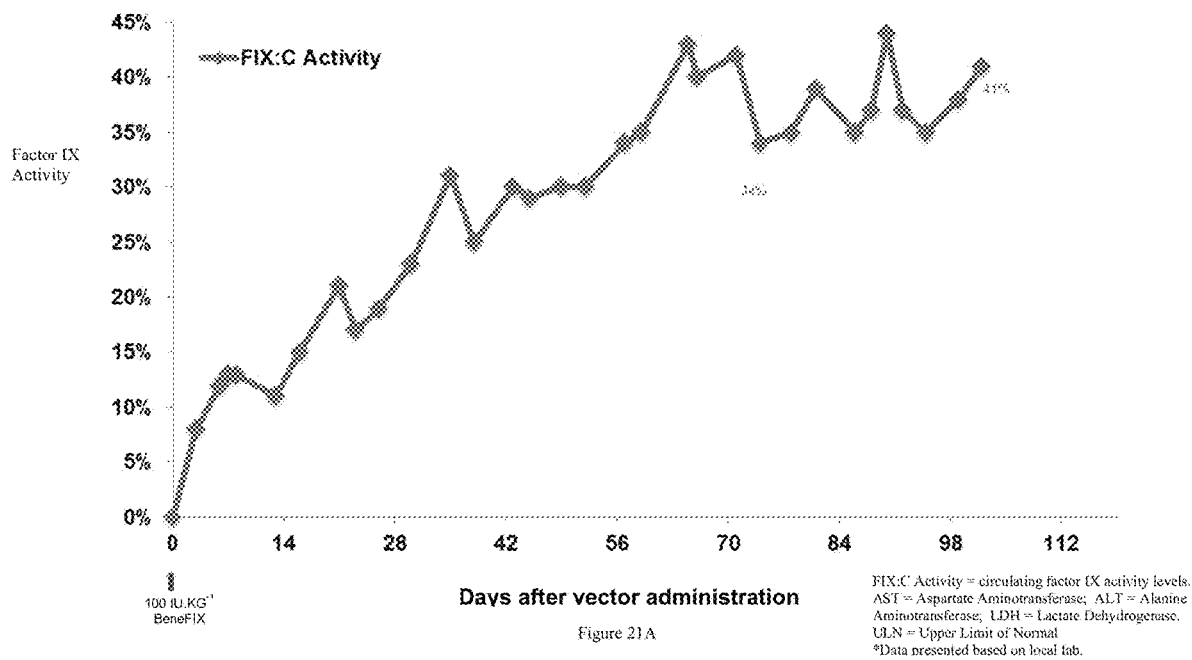
FIG. 21A shows the FIX activity (%) data of the second human hemophilia B patient administered the single infusion of AAV-FIX Padua variant (FIX39) bearing vector, over the 102 day evaluation period.
Figure 21B:
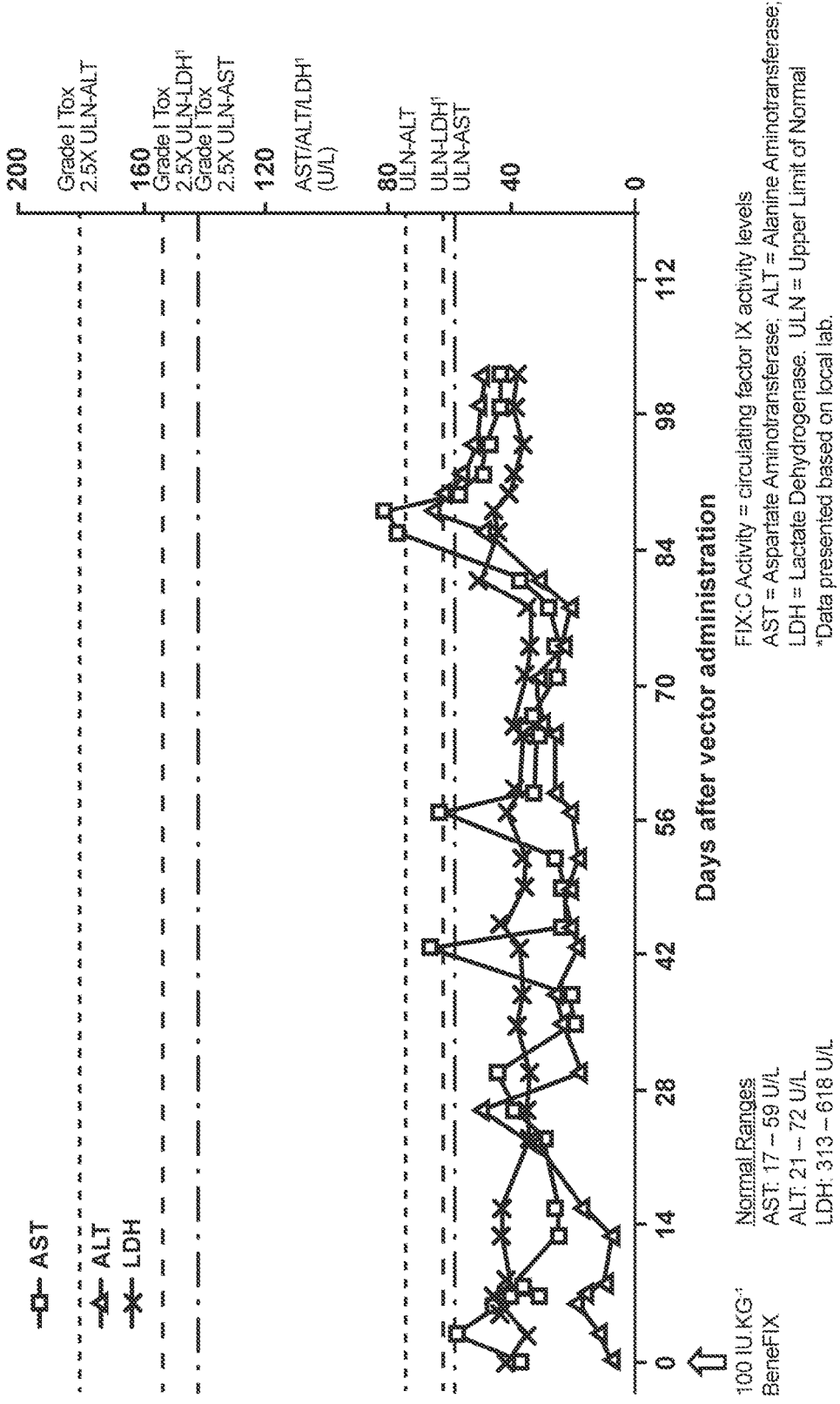
FIG. 21B shows liver function test (ALT, AST and LDH enzymes) data of the second human hemophilia B patient administered the single infusion of AAV-FIX Padua variant (FIX39) bearing vector, over the 102 day evaluation period. The plotted LDH values (LDH$^1$) have been divided by 10 in order to be shown with the ALT and AST values.
Figure 22A:
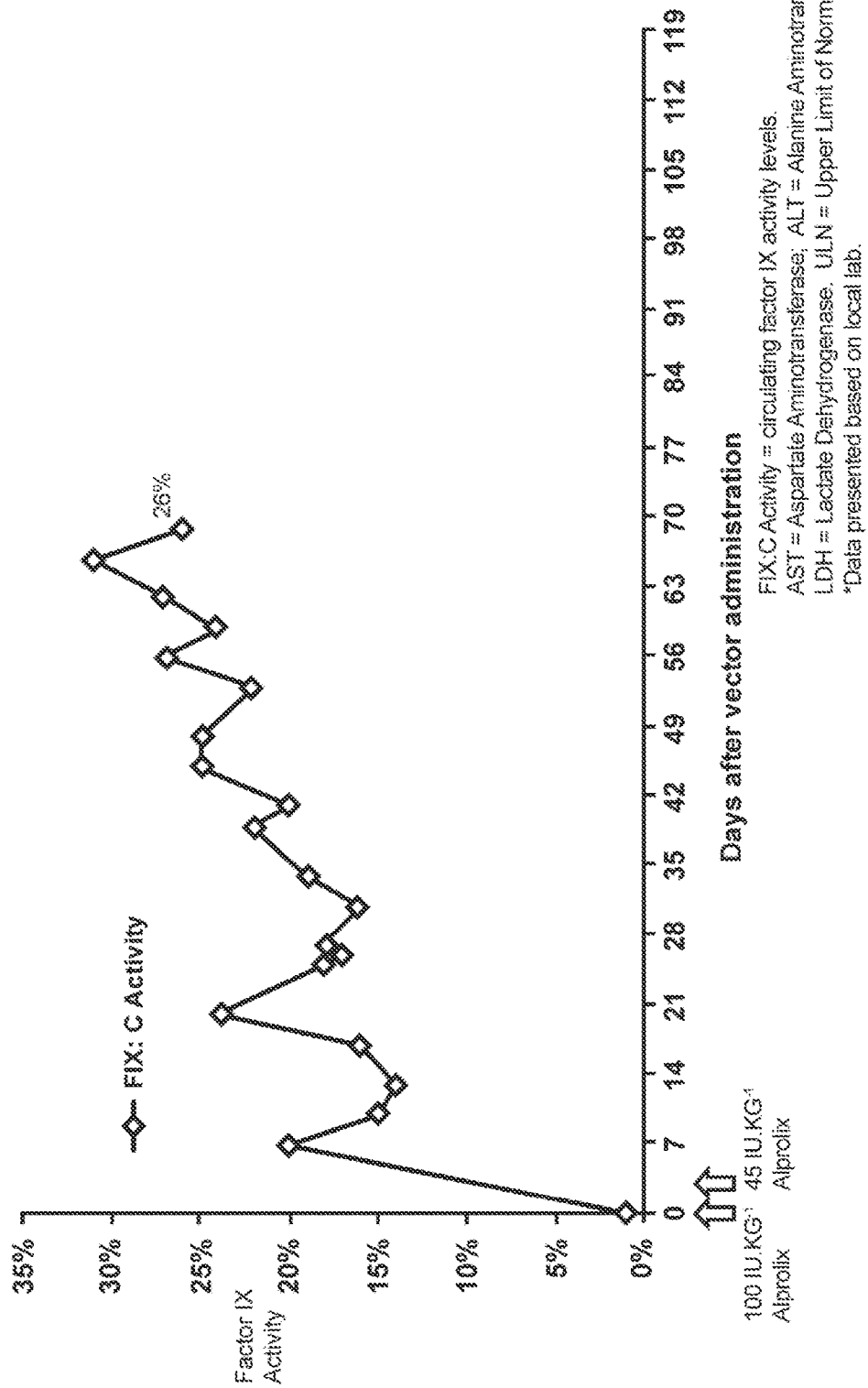
FIG. 22A shows the FIX activity (%) data of the third human hemophilia B patient administered the single infusion of AAV-FIX Padua variant (FIX39) bearing vector, over the 69 day evaluation period.
Figure 22B:
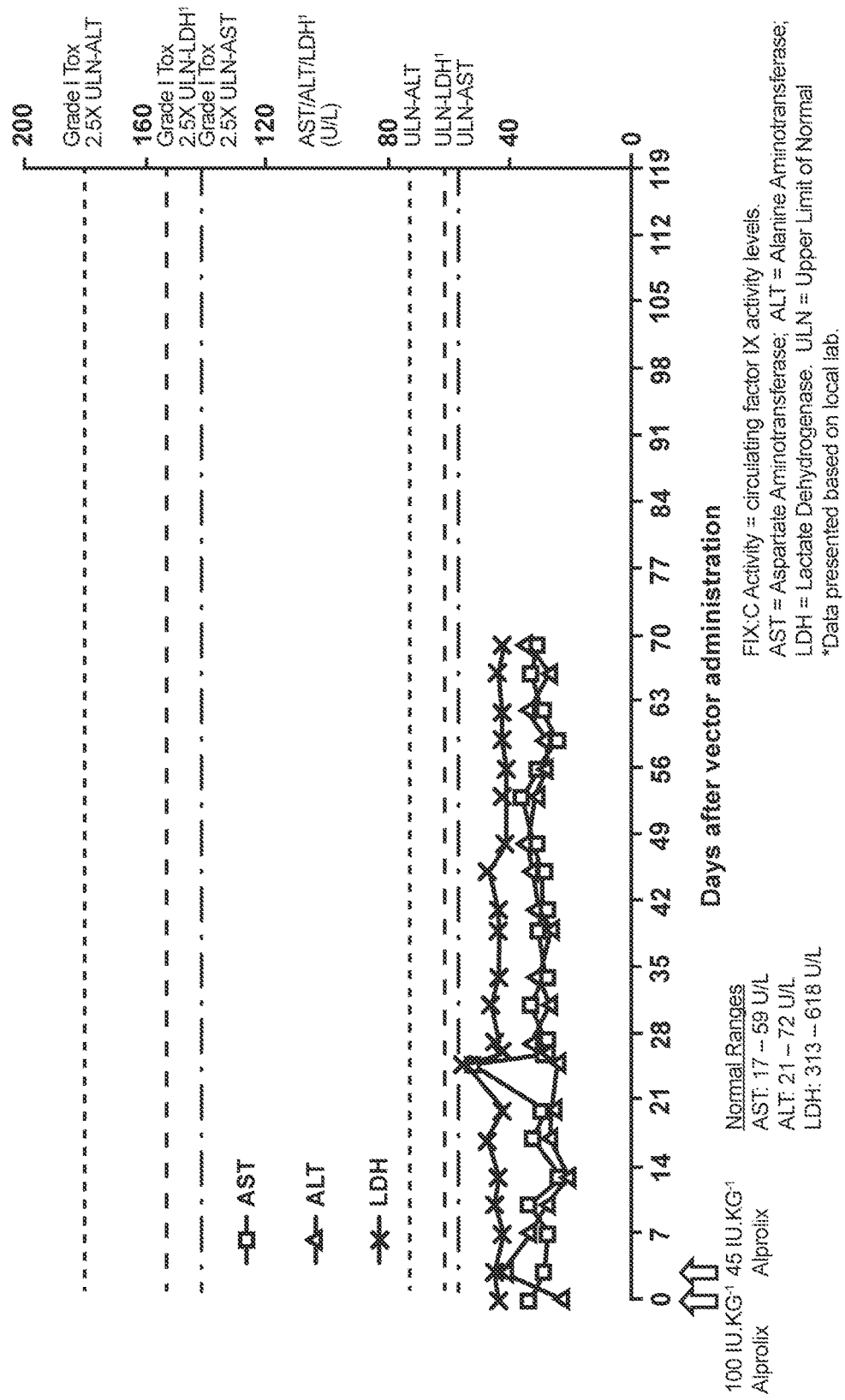
FIG. 22B shows liver function test (ALT, AST and LDH enzymes) data of the third human hemophilia B patient administered the single infusion of AAV-FIX Padua variant (FIX39) bearing vector, over the 69 day evaluation period. The plotted LDH values (LDH$^1$) have been divided by 10 in order to be shown with the ALT and AST values.
Figure 23A:
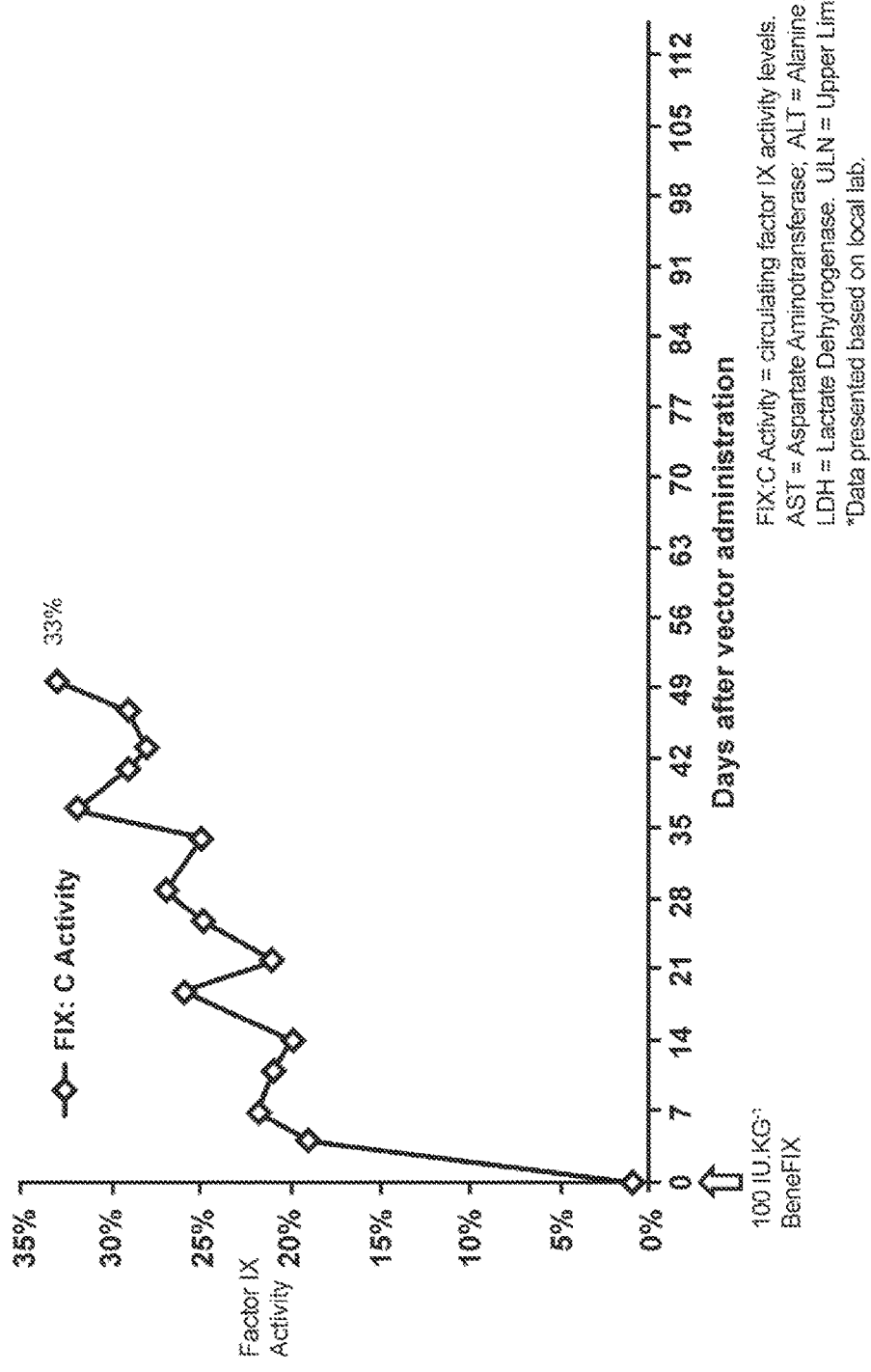
FIG. 23A shows the FIX activity (%) data of the fourth human hemophilia B patient administered the single infusion of AAV-FIX Padua variant (FIX39) bearing vector, over the 50 day evaluation period.
Figure 23B:
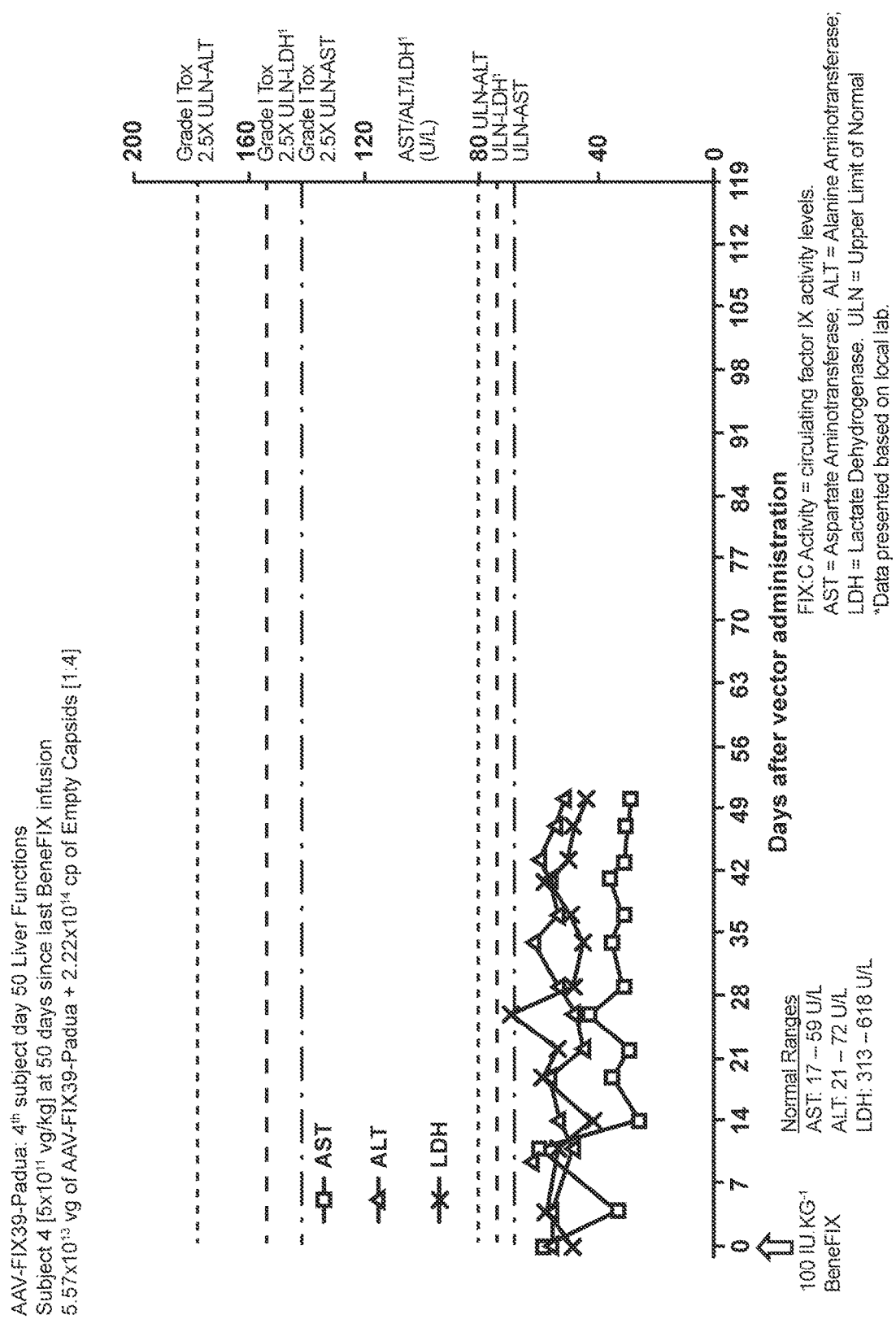
FIG. 23B shows liver function test (ALT, AST and LDH enzymes) data of the fourth human hemophilia B patient administered the single infusion of AAV-FIX Padua variant (FIX39) bearing vector, over the 50 day evaluation period. The plotted LDH values (LDH$^1$) have been divided by 10 in order to be shown with the ALT and AST values.

As summarized in FIG. 19 and shown for each individual subject in FIGS. 20, 21A, 22A and 23A, Factor IX activity gradually increased and appeared stable throughout the 183, 102, 69 and 50 day evaluation periods for all four subjects. These data indicate that a single infusion of $5\times10^{11}$ vg/kg of AAV-FIX39-Padua vector results in sufficient and sustained Factor IX production and activity to provide hemophilia B patients with meaningful and beneficial blood clotting activity to provide hemostasis.

As shown in FIGS. 19, 20A, 21A, 22A and 23A, Factor IX activity levels were at 28%, 41%, 26% and 33% of normal, for subjects 1-4 respectively, at 183, 102, 69 and 50 days after infusion. Subject #3 treated himself with an extended half-life product for a suspected ankle bleed 2 days after vector infusion; other than this there have been no factor infusions and no bleeds during the evaluation period.

Immunosuppressing agents (steroids) have not been administered to any of the subjects. In addition, in general there have been no sustained elevations of transaminases above the upper limit of normal, indicating no adverse effects of the treatment (FIGS. 20B, 21B, 22B and 23).

ELISPOTs were used to monitor T cell responses to AAV and to FIX in all four subjects and have shown no or very low responses. Of note, the time course of rise in Factor IX levels to a plateau level has been remarkably consistent to date (FIG. 19). Modest fluctuations in antigen levels lead to greater shifts in activity levels, given the 8-fold increase in specific activity of the Factor IX Padua variant.

Published data (Nathwani et al., N Engl J Med. 371(21): 1994-2004 (2014)) have shown long-term expression of Factor IX in men with hemophilia B infused with an AAV8 vector expressing wild-type Factor IX. However, levels of expression were low-ranging from 1.4%-2.2% normal at the lowest dose ($2\times10^{11}$ vector genomes [vg]/kg body weight) to 2.9-7.2% at the highest dose ($2\times10^{12}$ vg/kg). Moreover, 4/6 subjects infused at the highest dose required a course of immunosuppressant (prednisolone) to reduce rising transaminases associated with the highest dose (but not observed at lower doses of $2\times10^{11}$ or $6\times10^{11}$ vg/kg). Data from a natural history study of patients with hemophilia suggest that circulating levels of ~12% FIX are required to reduce the annual number of spontaneous joint bleeds to zero (den Uijl et al., Haemophilia 17(1):41-4 (2011)).

These are the first clinical results using a novel bioengineered AAV capsid expressing a high specific activity Factor IX transgene. The Factor IX activity levels seen in subjects 1-4 28%, 41%, 26% and 33% of normal are substantially greater circulating Factor IX levels than the those seen in prior studies, based on published data, and exceed the circulating Factor IX levels needed to reduce the annual number of spontaneous joint bleeds to zero.

Furthermore, the substantial Factor IX activity levels seen in this study were achieved with no recombinant Factor IX use since vector infusion, and without using immunosuppressing agents (steroids). These results show the development of an AAV-FIX vector that can direct high level clotting factor expression at low doses of AAV vector administration, so that immunosuppression is not required—an important goal for liver-directed gene therapy. Factor IX activity levels observed in this study have been sustained over the duration of the study period.

Example 6. Reduced Immunogenicity of AAV-FIX39-Padua Vector

For the current Phase I/II study, four subjects receiving 5e11 vg/kg of AAV-FIX39-Padua were monitored for potential immune responses against the AAV vector using a validated interferon-gamma (IFN-g) Enzyme Linked Immunospot (ELISPOT) assay. Purified PBMCs isolated from weekly blood draws were tested via interferon gamma ELISPOT assay. Six AAV capsid peptide pools, containing 24-25 peptides each were incubated with 2e5 cells in triplicate. T cell responses were detected using a biotinylated antibody against IFN-g, followed by colorimetric development and reported as spot-forming units (SFU) per million cells. The highest responding pool at each timepoint is shown as SFU/million cells. The historically used cutoff for positivity is >50 SFU and 3-fold media control (blue line). Subjects 840-003-001, 840-001-002, 840-001-004, and 840-001-005 (shown in black) have been followed as far out as weeks 26, 14, 11, and 8 respectively. ELISPOT results from a previous trial in which two subjects, CP-16 and PT17 received 1e12 vg/kg of the AAV8-FIX19 vector and one subject received 2e12 vg/kg of AAV8-FIX19, are shown in red.

Figure 24A:
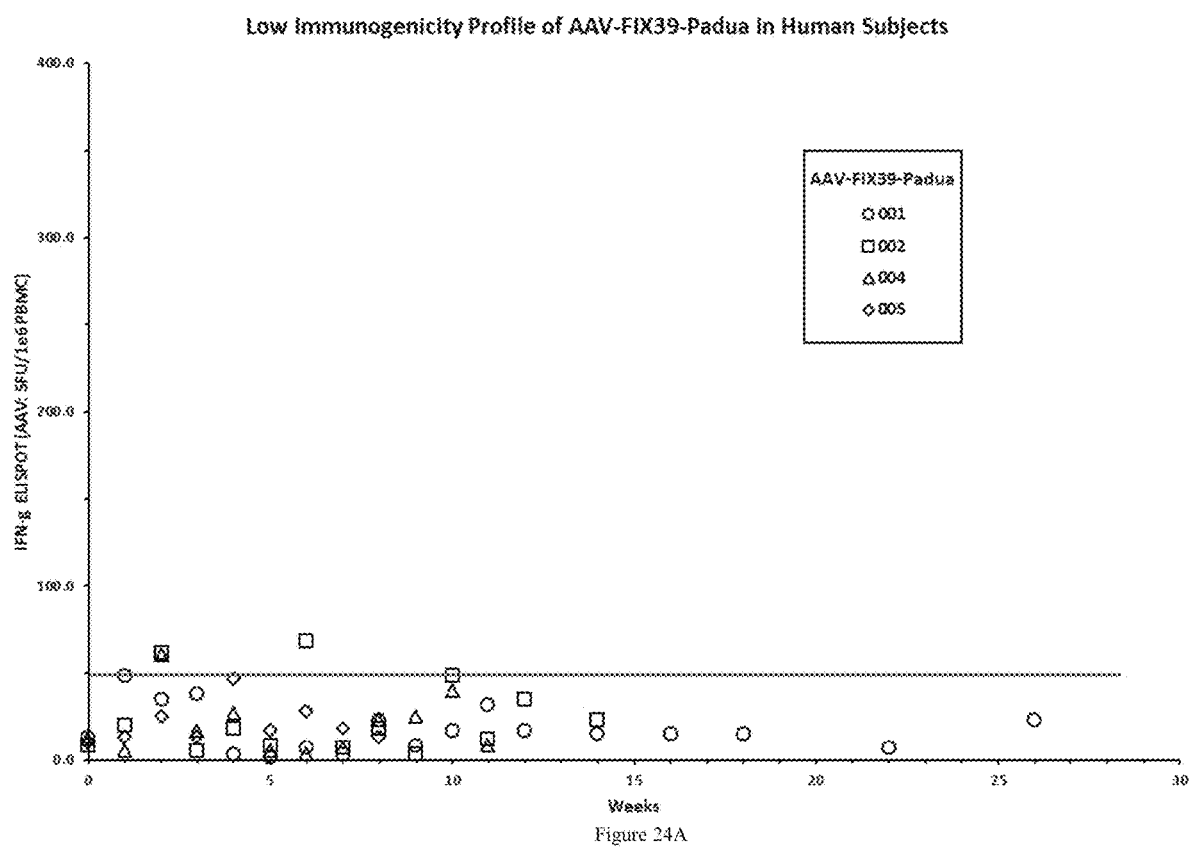
FIG. 24A shows low immunogenicity profile of AAV-FIX39-Padua in human subjects.
Figure 24B:
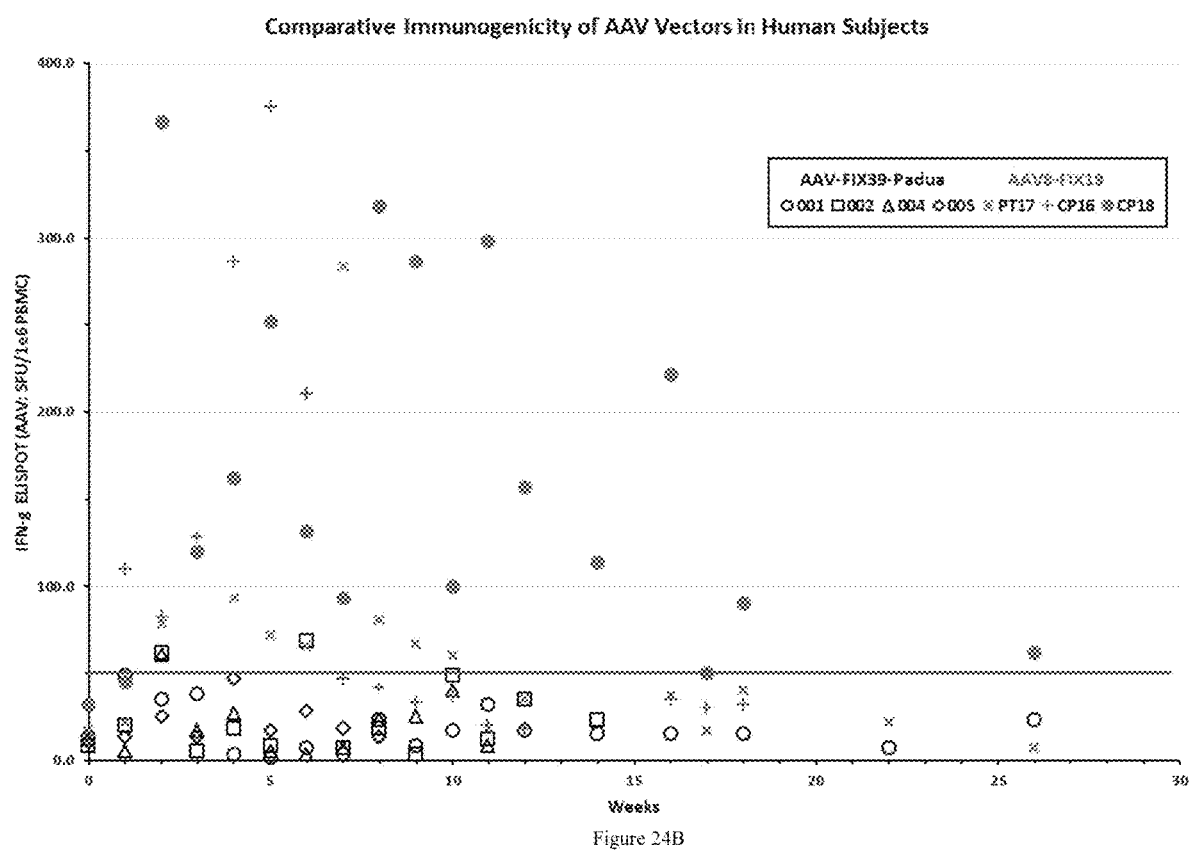
FIG. 24B shows a comparative immunogenicity profile of AAV-FIX39-Padua and AAV8-FIX19 in human subjects.

Using the historically accepted value of >50 SFU and 3-fold the background (media) control as criteria for positive T cell response, there has been very little to no response in the three subjects as far out as 26-weeks post infusion (FIG. 24A). This is in stark contrast to a previously unpublished study by our group using a codon optimized AAV8 vector to deliver the FIX transgene cassette to 3 subjects, in which robust IFN-g T cell responses were observed as early as the week 2 timepoint (FIG. 24B). Other previously published studies using AAV-2 (Manno et al., 2006 Nat Med) and AAV-8 self-complementary vectors (Nathwani et al., 2011 NEJM) have also shown evidence of early T cell responses to the AAV capsid as well. Importantly, no responses against the transgene product have been observed in this trial.

It is hypothesized that the activation of a T-cell mediated immune response against transduced hepatocytes presenting AAV capsid T cell epitopes may play a role in subjects that show short-lived and eventual loss of transgene expression. Therefore, the reduced immunogenicity profile of the AAV-FIX39-Padua vector represents a promising improvement towards overall efficacy.

```
                              SEQUENCE LISTING

Sequence total quantity: 27
SEQ ID NO: 1            moltype = AA  length = 738
FEATURE                 Location/Qualifiers
source                  1..738
                        mol_type = protein
                        organism = synthetic construct
SEQUENCE: 1
MAADGYLPDW LEDNLSEGIR EWWDLKPGAP KPKANQQKQD NGRGLVLPGY KYLGPFNGLD   60
KGEPVNAADA AALEHDKAYD QQLQAGDNPY LRYNHADAEF QERLQEDTSF GGNLGRAVFQ  120
AKKRVLEPLG LVESPVKTAP GKKRPVEPSP QRSPDSSTGI GKKGQQPAKK RLNFGQTGDS  180
ESVPDPQPIG EPPAGPSGLG SGTMAAGGGA PMADNNEGAD GVGSSSGNWH CDSTWLGDRV  240
ITTSTRTWAL PTYNNHLYKQ ISNGTSGGST NDNTYFGYST PWGYFDFNRF HCHFSPRDWQ  300
RLINNNWGFR PKRLNFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFEFSYNFED  420
VPFHSSYAHS QSLDRLMNPL IDQYLYYLSR TQSTGGTAGT QQLLFSQAGP NNMSAQAKNW  480
LPGPCYRQQR VSTTLSQNNN SNFAWTGATK YHLNGRDSLV NPGVAMATHK DDEERFFPSS  540
GVLMFGKQGA GKDNVDYSSV MLTSEEEIKT TNPVATEQYG VVADNLQQQN AAPIVGAVNS  600
QGALPGMVWQ NRDVYLQGPI WAKIPHTDGN FHPSPLMGGF GLKHPPPQIL IKNTPVPADP  660
PTTFNQAKLA SFITQYSTGQ VSVEIEWELQ KENSKRWNPE IQYTSNYYKS TNVDFAVNTE  720
GTYSEPRPIG TRYLTRNL                                                738

SEQ ID NO: 2            moltype = AA  length = 601
FEATURE                 Location/Qualifiers
source                  1..601
                        mol_type = protein
                        organism = synthetic construct
SEQUENCE: 2
TAPGKKRPVE PSPQRSPDSS TGIGKKGQQP AKKRLNFGQT GDSESVPDPQ PIGEPPAGPS   60
GLGSGTMAAG GGAPMADNNE GADGVGSSSG NWHCDSTWLG DRVITTSTRT WALPTYNNHL  120
YKQISNGTSG GSTNDNTYFG YSTPWGYFDF NRFHCHFSPR DWQRLINNNW GFRPKRLNFK  180
LFNIQVKEVT QNEGTKTIAN NLTSTIQVFT DSEYQLPYVL GSAHQGCLPP FPADVFMIPQ  240
YGYLTLNNGS QAVGRSSFYC LEYFPSQMLR TGNNFEFSYN FEDVPFHSSY AHSQSLDRLM  300
NPLIDQYLYY LSRTQSTGGT AGTQQLLFSQ AGPNNMSAQA KNWLPGPCYR QQRVSTTLSQ  360
NNNSNFAWTG ATKYHLNGRD SLVNPGVAMA THKDDEERFF PSSGVLMFGK QGAGKDNVDY  420
SSVMLTSEEE IKTTNPVATE QYGVVADNLQ QQNAAPIVGA VNSQGALPGM VWQNRDVYLQ  480
GPIWAKIPHT DGNFHPSPLM GGFGLKHPPP QILIKNTPVP ADPPTTFNQA KLASFITQYS  540
TGQVSVEIEW ELQKENSKRW NPEIQYTSNY YKSTNVDFAV NTEGTYSEPR PIGTRYLTRN  600
L                                                                  601

SEQ ID NO: 3            moltype = AA  length = 535
FEATURE                 Location/Qualifiers
source                  1..535
                        mol_type = protein
                        organism = synthetic construct
SEQUENCE: 3
MAAGGGAPMA DNNEGADGVG SSSGNWHCDS TWLGDRVITT STRTWALPTY NNHLYKQISN   60
GTSGGSTNDN TYFGYSTPWG YFDFNRFHCH FSPRDWQRLI NNNWGFRPKR LNFKLFNIQV  120
KEVTQNEGTK TIANNLTSTI QVFTDSEYQL PYVLGSAHQG CLPPFPADVF MIPQYGYLTL  180
NNGSQAVGRS SFYCLEYFPS QMLRTGNNFE FSYNFEDVPF HSSYAHSQSL DRLMNPLIDQ  240
YLYYLSRTQS TGGTAGTQQL LFSQAGPNNM SAQAKNWLPG PCYRQQRVST TLSQNNNSNF  300
AWTGATKYHL NGRDSLVNPG VAMATHKDDE ERFFPSSGVL MFGKQGAGKD NVDYSSVMLT  360
SEEEIKTTNP VATEQYGVVA DNLQQQNAAP IVGAVNSQGA LPGMVWQNRD VYLQGPIWAK  420
IPHTDGNFHP SPLMGGFGLK HPPPQILIKN TPVPADPPTT FNQAKLASFI TQYSTGQVSV  480
EIEWELQKEN SKRWNPEIQY TSNYYKSTNV DFAVNTEGTY SEPRPIGTRY LTRNL        535

SEQ ID NO: 4            moltype = AA  length = 738
FEATURE                 Location/Qualifiers
source                  1..738
                        mol_type = protein
                        organism = synthetic construct
SEQUENCE: 4
MAADGYLPDW LEDNLSEGIR EWWDLKPGAP KPKANQQKQD NGRGLVLPGY KYLGPFNGLD   60
KGEPVNAADA AALEHDKAYD QQLQAGDNPY LRYNHADAEF QERLQEDTSF GGNLGRAVFQ  120
AKKRVLEPLG LVESPVKTAP GKKRPVEPSP QRSPDSSTGI GKKGQQPAKK RLNFGQTGDS  180
ESVPDPQPIG EPPAAPSGVG PNTMAAGGGA PMADNNEGAD GVGSSSGNWH CDSTWLGDRV  240
ITTSTRTWAL PTYNNHLYKQ ISNGTSGGST NDNTYFGYST PWGYFDFNRF HCHFSPRDWQ  300
```

```
RLINNNWGFR PKRLNFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFEFSYNFED    420
VPFHSSYAHS QSLDRLMNPL IDQYLYYLSR TQSTGGTAGT QQLLFSQAGP NNMSAQAKNW    480
LPGPCYRQQR VSTTLSQNNN SNFAWTGATK YHLNGRDSLV NPGVAMATHK DDEERFFPSS    540
GVLMFGKQGA GKDNVDYSSV MLTSEEEIKT TNPVATEQYG VVADNLQQQN AAPIVGAVNS    600
QGALPGMVWQ NRDVYLQGPI WAKIPHTDGN FHPSPLMGGF GLKHPPPQIL IKNTPVPADP    660
PTTFNQAKLA SFITQYSTGQ VSVEIEWELQ KENSKRWNPE IQYTSNYYKS TNVDFAVNTE    720
GTYSEPRPIG TRYLTRNL                                                 738

SEQ ID NO: 5            moltype = AA   length = 738
FEATURE                 Location/Qualifiers
source                  1..738
                        mol_type = protein
                        organism = synthetic construct
SEQUENCE: 5
MAADGYLPDW LEDNLSEGIR EWWDLKPGAP KPKANQQRQD NGRGLVLPGY RYLGPFNGLD     60
KGEPVNAADA AALEHDRAYD QQLQAGDNPY LRYNHADAEF QERLQEDTSF GGNLGRAVFQ    120
AKKRVLEPLG LVESPVRTAP GKKRPVEPSP QRSPDSSTGI GKKGQQPARK RLNFGQTGDS    180
ESVPDPQPIG EPPAAPSGVG PNTMAAGGGA PMADNNEGAD GVGSSSGNWH CDSTWLGDRV    240
ITTSTRTWAL PTYNNHLYRQ ISNGTSGGST NDNTYFGYST PWGYFDFNRF HCHFSPRDWQ    300
RLINNNWGFR PKRLNFKLFN IQVKEVTQNE GTRTIANNLT STIQVFTDSE YQLPYVLGSA    360
HQGCLPPFPA DVFMIPQYGY LTLNNGSQAV GRSSFYCLEY FPSQMLRTGN NFEFSYNFED    420
VPFHSSYAHS QSLDRLMNPL IDQYLYYLSR TQSTGGTAGT QQLLFSQAGP NNMSAQAKNW    480
LPGPCYRQQR VSTTLSQNNN SNFAWTGATK YHLNGRDSLV NPGVAMATHR DDEERFFPSS    540
GVLMFGRQGA GRDNVDYSSV MLTSEEEIRT TNPVATEQYG VVADNLQQQN AAPIVGAVNS    600
QGALPGMVWQ NRDVYLQGPI WAKIPHTDGN FHPSPLMGGF GLKHPPPQIL IKNTPVPADP    660
PTTFNQAKLA SFITQYSTGQ VSVEIEWELQ KENSKRWNPE IQYTSNYYKS TNVDFAVNTE    720
GTYSEPRPIG TRYLTRNL                                                 738

SEQ ID NO: 6            moltype = AA   length = 738
FEATURE                 Location/Qualifiers
source                  1..738
                        mol_type = protein
                        organism = synthetic construct
SEQUENCE: 6
MAADGYLPDW LEDNLSEGIR EWWDLKPGAP KPKANQQRQD NGRGLVLPGY RYLGPFNGLD     60
KGEPVNAADA AALEHDRAYD QQLQAGDNPY LRYNHADAEF QERLQEDTSF GGNLGRAVFQ    120
AKKRVLEPLG LVESPVRTAP GKKRPVEPSP QRSPDSSTGI GKKGQQPARK RLNFGQTGDS    180
ESVPDPQPIG EPPAAPSGVG PNTMAAGGGA PMADNNEGAD GVGSSSGNWH CDSTWLGDRV    240
ITTSTRTWAL PTYNNHLYRQ ISNGTSGGST NDNTYFGYST PWGYFDFNRF HCHFSPRDWQ    300
RLINNNWGFR PKRLNFKLFN IQVKEVTQNE GTRTIANNLT STIQVFTDSE YQLPYVLGSA    360
HQGCLPPFPA DVFMIPQYGY LTLNNGSQAV GRSSFYCLEY FPSQMLRTGN NFEFSYNFED    420
VPFHSSYAHS QSLDRLMNPL IDQYLYYLSR TQSTGGTAGT QQLLFSQAGP NNMSAQAKNW    480
LPGPCYRQQR VSTTLSQNNN SNFAWTGATK YHLNGRDSLV NPGVAMATHR DDEERFFPSS    540
GVLMFGKQGA GRDNVDYSSV MLTSEEEIRT TNPVATEQYG VVADNLQQQN AAPIVGAVNS    600
QGALPGMVWQ NRDVYLQGPI WAKIPHTDGN FHPSPLMGGF GLKHPPPQIL IKNTPVPADP    660
PTTFNQAKLA SFITQYSTGQ VSVEIEWELQ KENSKRWNPE IQYTSNYYKS TNVDFAVNTE    720
GTYSEPRPIG TRYLTRNL                                                 738

SEQ ID NO: 7            moltype = AA   length = 738
FEATURE                 Location/Qualifiers
source                  1..738
                        mol_type = protein
                        organism = synthetic construct
SEQUENCE: 7
MAADGYLPDW LEDNLSEGIR EWWDLKPGAP KPKANQQRQD NGRGLVLPGY RYLGPFNGLD     60
KGEPVNAADA AALEHDRAYD QQLQAGDNPY LRYNHADAEF QERLQEDTSF GGNLGRAVFQ    120
AKKRVLEPLG LVESPVRTAP GKKRPVEPSP QRSPDSSTGI GKRGQQPAKK RLNFGQTGDS    180
ESVPDPQPIG EPPAAPSGVG PNTMAAGGGA PMADNNEGAD GVGSSSGNWH CDSTWLGDRV    240
ITTSTRTWAL PTYNNHLYRQ ISNGTSGGST NDNTYFGYST PWGYFDFNRF HCHFSPRDWQ    300
RLINNNWGFR PKRLNFKLFN IQVKEVTQNE GTRTIANNLT STIQVFTDSE YQLPYVLGSA    360
HQGCLPPFPA DVFMIPQYGY LTLNNGSQAV GRSSFYCLEY FPSQMLRTGN NFEFSYNFED    420
VPFHSSYAHS QSLDRLMNPL IDQYLYYLSR TQSTGGTAGT QQLLFSQAGP NNMSAQAKNW    480
LPGPCYRQQR VSTTLSQNNN SNFAWTGATK YHLNGRDSLV NPGVAMATHR DDEERFFPSS    540
GVLMFGRQGA GRDNVDYSSV MLTSEEEIRT TNPVATEQYG VVADNLQQQN AAPIVGAVNS    600
QGALPGMVWQ NRDVYLQGPI WAKIPHTDGN FHPSPLMGGF GLKHPPPQIL IKNTPVPADP    660
PTTFNQAKLA SFITQYSTGQ VSVEIEWELQ KENSKRWNPE IQYTSNYYKS TNVDFAVNTE    720
GTYSEPRPIG TRYLTRNL                                                 738

SEQ ID NO: 8            moltype = AA   length = 738
FEATURE                 Location/Qualifiers
source                  1..738
                        mol_type = protein
                        organism = synthetic construct
SEQUENCE: 8
MAADGYLPDW LEDNLSEGIR EWWDLKPGAP KPKANQQRQD NGRGLVLPGY RYLGPFNGLD     60
KGEPVNAADA AALEHDRAYD QQLQAGDNPY LRYNHADAEF QERLQEDTSF GGNLGRAVFQ    120
AKKRVLEPLG LVESPVRTAP GKKRPVEPSP QRSPDSSTGI GKRGQQPAKK RLNFGQTGDS    180
ESVPDPQPIG EPPAAPSGVG PNTMAAGGGA PMADNNEGAD GVGSSSGNWH CDSTWLGDRV    240
```

```
                                    -continued
ITTSTRTWAL PTYNNHLYRQ ISNGTSGGST NDNTYFGYST PWGYFDFNRF HCHFSPRDWQ    300
RLINNNWGFR PKRLNFKLFN IQVKEVTQNE GTRTIANNLT STIQVFTDSE YQLPYVLGSA    360
HQGCLPPFPA DVFMIPQYGY LTLNNGSQAV GRSSFYCLEY FPSQMLRTGN NFEFSYNFED    420
VPFHSSYAHS QSLDRLMNPL IDQYLYYLSR TQSTGGTAGT QQLLFSQAGP NNMSAQAKNW    480
LPGPCYRQQR VSTTLSQNNN SNFAWTGATK YHLNGRDSLV NPGVAMATHR DDEERFFPSS    540
GVLMFGKQGA GRDNVDYSSV MLTSEEEIRT TNPVATEQYG VVADNLQQQN AAPIVGAVNS    600
QGALPGMVWQ NRDVYLQGPI WAKIPHTDGN FHPSPLMGGF GLKHPPPQIL IKNTPVPADP    660
PTTFNQARLA SFITQYSTGQ VSVEIEWELQ KENSKRWNPE IQYTSNYYKS TNVDFAVNTE    720
GTYSEPRPIG TRYLTRNL                                                  738

SEQ ID NO: 9            moltype = AA  length = 738
FEATURE                 Location/Qualifiers
source                  1..738
                        mol_type = protein
                        organism = synthetic construct
SEQUENCE: 9
MAADGYLPDW LEDNLSEGIR EWWDLKPGAP KPKANQQRQD NGRGLVLPGY RYLGPFNGLD     60
KGEPVNAADA AALEHDRAYD QQLQAGDNPY LRYNHADAEF QERLQEDTSF GGNLGRAVFQ    120
AKKRVLEPLG LVESPVRTAP GKKRPVEPSP QRSPDSSTGI GKKGQQPAKK RLNFGQTGDS    180
ESVPDPQPIG EPPAAPSGVG PNTMAAGGGA PMADNNEGAD GVGSSSGNWH CDSTWLGDRV    240
ITTSTRTWAL PTYNNHLYRQ ISNGTSGGST NDNTYFGYST PWGYFDFNRF HCHFSPRDWQ    300
RLINNNWGFR PKRLNFKLFN IQVKEVTQNE GTRTIANNLT STIQVFTDSE YQLPYVLGSA    360
HQGCLPPFPA DVFMIPQYGY LTLNNGSQAV GRSSFYCLEY FPSQMLRTGN NFEFSYNFED    420
VPFHSSYAHS QSLDRLMNPL IDQYLYYLSR TQSTGGTAGT QQLLFSQAGP NNMSAQAKNW    480
LPGPCYRQQR VSTTLSQNNN SNFAWTGATK YHLNGRDSLV NPGVAMATHR DDEERFFPSS    540
GVLMFGKQGA GRDNVDYSSV MLTSEEEIRT TNPVATEQYG VVADNLQQQN AAPIVGAVNS    600
QGALPGMVWQ NRDVYLQGPI WAKIPHTDGN FHPSPLMGGF GLKHPPPQIL IKNTPVPADP    660
PTTFNQARLA SFITQYSTGQ VSVEIEWELQ KENSKRWNPE IQYTSNYYKS TNVDFAVNTE    720
GTYSEPRPIG TRYLTRNL                                                  738

SEQ ID NO: 10           moltype = DNA  length = 1386
FEATURE                 Location/Qualifiers
source                  1..1386
                        mol_type = other DNA
                        organism = synthetic construct
SEQUENCE: 10
atgcagaggg tgaacatgat catggctgag agccctggcc tgatcaccat ctgcctgctg     60
ggctacctgc tgtctgctga atgtacagtt tttcttgatc atgaaaatgc caacaaaatt    120
ctgaatagac caaagaggta taactctggc aagcttgaaa agtttgtaca ggggaactg    180
gagagagagt gtatgaagaa gaagtgcagc tttgaggaag ccagagaagt gtttgaaaat    240
acagagagaa caactgaatt ttggaagcag tatgtggatg gtgatcaatg tgagagcaat    300
ccctgcctga atgggggag ctgtaaagat gatatcaaca gctatgaatg ttggtgtccc    360
tttggatttg aggggaaaaa ctgtgagctt gatgtgacct gtaatatcaa gaatggctgg    420
tgtgagcaat tttgcaagaa ttctgctgat aacaaagtgg tctgtagctg cactgaggga    480
tataggctgg ctgaaaacca gaagagctgt gaacctgcag tgcctttcc ctgtgggaga    540
gtgtctgtga gccaaaccag caagctgact agggctgaag cagtctttcc tgatgtagat    600
tatgtgaata gcactgaggc tgagacaatc cttgacaatc tcactcagag cacacagagc    660
ttcaatgact tcaccagggt ggtaggaggg aggatgcca agcctgggca gttcccctgg    720
caggtagtgc tcaatggaaa agtggatgcc ttttgtggag gttcaattgt aaatgagaag    780
tggattgtga ctgcagccca ctgtgtgaa actgagtca agattactgt ggtggctgga    840
gagcacaata ttgaggaaac tgagcacact gagcagaaga gaaatgtgat caggattatc    900
ccccaccaca actacaatgc tgctatcaac aagtacaacc atgacattgc cctcctggaa    960
ctggatgaac ccctggtctt gaacagctat gtgacaccca tctgtattgc tgataaagag   1020
tacaccaaca tctttctgaa atttgggtct ggatatgtgt ctggctgggg cagggtgttc   1080
cataaaggca ggtctgccct ggtattgcag tatttggtg tgcctctgga ggatagagca   1140
acctgcttgc tgagcaccaa gtttacaatc tacaacaata tgttctgtgc agggttccat   1200
gaaggtggta gagacagctg ccagggagat tctgggggtc cccatgtgac tgaggtggag   1260
ggaaccagct cctgactgg gattatcagc tgggtgagg agtgtgctat gaagggaaag   1320
tatgggatct acacaaagt atccagatat gtgaactgga ttaaggagaa aaccaagctg   1380
acttga                                                              1386

SEQ ID NO: 11           moltype = DNA  length = 1386
FEATURE                 Location/Qualifiers
source                  1..1386
                        mol_type = other DNA
                        organism = synthetic construct
SEQUENCE: 11
atgcagcgcg tgaacatgat catggccgag agccctggcc tgattaccat ctgcctgtta     60
ggatatctac tcagtgctga atgtacagtt tttcttgatc atgaaaacgc caacaaaatc    120
ctgaaccggc ccaagcggta caactcaggc aagctggaag agttcgtgca gggcaacctg    180
gaacgggagt gcatggaaga gaagtgcagc ttcgaggaag cccgggaggt gttcgagaac    240
accgagcgga ccaccgagtt ctggaagcag tacgtggacg gcgaccagtg cgagtcaaac    300
ccctgcctga acggcggcag ctgcaaggac gatatcaaca gctacgagtg ctggtgcccc    360
ttcggcttcg agggcaagaa ctgcgagctg gacgtgacct gcaacatcaa gaatggctgg    420
tgcgagcagt tctgcaagaa cagcgccgac aacaaggtgg tgtctcatg cactgagggc    480
taccggctgg ccgagaacca gaagagctgt gagcccgccg tgcctttcc ctgcggcaga    540
gtgtccgtga gccagaccag caagctgacc agggccgagg ccgtgttccc tgacgtggac    600
tacgtgaact caaccgaggc cgagacaatc ctggacaaca tcacccagag cacccagtcc    660
ttcaacgact tcaccgggt ggtggccgga gaagacgcca gcccggcca gttccctgg    720
```

```
caggtggtgc tgaacggcaa ggtggacgcc ttctgcggcg gctcaatcgt gaacgagaag    780
tggatcgtga cagccgccca ctgcgtggag acaggcgtga agatcaccgt ggtggccggc    840
gaacacaata tcgaggaaac cgagcacacc gagcagaaac ggaacgtgat ccggattatc    900
ccccaccaca actacaacgc cgccatcaac aagtacaacc acgatatcgc cctgctgaa    960
ctggacgagc ctctggtgct gaattctac gtgaccccca tctgtatcgc cgacaaagag   1020
tacaccaaca tctttctgaa gttcggcagc ggctacgtgt ccggctgggg cagggtgttc   1080
cacaagggcc gcagcgccct ggtgctgcag tacctgcggg tgcccctggt ggacagagcc   1140
acctgcctgc ggtcaaccaa gttcaccatc tacaacaaca tgttctgcgc cggcttccac   1200
gagggcggca gggacagctg ccagggcgac agcggcggac cccacgtgac cgaggtggag   1260
ggcaccagct ttctgaccgg catcatctca tggggcgagg aatgcgccat gaagggcaag   1320
tacgaatct acactaaggt gtcaagatac gtgaactgga tcaaagagaa aaccaagctg   1380
acctga                                                              1386

SEQ ID NO: 12         moltype = DNA   length = 11125
FEATURE               Location/Qualifiers
source                1..11125
                      mol_type = other DNA
                      organism = synthetic construct
SEQUENCE: 12
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccttag taggctcaga gcacacagg agtttctggg    180
ctcaccctgc ccccttccaa cccctcagtt cccatcctcc agcagctgtt tgtgtgctgc    240
ctctgaagtc cacactgaac aaacttcagc tactcatgt ccctaaaatg gcaaacatt     300
gcaagcagca aacagcaaac acacagccct ccctgcctgc tgaccttgga gctggggcag    360
aggtcagaga cctctctggg cccatgccaa ctccaacatc cactcgaccc cttgaattt    420
cggtggagag gagcagaggt tgtcctggcg tggtttaggt agtgtgagag gggtaccgg    480
ggatcttgct accagtggaa cagccactaa ggattctgca gtgagagcag agggccagct    540
aagtggtact ctcccagaga ctgtctgact cacgccaccc cctccacctt ggacacagga    600
cgctgtggtt tctgagccag gtacaatgac tcctttcggt aagtgcagtg gaagctgtac    660
actgccagg caaagcgtcc gggcagcgta ggcgggcgac tcagatccca gccagtggac    720
ttagcccctg tttgctcctc cgataactgg ggtgaccttg gttaatattc accagcagcc    780
tccccgttg ccctctgga tccactgctt aaatacggac gaggacaggg ccctgtctcc    840
tcagcttcag gcaccaccac tgacctggga cagtgaatac cactttcaca atctgctagc    900
aaaggttatg cagagggtga acatgatcat ggctgagagc cctggcctga tcaccatctg    960
cctgctgggc tacctgctgt ctgctgaatg tacaggtttg ttttcctttt tataatacat   1020
tgagtatgct tgccttttag atatagaaat atctgattct gtcttcttca ctaaattttg   1080
attacatgat ttgacagcaa tattgaagag tctaacagcc agcaccagg ttggtaagta    1140
ctggttctttt gttagtagg tttcttctt cttcactttt aaaactaaat agatggacaa   1200
tgcttatgat gcaataaggt ttaataaaca ctgttcagtt cagtatttgg tcatgtaatt   1260
cctgttaaaa aacagtcatc tccttggttt aaaaaaatta aaagtgggaa aacaaagaaa   1320
tagcagaata tagtgaaaaa aaataaccac agtatttttg tttggactta ccactttgaa   1380
atcaaattgg gaaacaaaag cacaaacagt ggccttattt acacaaaaag tctgatttta   1440
agatatgtga caattcaagg tttcagaagt atgtaaggag gtgtgtctct aatttttaa    1500
attatatatc ttcaattaa agttttagtt aaaaacataaa gattaacctt tcattagcaa   1560
gctgttagtt atcaccaaag cttttcatgg attaggaaaa aatcattttg tctctatctc   1620
aaacatcttg gagttgatat ttggggaaac acaatactca gttgagttcc ctaggggaga   1680
aaagcaagct taagaattga cacaaagagt aggaagttag ctattgcaac atatatcact   1740
ttgttttttc acaactacag tgactttatt tatttcccag aggaaggcat acagggaaga   1800
aattatccca tttggacaaa cagcatgttc tcacagtaag cacttatcac acttacttgt   1860
caacttttca gaatcaaatc tagtagctga cagtaccagg atcaggggtg caaccctaa   1920
gcaccccag aaagctgact ggccctgtgg ttcccactcc agacatgatg tcagctgtga   1980
aatccacctc cctggaccat aattaggctt ctgttcttca ggagacattt gttcaaagtc   2040
atttgggcaa ccatattctg aaaacagccc agccagggtg atggatcact ttgcaaagat   2100
cctcaatgag ctattttcaa gtgatgacaa agtgtgaagt taagggctca tttgagaact   2160
ttctttttca tccaaagtaa attcaaatat gattagaaat ctgaccttttt attactgaa    2220
ttctcttgac taaaagtaaa attgaatttt aattcctaaa tctccatgtg tatacagtac   2280
tgtgggaaca tcacagattt tggctccatg ccctaaagag aaattggctt tcagattatt   2340
tggattaaaa acaaagactt tcttaagaga tgtaaaattt tcatgatgtt ttcttttttg   2400
ctaaaactaa agaattattc tttacatttt cagttttttct tgatcatgaa aatgccaaca   2460
aaattctgaa tagaccaaag aggtataact ctggcaagct tgaagagttt gtacagggaa   2520
atctggagag agagtgtatg gaagagaagt gcagctttga ggaagccaga gaagtgtttg   2580
aaaatacaga gagaacaact gaattttgga agcagtatgt ggatggtgat caatgtgaga   2640
gcaatccctg cttgaatggg gggagctgta aagatgcat caacagctat gaatgttgat   2700
gtcccttgg atttgagggg aaaaactgtg agcttgatgt gacctgtaat atcaagaatg   2760
gcaggtgtga gcaattttgc aagaattctg ctgataacaa agtggtctgt agctgcactg   2820
agggatatag gctggctgaa aaccagaaga gctgtgaacc tgcagtgcct tttccctgtg   2880
ggagagtgtc tgtgagccaa accagcaagc tgactagggc tgaagcagtc tttcctgatg   2940
tagattatgt gaatagcact gaggctgaga atcctggaca caatatcact cagagcacac   3000
agagcttcaa tgacttcacc agggtggtag aggggagga tgccaagcct gggcagttcc   3060
cctgcaggt agtgctcaat ggaaaagtgg atgccttttg tggaggttca attgtaaatg   3120
agaagtggat tgtgactgca gcccactgtg tggaaactgg agtcaagatt actgtggtgg   3180
ctggagagca caatattgag gaaactgagc acactgagca gaagaggaat gtgatcagga   3240
ttatccccca ccacaactac aatgctgcta tcaacaagta caactccctg gcccttgatt   3300
tggaactgga tgaaccctg gtcttgaaca gctatgtgac acccatcgtt attgctgata   3360
aagagtacac caacatcttc ttgaaatttg ggtctggata tgtgtctggc tggggcaggg   3420
tgttccataa aggcaggtct gccctggtat tgcagtattt gagggtgcct ctggtggata   3480
gagcaaacctg cttgctgagc accaagttta caatctacaa caatatgttc tgtgcagggt   3540
tccatgaagg tggtagagac agctgccagg gagattctg gggtccccat gtgactgagg   3600
```

```
tggagggaac cagcttcctg actgggatta tcagctgggg tgaggagtgt gctatgaagg   3660
gaaagtatgg gatctacaca aaagtatcca gatatgtgaa ctggattaag gagaaaacca   3720
agctgacttg atgaaagatg gatttccaag gttaattcat tggaattgaa aattaacaga   3780
gatctagagc tgaattcctg cagccagggg gatcagcctc tactgtgcct tctagttgcc   3840
agccatctgt tgtttgcccc tcccccttgc cttccttgac cctggaaggt gccactccca   3900
ctgtcctttc ctaataaaat gaggaaattg catcacattg tctgagtagg tgtcattcta   3960
ttctgggggg tggggtgggg caggacagca agggggagga ttgggaagac aatagcaggc   4020
atgctgggga tgcagtgggc tctatggctt ctgaggcaga agaaccagc tggggctcga   4080
gatccactag ggccgcagga acccctagtg atggagttgg ccactccctc tctgcgcgct   4140
cgctcgctca ctgaggccgc ccgggctttg cccgggcggc ctcagtgagc gagcgagcgc   4200
gcagctgcct gcaggggcag cttgaaggaa atactaaggc aaaggtactg caagtgctcg   4260
caacattcgc ttatgcggat tattgccgta gtgccgcgac gccggggca agatgcagag   4320
attgccatgg tacaggccgt gcggttgata ttgccaaaac agagctgtgg gggagagttg   4380
tcgagaaaga gtgcggaaga tgcaaaggcg tcggctattc aaggatgcca gcaagcgcga   4440
catatcgcgc tgtgacgatg ctaatcccaa accttaccca acccacctgg tcacgcactg   4500
ttaagccgct gtatgacgct ctggtggtgc aatgccacaa agaagagtca atcgcagaca   4560
acattttgaa tgcggtcaca cgttagcagc atgattgcca cggatggcaa catattaacg   4620
gcatgatatt gacttattga ataaaattgg gtaaatttga ctcaacgatg ggttaattcg   4680
ctcgttgtgg tagtgagatg aaaagaggcg gcgcttacta ccgattccgc ctagttggtc   4740
acttcgacgt atcgtctgga actccaacca tcgcaggcag agaggtctgc aaaatgcaat   4800
cccgaaacag ttcgcaggta atagttagag cctgcataac ggtttcggga tttttttatat  4860
ctgcacaaca ggtaagagca ttgagtcgat aatcgtgaag agtcggcgag cctggttagc   4920
cagtgctctt tccgttgtgc tgaattaagc gaataccgaa agcagaaccg gatcaccaaa   4980
tgcgtacagg cgtcatcgcc gcccagcaac agcacaaccc aaactgagcc gtagccactg   5040
tctgtcctga attcattagt aatagttacg ctgcggcctt ttacacatga ccttcgtgaa   5100
agcgggtggc aggaggtcgc gctaacaacc tcctgccgtt ttgcccgtgc atatcggtca   5160
cgaacaaatc tgattactaa acacagtagc ctggatttgt tctatcagta atcgacctta   5220
ttcctaatta aatagagcaa atcccctta tgggggtaag acatgaagat gccagaaaaa   5280
catgacctgt tggccgccat tctcgcggca aaggaacaag gcatcgggc aatccttgcg   5340
tttgcaatgg cgtaccttcg cggcagatat aatggcgtg cgtttacaaa aacagtaatc   5400
gacgcaacga tgtgcgccat tatcgcctag ttcattcgtg accttctcga cttcgccgga   5460
ctaagtagca atctcgctta tataacgagc gtgtttatcg gctacatcgg tactgactcg   5520
attggttcgc ttatcaaacg cttcgctgct aaaaaagccg gagtagaaga tggtagaaat   5580
caataatcaa cgtaaggcgt tcctcgatat gctggcgtgg tcggagggaa ctgataacgg   5640
acgtcagaaa accagaaatc atggttatga cgtcattgta ggcggagagc tatttactga   5700
ttactccgat caccctcgca aacttgtcac gctaaaccca aaactcaaat caacaggcgc   5760
cggacgctac cagcttcttt cccgttggtg ggatgcctac cgcaagcagc ttggcctgaa   5820
agacttctct ccgaaaagtc aggacgctgt ggcattgcag cagattaagg agcgtggcgc   5880
tttacctatg attgatcgtg gtgatatccg tcaggcagac gaccgttgca gcaatatctg   5940
ggcttcactg ccgggcgctg gttatgtgca gttcgagcat aaggctgaca gcctgattgc   6000
aaaattcaaa gaagcgggcg gaacggtcag agagattgat gtatgagcag agtcaccgcg   6060
attatctccg ctctggttat ctgcatcatc gtctgcctgt catgggctgt taatcattac   6120
cgtgataacg ccattaccta caaagcccaa cgcgacaaaa ctgcagaga actgaagctg   6180
gcgaacgcgg caattactga catgcagatg cgtcagcgtg atgttgctgc ctcgatgca   6240
aaatacgca aggagttagc tgatgctaaa gctgaaatg atgctctgcg tgatgatgtt   6300
gccgctggtc gtcgtcggtt gcacatcaaa gcagtctgtc agtcagtgcg tgaagccacc   6360
accgcctccg gcgtggataa tgcagcctcc ccccgactgg cagacaccgc tgaacgggat   6420
tatttcaccc tcagagagag gctgatcact atgcaaaaac aactggaagg aacccagaag   6480
tatattaatg agcagtgcag atagagttgc ccatatcgat gggcaactca tgcaattatt   6540
gtgagcaata cacacgcgct tccagcgag tataaatgcc taaagtaata aaaccgagca   6600
atccatttac gaatgtttgc tgggtttctg ttttaacaac attttctgcg ccgccacaaa   6660
ttttggctgc atcgacagtt ttcttctgcc caattccaga aacgaagaaa tgatgggtga   6720
tggtttcctt tggtgctact gctgccggtt tgttttgaac agtaaacgtc tgttgagcac   6780
atcctgtaat aagcagggcc agcgcagtag cgagtagcat tttttttcatg tgttattcc   6840
cgatgctttt tgaagttcgc agaatcgtat gtgtagaaaa ttaaacaaac cctaaacaat   6900
gagttgaaat ttcatattgt taatatttat taatgtatgt caggtgcgat gaatcgtcat   6960
tgtattcccg gattaactat gtccacagcc ctgacgggga acttctctgc gggagtgtcc   7020
gggaataatt aaaacgatgc acacagggtt tagcgcgtac acgtattgca ttatgccaac   7080
gccccggtgc tgacacggaa gaaaccggac gttatgattt agcgtggaaa gatttgtgta   7140
gtgttctgaa tgctctcagt aaatagtaat gaattatcaa aggtatagta atatctttta   7200
tgttcatgga tatttgtaac ccatcggaaa actcctgctt tagcaagatt ttccctgtat   7260
tgctgaaatg tgatttctct tgatttcaac ctatcatagg acgtttctat aagatgcgtg   7320
tttcttgaga atttaacatt tacaaccttt ttaagtcctt ttattaacac ggtgttatcg   7380
ttttctaaca cgatgtgaat attatctgtg gctagatagt aaatataatg tgagacgttg   7440
tgacgtttta gttcagaata aaacaattca cagtctaaat cttttcgcac ttgatcgaat   7500
atttctttaa aaatggcaac ctgagccatt ggtaaaacct tccatgtgat acgagggcgc   7560
gtagtttgca ttatcgtttt tatcgtttca atctggtctg acctccttgt gttttgttga   7620
tgatttatgt caaatattag gaatgttttc acttaatagt attggttgcg taacaaagtg   7680
cggtcctgtc ggcattctgg agggaaatac aaccgacaga tgtatgtaag gccaacgtg    7740
tcaaatcttc atacagaaag atttgaagta atattttaac cgctagatga agagcaagcg   7800
catggagcga caaaatgaat aaagaacaat ctgctgatga tccctccgtg gatctgattc   7860
gtgtaaaaaa tatgcttaat agcaccattt ctatgagtta ccctgatgtt gtaattgcat   7920
gtatagaaca taaggtgtct ctggaagcat tcagagcaat tgaggcagcg ttggtgaagc   7980
acgataataa tatgaaggat tattccctgg tggttgactg atcaccataa ctgctaatca   8040
ttcaaactat ttagtctgtg acagagccaa cacgcagtcg gtcactgtca ggaaagtggt   8100
aaaactgcaa ctcaattact gcaatgccct cgtaattaag tgaatttaca atatcgtcct   8160
gttcggaggg aagaacgcgg gatgttcatt cttcatcact tttaattgat gtatatgctc   8220
tcttttctga cgttagtctc cgacggcagg cttcaatgac ccaggctgag aaattcccgg   8280
acccttttg ctcaagagcg atgttaattt gttcaatcat ttggttagga aagcggatgt   8340
```

```
tgcgggttgt tgttctgcgg gttctgttct tcgttgacat gaggttgccc cgtattcagt   8400
gtcgctgatt tgtattgtct gaagttgttt ttacgttaag ttgatgcaga tcaattaata   8460
cgatacctgc gtcataattg attatttgac gtggtttgat ggcctccacg cacgttgtga   8520
tatgtagatg ataatcatta tcactttacg ggtcctttcc ggtgatccga caggttacgg   8580
ggcgcgacc tgcctgatgc ggtattttct ccttacgcat ctgtgcggta tttcacaccg    8640
catacgtcaa agcaaccata gtacgcgccc tgtagcggcg cattaagcgc ggcgggtgtg   8700
gtggttacgc gcagcgtgac cgctacactt gccagcgcct tagcgcccgc tcctttcgct   8760
ttcttcccttt cctttctcgc cacgttcgcc ggctttcccc gtcaagctct aaatcggggg  8820
ctcccttag ggttccgatt tagtgcttta cggcaccctcg accccaaaaa acttgatttg   8880
ggtgatggtt cacgtagtgg gccatcgccc tgatagacgg ttttttcgccc tttgacgttg  8940
gagtccacgt tctttaatag tggactcttg ttccaaactg gaacaacact caactctatc   9000
tcgggctatt cttttgattt agacctgcag gcatgcaagc ttggcactgg ccgtcgtttt   9060
acaacgtcgt gactgggaaa accctggcgt tacccaactt aatcgccttg cagcacatcc   9120
cccttttcgcc agctggcgta atagcgaaga ggcccgcacc gatcgccctt cccaacagtt   9180
gcgcagcctg aatggcgaat gcgatttatt caacaaagcc gccgtcccgt caagtcagcg   9240
taatgctctg ccagtgttac aaccaattaa ccaattctga ttagaaaaac tcatcgagca   9300
tcaaatgaaa ctgcaattta ttcatatcag gattatcaat accatatttt tgaaaaagcc   9360
gtttctgtaa tgaaggagaa aactcaccga ggcagttcca taggatgcaa gatcctggt   9420
atcggtctgc gattccgact cgtccaacat caatacaacc tattaatttc ccctcgtcaa   9480
aaataaggtt atcaagtgag aaatcaccat gagtgacgac tgaatccggt gagaatggca   9540
aaagcttatg catttctttc cagacttgtt caacaggcca gccattacgc tcgtcatcaa   9600
aatcactcgc atcaaccaaa ccgttattca ttcgtgattg cgcctgagcg agacgaaata   9660
cgcgatcgct gttaaaagga caattacaaa caggaatcga atgcaaccgg cgcaggaaca   9720
ctgccagcgc atcaacaata ttttcacctg aatcaggata ttcttctaat acctggaatg   9780
ctgtttttccc ggggatcgca gtggtgagta accatgcatc atcaggagta cggataaaat   9840
gcttgatggt cggaagaggc ataaaattccg tcagccagtt tagtctgacc atctcatctg   9900
taacatcatt ggcaacgcta cctttgccat gtttcagaaa caactctggc gcatcgggct   9960
tcccatacaa tcgatagatt gtcgcacctg attgcccgac attatcgcga gcccatttat  10020
acccatataa atcagcatcc atgttggaat ttaatcgcgg cttcgagcaa gacgtttccc  10080
gttgaatatg gctcataaca cccccttgtat tactgtttat gtaagcagac agttttattg  10140
ttcatgatga tatattttta tcttgtgcaa tgtaacatca gagattttga gacacaacgt   10200
ggctttgttg aataaatcga acttttgctg agttgaagga tcagatcacg catcttcccg   10260
acaacgcaga ccgttccgtg gcaaagcaaa agttcaaaat caccaactgg tccacctaca   10320
acaaagctct catcaaccgt ggctccctca cttttctggc tggatgatggg gcgattcagg  10380
cctggtatga gtcagcaaca ccttcttcac gaggcagacc tctcgacgga gttccactga  10440
gcgtcagacc ccgtagaaaa gatcaaagga tcttcttgag atcctttttt tctgcgcgta  10500
atctgctgct tgcaaacaaa aaaaccaccg ctaccagcgg tggtttgttt gccggatcaa  10560
gagctaccaa ctctttttcc gaaggtaact ggcttcagca gagcgcagat accaaatact  10620
gttcttctag tgtagccgta gttaggccac cacttcaaga actctgtagc accgcctaca  10680
tacctcgctc tgctaatcct gttaccagtg gctgctgcca gtggcgataa gtcgtgtctt  10740
accgggttgg actcaagacg atagttaccg gataagcgc agcggtcggg ctgaacgggg  10800
ggttcgtgca cacagcccag cttggagcga acgacctaca ccgaactgag atacctacag  10860
gcgtgagcta tgagaaagcg ccacgcttcc cgaagggaga aaggcggaca ggtatccggt  10920
aagcggcaggg tcggaacagg agagcgcacg agggagcttc caggggaaa cgcctggtat  10980
ctttatagtc ctgtcgggtt tcgccacctc tgacttgagc gtcgatttt tgtgatgctcg  11040
tcagggggc ggagcctatg gaaaaacgcc agcaacgcgg cctttttacg gttcctggcc   11100
ttttgctggc cttttgctca catgt                                         11125

SEQ ID NO: 13         moltype = DNA   length = 141
FEATURE               Location/Qualifiers
source                1..141
                      mol_type = other DNA
                      organism = synthetic construct
SEQUENCE: 13
cctgcaggca gctgcgcgct cgctcgctca ctgaggccgc ccgggcaaag cccgggcgtc   60
gggcgacctt tggtcgcccg gcctcagtga gcgagcgagc gcgcagagag ggagtggcca   120
actccatcac tagggggttcc t                                            141

SEQ ID NO: 14         moltype = DNA   length = 321
FEATURE               Location/Qualifiers
source                1..321
                      mol_type = other DNA
                      organism = synthetic construct
SEQUENCE: 14
aggctcagag gcacacagga gtttctgggc tcaccctgcc cccttccaac ccctcagttc   60
ccatcctcca gcagctgttt gtgtgctgcc tctgaagtcc acactgaaca aacttcagcc   120
tactcatgtc cctaaaatgg gcaaacattg caagcagcaa acagcaaaca cacagccctc   180
cctgcctgct gaccttggag ctggggcaga ggtcagagac ctctctgggc ccatgccacc   240
tccaacatcc actcgacccc ttggaatttc ggtggagagg agcagaggtt gtcctggcgt   300
ggtttaggta gtgtgagagg g                                             321

SEQ ID NO: 15         moltype = DNA   length = 397
FEATURE               Location/Qualifiers
source                1..397
                      mol_type = other DNA
                      organism = synthetic construct
SEQUENCE: 15
gatcttgcta ccagtggaac agccactaag gattctgcag tgagagcaga gggccagcta   60
agtggtactc tcccagagac tgtctgactc acgccacccc ctccaccttg gacacaggac  120
```

```
gctgtggttt ctgagccagg tacaatgact cctttcggta agtgcagtgg aagctgtaca    180
ctgcccaggc aaagcgtccg ggcagcgtag gcgggcgact cagatcccag ccagtggact    240
tagcccctgt ttgctcctcc gataactggg gtgaccttgg ttaatattca ccagcagcct    300
cccccgttgc ccctctggat ccactgctta aatacgacg aggacagggc cctgtctcct     360
cagcttcagg caccaccact gacctgggac agtgaat                              397

SEQ ID NO: 16           moltype = DNA   length = 29
FEATURE                 Location/Qualifiers
source                  1..29
                        mol_type = other DNA
                        organism = synthetic construct
SEQUENCE: 16
accactttca caatctgcta gcaaaggtt                                       29

SEQ ID NO: 17           moltype = DNA   length = 1438
FEATURE                 Location/Qualifiers
source                  1..1438
                        mol_type = other DNA
                        organism = synthetic construct
SEQUENCE: 17
gtttgtttcc tttttataa tacattgagt atgcttgcct tttagatata gaaatatctg      60
attctgtctt cttcactaaa ttttgattac atgatttgac agcaatattg aagagtctaa    120
cagccagcac ccaggttggt aagtactggt tctttgttag ctaggttttc ttcttcttca    180
cttttaaaac taaatagatg gacaatgctt atgatgcaat aaggtttaat aaacactgtt    240
cagttcagta tttggtcatg taattcctgt taaaaacag tcatctcctt ggtttaaaaa     300
aattaaaagt gggaaaacaa agaaatagca gaatatatgt aaaaaaaata accacagtat   360
ttttgtttgg acttaccact ttgaaatcaa attgggaaac aaaagcacaa acagtggcct    420
tatttacaca aaaagtctga ttttaagata tgtgacaatt caaggtttca gaagtatgta    480
aggaggtgtg tctctaattt tttaaattat atatcttcaa tttaaagttt tagttaaaac    540
ataaagatta acctttcatt agcaagctgt tagttatcac caaagctttt catggattag    600
gaaaaaatca ttttgtctct atctcaaaca tcttggagtt gatatttggg gaaacacaat    660
actcagttga gttccctagg ggagaaaagc aagcttaaga attgacacaa agagtaggaa    720
gttagctatt gcaacatata tcactttgtt ttttcacaac tacagtgact ttatttattt    780
cccagaggaa ggcatacagg gaagaaatta tcccatttgg acaaacagca tgttctcaca    840
gtaagcactt atcacactta cttgtcaact ttctagaatc aaatctagta gctgacagta    900
ccaggatcag gggtgccaac cctaagcacc ccagaaagc tgactggccc tgtggttccc     960
actccagaca tgatgtcagc tgtgaaatcc acctccctgg accataatta ggcttctgtt   1020
cttcaggaga catttgttca aagtcatttg ggcaaccata ttctgaaaac agcccagcca   1080
gggtgatgga tcactttgca aagatcctca atgagctatt ttcaagtgat gacaaagtgt   1140
gaagttaagg gctcatttga aactttctt tttcatccaa agtaaattca aatatgatta    1200
gaaatctgac cttttattac tggaattctc ttgactaaaa gtaaaattga attttaattc   1260
ctaaatctcc atgtgtatac agtactgtgg gaacatcaca gattttggct ccatgcccta   1320
aagagaaatt ggctttcaga ttattggat taaaaacaaa gacttttctta agagatgtaa   1380
aattttcatg atgttttctt ttttgctaaa actaaagaat tattcttta catttcag     1438

SEQ ID NO: 18           moltype = DNA   length = 48
FEATURE                 Location/Qualifiers
source                  1..48
                        mol_type = other DNA
                        organism = synthetic construct
SEQUENCE: 18
tgaaagatgg atttccaagg ttaattcatt ggaattgaaa attaacag                  48

SEQ ID NO: 19           moltype = DNA   length = 228
FEATURE                 Location/Qualifiers
source                  1..228
                        mol_type = other DNA
                        organism = synthetic construct
SEQUENCE: 19
ctactgtgcc ttctagttgc cagccatctg ttgtttgccc ctcccccttg ccttccttga     60
ccctggaagg tgccactccc actgtccttt cctaataaaa tgaggaaatt gcatcacatt    120
gtctgagtag gtgtcattct attctggggg gtggggtggg gcaggacagc aagggggagg    180
attgggaaga caatagcagg catgctgggg atgcagtggg ctctatgg                 228

SEQ ID NO: 20           moltype = DNA   length = 108
FEATURE                 Location/Qualifiers
source                  1..108
                        mol_type = other DNA
                        organism = synthetic construct
SEQUENCE: 20
aggaacccct agtgatggag ttggccactc cctctctgcg cgctcgctcg ctcactgagg     60
ccgcccgggc tttgcccggg cggcctcagt gagcgagcga gcgcgcag                 108

SEQ ID NO: 21           moltype = DNA   length = 3631
FEATURE                 Location/Qualifiers
source                  1..3631
                        mol_type = other DNA
                        organism = synthetic construct
SEQUENCE: 21
```

```
agcttgaagg aaatactaag gcaaaggtac tgcaagtgct cgcaacattc gcttatgcgg    60
attattgccg tagtgccgcg acgccggggg caagatgcag agattgccat ggtacaggcc   120
gtgcggttga tattgccaaa acagagctgt gggggagagt tgtcgagaaa gagtgcggaa   180
gatgcaaagg cgtcggctat tcaaggatgc cagcaagcgc agcatatcgc gctgtgacga   240
tgctaatccc aaaccttacc caacccacct ggtcacgcac tgttaagccg ctgtatgacg   300
ctctggtggt gcaatgccac aaagaagagt caatcgcaga caacattttg aatgcggtca   360
cacgttagca gcatgattgc cacggatggc aacatattaa cggcatgata ttgacttatt   420
gaataaaatt gggtaaattt gactcaacga tgggttaatt cgctcgttgt ggtagtgaga   480
tgaaaagagg cggcgcttac taccgattcc gcctagttgg tcacttcgac gtatcgtctg   540
gaactccaac catcgcaggc agagaggtct gcaaaatgca atcccgaaac agttcgcagg   600
taatagttag agcctgcata acggtttcgg gattttttat atctgcacaa caggtaagag   660
cattgagtcg ataatcgtga agagtcggcg agcctggtta gccagtgctc tttccgttgt   720
gctgaattaa gcgaataccg gaagcagaac cggatcacca aatgcgtaca ggcgtcatcg   780
ccgcccagca acagcacaac ccaaactgag cgtagccac tgtctgtcct gaattcatta   840
gtaatagtta cgctgcggcc ttttacacat gaccttcgtg aaagcgggtg gcaggaggtc   900
gcgctaacaa cctcctgccg ttttgcccgt gcatatcggt cacgaacaaa tctgattact   960
aaacacagta gcctggattt gttctatcag taatcgacct tattcctaat aaatagagc   1020
aaatcccctt attggggta agacatgaag atgccagaaa aacatgacct gttggccgcc   1080
attctcgcgg caaaggaaca aggcatcggg gcaatccttg cgtttgcaat ggcgtacctt   1140
cgcggcagat ataatggcgg tgcgtttaca aaaacagtaa tcgacgcaac gatgtgcgcc   1200
attatcgcct agttcattcg tgaccttctc gacttcgccg gactaagtag caatctcgct   1260
tatataacga gcgtgtttat cggctacatc ggtactgact cgattggttc gcttatcaaa   1320
cgcttcgctg ctaaaaaagc cggagtagaa gatggtagaa atcaataatc aacgtaaggc   1380
gttcctcgat atgctggcgt ggtcggaggg aactgataac ggacgtcaga aaaccagaaa   1440
tcatggttat gacgtcattg taggcggaga gctatttact gattactccg atcaccctcg   1500
caaactttgtc acgctaaacc caaaactcaa atcaacagcc gccggacgct accagcttct   1560
ttcccgttgg tgggatgcct accgcaagca gcttggcctg aaagacttct ctccgaaaag   1620
tcaggacgct gtggcattgc agcagattaa ggagcgtggc gctttaccta tgattgatcg   1680
tggtgatatc cgtcaggcaa tcgaccgttg cagcaatatc tgggcttcac tgccgggcgc   1740
tggttatggt cagttcgagc ataaggctga cagcctgatt gcaaaattca aagaagcggg   1800
cggaacggtc agagagattg atgtatgagc agagtcaccg cgattatctc cgctctggtt   1860
atctgcatca tcgtctgcct gtcatgggct gttaatcatt accgtgataa cgccattacc   1920
tacaaagccc agcgcgacaa aaatgccaga gaactgaagc tggcgaacgc ggcaattact   1980
gacatgcaga tgcgtcagcg tgatgttgct gcgctgatcg caaaatacac gaaggagtta   2040
gctgatgcta aagctgaaaa tgatgctctg cgtgatgatg ttgccgctgg tcgtcgtcgg   2100
ttgcacatca aagcagtctg tcagtcagtg cgtgaagcca ccaccgcctc cggcgtggat   2160
aatgcagcct ccccccgact ggcagacacc gctgaacggg attatttcac cctcagagag   2220
aggctgatca ctatgcaaaa acaactggaa ggaacccaga agtatattaa tgagcagtgc   2280
agatagagtt gcccatatcg atgggcaact catgcaatta ttgtgagcaa tacacacgcg   2340
cttccagcgg agtataaatg cctaaagtaa taaaaccgag caatccatt acgaatgttt   2400
gctgggtttc tgttttaaca acattttctg cgccgccaca aattttggct gcatcgacag   2460
ttttcttctg cccaattcca gaaacgaaga aatgatgggt gatggtttcc tttggtgcta   2520
ctgctgccgg tttgttttga acagtaaacg tctgttgagc acatcctgta ataagcaggg   2580
ccagcgcagt agcgagtagc attttttttca tggtgttatt cccgatgctt tttgaagttc   2640
gcagaatcgt atgtgtagaa aattaaacaa acctaaaca atgagttgaa atttcatatt   2700
gttaatattt attaatgtat gtcaggtgcg atgaatcgtc attgtattcc cggattaact   2760
atgtccacag ccctgacggg gaacttctct gcgggagtgt ccgggaataa ttaaaacgat   2820
gcacacaggg tttagcgcgt acacgtattg cattatgcca acgccccggt gctgacacgg   2880
aagaaaccgg acgttatgat ttagcgtgga aagatttgtg tagtgttctg aatgctctca   2940
gtaaatagta atgaattatc aaaggtatag taatatcttt tatgttcatg gatatttgta   3000
acccatcgga aaactcctgc tttagcaaga ttttcccgt attgctgaaa tgtgattcn    3060
cttgatttca acctatcata ggacgttct ataagatgcg tgtttcttga gatttaaca    3120
tttacaacct ttttaagtcc ttttattaac acggtgttat cgttttctaa cacgatgtga   3180
atattatctg tggctagata gtaaaataaa tgtgagacgt tgtgacgttt tagttcgaaa   3240
taaaacaatt cacagtctaa atcttttcgc acttgatcga atatttcttt aaaaatggca   3300
acctgagcca ttggtaaaac cttccatgtg atacgagggc gcgtagtttg cattatcgtt   3360
tttatcgttt caatctggtc tgacctcctt gtgttttgtt gatgatttat gtcaaatatt   3420
aggaatgttt tcacttaata gtattggttg cgtaacaaag tgcggtcctg ctggcattct   3480
ggagggaaat acaaccgaca gatgtatgta aggccaacgt gctcaaatct tcatacagaa   3540
agatttgaag taatatttta accgctagat gaagagcaag cgcatggagc gacaaaatga   3600
ataaagaaca atctgctgat gatccctccg t                                  3631

SEQ ID NO: 22          moltype = DNA  length = 307
FEATURE                Location/Qualifiers
source                 1..307
                       mol_type = other DNA
                       organism = synthetic construct
SEQUENCE: 22
gcattaagcg cggcgggtgt ggtggttacg cgcagcgtga ccgctacact tgccagcgcc    60
ttagcgcccg ctcctttcgc tttcttccct tcctttctcg ccacgttcgc cggctttccc   120
cgtcaagctc taaatcgggg gctccctttta gggttccgat ttagtgcttt acggcacctc   180
gaccccaaaa aacttgattt gggtgatggt tcacgtagtg ggccatcgcc ctgatagacg   240
gttttcgcc ctttgacgtt ggagtccacg ttctttaata gtggactctt gttccaaact   300
ggaacaa                                                             307

SEQ ID NO: 23          moltype = DNA  length = 813
FEATURE                Location/Qualifiers
source                 1..813
                       mol_type = other DNA
```

```
                        organism = synthetic construct
SEQUENCE: 23
gaaaaactca tcgagcatca aatgaaactg caatttattc atatcaggat tatcaatacc   60
atattttga aaaagccgtt tctgtaatga aggagaaaac tcaccgaggc agttccatag   120
gatggcaaga tcctggtatc ggtctgcgat tccgactcgt ccaacatcaa tacaacctat   180
taatttcccc tcgtcaaaaa taaggttatc aagtgagaaa tcaccatgag tgacgactga   240
atccggtgag aatggcaaaa gcttatgcat ttctttccag acttgttcaa caggccagcc   300
attacgctcg tcatcaaaat cactcgcatc aaccaaaccg ttattcattc gtgattgcgc   360
ctgagcgaga cgaaatacgc gatcgctgtt aaaaggacaa ttacaaacag gaatcgaatg   420
caaccggcgc aggaacactg ccagcgcatc aacaatattt tcacctgaat caggatattc   480
ttctaatacc tggaatgctg ttttcccggg gatcgcagtg gtgagtaacc atgcatcatc   540
aggagtacgg ataaaatgct tgatggtcgg aagaggcata aattccgtca gccagtttag   600
tctgaccatc tcatctgtaa catcattggc aacgctacct ttgccatgtt tcagaaacaa   660
ctctggcgca tcgggcttcc catacaatcg atagattgtc gcacctgatt gcccgacatt   720
atcgcgagcc catttatacc catataaatc agcatccatg ttggaattta atcgcggctt   780
cgagcaagac gtttcccgtt gaatatggct cat                               813

SEQ ID NO: 24          moltype = DNA  length = 668
FEATURE                Location/Qualifiers
source                 1..668
                       mol_type = other DNA
                       organism = synthetic construct
SEQUENCE: 24
gtagaaaaga tcaaaggatc ttcttgagat ccttttttc tgcgcgtaat ctgctgcttg    60
caaacaaaaa aaccaccgct accagcggtg gtttgtttgc cggatcaaga gctaccaact   120
cttttccgaa ggtaactggc ttcagcagag cgcagatacc aaatactgtt cttctagtg   180
tagccgtagt taggccacca cttcaagaac tctgtagcac cgcctacata cctcgctctg   240
ctaatcctgt taccagtggc tgctgccagt ggcgataagt cgtgtcttac cgggttggac   300
tcaagacgat agttaccgga taaggcgcag cggtcgggct gaacggggggg ttcgtgcaca   360
cagcccagct tggagcgaac gacctacacc gaactgagat acctacagcg tgagctatga   420
gaaagcgcca cgcttcccga agggagaaag gcggacaggt atccggtaag cggcagggtc   480
ggaacaggag agcgcacgag ggagcttcca gggggaaacg cctggtatct ttatagtcct   540
gtcgggtttc gccacctctg acttgagcgt cgatttttgt gatgctcgtc aggggggcgg   600
agcctatgga aaaacgccag caacgcggcc tttttacggt tcctggcctt ttgctggcct   660
tttgctca                                                           668

SEQ ID NO: 25          moltype = DNA  length = 2824
FEATURE                Location/Qualifiers
source                 1..2824
                       mol_type = other DNA
                       organism = synthetic construct
SEQUENCE: 25
atgcagaggg tgaacatgat catggctgag agccctggcc tgatcaccat ctgcctgctg    60
ggctacctgc tgtctgctga atgtacaggt ttgtttcctt ttttataata cattgagtat   120
gcttgccttt tagatataga aatatctgat tctgtcttct tcactaaatt ttgattacat   180
gatttgacag caatattgaa gagtctaaca gccagcaccc aggttggtaa gtactggttc   240
tttgttagct aggttttctt cttcttcact tttaaaacta aatagatgga caatgcttat   300
gatgcaataa ggtttaataa acactgttca gttcagtatt tggtcatgta attcctgtta   360
aaaaacagtc atctccttgg tttaaaaaaa ttaaaagtgg gaaaacaaag aaatagcaga   420
atatagtgaa aaaaaataac cacagtattt ttgtttggac ttaccacttt gaaatcaaat   480
tgggaaacaa aagcacaaac agtggccttta tttacacaaa aagtctgatt ttaagatatg   540
tgacaattca aggtttcaga agtatgtaag gaggtgtgtc tctaatttt taaattatat   600
atcttcaatt taaagttttta gttaaaacat aaagattaac ctttcattag caagctgtta   660
gttatccacca aagcttttca tggattagga aaaaatcatt ttgtctctat ctcaaacatc   720
ttggagttga tatttgggga aacacaatac tcagttgagt tccctagggg agaaaagcaa   780
gcttaagaat tgacacaaag gtaggaagt tagctattgc aacatatatc actttgtttt   840
ttcacaacta cagtgacttt atttatttcc cagaggaagg catacaggga agaaattatc   900
ccatttggac aaacagcatg ttctcacagt aagcacttat cacacttact tgtcaacttt   960
ctagaatcaa atctagtagc tgacagtacc aggataccgg gtgccaaccc taagcaccgc  1020
cagaaagctg actggccctg tggttcccac tccagacatg atgtcagctg tgaaatccac  1080
ctccctggac cataattagg cttctgttct tcaggagaca tttgttcaaa gtcatttggg  1140
caaccatatt ctgaaaacag cccagccagg gtgatggatc actttgcaaa gatcctcaat  1200
gagctatttt caagtgatga caaagtgtga agttaagggc tcatttgaga actttctttt  1260
tcatccaaag taaattcaaa tatgattaga aatctgacct tttattactg gaattctctt  1320
gactaaaagt aaaattgaat tttaattcct aaatctccat gtgtatacag tactgtggga  1380
acatcacaga ttttggctcc atgccctaaa gagaaattgg ctttcagatt atttggatta  1440
aaaacaaaga ctttcttaag agatgtaaaa ttttcatgat gttttctttt ttgctaaaac  1500
taaagaatta ttcttttaca tttcagtttt tcttgatcat gaaaatgcca acaaaattct  1560
gaatagacca aagaggtata actctggcaa gcttgaagag tttgtacagg ggaatctgga  1620
gagagagtgt atggaagaga agtgcagctt tgaggaagcc agagaagtgt ttgaaaatac  1680
agagagaaca actgaatttt ggaagcagta tgtggatggt gatcaatgtg agagcaatcc  1740
ctgcttgaat ggggggagct gtaaagatga tatcaacagc tatgaatgtt ggtgtccctt  1800
tggatttgag gggaaaaact gtgagcttga tgtgacctgt aatatcaaga atggcaggtg  1860
tgagcaattt tgcaagaatt ctgctgataa caaagtggtc tgtagctgca ctgagggata  1920
taggctggct gaaaaccaga gagctgtgaa acctgcagtg cctttttcct gtgggagagt  1980
gtctgtgagc caaaccagca agctgactag ggctgaagca gtcttcctg atgtagatta  2040
tgtgaatagc actgaggctg agacaatcct tgacaatatc actcagagca cacagagctt  2100
caatgacttc accagggtgg taggagggga ggatgccaag cctgggcagt tcccctggca  2160
ggtagtgctc aatggaaaag tggatgcctt ttgtggaggt tcaattgtaa atgagaagtg  2220
```

```
gattgtgact gcagcccact gtgtggaaac tggagtcaag attactgtgg tggctggaga    2280
gcacaatatt gaggaaactg agcacactga gcagaagagg aatgtgatca ggattatccc    2340
ccaccacaac tacaatgctg ctatcaacaa gtacaaccat gacattgccc tcctggaact    2400
ggatgaaccc ctggtcttga acagctatgt gacacccatc tgtattgctg ataaagagta    2460
caccaacatc ttcttgaaat ttgggtctgg atatgtgtct ggctgggca gggtgttcca    2520
taaaggcagg tctgccctgg tattgcagta tttgagggtg cctctggtgg atagagcaac    2580
ctgcttgctg agcaccaagt ttacaatcta acaatatg ttctgtgcag ggttccatga     2640
aggtggtaga gacagctgcc agggagattc tgggggtccc catgtgactg aggtggaggg    2700
aaccagcttc ctgactggga ttatcagctg gggtgaggag tgtgctatga agggaaagta    2760
tgggatctac acaaaagtat ccagatatgt gaactggatt aaggagaaaa ccaagctgac    2820
ttga                                                                 2824

SEQ ID NO: 26        moltype = DNA  length = 10659
FEATURE              Location/Qualifiers
source               1..10659
                     mol_type = other DNA
                     organism = synthetic construct
SEQUENCE: 26
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggcctag taggctcaga ggcacacagg agtttctggg    180
ctcaccctgc ccccttccaa cccctcagtt cccatcctcc agcagctgtt tgtgtgctgc    240
ctctgaagtc cacactgaac aaacttcagc ctactcatgt ccctaaaatg ggcaaacatt    300
gcaagcagca aacagcaaac acacagccct ccctgcctgc tgaccttgga gctggggcag    360
aggtcagaga cctctctggg cccatgccac ctccaacatc cactcgaccc cttggaattt    420
cggtgtggag gagcagaggt tgtcctggcg tggtttaagt agtgtgaagg agtgtacccgg    480
ggatcttgct accagtggaa cagccactaa ggattctgca gtgagagcag agggccagct    540
aagtggtact ctcccagaga ctgtctgact cacgccaccc cctccacctt ggacacagga    600
cgctgtggtt tctgagccag gtacaatgac tcctttcggt aagtgcagtg gaagctgtac    660
actgccagg caaagcgtcc gggcagcgta ggcgggcgac tcagatccca gccagtggac    720
ttagcccctg tttgctcctc cgataactga ggtgaccttg gttaatattc accagcagcc    780
tccccgttg ccctctgga tccactgctt aaatacggac gaggacaggg ccctgtctcc    840
tcagcttcag gcaccaccac tgacctggga cagtgaatac cactttcaca atctgctagc    900
aaaggttatg cagagggtga acatgatcat ggctggagagc cctggcctga tcaccatctg    960
cctgctgggc tacctgctgt ctgctgaatg tacaggtttg tttccttttt tataatacat   1020
tgagtatgct tgcccttttag atatagaaat atctgcattct gtcttcttca ctaaattttg   1080
attacatgat ttgacagcaa tattgaagag tctaacagcc agcacccagg ttggtaagta   1140
ctggttcttt gttagctagg ttttcttctt cttcacttttt aaaactaaat agatggacaa   1200
tgcttatgat gcaataaggt ttaataaaca ctgttcagtt cagtatttgg tcatgtaatt   1260
cctgttaaaa aacagtcatc tccttggttt aaaaaaatta aaagtgggaa aacaaagaaa   1320
tagcagaata tagtgaaaaa aaataaccac agtattttg tttggactta ccactttgaa   1380
atcaaattgg gaaacaaaag cacaaacagt ggccttattt acacaaaaag tctgatttta   1440
agatatgtga caattcaagg tttcagaagt atgtaaggag gtgtgtctct aattttttaa   1500
attatatatc ttcaatttaa agttttagtt aaaaacataa gattaacctt tcattagcaa   1560
cctcaatgag ctattttcaa gtgatgacaa agtgtgaagt taagggctca tttgagaact   1620
ttcttttca tccaaagtaa attcaaatat gattagaaat ctgaccttt attactgaa    1680
ttctcttgac taaaagtaaa attgaatttt aattcctaaa tctccatgtg tatacagtac   1740
tgtgggaaca tcacagattt tggctccatg ccctaaagag aaattggctt tcagattatt   1800
tggattaaaa acaaagactt tcttaagaga tgtaaaattt tcatgatgtt ttctttttg   1860
ctaaaactaa agaattattc ttttacattt cagttttcct tgatcatgaa aatgccaaca   1920
aaattctgaa tagaccaaag aggtataact ctggcaagtt tgaagagttt gtacagggga   1980
atctggagag agagtgtatg gaagagaagt gcagctttg ggaagccaga gaagtgttg    2040
aaaatacaga gagaacaact gaattttgga agcagtatgt ggatggtgat caatgtgaga   2100
gcaatccctg cttgaatggg gggagctgta aagatgtat caacagctat gaatgttggt   2160
gtcccttggg atttgagggg aaaaactgtg agcttgatgt gacctgtaat atcaagaatg   2220
gcaggtgtga gcaattttgc aagaattctg ctgataacaa agtggtctgt agctgcactg   2280
agggatatag gctggctgaa accagaagag ctgtgaacc tgcagtgcct tttccctgtg   2340
ggagagtgtc tgtgagccaa accagcaagc tgactagggc tgaagcagtc tttcctgatg   2400
tagattatgt gaatagcact gaggctgaga caatccttga caatatcact cagagcacac   2460
agagcttcaa tgacttcacc agggtggtag gaggggagga tgccaagcct gggcagttcc   2520
cctggcaggt agtgctcaat ggaaagtgg atgcctttg tggaggttca attgtaaatg   2580
agaagtggat tgtgactgca gcccactgtg tggaaactgg agtcaagatt actgtggtgg   2640
ctggagagca caatattgag gaaactgagc acactgagca gaagaggaat gtgatcagga   2700
ttatccccca ccacaactac aatgctgcta tcaacaagta caaccatgac attgccctcc   2760
tggaactgga tgaaccccctg gtcttgaaca gctatgtgac acccatcgt attgctgata   2820
aagagtacac caacatcttc ttgaaatttg gtctggata tgtgtctggc tggggcaggg   2880
tgttccataa aggcaggtct gccctggtat tgcagtattt gagggtgcct ctggtggata   2940
gagcaacctg cttgctgagc accaagttta catctacaa caatatgttc tgtgcaggt    3000
tccatgaagg tggtagagac agctgccagg gagattctgg ggtccccat gtgactggga   3060
tggagggaac cagcttcctg actgggatta tcagctgggg tgaggagtgt gctatgaagg   3120
gaaagtatgg gatctacaca aaagtatcca gatatgtgaa ctggattaag gagaaaacca   3180
agctgacttg atgaaagatg gatttccaag gttaattcat tggaattgaa aattaacaga   3240
gatctagagc tgaattcctg cagccagggg atcagcctc tactgtgcct tctagttgcc    3300
agccatctgt tgtttgcccc tccccttgc cttccttgac cctggaaggt gccactccca   3360
ctgtcctttc ctaataaaat gaggaaattg catcacattg tctgagtagg tgtcattcta   3420
ttctgggggg tggggtgggg caggacagca aggggggagga ttggaagac aatagcaggc   3480
atgctgggga tgcagtgggc tctatggctt ctgaggcaga aagaaccagc tggggctcga   3540
gatcactag gccgcagga accccctagtg atggagttgg ccactcccctc tctgcgcgct   3600
cgctcgctca ctgaggccgg cgaccaaag gtcgcccgac gcccgggctt tgcccgggcg   3660
```

```
gcctcagtga gcgagcgagc gcgcagctgc ctgcagggc ccatgggcag atgcaccacc    3720
tgtctcagtg caaagccctg cctaagtagg ctggtcataa gaccatgtgt ctggctgtaa    3780
ctccaattga ttgtcagcat caataaaact tggccaacac tgttatatac tggtattgat    3840
agttacaact gaacatattt gtttaagcaa ttggaattaa gaattcacat gcaatgatat    3900
caggtccctt ctcctctggt tagtgtattg ggggaaatt ggacatctct cagctcagta    3960
ggctagttag gccaggatgg atgacatcca cagcccctgg gcagagagat tatgatgtag    4020
ctagtctgac tcctgacaaa gacttgcttc ctggagcttc tactactttc tggtggatgg    4080
ctaagaaata tggttgtgtt ctttttaagtc tgaagagcat tattttttgcc aaccctgac    4140
caaacatcct tgccaaggaa aaggcctaaa atatatttgc atttaaagat attacaaact    4200
acttggtttt ggaatgtttg gccttttcagg atcatagcta tcaaaatatt agctatttgg    4260
ggtatgagat gtctgcttgg tcaaggacaa gttcttaaag acatcatgtt ggggaataat    4320
ggggaaaatg ggaaggctta tgctctgagt aagacatctg agttatcatc tgtcaaacat    4380
ttttgttagt catagtctaa tgggagcctg tttttccctct ttaatataca ttcacatctg    4440
aatttatgct cttcattgac aatgccagcc cagaacaaca gctcttaccc tttggttttc    4500
ttcctaacct ttaactccaa tgtaaccatt acctgccatt tcagtaaaac cattattctc    4560
cctacttacc cacccaagtt gtacaataaa gagtgtttgc tctcactcat atacaaagca    4620
aattcatttg tttgtgatgt acagcttgct atgcccacag atgtggtttg cctagtcctt    4680
tgctctaggt catttgactg ggaacagatg ggatgctcag tttggttttt aatgttaac    4740
tagtcattga aatgcatttc atcaaataat cttagaggat aattgtttaa atgtctgtcc    4800
agactagctt tgtagagcca ggtgccatta cacatgtcac cttcttattt ctcttaattg    4860
aattttttatc atctgagata ggaataatag agggcttttt caagtgaaga tattactata    4920
gtctaaagac cttagtgtaa catccctggc cctaaggaaa acaagttct ggttcataca    4980
tataataact ttgcatgtta tctgccactg agatgtgtcc taatccaaca gaaaggattg    5040
aatctctgta gctaggtgta cagggcaaga gctgtacagg gaacctttaa agatagcttc    5100
aggccaaagc tgaggaaagt ggatggagac tgggaaaat gctaagacat tttaaagatt    5160
ttctttaggt caaaaataga ataagaaata gaccatttcc ctggacatttt tctgtaggtt    5220
aatactgtta actattggta aatgcatatg ctacaactta atatgtctgc tttgtgagtt    5280
tagcattgtc tccttgtcat tccagaaatg aaatggcaaa tacatttaaa tcagaactaa    5340
aaaggggaac agggtataaa ggctcaattt agtcacatca tttcccttc tcacccaccc    5400
ccttttaaacc agatgtttgc caatgcatta acaatgcaga tgtttcctga aagaaagttt    5460
agtaactcaa gcagacacct tatttttctt tcaagcagaa aagactatga gatggtggtt    5520
gtggttgttc tgggagggag aagatataaa tgatacacat tatttcaaat catttcatga    5580
cctcactgca cacttatagt tattgtacct gttgtcttt tgctgtcaag cctagctaag    5640
atcatttgga atgttcaaga tcactcatac atgcatgtgc acacatacac atgcacatat    5700
gttcactccc tatttcatcc acatgaacta agattactga tgtgtacaga ttcaaagcac    5760
ttttattctt ttccaaaggc aagaagctga gctactttcc agaatagttg tgaaagaccc    5820
tgtcatactt ctgcattgtt tcctccacac cacctccatc cagttcctta tgaatggtta    5880
ctggttttca aaaatatgag ataaattgag tgtataaaag tcattttag acaaaatgaa    5940
acaggaaatg aaagaaacca gaatctctcc tcatttgtgg atgggccagc tccaccatgt    6000
catggttaat ctgcagggag gaaatactag atttgattgc agatcagact gcagcaaacc    6060
tgctgtgact aaggcatcaa gagaaagcaa gcaacagctg gggcttcagt ggtgaaaaca    6120
ttatatatct agctttgaaa tatgaaatac tgtttagcag tgtcacctag aaaagagtgt    6180
ttcaaaatgc tgatgcttca taagaaacctt tctcttcaga gttgtttctt ttatcttttca    6240
aattagccag ggtgggaaat aaagtgatca cttggtgaag aaatctcaca agaagaaca    6300
tagagagttc actttcatct ggagtaatga acagattgaa caaactagaa atggttagtc    6360
tgttaaagaa aaggtgtagg tgagctgttt gcaagagcca caagggaaag gggaagacaa    6420
cttcttttgtg gacttaaggg tgaaagttgc aagcaggcaa gaccattctg acctccatta    6480
agaaagccct ttccaaccaa caaccactgg gttggttact caggttgggc agcattggga    6540
gcaaatgttg attgaacaaa tgtttgtcag aattgttgac ttaaagagct gttctgtcac    6600
tggggacagc agcagctaga tagccccatt cagggagagg gcatttgttc acctggccag    6660
agatcagaga aggctaaggg actgctggga tcctgtccag ctttgagacc ctacagaaagc    6720
atgttcacct agcaggtatc ccttctgagg tcactctcat ttcttacctt attccagggc    6780
tttcacctca gcttgccagg ctggagccaa gggccaaggc agcctcacct tgttggctat    6840
ggtagcttcc caggagcccc ctatggttca ggaacagctc tgcctgcccc atcctgtttg    6900
ctacctccta aagccaaagg cactggtggg ccaggccagc ttctaaagtc acacaaggtt    6960
agaaggttcc tgacaggaag ggcttgaggc caatgggagg aggtacttca gtttccctcc    7020
agatgcccag tgatgggctc agagctcctg gagaacttgg gaaaggaagc agggtctctg    7080
aagaaatact tcaggagtag aaagaggaag ctagagggtt aaatgcacta cacaggaaca    7140
gaaatgagtt tttcttagag ttagtatatg tctagaggtg tagtaaacta aaaacaagtct    7200
tgaattgcat acagccactt agggaagaaa tgaaaaccttt tgaatattag tgaaaaaggg    7260
gaaactgcaa cccctgtatt actagatagc tttcatcaac agctcaaaac agacagattt    7320
ttataggttt actgtgtgca ctttaataca agggcagtgg ttcagaacta gtcaggtcct    7380
gaaaaggatt taccaaatgt tgagtgtgcc ctctagtgtt cacacttccc agctttcttc    7440
ctataaaggt ggatcaaggc acttgcttac aactggaact gaaatcctcc aagtggaact    7500
agacattgag atggagaaaa tattcattgt ccactgtaat tatgcaagga atatccagtt    7560
gagataatgg acttgcctct tatctaataa tacccaggct caatgggtca ctgctttgtc    7620
cactttgccc aaaattcaag cacagctaag ttgatatttt aggacaaagg cagcttacta    7680
tccagccaga ggggagtaga atatgtttaa gagagagtgg aaagaatgaa tgagccctgc    7740
tattcctcac tgcctggatg gctataagca cagcccttat ggaggccttta ggtcttgctt    7800
cataatattc cagtttgaaa agggtttgaa aagacctcct agaaaaatca gtagttttttc    7860
tcttttgagt aacatgtagc aaaaaaaatt tcatcatgta ggtacaggga cacccctaat    7920
aactattaat ctcaaggagt caagccagtg tgtttcctaa tgtatctgct gtatcccccat    7980
gaagcaaatt ttgccatcag agaaactgac tcatgggaa aaaatccaag gacctcaaat    8040
caccaaaaga agccattcct cagatttgcc taagcttaag tttccctgtc tctcattgtg    8100
tgttgctttc aatgcagtta cataaatggc ttttttgttt atgcaccaaa aacactaatt    8160
catctgcaaa gctataggtc aaagcaacca tagtatgcac cctgctagct ggcgcattaa    8220
gcgcggcggg tgtggtggtt acgcgcagcg tgaccgctac acttgccagc gccttagcgc    8280
ccgctccttt cgctttcttc ccttcctttc tcgccacgtt cgccggcttt ccccgtcaag    8340
ctctaaatcg ggggctccct ttagggttcc gatttagtgc tttacggcac ctcgacccca    8400
```

```
aaaaacttga tttgggtgat ggttcacgta gtgggccatc gccctgatag acgttttttc  8460
gcccttttgac gttggagtcc acgttcttta atagtggact cttgttccaa actggaacaa  8520
cactcaactc tatctcgggc tattcttttg atttagacct gcaggcatgc aagcttggca  8580
ctggccgtcg ttttacaacg tcgtgactgg gaaaaccctg gcgttaccca acttaatcgc  8640
cttgcagcac atccccttt cgccagctgg cgtaatagcg aagaggcccg caccgatcgc  8700
ccttcccaac agttgcgcag cctgaatggc gaatgcgatt tattcaacaa agccgccgtc  8760
ccgtcaagtc agcgtaatgc tctgccagtg ttacaaccaa ttaaccaatt ctgattagaa  8820
aaactcatcg agcatcaaat gaaactgcaa tttattcata tcaggattat caataccata  8880
tttttgaaaa agccgtttct gtaatgaagg agaaaactca ccgaggcagt tccataggat  8940
ggcaagatcc tggtatcggt ctgcgattcc gactcgtcca acatcaatac aacctattaa  9000
tttcccctcg tcaaaaataa ggttatcaag tgagaaatca ccatgagtga cgactgaatc  9060
cggtgagaat ggcaaaagct tatgcatttc tttccagact tgttcaacag gccagccatt  9120
acgctcgtca tcaaaatcac tcgcatcaac caaaccgtta ttcattcgtg attgcgcctg  9180
agcgagacga aatacgcgat cgctgttaaa aggacaatta caaacaggaa tcgaatgcaa  9240
ccggcgcagg aacactgcca gcgcatcaac aatattttca cctgaatcag gatattcttc  9300
taatacctgg aatgctgttt tcccggggat cgcagtggtg agtaaccatg catcatcagg  9360
agtacggata aaatgcttga tggtcggaag aggcataaat tccgtcagcc agtttagtct  9420
gaccatctca tctgtaacat cattggcaac gctacctttg ccatgtttca gaaacaactc  9480
tggcgcatcg ggcttcccat acaatcgata gattgtcgca cctgattgcc cgacattatc  9540
gcgagcccat ttatacccat ataaatcagc atccatgttg gaatttaatc gcggcttcga  9600
gcaagacgtt tcccgttgaa tatggctcat aacaccccctt gtattactgt ttatgtaagc  9660
agacagtttt attgttcatg atgatatatt tttatcttgt gcaatgtaac atcagagatt  9720
ttgagacaca acgtggcttt gttgaataaa tcgaacttt gctgagttga aggatcagat  9780
cacgcatctt cccgacaacg cagaccgttc cgtggcaaag caaaagttca aaatcaccaa  9840
ctggtccacc tacaacaaag ctctcatcaa ccgtggctcc ctcactttct ggctggatga  9900
tggggcgatt caggcctggt atgagtcagc aacaccttct tcacgaggca gacctctcga  9960
cggagttcca ctgagcgtca gaccccgtag aaaagatcaa aggatcttct tgagatcctt 10020
tttttctgcg cgtaatctgc tgcttgcaaa caaaaaaacc accgctacca gcggtggttt 10080
gtttgccgga tcaagagcta ccaactcttt ttccgaaggt aactggcttc agcagagcgc 10140
agataccaaa tactgttctt ctagtgtagc cgtagttagg ccaccacttc aagaactctg 10200
tagcaccgcc tacatacctc gctctgctaa tcctgttacc agtggctgct gccagtggcg 10260
ataagtcgtg tcttaccggg ttggactcaa gacgatagtt accggataag cgcagcggt 10320
cgggctgaac ggggggttcg tgcacacagc ccagcttgga gcgaacgacc tacaccgaac 10380
tgagatacct acagcgtgag ctatgagaaa gcgccacgct tcccgaaggg agaaaggcgg 10440
acaggtatcc ggtaagcggc agggtcggaa caggagagcg cacgagggag cttccagggg 10500
gaaacgcctg gtatctttat agtcctgtcg ggtttcgcca cctctgactt gagcgtcgat 10560
ttttgtgatg ctcgtcaggg gggcggagcc tatggaaaaa cgccagcaac gcggcctttt 10620
tacggttcct ggccttttgc tggccttttg ctcacatgt                        10659

SEQ ID NO: 27        moltype = AA  length = 601
FEATURE              Location/Qualifiers
source               1..601
                     mol_type = protein
                     organism = synthetic construct
SEQUENCE: 27
TAPGKKRPVE PSPQRSPDSS TGIGKKGQQP AKKRLNFGQT GDSESVPDPQ PIGEPPAAPS   60
GVGPNTMAAG GGAPMADNNE GADGVGSSSG NWHCDSTWLG DRVITTSTRT WALPTYNNHL  120
YKQISNGTSG GSTNDNTYFG YSTPWGYFDF NRFHCHFSPR DWQRLINNNW GFRPKRLNFK  180
LFNIQVKEVT QNEGTKTIAN NLTSTIQVFT DSEYQLPYVL GSAHQGCLPP FPADVFMIPQ  240
YGYLTLNNGS QAVGRSSFYC LEYFPSQMLR TGNNFEFSYN FEDVPFHSSY AHSQSLDRLM  300
NPLIDQYLYY LSRTQSTGGT AGTQQLLFSQ AGPNNMSAQA KNWLPGPCYR QQRVSTTLSQ  360
NNNSNFAWTG ATKYHLNGRD SLVNPGVAMA THKDDEERFF PSSGVLMFGK QGAGKDNVDY  420
SSVMLTSEEE IKTTNPVATE QYGVVADNLQ QQNAAPIVGA VNSQGALPGM VWQNRDVYLQ  480
GPIWAKIPHT DGNFHPSPLM GGFGLKHPPP QILIKNTPVP ADPPTTFNQA KLASFITQYS  540
TGQVSVEIEW ELQKENSKRW NPEIQYTSNY YKSTNVDFAV NTEGTYSEPR PIGTRYLTRN  600
L                                                                 601
```

What is claimed:

1. A method of treating a human subject with hemophilia B comprising: administering to said subject a therapeutically effective amount of a recombinant adeno-associated virus (rAAV) vector comprising a vector genome encapsidated by an AAV5 capsid, wherein said vector genome comprises at least two AAV inverted terminal repeats (ITR), an expression control element conferring liver tissue-specific expression operably linked with a nucleic acid sequence encoding human Factor IX (FIX) protein, and a polyadenylation signal sequence, wherein said nucleic acid sequence encoding human FIX protein is at least 70% identical to SEQ ID NO:10, has a reduced number of CpG dinucleotides compared to wild-type nucleic acid sequence encoding human FIX protein and encodes the same human FIX protein encoded by SEQ ID NO:10, and wherein said therapeutically effective amount of said rAAV vector is a dose ranging from $1\times10^{13}$ to $1\times10^{14}$ vector genomes per kilogram (vg/kg) human subject body weight.

2. The method of claim 1, wherein said nucleic acid sequence encoding human FIX protein is at least 80% identical to SEQ ID NO:10.

3. The method of claim 2, wherein said nucleic acid sequence encoding human FIX protein is at least 85% identical to SEQ ID NO:10.

4. The method of claim 1, wherein said vector genome further comprises an intron.

5. The method of claim 4, wherein said intron is positioned within said nucleic acid sequence encoding human FIX protein.

6. The method of claim 4, wherein said intron is positioned between said promoter and said nucleic acid sequence encoding human FIX protein.

7. The method of claim 1, wherein said vector genome is linear single-stranded DNA.

8. The method of claim 1, wherein an AAV ITR is positioned at each end of the vector genome, and said expression control element comprises an enhancer and a promoter.

9. The method of claim 8, wherein said AAV ITRs are AAV2 ITRs, said enhancer is a human apolipoprotein HCR enhancer, and said promoter is a human alpha-1-antitrypsin gene promoter.

10. The method of claim 1, wherein said therapeutically effective amount of said rAAV vector is a dose selected from the group consisting of $1\times10^{13}$, $2\times10^{13}$, $3\times10^{13}$, $4\times10^{13}$, $5\times10^{13}$, $6\times10^{13}$ $7\times10^{13}$, $8\times10^{13}$, $9\times10^{13}$ and $1\times10^{14}$ vg/kg human subject body weight.

11. The method of claim 10, wherein said therapeutically effective amount of said rAAV vector is a dose of $2\times10^{13}$ vg/kg human subject body weight.

12. The method of claim 11, wherein the disease phenotype of said hemophilia B is severe or moderate hemophilia B and said treatment is effective to convert the disease phenotype to mild hemophilia B.

13. The method of claim 1, wherein said treatment does not cause circulating liver enzyme levels to exceed 100% of the upper limit of normal value.

14. The method of claim 1, wherein the disease phenotype of said hemophilia B is severe or moderate hemophilia B and said treatment is effective to convert the disease phenotype to mild hemophilia B.

15. The method of claim 14, wherein said treatment is effective to produce greater than 5% of normal FIX activity.

16. The method of claim 14, wherein said treatment is effective to produce greater than 30% of normal FIX activity.

17. The method of claim 14, wherein said treatment is effective to produce 6% to 40% of normal FIX activity.

18. The method of claim 14, wherein said treatment is effective for a sustained period of at least 12 months without immunosuppression.

19. The method of claim 1, wherein the disease phenotype of said hemophilia B is severe or moderate hemophilia B and said treatment is effective to convert the disease phenotype to a hemophilia B disease-free state.

20. The method of claim 19, wherein said treatment is effective to produce about 50% to 150% of normal FIX activity.

21. The method of claim 19, wherein said treatment is effective for a sustained period of at least 12 months without immunosuppression.

22. A method of treating a human subject with hemophilia B comprising:
administering to said human subject a therapeutically effective amount of a recombinant adeno-associated virus (rAAV) vector comprising a vector genome encapsidated by an AAV5 capsid,
wherein said vector genome comprises at least two AAV inverted terminal repeats (ITR), an expression control element conferring liver tissue-specific expression operably linked with a nucleic acid sequence encoding human Factor IX (FIX) protein, and a polyadenylation signal sequence, wherein said nucleic acid sequence encoding human FIX protein is at least 70% identical to SEQ ID NO:10 and encodes the same human FIX protein encoded by SEQ ID NO:10, and
wherein said therapeutically effective amount of said rAAV vector is a dose ranging from $1\times10^{13}$ to $1\times10^{14}$ vector genomes per kilogram (vg/kg) human subject body weight.

23. A method of treating a human subject with hemophilia B comprising:
administering to said human subject a therapeutically effective amount of a recombinant adeno-associated virus (rAAV) vector comprising a vector genome encapsidated by an AAV5 capsid,
wherein said vector genome comprises at least two AAV inverted terminal repeats (ITR), an expression control element conferring liver tissue-specific expression operably linked with a nucleic acid sequence encoding human Factor IX (FIX) protein, and a polyadenylation signal sequence, wherein said nucleic acid sequence encoding human FIX protein is at least 70% identical to SEQ ID NO:10 and encodes a human FIX protein variant having an amino acid sequence at least 99% identical to that encoded by SEQ ID NO:10, amino acid number 338 thereof being leucine and invariant, and
wherein said therapeutically effective amount of said rAAV vector is a dose ranging from $1\times10^{13}$ to $1\times10^{14}$ vector genomes per kilogram (vg/kg) human subject body weight.

* * * * *